(12) United States Patent
Mead et al.

(10) Patent No.: US 7,723,103 B2
(45) Date of Patent: May 25, 2010

(54) VECTORS, KITS AND METHODS FOR CLONING DNA

(75) Inventors: David A. Mead, Middleton, WI (US); Ronald Godiska, Verona, WI (US); Thomas W. Schoenfeld, Madison, WI (US); Spencer Hermanson, Watertown, WI (US)

(73) Assignee: Lucigen Corporation WI (US)

( * ) Notice: Subject to any disclaimer, the term of this patent is extended or adjusted under 35 U.S.C. 154(b) by 464 days.

(21) Appl. No.: 11/621,031

(22) Filed: Jan. 8, 2007

(65) Prior Publication Data

US 2008/0166773 A1 Jul. 10, 2008

(51) Int. Cl.
*C12N 15/74* (2006.01)
(52) U.S. Cl. .................. 435/320.1; 536/23.1
(58) Field of Classification Search ............. None
See application file for complete search history.

(56) References Cited

U.S. PATENT DOCUMENTS

| | | | | |
|---|---|---|---|---|
| 5,487,993 A | * | 1/1996 | Herrnstadt et al. | 435/488 |
| 5,827,657 A | | 10/1998 | Herrnstadt et al. | |
| 5,847,993 A | | 12/1998 | Dejenfelt | |
| 5,856,144 A | | 1/1999 | Mierendort et al. | |
| 6,586,237 B1 | * | 7/2003 | Yesland | 435/320.1 |
| 6,589,783 B2 | * | 7/2003 | Novy et al. | 435/320.1 |
| 6,916,632 B2 | | 7/2005 | Chesnut et al. | |

OTHER PUBLICATIONS

Gayle et al. Gene 1987;54: 221-228.*
Day, J.P. et al., "Nucleotide analogs facilitate base conversion with 3' mismatch primers," Nuc. Acid. Res. (1999) 27 (8)1810-1818.
Kong, H. et al., "Characterization of a DNA polymerase from the hyperthermophile archaea thermococcus litoralis," J. Biol. Chem. (1993) 268(3):1965-1975.
Mardanov, A.V. et al., (2004) Abstracts of the conference "Lomonosov-2004" 1:21, Moscow, Russia.
Reynolds, R. et al., "Parameters affecting transcription termination by *Escherichia coli* RNA polymerase," J. Mol. Biol. (1992) 224(1):31-51.
Wild, J. et al., "Conditionally amplifiable BACs: switching from single-copy to high-copy vectors and genomic clones," Genome Res. (2002) 12:1434-1444.
Mead, D.A. et al., "Chimera free method for capturing single DNA inserts using a new GC cloning technology," Plant & Animal Genomes XV Conference, Jan. 13-17, 2007, San Diego, California, Abstract.

* cited by examiner

*Primary Examiner*—Q. Janice Li
(74) *Attorney, Agent, or Firm*—Joseph T. Leone, Esq.; DeWitt Ross & Stevens S.C.

(57) ABSTRACT

Vector preparations and cloning constructs suitable for use in cloning are provided. Vector preparations are double-stranded DNA molecules having two 3' termini, each terminus having a single base pair overhang that is capable of hybridizing to a single base pair overhang on a double stranded polynucleotide sequence to be cloned. The overhang of the vector preparation is suitably a dCMP and the overhang of the polynucleotide sequence to be cloned is suitably a dGMP. In other embodiments, the overhang of the polynucleotide sequence to be cloned is any ddNTP and the corresponding overhang of the vector preparation is any base that pairs to the ddNTP. The latter embodiment is particularly suited to preparing recombinant molecules having only a single insert. Methods of cloning, methods of preparing libraries of recombinant molecules and kits for carrying out the methods are also provided.

11 Claims, 7 Drawing Sheets

M  0  A  T  G  C  Blunt

A)

B)

A)

B)

SEQUENCE LISTING

<160> NUMBER OF SEQ ID NOS: 72

<210> SEQ ID NO 1
<211> LENGTH: 1788
<212> TYPE: DNA
<213> ORGANISM: Artificial
<220> FEATURE:
<223> OTHER INFORMATION: pSMART HCKan

<400> SEQUENCE: 1

```
gacgaattct ctagatatcg ctcaatactg accatttaaa tcatacctga cctccatagc      60
agaaagtcaa aagcctccga ccggaggctt ttgacttgat cggcacgtaa gaggttccaa     120
ctttcaccat aatgaaataa gatcactacc gggcgtattt tttgagttat cgagattttc     180
aggagctaag gaagctaaaa tgagccatat tcaacgggaa acgtcttgct cgaggccgcg     240
attaaattcc aacatggatg ctgatttata tgggtataaa tgggctcgcg ataatgtcgg     300
gcaatcaggt gcgacaatct atcgattgta tgggaagccc gatgcgccag agttgtttct     360
gaaacatggc aaaggtagcg ttgccaatga tgttacagat gagatggtca ggctaaactg     420
gctgacggaa tttatgcctc ttccgaccat caagcatttt atccgtactc ctgatgatgc     480
atggttactc accactgcga tcccagggaa aacagcattc caggtattag aagaatatcc     540
tgattcaggt gaaaatattg ttgatgcgct ggcagtgttc ctgcgccggt tgcattcgat     600
tcctgtttgt aattgtcctt ttaacggcga tcgcgtattt cgtctcgctc aggcgcaatc     660
acgaatgaat aacggtttgg ttggtgcgag tgattttgat gacgagcgta atggctggcc     720
tgttgaacaa gtctggaaag aaatgcataa gcttttgcca ttctcaccgg attcagtcgt     780
cactcatggt gatttctcac ttgataacct tatttttgac gaggggaaat taataggttg     840
tattgatgtt ggacgagtcg gaatcgcaga ccgataccag gatcttgcca tcctatggaa     900
ctgcctcggt gagttttctc cttcattaca gaaacggctt tttcaaaaat atggtattga     960
taatcctgat atgaataaat tgcagtttca cttgatgctc gatgagtttt tctaatgagg    1020
gcccaaatgt aatcacctgg ctcaccttcg ggtgggcctt tctgcgttgc tggcgttttt    1080
ccataggctc cgcccccctg acgagcatca caaaaatcga tgctcaagtc agaggtggcg    1140
aaacccgaca ggactataaa gataccaggc gtttccccct ggaagctccc tcgtgcgctc    1200
tcctgttccg accctgccgc ttaccggata cctgtccgcc tttctccctt cgggaagcgt    1260
```

-continued

```
ggcgctttct catagctcac gctgtaggta tctcagttcg gtgtaggtcg ttcgctccaa    1320
gctgggctgt gtgcacgaac ccccgttca gcccgaccgc tgcgccttat ccggtaacta    1380
tcgtcttgag tccaacccgg taagacacga cttatcgcca ctggcagcag ccactggtaa    1440
caggattagc agagcgaggt atgtaggcgg tgctacagag ttcttgaagt ggtggcctaa    1500
ctacggctac actagaagaa cagtatttgg tatctgcgct ctgctgaagc cagttacctc    1560 ggaaaagag ttggtagctc ttgatccggc aaacaaacca ccgctggtag cggtggtttt    1620
tttgtttgca gcagcagat tacgcgcaga aaaaaaggat ctcaagaaga tcctttgatt    1680
ttctaccgaa gaaaggccca cccgtgaagg tgagccagtg agttgattgc agtccagtta    1740
cgctggagtc tgaggctcgt cctgaatgat atcaagcttg aattcgtt    1788
```

```
<210> SEQ ID NO 2
<211> LENGTH: 1980
<212> TYPE: DNA
<213> ORGANISM: Artificial
<220> FEATURE:
<223> OTHER INFORMATION: pSMART LCKan

<400> SEQUENCE: 2
gacgaattct ctagatatcg ctcaatactg accatttaaa tcatacctga cctccatagc      60
agaaagtcaa aagcctccga ccggaggctt ttgacttgat cggcacgtaa gaggttccaa     120
ctttcaccat aatgaaataa gatcactacc gggcgtattt tttgagttat cgagattttc     180
aggagctaag gaagctaaaa tgagccatat tcaacgggaa acgtcttgct cgaggccgcg     240
attaaattcc aacatggatg ctgatttata tgggtataaa tgggctcgcg ataatgtcgg     300
gcaatcaggt gcgacaatct atcgattgta tgggaagccc gatgcgccag agttgtttct     360
gaaacatggc aaaggtagcg ttgccaatga tgttacagat gagatggtca ggctaaactg     420
gctgacggaa tttatgcctc ttccgaccat caagcatttt atccgtactc ctgatgatgc     480
atggttactc accactgcga tcccagggaa acagcattc aggtattag aagaatatcc     540 tgattcaggt gaaaatattg ttgatgcgct ggcagtgttc ctgcgccggt tgcattcgat     600
tcctgtttgt aattgtcctt ttaacggcga tcgcgtattt cgtctcgctc aggcgcaatc     660
acgaatgaat aacggtttgg ttggtgcgag tgattttgat gacgagcgta atggctggcc     720
tgttgaacaa gtctggaaag aaatgcataa gcttttgcca ttctcaccgg attcagtcgt     780
cactcatggt gatttctcac ttgataacct tattttgac gagggaaat taataggttg     840 tattgatgtt ggacgagtcg gaatcgcaga ccgataccag gatcttgcca tcctatggaa     900
ctgcctcggt gagttttctc cttcattaca gaaacggctt tttcaaaaat atggtattga     960
taatcctgat atgaataaat tgcagtttca cttgatgctc gatgagtttt tctaaatgac    1020
caaacaggaa aaaccgccc ttaacatggc ccgctttatc agaagccaga cattaacgct    1080
tctggagaaa ctcaacgagc tggacgcgga tgaacaggca gacatctgtg aatcgcttca    1140
cgaccacgct gatgagcttt accgcagctg cctcgcgcgt ttcggtgatg acggtgaaaa    1200
cctctgatga gggcccaaat gtaatcacct ggctcacctt cgggtgggcc tttctgcgtt    1260
gctggcgttt ttccataggc tccgcccccc tgacgagcat cacaaaaatc gatgctcaag    1320
tcagaggtgg cgaaacccga caggactata aagataccag gcgtttcccc ctggaagctc    1380
cctcgtgcgc tctcctgttc cgaccctgcc gcttaccgga tacctgtccg cctttctccc    1440
ttcgggaagc gtggcgcttt ctcatagctc acgctgtagg tatctcagtt cggtgtaggt    1500
```

| | |
|---|---:|
| cgttcgctcc aagctgggct gtgtgcacga accccccgtt cagcccgacc gctgcgcctt | 1560 |
| atccggtaac tatcgtcttg agtccaaccc ggtaagacac gacttatcgc cactggcagc | 1620 |
| agccactggt aacaggatta gcagagcgag gtatgtaggc ggtgctacag agttcttgaa | 1680 |
| gtggtggcct aactacggct acactagaag aacagtattt ggtatctgcg ctctgctgaa | 1740 |
| gccagttacc tcggaaaaag agttggtagc tcttgatccg gcaaacaaac caccgctggt | 1800 |
| agcggtggtt ttttttgtttg caagcagcag attacgcgca gaaaaaaagg atctcaagaa | 1860 |
| gatcctttga ttttctaccg aagaaaggcc caccccgtgaa ggtgagccag tgagttgatt | 1920 |
| gcagtccagt tacgctggag tctgaggctc gtcctgaatg atatcaagct tgaattcgtt | 1980 |

<210> SEQ ID NO 3
<211> LENGTH: 3973
<212> TYPE: DNA
<213> ORGANISM: Artificial
<220> FEATURE:
<223> OTHER INFORMATION: pCRII-TOPO

<400> SEQUENCE: 3

| | |
|---|---:|
| agcgcccaat acgcaaaccg cctctccccg cgcgttggcc gattcattaa tgcagctggc | 60 |
| acgacaggtt tcccgactgg aaagcgggca gtgagcgcaa cgcaattaat gtgagttagc | 120 |
| tcactcatta ggcaccccag gctttacact ttatgcttcc ggctcgtatg ttgtgtggaa | 180 |
| ttgtgagcgg ataacaattt cacacaggaa acagctatga ccatgattac gccaagctat | 240 |
| ttaggtgaca ctatagaata ctcaagctat gcatcaagct tggtaccgag ctcggatcca | 300 |
| ctagtaacgg ccgccagtgt gctggaattc gcccttaagg gcgaattctg cagatatcca | 360 |
| tcacactggc ggccgctcga gcatgcatct agagggccca attcgcccta tagtgagtcg | 420 |
| tattacaatt cactggccgt cgttttacaa cgtcgtgact gggaaaaccc tggcgttacc | 480 |
| caacttaatc gccttgcagc acatccccct ttcgccagct ggcgtaatag cgaagaggcc | 540 |
| cgcaccgatc gcccttccca acagttgcgc agcctgaatg gcgaatggac gcgccctgta | 600 |
| gcggcgcatt aagcgcggcg ggtgtggtgg ttacgcgcag cgtgaccgct acacttgcca | 660 |
| gcgccctagc gcccgctcct ttcgctttct tcccttcctt tctcgccacg ttcgccggct | 720 |
| ttccccgtca agctctaaat cgggggctcc ctttagggtt ccgatttagt gctttacggc | 780 |
| acctcgaccc caaaaaactt gattagggtg atggttcacg tagtgggcca tcgccctgat | 840 |
| agacggtttt tcgccctttg acgttggagt ccacgttctt taatagtgga ctcttgttcc | 900 |
| aaactggaac aacactcaac cctatctcgg tctattcttt tgatttataa gggattttgc | 960 |
| cgatttcggc ctattggtta aaaaatgagc tgatttaaca aaaatttaac gcgaattta | 1020 |
| acaaaattca gggcgcaagg gctgctaaag gaagcggaac acgtagaaag ccagtccgca | 1080 |
| gaaacggtgc tgaccccgga tgaatgtcag ctactgggct atctggacaa gggaaaacgc | 1140 |
| aagcgcaaag agaaagcagg tagcttgcag tgggcttaca tggcgatagc tagactgggc | 1200 |
| ggttttatgg acagcaagcg aaccggaatt gccagctggg gcgccctctg gtaaggttgg | 1260 |
| gaagccctgc aaagtaaact ggatggcttt cttgccgcca aggatctgat ggcgcagggg | 1320 |
| atcaagatct gatcaagaga caggatgagg atcgtttcgc atgattgaac aagatggatt | 1380 |
| gcacgcaggt tctccggccg cttgggtgga gaggctattc ggctatgact gggcacaaca | 1440 |
| gacaatcggc tgctctgatg ccgccgtgtt ccggctgtca gcgcaggggc gcccggttct | 1500 |
| ttttgtcaag accgacctgt ccggtgccct gaatgaactg caggacgagg cagcgcggct | 1560 |
| atcgtggctg gccacgacgg gcgttccttg cgcagctgtg ctcgacgttg tcactgaagc | 1620 |

-continued

```
gggaagggac tggctgctat tgggcgaagt gccggggcag gatctcctgt catcccacct     1680
tgctcctgcc gagaaagtat ccatcatggc tgatgcaatg cggcggctgc atacgcttga     1740
tccggctacc tgcccattcg accaccaagc gaaacatcgc atcgagcgag cacgtactcg     1800
gatggaagcc ggtcttgtcg atcaggatga tctggacgaa gagcatcagg ggctcgcgcc     1860
agccgaactg ttcgccaggc tcaaggcgcg catgcccgac ggcgaggatc tcgtcgtgac     1920
ccatggcgat gcctgcttgc cgaatatcat ggtggaaaat ggccgctttt ctggattcat     1980
cgactgtggc cggctgggtg tggcggaccg ctatcaggac atagcgttgg ctacccgtga     2040
tattgctgaa gagcttggcg gcgaatgggc tgaccgcttc ctcgtgcttt acggtatcgc     2100
cgctccccgat tcgcagcgca tcgccttcta tcgccttctt gacgagttct tctgaattga    2160
aaaaggaaga gtatgagtat caacatttc cgtgtcgccc ttattccctt ttttgcggca      2220
ttttgccttc ctgtttttgc tcacccagaa acgctggtga agtaaaaga tgctgaagat      2280
cagttgggtg cacgagtggg ttacatcgaa ctggatctca acagcggtaa gatccttgag     2340
agttttcgcc ccgaagaacg ttttccaatg atgagcactt ttaaagttct gctatgtggc    2400
gcggtattat cccgtattga cgccgggcaa gagcaactcg gtcgccgcat acactattct    2460
cagaatgact tggttgagta ctcaccagtc acagaaaagc atcttacgga tggcatgaca    2520
gtaagagaat tatgcagtgc tgccataacc atgagtgata acactgcggc caacttactt    2580
ctgacaacga tcggaggacc gaaggagcta accgcttttt tgcacaacat ggggatcat     2640
gtaactcgcc ttgatcgttg ggaaccggag ctgaatgaag ccataccaaa cgacgagcgt    2700
gacaccacga tgcctgtagc aatggcaaca acgttgcgca aactattaac tggcgaacta    2760
cttactctag cttcccggca acaattaata gactggatgg aggcggataa agttgcagga    2820
ccacttctgc gctcggccct tccggctggc tggtttattg ctgataaatc tggagccggt    2880
gagcgtgggt ctcgcggtat cattgcagca ctggggccag atggtaagcc ctcccgtatc    2940
gtagttatct acacgacggg gagtcaggca actatggatg aacgaaatag acagatcgct    3000
gagataggtg cctcactgat taagcattgg taactgtcag accaagttta ctcatatata    3060
ctttagattg atttaaaact tcatttttaa tttaaaagga tctaggtgaa gatcctttt    3120
gataatctca tgaccaaaat cccttaacgt gagttttcgt tccactgagc gtcagacccc    3180
gtagaaaaga tcaaaggatc ttcttgagat cctttttttc tgcgcgtaat ctgctgcttg    3240
caaacaaaaa aaccaccgct accagcggtg gtttgtttgc cggatcaaga gctaccaact    3300
ctttttccga aggtaactgg cttcagcaga gcgcagatac caaatactgt tcttctagtg    3360
tagccgtagt taggccacca cttcaagaac tctgtagcac cgcctacata cctcgctctg    3420
ctaatcctgt taccagtggc tgctgccagt ggcgataagt cgtgtcttac cgggttggac    3480
tcaagacgat agttaccgga taaggcgcag cggtcgggct gaacggggggg ttcgtgcaca    3540
cagcccagct tggagcgaac gacctacacc gaactgagat acctacagcg tgagctatga    3600
gaaagcgcca cgcttcccga agggagaaag gcggacaggt atccggtaag cggcagggtc    3660
ggaacaggag agcgcacgag ggagcttcca gggggaaacg cctggtatct ttatagtcct    3720
gtcgggtttc gccacctctg acttgagcgt cgatttttgt gatgctcgtc aggggggcgg    3780
agcctatgga aaaacgccag caacgcggcc tttttacggt tcctggcctt ttgctggcct    3840
tttgctcaca tgttctttcc tgcgttatcc cctgattctg tggataaccg tattaccgcc    3900
tttgagtgag ctgataccgc tcgccgcagc cgaacgaccg agcgcagcga gtcagtgagc    3960
```

-continued

| | |
|---|---|
| gaggaagcgg aag | 3973 |

<210> SEQ ID NO 4
<211> LENGTH: 6900
<212> TYPE: DNA
<213> ORGANISM: Artificial
<220> FEATURE:
<223> OTHER INFORMATION: pSMART VC vector

<400> SEQUENCE: 4

| | |
|---|---|
| aaggaatatt cagcaatttg cccgtgccga agaaaggccc acccgtgaag gtgagccagt | 60 |
| gagttgattg ctacgtaaat aacttcgtat agcatacatt atacgaagtt atggactagg | 120 |
| cgcgccagaa gagagaaaga aggaaagcgg ccgccagggt tttcccagtc acgacaagct | 180 |
| tgcatgcgat acgtatcgtt aacgatggat ccgacgcacg tgcgaattcc tctagaggtt | 240 |
| cctagttgta actgccaggg cggccacttg acataacttc gtatagcata cattatacga | 300 |
| agttatgttt aaacattagc agaaagtcaa agcctccga ccggaggctt ttgactaaaa | 360 |
| cttcccttgg ggttatcatt gggccgagac cgcctgaaga ggacttccat tgttcattcc | 420 |
| acggacaaaa acagagaaag gaaacgcacg aggccaaaaa gctcgctttc agcacctgtc | 480 |
| gtttcctttc ttttcagagg gtatttttaaa taaaaacatt aagttatgac gaagaagaac | 540 |
| ggaaacgcct taaaccggaa aattttcata aatagcgaaa acccgcgagg tcgccgcccc | 600 |
| gtaacctgtc ggatcaccgg aaaggacccg taaagtgata atgattatca tctacatatc | 660 |
| acaacgtgcg tggaggccat caaaccacgt caaataatca attatgacgc aggtatcgta | 720 |
| ttaattgatc tgcatcaact aacgtaaaaa gcaacttcag acaatacaaa tcagcgacac | 780 |
| tgaatacggg gcaacctcat gtcgcctgaa gagtgagacc gccctgatcg cacgtaaga | 840 |
| ggttccgact ttcaccataa tgaaataaga tcactaccgg gcgtattttt tgagttatcg | 900 |
| agattttcag gagctaagga agctaaaatg gagaaaaaaa tcactggata taccaccgtt | 960 |
| gatatatccc aatggcatcg taaagaacat tttgaggcat ttcagtcagt tgctcaatgt | 1020 |
| acctataacc agaccgttca gctggatatt acggcctttt taaagaccgt aaagaaaaat | 1080 |
| aagcacaagt tttatccggc ctttattcac attcttgccc gcctgatgaa tgctcatccg | 1140 |
| gaatttcgta tggcaatgaa agacggtgag ctggtgatat gggatagtgt tcacccttgt | 1200 |
| tacaccgttt tccatgagca aactgaaacg ttttcatcgc tctggagtga ataccacgac | 1260 |
| gatttccggc agtttctaca catatattcg caagatgtgg cgtgttacgg tgaaaacctg | 1320 |
| gcctatttcc ctaaagggtt tattgagaat atgttttcg tctcagccaa tccctgggtg | 1380 |
| agtttcacca gttttgattt aaacgtggcc aatatggaca acttcttcgc cccgttttc | 1440 |
| accatgggca aatattatac gcaaggcgac aaggtgctga tgccgctggc gattcaggtt | 1500 |
| catcatgccg tttgtgatgg cttccatgtc ggcagaatgc ttaatgaatt acaacagtac | 1560 |
| tgcgatgagt ggcagggcgg ggcgtaaaaa tgtaatcacc tggctcacct tcgggtgggc | 1620 |
| ctttcacact tgcatcggat gcagcccggt gaacgtgccg gcacggcctg gtaaccagg | 1680 |
| tattttgtcc acataaccgt gcgcaaaatg ttgtggataa gcaggacaca gcagcaatcc | 1740 |
| acagcaggca tacaaccgca caccgaggtt actccgttct acaggttacg acgacatgtc | 1800 |
| aatacttgcc cttgacaggc attgatgaa tcgtagtctc acgctgatag tctgatcgac | 1860 |
| aatacaagtg ggaccgtggt cccagaccga taatcagacc gacaacacga gtgggatcgt | 1920 |
| ggtcccagac taataatcag accgacgata cgagtgggac cgtggtccca gactaataat | 1980 |
| cagaccgacg atacgagtgg gaccgtggtt ccagactaat aatcagaccg acgatacgag | 2040 |

```
tgggaccgtg gtcccagact aataatcaga ccgacgatac gagtgggacc atggtcccag      2100
actaataatc agaccgacga tacgagtggg accgtggtcc cagtctgatt atcagaccga      2160
cgatacgagt gggaccgtgg tcccagacta ataatcagac cgacgatacg agtgggaccg      2220
tggtcccaga ctaataatca gaccgacgat acgagtggga ccgtggtccc agtctgatta      2280
tcagaccgac gatacaagtg gaacagtggg cccagagaga atattcaggc cagttatgct      2340
ttctggcctg taacaaagga cattaagtaa agacagataa acgtagacta aaacgtggtc      2400
gcatcagggt gctggctttt caagttcctt aagaatggcc tcaattttct ctatacactc      2460
agttggaaca cgagacctgt ccaggttaag caccatttta tcgcccttat acaatactgt      2520
cgctccagga gcaaactgat gtcgtgagct taaactagtt cttgatgcag atgacgtttt      2580
aagcacagaa gttaaaagag tgataacttc ttcagcttca aatatcaccc cagctttttt      2640
ctgctcatga aggttagatg cctgctgctt aagtaattcc tctttatctg taaaggcttt      2700
ttgaagtgca tcacctgacc gggcagatag ttcaccgggg tgagaaaaaa gagcaacaac      2760
tgatttaggc aatttggcgg tgttgataca gcgggtaata atcttacgtg aaatattttc      2820
cgcatcagcc agcgcagaaa tatttccagc aaattcattc tgcaatcggc ttgcataacg      2880
ctgaccacgt tcataagcac ttgttgggcg ataatcgtta cccaatctgg ataatgcagc      2940
catctgctca tcatccagct cgccaaccag aacacgataa tcactttcgg taagtgcagc      3000
agctttacga cggcgactcc catcggcaat ttctatgaca ccagatactc ttcgaccgaa      3060
cgccggtgtc tgttgaccag tcagtagaaa agaagggatg agatcatcca gtgcgtcctc      3120
agtaagcagc tcctggtcac gttcattacc tgaccatacc cgagaggtct tctcaacact      3180
atcaccccgg agcacttcaa gagtaaactt cacatcccga ccacatacag gcaaagtaat      3240
ggcattaccg cgagccatta ctcctacgcg cgcaattaac gaatccacca tcggggcagc      3300
tggtgtcgat aacgaagtat cttcaaccgg ttgagtattg agcgtatgtt ttggaataac      3360
aggcgcacgc ttcattatct aatctcccag cgtggtttaa tcagacgatc gaaaatttca      3420
ttgcagacag gttcccaaat agaaagagca tttctccagg caccagttga agagcgttga      3480
tcaatggcct gttcaaaaac agttctcatc cggatctgac ctttaccaac ttcatccgtt      3540
tcacgtacaa catttttag aaccatgctt cccccaggcat cccgaatttg ctcctccatc      3600
cacggggact gagagccatt actattgctg tatttggtaa gcaaaatacg tacatcaggc      3660
tcgaacccct taagatcaac gttcttgagc agatacgaa gcatatcgaa aaactgcagt      3720
gcggaggtgt agtcaaacaa ctcagcaggc gtgggaacaa tcagcacatc agcagcacat      3780
acgacattaa tcgtgccgat acccaggtta ggcgcgctgt caataactat gacatcatag      3840
tcatgagcaa cagtttcaat ggccagtcgg agcatcaggt gtggatcggt gggcagttta      3900
ccttcatcaa atttgcccat taactcagtt tcaatacggt gcagagccag acaggaagga      3960
ataatgtcaa gccccggcca gcaagtgggc tttattgcat aagtgacatc gtcctttttcc      4020 ccaagataga aaggcaggag agtgtcttct gcatgaatat gaagatctgg tacccatccg      4080
tgatacattg aggctgttcc ctgggggtcg ttaccttcca cgagcaaaac acgtagcccc      4140
ttcagagcca gatcctgagc aagatgaaca gaaactgagg ttttgtaaac gccacccttta      4200 tgggcagcaa ccccgatcac cggtggaaat acgtcttcag cacgtcgcaa tcgcgtacca      4260
aacacatcac gcatatgatt aatttgttca attgtataac caacacgttg ctcaacccgt      4320
cctcgaattt ccatatccgg gtgcggtagt cgccctgctt tctcggcatc tctgatagcc      4380
```

```
tgagaagaaa ccccaactaa atccgctgct tcacctattc tccagcgccg ggttattttc    4440
ctcgcttccg ggctgtcatc attaaactgt gcaatggcga tagccttcgt catttcatga    4500
ccagcgttta tgcactggtt aagtgtttcc atgagtttca ttctgaacat cctttaatca    4560
ttgctttgcg tttttttatt aaatcttgca atttactgca aagcaacaac aaaatcgcaa    4620
agtcatcaaa aaaccgcaaa gttgtttaaa ataagagcaa cactacaaaa ggagataaga    4680
agagcacata cctcagtcac ttattatcac tagcgctcgc cgcagccgtg taaccgagca    4740
tagcgagcga actggcgagg aagcaaagaa gaactgttct gtcagatagc tcttacgctc    4800
agcgcaagaa gaaatatcca ccgtgggaaa actccaggt agaggtacac acgcggatag    4860
ccaattcaga gtaataaact gtgataatca accctcatca atgatgacga actaaccccc    4920
gatatcaagt cacatgacga agggaaagag aaggaaatca actgtgacaa actgccctca    4980
aatttggctt ccttaaaaat tacagttcaa aaagtatgag aaaatccatg caggctgaag    5040
gaaacagcaa aactgtgaca aattaccctc agtaggtcag aacaaatgtg acgaaccacc    5100
ctcaaatctg tgacagataa ccctcagact atcctgtcgt catggaagtg atatcgcgga    5160
aggaaaatac gatatgagtc gtctggcggc ctttcttttt ctcaatgtat gagaggcgca    5220
ttggagttct gctgttgatc tcattaacac agacctgcag gaagcggcgg cggaagtcag    5280
gcatacgctg gtaactttga ggcagctggt aacgctctat gatccagtcg attttcagag    5340
agacgatgcc tgagccatcc ggcttacgat actgacacag ggattcgtat aaacgcatgg    5400
catacggatt ggtgatttct tttgtttcac taagccgaaa ctgcgtaaac cggttctgta    5460
acccgataaa gaagggaatg agatatgggt tgatatgtac actgtaaagc cctctggatg    5520
gactgtgcgc acgtttgata aaccaaggaa aagattcata gccttttca tcgccggcat    5580 cctcttcagg gcgataaaaa accacttcct tccccgcgaa actcttcaat gcctgccgta    5640
tatccttact ggcttccgca gaggtcaatc cgaatatttc agcatattta gcaacatgga    5700
tctcgcagat accgtcatgt tcctgtaggg tgccatcaga ttttctgatc tggtcaacga    5760
acagatacag catacgtttt tgatcccggg agagactata tgccgcctca gtgaggtcgt    5820
ttgactggac gattcgcggg ctatttttac gtttcttgtg attgataacc gctgtttccg    5880
ccatgacaga tccatgtgaa gtgtgacaag ttttagatt gtcacactaa ataaaaaga    5940 gtcaataagc agggataact ttgtgaaaaa acagcttctt ctgagggcaa tttgtcacag    6000
ggttaagggc aatttgtcac agacaggact gtcatttgag ggtgatttgt cacactgaaa    6060
gggcaatttg tcaacacacc ttctctagaa ccagcatgga taaaggccta caaggcgctc    6120 taaaaagaa gatctaaaaa ctataaaaaa aataattata aaatatcccc cgtggataag    6180
tggataaccc caagggaagt tttttcaggc atcgtgtgta agcagaatat ataagtgctg    6240
ttccctggtg cttcctcgct cactcgaccg ggagggttcg agaaggggggg cacccccct    6300 tcggcgtgcg cggtcacgcg cacagggcgc agccctggtt aaaaacaagg tttataaata    6360
ttggtttaaa agcaggttaa aagacaggtt agcggtggcc gaaaacgggc ggaaaccct    6420 tgcaaatgct ggattttctg cctgtggaca gcccctcaaa tgtcaatagg tgcgcccctc    6480
atctgtcagc actctgcccc tcaagtgtca aggatcgcgc ccctcatctg tcagtagtcg    6540
cgcccctcaa gtgtcaatac cgcagggcac ttatccccag gcttgtccac atcatctgtg    6600
ggaaactcgc gtaaaatcag gcgttttcgc cgatttgcga ggctggccag ctccacgtcg    6660
ccggccgaaa tcgagcctgc ccctcatctg tcaacgccgc gccgggtgag tcggcccctc    6720
aagtgtcaac gtccgcccct catctgtcag tgagggccaa gttttccgcg aggtatccac    6780
```

```
aacgccggcg gccggccgcg gtgtctcgca cacggcttcg acggcgtttc tggcgcgttt    6840
gcagggccat agacggccgc cagcccagcg gcgagggcaa ccagcccggt gagcgtcgga    6900

<210> SEQ ID NO 5
<211> LENGTH: 14600
<212> TYPE: DNA
<213> ORGANISM: Artificial
<220> FEATURE:
<223> OTHER INFORMATION: pJAZZ-KA (NZAN)

<400> SEQUENCE: 5
gcgtataatg gactattgtg tgctgataag gagaacataa gcgcagaaca atatgtatct      60
attccggtgt tgtgttcctt tgttattctg ctattatgtt ctcttatagt gtgacgaaag     120
cagcataatt aatcgtcact tgttctttga ttgtgttacg atatccagag acttagaaac     180
gggggaaccg ggatgagcaa ggtaaaaatc ggtgagttga tcaacacgct tgtgaatgag     240
gtagaggcaa ttgatgcctc agaccgccca caaggcgaca aaacgaagag aattaaagcc     300
gcagccgcac ggtataagaa cgcgttattt aatgataaaa gaaagttccg tgggaaagga     360
ttgcagaaaa gaataaccgc gaatactttt aacgcctata tgagcagggc aagaaagcgg     420
tttgatgata aattacatca tagctttgat aaaaatatta ataaattatc ggaaaagtat     480 cctctcttaca gcgaagaatt atcttcatgg ctttctatgc ctacggctaa tattcgccag     540
cacatgtcat cgttacaatc taaattgaaa gaataatgc cgcttgccga agagttatca     600
aatgtaagaa taggctctaa aggcagtgat gcaaaaatag caagactaat aaaaaaatat     660
ccagattgga gttttgctct tagtgattta acagtgatg attggaagga gcgccgtgac     720
tatctttata agttattcca acaaggctct gcgttgttag aagaactaca ccagctcaag     780
gtcaaccatg aggttctgta ccatctgcag ctaagccctg cggagcgtac atctatacag     840
caacgatggg ccgatgttct gcgcgagaag aagcgtaatg ttgtggttat tgactaccca     900
acatacatgc agtctatcta tgatattttg aataatcctg cgactttatt tagtttaaac     960
actcgttctg gaatggcacc tttggccttt gctctggctg cggtatcagg gcgaagaatg    1020
attgagataa tgtttcaggg tgaatttgcc gtttcaggaa agtatacggt taatttctca    1080
gggcaagcta aaaacgctc tgaagataaa agcgtaacca gaacgattta actttatgc    1140 gaagcaaaat tattcgttga attattaaca gaattgcgtt cttgctctgc tgcatctgat    1200
ttcgatgagg ttgttaaagg atatggaaag gatgatacaa ggtctgagaa cggcaggata    1260
aatgctattt tagcaaaagc atttaaccct tgggttaaat catttttcgg cgatgaccgt    1320 cgtgttatata agatagccg cgctatttac gctcgcatcg cttatgagat gttcttccgc    1380
gtcgatccac ggtggaaaaa cgtcgacgag gatgtgttct tcatggagat tctcggacac    1440
gacgatgaga acacccagct gcactataag cagttcaagc tggccaactt ctccagaacc    1500
tggcgacctg aagttgggga tgaaacacc aggctggtgg ctctgcagaa actggacgat    1560
gaaatgccag gctttgccag aggtgacgct ggcgtccgtc tccatgaaac cgttaagcag    1620
ctggtggagc aggacccatc agcaaaaata accaacagca ctctccgggc ctttaaattt    1680
agcccgacga tgattagccg gtacctggag tttgccgctg atgcattggg gcagttcgtt    1740
ggcgagaacg ggcagtggca gctgaagata gagacacctg caatcgtcct gcctgatgaa    1800
gaatccgttg agaccatcga cgaaccggat gatgagtccc aagacgacga gctgatgaa    1860 gatgaaattg agctcgacga gggtggcggc gatgaaccaa ccgaagagga agggccagaa    1920
```

```
gaacatcagc caactgctct aaaacccgtc ttcaagcctg caaaaaataa cggggacgga    1980
acgtacaaga tagagtttga atacgatgga aagcattatg cctggtccgg ccccgccgat    2040
agccctatgg ccgcaatgcg atccgcatgg gaaacgtact acagctaaaa gaaaagccac    2100
cggtgttaat cggtggcttt tttattgagg cctgtcccta cccatcccct gcaagggacg    2160
gaaggattag gcggaaactg cagctgcaac tacggacatc gccgtcccga ctgcagggac    2220
ttccccgcgt aaagcggggc ttaaattcgg gctggccaac cctatttttc tgcaatcgct    2280
ggcgatgtta gtttcgtgga tagcgtttcc agcttttcaa tggccagctc aaaatgtgct    2340
ggcagcacct tctccagttc cgtatcaata tcggtgatcg gcagctctcc acaagacata    2400
ctccggcgac cgccacgaac tacatcgcgc agcagctccc gttcgtagac acgcatgttg    2460
cccagagccg tttctgcagc cgttaatatc cggcgcagct cggcgatgat tgccgggaga    2520
tcatccacgg ttattgggtt cggtgatggg ttcctgcagg cgcggcggag agccatccag    2580
acgccgctaa cccatgcgtt acggtactga aaactttgtg ctatgtcgtt tatcaggccc    2640
cgaagttctt ctttctgccg ccagtccagt ggttcaccgg cgttcttagg ctcaggctcg    2700
acaaaagcat actcgccgtt tttccggata gctggcagaa cctcgttcgt cacccacttg    2760
cggaaccgcc aggctgtcgt cccctgtttc accgcgtcgc ggcagcggag gattatggtg    2820
tagagaccag attccgatac cacatttact tccctggcca tccgatcaag ttttttgtgcc    2880 tcggttaaac cgagggtcaa ttttttcatca tgatccagct tacgcaatgc atcagaaggg    2940
ttggctatat tcaatgcagc acagatatcc agcgccacaa accacgggtc accaccgaca    3000
agaaccaccc gtataggtg gctttcctga atgaaaaga cggagagagc cttcattgcg    3060
cctccccgga tttcagctgc tcagaaaggg acagggagca gccgcgagct tcctgcgtga    3120
gttcgcgcgc gacctgcaga agttccgcag cttcctgcaa atacagcgtg gcctcataac    3180
tggagatagt gcggtgagca gagcccacaa gcgcttcaac ctgcagcagg cgttcctcaa    3240
tcgtctccag caggccctgg gcgtttaact gaatctggtt catgcgatca cctcgctgac    3300
cgggatacgg gctgacagaa cgaggacaaa acggctggcg aactggcgac gagcttctcg    3360
ctcggatgat gcaatggtgg aaaggcggtg gatatgggat tttttgtccg tgcggacgac    3420
agctgcaaat ttgaatttga acatggtatg cattcctatc ttgtataggg tgctaccacc    3480
agagttgaga atctctatag gggtggtagc ccagacaggg ttctcaacac cggtacaaga    3540
agaaaccggc ccaaccgaag ttggccccat ctgagccacc ataattcagg tatgcgcaga    3600
tttaacacac aaaaaaacac gctggcgcgt gttgtgcgct tcttgtcatt cggggttgag    3660
aggcccggct gcagatttg ctgcagcggg gtaactctac cgccaaagca gaacgcacgt    3720
caataattta ggtggatatt ttaccccgtg accagtcacg tgcacaggtg ttttatagt    3780 ttgctttact gactgatcag aacctgatca gttattggag tccggtaatc ttattgatga    3840
ccgcagccac cttagatgtt gtctcaaacc ccatacggcc acgaatgagc cactggaacg    3900
gaatagtcag caggtacagc ggaacgaacc acaaacggtt cagacgctgc cagaacgtcg    3960
catcacgacg ttccatccat tcggtattgt cgacgacctg gtaagcgtat tgtcctggcg    4020
tttttgctgc ttccgagtag caatcctctt caccacaaag aaagttactt atctgcttcc    4080
agttttcgaa cccttcttct ttgagccgct tttccagctc attcctccac aaaacaggca    4140
cccatcctct gcgataaatc atgattattt gtcctttaaa taaggctgta gaactgcaaa    4200
atcgctctcg ttcacatgct gtacgtagat gcgtagcaaa ttgccgttcc atccctgtaa    4260
tccaccttct ttggaaagat cgtccttgac ctcacgaaga accttatcca atagccctgc    4320
```

```
ggcacaagaa attgcctgct ctggatcagc aaattcatat tgattaatag gtgattgcca      4380
cacaccaaaa acaggaatca tcttttcggc taaacgcctc tcctgttctt tcttaatctc      4440
aagttgtaag cggaccagct caccatccat cattttttgt agatcatgcg ccactattca      4500
cccccactgg ccatcagcaa ataaagcttc atactcggac accggcaggc ggcttccacg      4560
gattgaaagg tcaagccaac cacgtccaga tgggtcagcc ttatccgatt cttcccaccg      4620
ttctgcagct gtagcaacca ggcattctac cgccttcatg tagtcttctg tacggaacca      4680
gccgtagtta atgccaccat cagtaactgc ccaggccatc ttttctctt cggcctcaat       4740 agcccggatg cggttatcgc acagctcgcg acagtacttc agctgttcgt aatccagttg      4800
cttcaggaac tctggtgtcg acgtcatagt ggcttcacct tataggcttt tagaagcgcc      4860
ctggcttcgt ctgtgtggtc ttccatgctc ttatcgctgg caatgcagca ataaactccc      4920
tcactatctg agaacccgtt catccgaata atcgtgaatg gaagttcccg gccagtttta     4980
taatcgctat agcttgtcgc gtcgtggctg accttgacca cataagggtc gtagccctcc      5040
acgatgacaa ggcattcccg ttgttttccc attaccctc cggttatatc gccacgctt       5100 gccgctggct tagaaacgct ttcagcagcc ttatttcgcg tactgatagc aggtccataa      5160
attcggtcat gtacagcgag gcgaacgttc tcgcgatgct ggccactggc cacaggcgta      5220
ccgcctccat ttcggttgct ggcaacgcgt tctccgccca cgcctccggt accgccaccg      5280
ggatagcctc cagtgcctgg ataattactg attgtggggc gtccggaacg tgctctgttt      5340
tggatcgagg gttaccatgt atatctatat ttagatccaa atcgcgatcc acttcgatgg      5400
tggttttttc caccttacgt gcgtgaattg ataaaccggc ctcgcggcgc ttctccacga     5460
tattcatgag gaactcgacc gagtccgggt caatggaacg catcgtgggg cgtgcatcgc      5520
cgtctctggc gcgtctggtc ttactggata gccccataga ctccaggatg cctatgcaga     5580
ggtctgcagg cgctttcttc ttgcctttct ctgtgttgaa gccgccgatg cgtaaaacgt      5640
tgtttagcag atcgcgccgt tccggcgtga gcaggttatc tctggcgcgt ttgagggcgt      5700
ccatgtctgc ttccaccttcc agggttttg gatcgatacc gcagtcgcgg aagtactgct      5760
gcagcgtcgc cgatttgagg gtgtagaaac cacgcatgcc tatctcaaca gcaggggtcg      5820
atttcactcg gtaatcggtt atggccggga atttagcctg gaactctgcg tcggcctgtt      5880
cccgcgtcat ggccgtagtg acgaactgct gccatcttcc ggcaacgcga taagcgtagg      5940
taaagtgaat caacgcttct tcacggtcaa ggcgacgggc ggttatctca tccagctgca      6000
tggtttcaaa caggcgcact tttttcaggc cgccgtcgaa atagaatttt aacgccacct      6060
cgtcgacatc cagctgcagc tccttttcga tgtcccagcg gaccagctgg gcctgctcat      6120
ccagggacag ggtgcgtttt tttatcaact catcgtgttc ggcctggtca ggagtatcga      6180
cactcaggtg gcgctccata agctgctcaa agaccagttc acgggcttct ttacgtaaat      6240
ccttaccgat gctgtttgca agcgcgtcgg tggccatagg cgcgacctga tagccatcat      6300
catgcatgat gcaaatcatg ttgctggcat aatcatttct ggccgatgcc tcgagcgcgg      6360
cggctttaat tttgagctgc atgaatgaag agttagccac gccgagtgaa attcggtcac      6420
cgtcaaagac aacgtctgtc agcagcccgg agtggccagc cgtttcgagc aaggcctgcg      6480
cgtaggcgcg tttgattttt tccggatcgg tttcacgttt accgcgaagc ttgtcgaaac      6540
cgataatgta ttcctgagct gtacggtcgc ggcgcagcat ctggatgcg tcgctgggga       6600 ccacttcgcc gcagaacatg ccgaaatggc ggtggaagtg tttctcctca atcgatacac      6660
```

```
ctgaagatat cgacgggctg tagatgaggc cgtcatattt tttcaccatc actttaggct    6720
ggttggtgaa atcgtcgact tccttctcct gtttgttttt ctggttaacg cagagaaact    6780
ttttgtcagg gaactgtagt ctcagctgca tggtaacgtc ttcggcgaac gtcgaactgt    6840
cggtggccag catgattcgt tcgccgcgtt gcactgcagc gataacctcg gtcatgatcc    6900 gattttctc  ggtataaaat acgcggatag gcttgttggt ttcgcggttg cgaacgtcga    6960
ccgggagttc aatcacgtga atttgcagcc aggcaggtag gcccagctcc tcgcgtcgct    7020
tcatcgccag ttcagccagg tcaacaagca gatcgttggc atcggcatcc accataatgg    7080
catgctcttc agtacgcgcc agcgcgtcga taagcgtgtt gaatacgcct accgggtttt    7140
ccatcgcacg cccggccaga atggcacgca ggccctgtgt tgcttcatcg aagccgaaga    7200
agtcatgctg gcgcatcagc ggttgccagc agcctttaag tatggagttg atgcaaatag    7260
tcagcttgtt ggcatatggc gccatttcct gatagccggg atcctgataa tgcagaatgt    7320
cggctttcgc gccttttccct tcggtcatca tttcatgcag gccgcctatc agggatacgc    7380
ggtgcgcgac ggaaacgcca cgcgtggact gcagcatcag tggacgcagg aggcctgtcg    7440
atttacccga ccccatcccg gcgcggacaa taacgatgcc ctgcagctgt gcggcgtatg    7500
tcatcacctc atcggtcatc ctggaggttt caaaccgttt gtaagtgatg tgtgacgggc    7560
gaaggttcgg gttggtgatg cgttcactga acgaacgtga tgtttgcgcg gcacggcatt    7620
tgcgattcaa ccggcgcgta atgtgatctt taacggtacc gttataaatt tctgcgatac    7680
ccatatcccg cagcgtgctg ctgaaaaggc gcataagttc tttcgggctg tttggtaccg    7740
ggcatgtcag catgccaata tcaacggcgc gaagcagttc tttggcaaaa gtgcgtctgt    7800
tcagacgcgg gagagtacgc agcttattca gcgtgatcga caacaggtcg gttgcacggc    7860
tcagatgatt tctcgttaac tggcgagcga cttccttcag ccctctcagg ctgtgcaggt    7920
cgttaaaatc gctgcattcc agctcagggt catcctcaaa agttgggtaa acacatttga    7980
cgccggaaaa cttctccatg atgtcgaatc cggtgcggag gcctgtgttg ccttttcctt    8040
cagctgagga tttgcggtcg ttatcgagag cgcaagtgat ttgcgcagcc gggtacatgt    8100
tcaccagctg ctcgacaacg tgaatcatgt tgttagcgga aaccgcaatg actaccgcgt    8160
caaagcgttt tttcgggtcg tttctggtcg ccagccagat ggatgccccg gtggcgaaac    8220
cctctgcagt cgcaattttt tgcgcccccct gcaggtcgcc aataacaaag catgcaccga    8280
cgaaatcacc gttagtgatg cgctggtct  ggaacttgcc accattcaga tcgatacgtt    8340
gccagccaac aatccgcccg tcttttcttc cgtccaggtg ggacagaggt atcgccatgt    8400
aagttgttgg tccacggctc catttcgcac tgtcgtgact ggtcacgcga cgtatatcac    8460
aagcgccaaa tacgtcacga attccctttt ttaccgcata aggccaggag ccatcttcag    8520
ctggcgaatg ttcccaggcg cgatggaaag ccaaccatcc aagcaggcgt tcctgctcca    8580
tctgattgtt ttttaaatca ttaacgcgtt gttgttcagc tcgaggcgg  cgtgcttcag    8640 cctggcgctc catgcgtgca cgttcttctt ccggctgagc gaccacggtc gcaccattcc    8700
gttgctgttc acggcgatac tccgaaaaca ggaatgaaaa gccactccag gagccagcgt    8760
catcgctttt tcaacgaagt taacgaaagt gataactgat gccatccttg ctctgctcaa    8820
ggcgtgaata gatttccaca cggcctttaa ggctcttctg cagagcttcc ggggaggaat    8880
tattgtaggt ggtatagcgc tctacaccac cgcgcggatt gagctgaatc ttatcagcac    8940
acgcaggcca gttgataccg gccatcttcg ccagctcagt cagctcatca cgtgccgcgt    9000
caagcagtga aaacggatcg ctgccaaagc gctccgcgta gaattcttgt aaggtcattt    9060
```

```
tttagccttt ccatgcgaat tagcattttt tcgggttgaa aaaatccgca ggagcagcca    9120
caataaacgc actatctttc tgaaggacgt atctgcgtta tcgtggctac ttcctgaaaa    9180
aggcccgagt tgccgactc gggtttttt tcgtctttt tcggctgcta cggtctggtt    9240
caaccccgac aaagtataga tcggattaaa ccagaattat agtcagcaat aaaccctgtt    9300
attgtatcat ctaccctcaa ccatgaacga tttgatcgta ccgactactt ggtgcacaaa    9360
ttgaagatca cttttatcat ggataacccg ttgagagtta gcactatcaa ggtagtaatg    9420
ctgctcgtca taacgggcta atcgttgaat tgtgatctcg ccgttattat cacaaaccag    9480
tacatcctca cccggtacaa gcgtaagtga agaatcgacc aggataacgt ctcccggctg    9540
gtagtttcgc tgaatctggt tcccgaccgt cagtgcgtaa acggtgttcc gttgactcac    9600
gaacggcagg aatcgctctg tgttggcagg ttctccaggc tgccagtctc tatccggtcc    9660
ggtctctgtc gtaccaataa caggaacgcg gtctggatca gattcagtgc catacagtat    9720
ccattgcacg ggcttacgca ggcattttgc cagcgatagc ccgatctcca gcgacggcat    9780
cacgtcgcca cgttctaagt tttggacgcc cggaagagag attcctacag cttctgccac    9840
ttgcttcagc gtcagtttca gctctaaacg gcgtgctttc agtcgttcgc ctcgtgtttt    9900 catacccctta atcataaatg atctctttat agctggctat aatttttata aattatacct    9960
agctttaatt ttcacttatt gattataata atccccatga aacccgaaga acttgtgcgc   10020
catttcggcg atgtggaaaa agcagcggtt ggcgtgggcg tgacaccccgg cgcagtctat   10080 caatggctgc aagctgggga gattccacct ctacgacaaa gcgatataga ggtccgtacc   10140
gcgtacaaat taagagtgaa tttcacctct cagcgcatgg gtaaggaagg gcataacagg   10200
ggatcctcta gagtcgacct gcaggcatgc aagcttcctg aatcgcccca tcatccagcc   10260
agaaagtgag ggagccacgg ttgatgagag ctttgttgta ggtggaccag ttggtgattt   10320
tgaacttttg ctttgccacg gaacggtctg cgttgtcggg aagatgcgtg atctgatcct   10380
tcaactcagc aaaagttcga tttattcaac aaagccgccg tcccgtcaag tcagcgtaat   10440
gctctgccag tgttacaacc aattaaccaa ttctgattag aaaaactcat cgagcatcaa   10500
atgaaactgc aatttattca tcatcaggatt atcaatacca tatttttgaa aaagccgttt   10560
ctgtaatgaa ggagaaaact caccgaggca gttccatagg atggcaagat cctggtatcg   10620
gtctgcgatt ccgactcgtc caacatcaat acaacctatt aatttcccct cgtcaaaaat   10680
aaggttatca agtgagaaat caccatgagt gacgactgaa tccggtgaga atggcaaaag   10740
cttatgcatt tctttccaga cttgttcaac aggccagcca ttacgctcgt catcaaaatc   10800
actcgcatca accaaaccgt tattcattcg tgattgcgcc tgagcgagac gaaatacgcg   10860
atcgctgtta aaaggacaat tacaaacagg aatcgaatgc aaccggcgca ggaacactgc   10920
cagcgcatca acaatatttt cacctgaatc aggatattct tctaatacct ggaatgctgt   10980
tttccctggg atcgcagtgg tgagtaacca tgcatcatca ggagtacgga taaaatgctt   11040
gatggtcgga agaggcataa attccgtcag ccagtttagt ctgaccatct catctgtaac   11100
atcattggca acgctacctt tgccatgttt cagaaacaac tctggcgcat cgggcttccc   11160
atacaatcga tagattgtcg cacctgattg cccgacatta tcgcgagccc atttataccc   11220
atataaatca gcatccatgt tggaatttaa tcgcggcctc gagcaagacg tttcccgttg   11280
aatatggctc ataacacccc ttgtattact gtttatgtaa gcagacagtt ttattgttca   11340
tgatgatata tttttatctt gtgcaatgta acatcagaga ttttgagaca caacgtggct   11400
```

```
ttgttgaata aatcgaactt ttgctgagtt gaaggatcag atcacgcatc ttcccgacaa    11460
cgcagaccgt tccgtggcaa agcaaaagtt caaaatcacc aactggtcca cctacaacaa    11520
agctctcatc aaccgtggct ccctcacttt ctggctggat gatggggcga ttcaggaagc    11580
ttgcatgcct gcaggtcgac tctagaggat ccccgagaac ccgataatcg ctaccagtga    11640
tgatggctgt tttgcggcgg cgtgagccat cggcaatttc gataatgcct gacgtccttc    11700
tggcgaacgc ggggttctgc tgtcctgaag tgaggaatga agggataagg tcggccagcg    11760
ctgattcgtt cagcaattcc tgatcacgtt cattaccgag ccaaaccatt gtggcctttt    11820
cgactttatc agcaggaatg gtttccagct taaaagtcac gttgcggcca tcaagcttga    11880
attcgtacgc agaaaggccc acccgaaggt gagccagtgt gattacattt gcggccgcat    11940
ttaaatgggc ccgggacagg tttcccgact ggaaagcggg cagtgagcgc aacgcaatta    12000
atgtgagtta gctcactcat taggcacccc aggctttaca ctttatgctt ccggctcgta    12060
tgttgtgtgg aattgtgagc ggacaacaat ttcacacagg aaacagctat gaccatgatt    12120
acgccaagct atttaggtga gactatagaa tactcaagct tgcatgcgat acgtatcgtt    12180
tacgatggat ccgacgcacg tgcgaattcg ccctatagtg agtcgtatta caattcactg    12240
gccgtcgttt tacaacgtcg tgactgggaa accctggcg tcacccaact taatcgcctt    12300
gcagcacatc ccccttcgc cagctggcgt aatagcgaag aggcccgcac cgatcgccct    12360
tcccaacagt tgcgcagctg aatggcgaat ggcgcctgag ggcccgggat ggcgcgccat    12420
gcggccgcca tggtcaaata aaacgaaagg ctcagtcgaa agactgggcc tttcgtttta    12480
atctgatcgg cacgtaagag gttccaactt tcaccataat gaaataagat cactaccggg    12540
cgtatttttt gagttatcga gattttcagg agctaaggaa gctaaaatga gtattcaaca    12600
tttccgtgtc gcccttattc ccttttttgc ggcattttgc cttcctgttt ttgctcaccc    12660
agaaacgctg gtgaaagtaa aagatgctga agatcagttg ggtgcacgag tgggttacat    12720
cgaactggat ctcaacagcg gtaagatcct tgagagttta cgccccgaag aacgttttcc    12780
aatgatgagc acttttaaag ttctgctatg tggcgcggta ttatcccgta ttgacgccgg    12840
gcaagagcaa ctcggtcgcc gcatacacta ttctcagaat gacttggttg agtactcacc    12900
agtcacagaa aagcatctca cggatggcat gacagtaaga gaattatgca gtgctgccat    12960
aaccatgagt gataacactg cggccaactt acttctggca acgatcggag gaccgaagga    13020
gctaaccgct tttttgcaca acatggggga tcatgtaact cgccttgatc gttgggaacc    13080
ggagctgaat gaagccatac caaacgacga gcgtgacacc acgatgcctg tagcaatggc    13140
aacaacgttg cgcaaactat taactggcga actacttact ctagcttccc ggcaacaatt    13200
aatagactgg atggaggcgg ataaagttgc aggatcactt ctgcgctcgg cctcccggc    13260 tggctggttt attgctgata atctggagc cggtgagcgt gggtctcgcg gtatcattgc    13320
agcactgggg ccagatggta agccctcccg catcgtagtt atctacacga cggggagtca    13380
ggcaactatg gatgaacgaa atagacagat cgctgagata ggtgcctcac tgattaagca    13440
ttggtaatga cagaagtcaa aagcctccg tcggaggctt ttgactttct gctagatctg    13500
tttcaatgcg gtgaagggcc aggcagctgg ggattatgtc gagacccggc cagcatgttg    13560
gttttatcgc atattcagcg ttgtcgcgtt tacccaggta aaatgaaagc agtgtatcgt    13620
ctgcgtgaat gtgcaaatca ggaacgtaac cgtggtacat agatgcagtc ccttgcgggt    13680
cgttcccttc aacagtagg acgcggtgcc cttcaaggc taaccattgc gcctggtgta    13740
ctgcagatga ggttttataa acccctccct tgtgtgacat aacggaaagt acaaccgggt    13800
```

-continued

```
ttttatcgtc aggtctttgg tttgggttac caaacacact ccgcatatgg ctaatttggt     13860
caattgtgta gccagcgcga cgttctactc ggcccctcat ctcaaaatca ggagccggta     13920
gacgaccagc tttttccgcg tctctgatag cctgcggtgt tacgccgatc aggtctgcaa     13980
cttctgttat accccagcgg cgagtaatac gacgcgcttc cgggctgtca tcgccgaact     14040
gtgcgatggc aatagcgcgc gtcatttcct gaccgcgatt gatacagtct ttcagcaaat     14100
taattaacga catcctgttt cctctcaaac atgcccttat ctttgtgttt ttcatcatac     14160
tttacgtttt taaagcaaag caacataaaa aaagcaaagt gacttagaaa acgcaaagtt     14220
aaggttcaaa tcaattttttt gatgcgctac agaagctatt tagcttcatc taagcgcaac     14280
ggtattactt acgttggtat atttaaaacc taacttaatg attttaaatg ataataaatc     14340
ataccaattg ctatcaaaag ttaagcgaac atgctgattt tcacgctgtt tatacacttt     14400
gaggcatctc tatctcttcc gtctctatat tgaaacacaa tcaaagaaca tcaatccatg     14460
tgacatcccc cactatctaa gaacaccata acagaacaca acataggaat gcaacattaa     14520
tgtatcaata attcggaaca tatgcactat atcatatctc aattacggaa catatcagca     14580
cacaattgcc cattatacgc                                                 14600
```

<210> SEQ ID NO 6
<211> LENGTH: 2238
<212> TYPE: DNA
<213> ORGANISM: Artificial
<220> FEATURE:
<223> OTHER INFORMATION: telN

<400> SEQUENCE: 6

```
gaattgcaag ctgatccggg cttatcgact gcacggtgca ccaatgcttc tggcgtcagg       60
cagccatcgg aagctgtggt atggctgtgc aggtcgtaaa tcactgcata attcgtgtcg      120
ctcaaggcgc actcccgttc tggataatgt ttttgcgcc gacatcataa cggttctggc       180
aaatattctg aaatgagctg ttgacaatta atcatcggct cgtataatgt gtggaattgt      240
gagcggataa caatttcaca caggaaacag aattcgagct cggtacccgg atcggatccc      300
gatatccaga gacttagaaa cgggggaacc gggatgagca aggtaaaaat cggtgagttg      360
atcaacacgc ttgtgaatga ggtagaggca attgatgcct cagaccgccc acaaggcgac      420
aaaacgaaga gaattaaagc cgcagccgca cggtataaga acgcgttatt taatgataaa      480
agaaagttcc gtgggaaagg attgcagaaa agaataaccg cgaatacttt taacgcctat      540
atgagcaggg caagaaagcg gtttgatgat aaattacatc atagctttga taaaaatatt      600
aataaattat cggaaaagta tcctctttac agcgaagaat tatcttcatg gctttctatg      660
cctacggcta atattcgcca gcacatgtca tcgttacaat ctaaattgaa agaaataatg      720
ccgcttgccg aagagttatc aaatgtaaga ataggctcta aaggcagtga tgcaaaaata      780
gcaagactaa taaaaaaata tccagattgg agttttgctc ttagtgattt aaacagtgat      840
gattggaagg agcgccgtga ctatctttat aagttattcc aacaaggctc tgcgttgtta      900
gaagaactac accagctcaa ggtcaaccat gaggttctgt accatctgca gctaagccct      960
gcggagcgta catctataca gcaacgatgg gccgatgttc tgcgcgagaa gaagcgtaat     1020
gttgtggtta ttgactaccc aacatacatg cagtctatct atgatatttt gaataatcct     1080
gcgactttat ttagtttaaa cactcgttct ggaatggcac ctttggcctt tgctctggct     1140
gcggtatcag ggcgaagaat gattgagata atgtttcagg gtgaatttgc cgtttcagga     1200
```

-continued

```
aagtatacgg ttaatttctc agggcaagct aaaaaacgct ctgaagataa aagcgtaacc    1260
agaacgattt atactttatg cgaagcaaaa ttattcgttg aattattaac agaattgcgt    1320
tcttgctctg ctgcatctga tttcgatgag gttgttaaag gatatggaaa ggatgataca    1380
aggtctgaga acggcaggat aaatgctatt ttagcaaaag catttaaccc ttgggttaaa    1440 tcattttcg gcgatgaccg tcgtgtttat aaagatagcc gcgctattta cgctcgcatc    1500
gcttatgaga tgttcttccg cgtcgatcca cggtggaaaa acgtcgacga ggatgtgttc    1560
ttcatggaga ttctcggaca cgacgatgag aacacccagc tgcactataa gcagttcaag    1620
ctggccaact tctccagaac ctggcgacct gaagttgggg atgaaaacac caggctggtg    1680
gctctgcaga aactggacga tgaaatgcca ggctttgcca gaggtgacgc tggcgtccgt    1740
ctccatgaaa ccgttaagca gctggtggag caggacccat cagcaaaaat aaccaacagc    1800
actctccggg cctttaaatt tagcccgacg atgattagcc ggtacctgga gtttgccgct    1860
gatgcattgg ggcagttcgt tggcgagaac gggcagtggc agctgaagat agagacacct    1920
gcaatcgtcc tgcctgatga agaatccgtt gagaccatcg acgaaccgga tgatgagtcc    1980
caagacgacg agctggatga agatgaaatt gagctcgacg agggtggcgg cgatgaacca    2040
accgaagagg aagggccaga agaacatcag ccaactgctc taaaacccgt cttcaagcct    2100
gcaaaaaata acgggacgg aacgtacaag atagagtttg aatacgatgg aaagcattat    2160
gcctggtccg gccccgccga tagccctatg gccgcaatgc gatccgcatg ggaaacgtac    2220
tacagctaaa agaagctt                                                  2238
```

<210> SEQ ID NO 7
<211> LENGTH: 59
<212> TYPE: DNA
<213> ORGANISM: Artificial
<220> FEATURE:
<223> OTHER INFORMATION: AHDAMPL

<400> SEQUENCE: 7

```
gacgacatca tgtccctat ttgtttattt ttctaaatac attcaaatat gtatccgct         59
```

<210> SEQ ID NO 8
<211> LENGTH: 46
<212> TYPE: DNA
<213> ORGANISM: Artificial
<220> FEATURE:
<223> OTHER INFORMATION: ADHAMPR

<400> SEQUENCE: 8

```
gacgacgtct agtcttacca atgcttaatc agtgaggcac ctatct                     46
```

<210> SEQ ID NO 9
<211> LENGTH: 36
<212> TYPE: DNA
<213> ORGANISM: Artificial
<220> FEATURE:
<223> OTHER INFORMATION: S-MCSL

<400> SEQUENCE: 9

```
tacggctagc actgaccatt taaatcatac ctgacc                                 36
```

<210> SEQ ID NO 10
<211> LENGTH: 34
<212> TYPE: DNA
<213> ORGANISM: Artificial
<220> FEATURE:
<223> OTHER INFORMATION: S-MCSR

<400> SEQUENCE: 10
atcgcatatg tcagactcca gagtaactgg actg        34

<210> SEQ ID NO 11
<211> LENGTH: 33
<212> TYPE: DNA
<213> ORGANISM: Artificial
<220> FEATURE:
<223> OTHER INFORMATION: CR2ZL

<400> SEQUENCE: 11
aaggcatatg aatgtgagtt agctcactca tta        33

<210> SEQ ID NO 12
<211> LENGTH: 34
<212> TYPE: DNA
<213> ORGANISM: Artificial
<220> FEATURE:
<223> OTHER INFORMATION: CR2ZR

<400> SEQUENCE: 12
aagggctacg ttaatgcgcc gctacagggc gcgt        34

<210> SEQ ID NO 13
<211> LENGTH: 41
<212> TYPE: DNA
<213> ORGANISM: Artificial
<220> FEATURE:
<223> OTHER INFORMATION: AhdMCSL

<400> SEQUENCE: 13
aacgcacgac tcggggtcga attctgcaga tatccatcac a        41

<210> SEQ ID NO 14
<211> LENGTH: 42
<212> TYPE: DNA
<213> ORGANISM: Artificial
<220> FEATURE:
<223> OTHER INFORMATION: AhdMCSR

<400> SEQUENCE: 14
aacacacgac acgaggtcga attccagcac actggcggcc gt        42

<210> SEQ ID NO 15
<211> LENGTH: 30
<212> TYPE: DNA
<213> ORGANISM: Artificial
<220> FEATURE:
<223> OTHER INFORMATION: HCKanNoKL

<400> SEQUENCE: 15
agatctaaat gtaatcacct ggctcacctt        30

<210> SEQ ID NO 16
<211> LENGTH: 23
<212> TYPE: DNA
<213> ORGANISM: Artificial
<220> FEATURE:
<223> OTHER INFORMATION: HCKanNoKR

<400> SEQUENCE: 16
tttagcttcc ttagctcctg aaa        23

<210> SEQ ID NO 17

```
<211> LENGTH: 23
<212> TYPE: DNA
<213> ORGANISM: Artificial
<220> FEATURE:
<223> OTHER INFORMATION: CR2ResL

<400> SEQUENCE: 17
atgattgaac aagatggatt gca                                              23

<210> SEQ ID NO 18
<211> LENGTH: 29
<212> TYPE: DNA
<213> ORGANISM: Artificial
<220> FEATURE:
<223> OTHER INFORMATION: CR2ResR

<400> SEQUENCE: 18
ttatcagaag aactcgtcaa gaaggcgat                                        29

<210> SEQ ID NO 19
<211> LENGTH: 21
<212> TYPE: DNA
<213> ORGANISM: Artificial
<220> FEATURE:
<223> OTHER INFORMATION: SL1

<400> SEQUENCE: 19
cagtccagtt acgctggagt c                                                21

<210> SEQ ID NO 20
<211> LENGTH: 18
<212> TYPE: DNA
<213> ORGANISM: Artificial
<220> FEATURE:
<223> OTHER INFORMATION: pCmOR

<400> SEQUENCE: 20
tttagcttcc ttagctcc                                                    18

<210> SEQ ID NO 21
<211> LENGTH: 29
<212> TYPE: DNA
<213> ORGANISM: Artificial
<220> FEATURE:
<223> OTHER INFORMATION: pCmF

<400> SEQUENCE: 21
tgatcggcac gtaagaggtt ccaactttc                                        29

<210> SEQ ID NO 22
<211> LENGTH: 81
<212> TYPE: DNA
<213> ORGANISM: Artificial
<220> FEATURE:
<223> OTHER INFORMATION: CamTonB-Rev

<400> SEQUENCE: 22
gaaacagatc tgatctagca gaaagtcaaa agcctccgac cggaggcttt tgacttctgt      60
cacctaggtt acgccccgcc c                                                81

<210> SEQ ID NO 23
<211> LENGTH: 22
<212> TYPE: DNA
<213> ORGANISM: Artificial
<220> FEATURE:
<223> OTHER INFORMATION: T7RC-del
```

<400> SEQUENCE: 23
acgcagaaag gcccacccga ag          22

<210> SEQ ID NO 24
<211> LENGTH: 24
<212> TYPE: DNA
<213> ORGANISM: Artificial
<220> FEATURE:
<223> OTHER INFORMATION: 2370F

<400> SEQUENCE: 24
ttggggttat ccacttatcc acgg        24

<210> SEQ ID NO 25
<211> LENGTH: 39
<212> TYPE: DNA
<213> ORGANISM: Artificial
<220> FEATURE:
<223> OTHER INFORMATION: dBstX4382R

<400> SEQUENCE: 25
gttttgtaaa cgcctccttt atgggcagca accccgatc        39

<210> SEQ ID NO 26
<211> LENGTH: 29
<212> TYPE: DNA
<213> ORGANISM: Artificial
<220> FEATURE:
<223> OTHER INFORMATION: dBstXI5185F

<400> SEQUENCE: 26
aaaggaggcg tttacaaaac ctcagtttc          29

<210> SEQ ID NO 27
<211> LENGTH: 21
<212> TYPE: DNA
<213> ORGANISM: Artificial
<220> FEATURE:
<223> OTHER INFORMATION: Stu5741R

<400> SEQUENCE: 27
gtacatcagg ctcgaaccct t           21

<210> SEQ ID NO 28
<211> LENGTH: 62
<212> TYPE: DNA
<213> ORGANISM: Artificial
<220> FEATURE:
<223> OTHER INFORMATION: dPRHBBlacR

<400> SEQUENCE: 28
aagtcacgtg aattccaagc ttcggatccc actgtgatgg ctatgcggca tcagagcaga        60
tt        62

<210> SEQ ID NO 29
<211> LENGTH: 63
<212> TYPE: DNA
<213> ORGANISM: Artificial
<220> FEATURE:
<223> OTHER INFORMATION: dPRHBBoriF

<400> SEQUENCE: 29
ttgtccacgt ggaattctaa gcttaggatc ccaatgtgct ggtagaaaag atcaaaggat        60

```
ctt                                                          63

<210> SEQ ID NO 30
<211> LENGTH: 38
<212> TYPE: DNA
<213> ORGANISM: Artificial
<220> FEATURE:
<223> OTHER INFORMATION: NotLacR

<400> SEQUENCE: 30
tggtcagtgc ggccgcgact tcaagtcacg tgaattcc                    38

<210> SEQ ID NO 31
<211> LENGTH: 40
<212> TYPE: DNA
<213> ORGANISM: Artificial
<220> FEATURE:
<223> OTHER INFORMATION: NotOriF

<400> SEQUENCE: 31
tcactagtgc ggccgcgaca acttgtccac gtggaattct                  40

<210> SEQ ID NO 32
<211> LENGTH: 48
<212> TYPE: DNA
<213> ORGANISM: Artificial
<220> FEATURE:
<223> OTHER INFORMATION: LacANN-For

<400> SEQUENCE: 32
tacttaagta agccggctta gctagcggga caggtttccc gactggaa         48

<210> SEQ ID NO 33
<211> LENGTH: 49
<212> TYPE: DNA
<213> ORGANISM: Artificial
<220> FEATURE:
<223> OTHER INFORMATION: LacANN-Rev

<400> SEQUENCE: 33
acttaagaat gccggcaatg ctagctcagg cgccattcgc cattcagct        49

<210> SEQ ID NO 34
<211> LENGTH: 47
<212> TYPE: DNA
<213> ORGANISM: Artificial
<220> FEATURE:
<223> OTHER INFORMATION: LacApSA-For

<400> SEQUENCE: 34
ttatatgggc ccaatggccc gggaggccta cttaagtaag ccggctt          47

<210> SEQ ID NO 35
<211> LENGTH: 50
<212> TYPE: DNA
<213> ORGANISM: Artificial
<220> FEATURE:
<223> OTHER INFORMATION: LacAsSA-Rev

<400> SEQUENCE: 35
aatagttggc gcgccaatgg cccgggaggc ctacttaaga atgccggcaa       50

<210> SEQ ID NO 36
<211> LENGTH: 78
<212> TYPE: DNA
<213> ORGANISM: Artificial
```

```
<220> FEATURE:
<223> OTHER INFORMATION: LacE-SL1-F

<400> SEQUENCE: 36
taactgtggc cagtccagtt acgctggagt cactagtgcg gccgcgacaa cttgtctagg      60
gcccaatggc ccgggagg                                                    78

<210> SEQ ID NO 37
<211> LENGTH: 70
<212> TYPE: DNA
<213> ORGANISM: Artificial
<220> FEATURE:
<223> OTHER INFORMATION: LacA SR2-Rev

<400> SEQUENCE: 37
ctaggaacat gttggtatga tttaaatggt cagtgcggcc gcgacttcaa gtctggcgcg      60
ccaatggccc                                                             70

<210> SEQ ID NO 38
<211> LENGTH: 28
<212> TYPE: DNA
<213> ORGANISM: Artificial
<220> FEATURE:
<223> OTHER INFORMATION: telN-For

<400> SEQUENCE: 38
gcggatcccg atatccagag acttagaa                                         28

<210> SEQ ID NO 39
<211> LENGTH: 29
<212> TYPE: DNA
<213> ORGANISM: Artificial
<220> FEATURE:
<223> OTHER INFORMATION: telN-Rev

<400> SEQUENCE: 39
cgaagcttct tttagctgta gtacgtttc                                        29

<210> SEQ ID NO 40
<211> LENGTH: 39
<212> TYPE: DNA
<213> ORGANISM: Artificial
<220> FEATURE:
<223> OTHER INFORMATION: 7847-F2

<400> SEQUENCE: 40
agatcggttg cacggctcag atgatttctc gttaactgg                             39

<210> SEQ ID NO 41
<211> LENGTH: 22
<212> TYPE: DNA
<213> ORGANISM: Artificial
<220> FEATURE:
<223> OTHER INFORMATION: T7 -RC-Del

<400> SEQUENCE: 41
acgcagaaag gcccacccga ag                                               22

<210> SEQ ID NO 42
<211> LENGTH: 39
<212> TYPE: DNA
<213> ORGANISM: Artificial
<220> FEATURE:
<223> OTHER INFORMATION: NZg7847a-F2
```

<400> SEQUENCE: 42
agatcggttg cacggctcag atgatttctc gttaactgg                                39

<210> SEQ ID NO 43
<211> LENGTH: 49
<212> TYPE: DNA
<213> ORGANISM: Artificial
<220> FEATURE:
<223> OTHER INFORMATION: NZg7847a-F3

<400> SEQUENCE: 43
agatcggttg cacggctcag atgatttctc gttaactggc gagcgactt                     49

<210> SEQ ID NO 44
<211> LENGTH: 74
<212> TYPE: DNA
<213> ORGANISM: Artificial
<220> FEATURE:
<223> OTHER INFORMATION: NZ-RevB

<400> SEQUENCE: 44
gccgcttgac ttcaagtcta atggcccggg aggcctactt aagattcgcc attcagctgc         60
gcaactgttg ggaa                                                           74

<210> SEQ ID NO 45
<211> LENGTH: 74
<212> TYPE: DNA
<213> ORGANISM: Artificial
<220> FEATURE:
<223> OTHER INFORMATION: NZ-RevA

<400> SEQUENCE: 45
aaatggtcag ttaatcagtt ctatgtacca gcaaggtcca gttgtaagcg gccgcttgac         60
ttcaagtcta atgg                                                           74

<210> SEQ ID NO 46
<211> LENGTH: 22
<212> TYPE: DNA
<213> ORGANISM: Artificial
<220> FEATURE:
<223> OTHER INFORMATION: NZ-RevC

<400> SEQUENCE: 46
aaatggtcag ttaatcagtt ct                                                  22

<210> SEQ ID NO 47
<211> LENGTH: 39
<212> TYPE: DNA
<213> ORGANISM: Artificial
<220> FEATURE:
<223> OTHER INFORMATION: SSB L

<400> SEQUENCE: 47
ctctgtccat ggcaagaggc ctgaaccgcg tatacctca                                39

<210> SEQ ID NO 48
<211> LENGTH: 50
<212> TYPE: DNA
<213> ORGANISM: Artificial
<220> FEATURE:
<223> OTHER INFORMATION: SSB R

<400> SEQUENCE: 48
catctctgcg gccgcgtcga ctcaaaacgg cagatcctcc tccggcggga                    50

<210> SEQ ID NO 49
<211> LENGTH: 30
<212> TYPE: DNA
<213> ORGANISM: Artificial
<220> FEATURE:
<223> OTHER INFORMATION: TBRPOLAL

<400> SEQUENCE: 49
ctctgtgcat gcttccctc tttgagccca                               30

<210> SEQ ID NO 50
<211> LENGTH: 38
<212> TYPE: DNA
<213> ORGANISM: Artificial
<220> FEATURE:
<223> OTHER INFORMATION: TBRPOLAR

<400> SEQUENCE: 50
ctctgtgtcg acctagccct tggcggaaag ccagtcct                     38

<210> SEQ ID NO 51
<211> LENGTH: 32
<212> TYPE: DNA
<213> ORGANISM: Artificial
<220> FEATURE:
<223> OTHER INFORMATION: CAp29F

<400> SEQUENCE: 51
caacggtctc ttacgccccg ccctgccact ca                           32

<210> SEQ ID NO 52
<211> LENGTH: 29
<212> TYPE: DNA
<213> ORGANISM: Artificial
<220> FEATURE:
<223> OTHER INFORMATION: cam792R

<400> SEQUENCE: 52
tattgggccc ctgatcggca cgtaagagg                               29

<210> SEQ ID NO 53
<211> LENGTH: 48
<212> TYPE: DNA
<213> ORGANISM: Artificial
<220> FEATURE:
<223> OTHER INFORMATION: ANNLacFor

<400> SEQUENCE: 53
tacttaagta agccggctta gctagcggga caggtttccc gactggaa          48

<210> SEQ ID NO 54
<211> LENGTH: 48
<212> TYPE: DNA
<213> ORGANISM: Artificial
<220> FEATURE:
<223> OTHER INFORMATION: ANNLacRev

<400> SEQUENCE: 54
acttaagaat gccggcaatg ctagctcagg cgccattcgc cattcagc          48

<210> SEQ ID NO 55
<211> LENGTH: 28
<212> TYPE: DNA
<213> ORGANISM: Artificial
<220> FEATURE:

<223> OTHER INFORMATION: 28T4

<400> SEQUENCE: 55
agcagtatca gatacaagcg gccgcatc 28

<210> SEQ ID NO 56
<211> LENGTH: 2275
<212> TYPE: DNA
<213> ORGANISM: Artificial
<220> FEATURE:
<223> OTHER INFORMATION: pGC Blue

<400> SEQUENCE: 56

| | |
|---|---|
| atttaaatgg tcagtgctag ccgtaaaggc atatgaatgt gagttagctc actcattagg | 60 |
| cacccccaggc tttacacttt atgcttccgg ctcgtatgtt gtgtggaatt gtgagcggat | 120 |
| aacaatttca cacaggaaac agctatgacc atgattacgc caagctattt aggtgacact | 180 |
| atagaatact caagctatgc atcaagcttg gtaccgagct cggatccact agtaacggcc | 240 |
| gccagtgtgc tggaattcga cctcgtgtcg tgtgttaacg cacgactcgg ggtcgaattc | 300 |
| tgcagatatc catcacactg gcggccgctc gagcatgcat ctagagggcc caattcgccc | 360 |
| tatagtgagt cgtattacaa ttcactggcc gtcgttttac aacgtcgtga ctgggaaaac | 420 |
| cctggcgtta cccaacttaa tcgccttgca gcacatcccc ctttcgccag ctggcgtaat | 480 |
| agcgaagagg cccgcaccga tcgcccttcc caacagttgc gcagcctgaa tggcgaatgg | 540 |
| acgcgccctg tagcggcgca ttaacgtagc cctatcgca tatgtcagac tccagcgtaa | 600 |
| ctggactgca atcaactcac tggctcacct tcacggtgg gcctttcttc ggtagaaaat | 660 |
| caaaggatct tcttgagatc cttttttct gcgcgtaatc tgctgcttgc aaacaaaaaa | 720 |
| accaccgcta ccagcggtgg tttgtttgcc ggatcaagag ctaccaactc ttttccgag | 780 |
| gtaactggct tcagcagagc gcagatacca aatactgttc ttctagtgta gccgtagtta | 840 |
| ggccaccact tcaagaactc tgtagcaccg cctacatacc tcgctctgct aatcctgtta | 900 |
| ccagtggctg ctgccagtgg cgataagtcg tgtcttaccg ggttggactc aagacgatag | 960 |
| ttaccggata aggcgcagcg gtcgggctga acggggggtt cgtgcacaca gcccagcttg | 1020 |
| gagcgaacga cctacaccga actgagatac ctacagcgtg agctatgaga aagcgccacg | 1080 |
| cttcccgaag ggagaaaggc ggacaggtat ccggtaagcg gcagggtcgg aacaggagag | 1140 |
| cgcacgaggg agcttccagg gggaaacgcc tggtatcttt atagtcctgt cgggtttcgc | 1200 |
| cacctctgac ttgagcatcg atttttgtga tgctcgtcag ggggcggag cctatggaaa | 1260 |
| aacgccagca acgcagaaag gcccacccga aggtgagcca ggtgattaca tttagatctt | 1320 |
| tatcagaaga actcgtcaag aaggcgatag aaggcgatgc gctgcgaatc gggagcggcg | 1380 |
| ataccgtaaa gcacgaggaa gcggtcagcc cattcgccgc caagctcttc agcaatatca | 1440 |
| cgggtagcca acgctatgtc ctgatagcgg tccgccacac ccagccggcc acagtcgatg | 1500 |
| aatccagaaa agcggccatt ttccaccatg atattcggca agcaggcatc gccatgggtc | 1560 |
| acgacgagat cctcgccgtc gggcatgcgc gccttgagcc tggcgaacag ttcggctggc | 1620 |
| gcgagcccct gatgctcttc gtccagatca tcctgatcga caagaccggc ttccatccga | 1680 |
| gtacgtgctc gctcgatgcg atgtttcgct tggtggtcga atgggcaggt agccggatca | 1740 |
| agcgtatgca gccgccgcat tgcatcagcc atgatggata ctttctcggc aggagcaagg | 1800 |
| tgggatgaca ggagatcctg ccccggcact tcgcccaata gcagccagtc ccttcccgct | 1860 |
| tcagtgacaa cgtcgagcac agctgcgcaa ggaacgcccg tcgtggccag ccacgatagc | 1920 |

```
cgcgctgcct cgtcctgcag ttcattcagg gcaccggaca ggtcggtctt gacaaaaaga   1980
accgggcgcc cctgcgctga cagccggaac acggcggcat cagagcagcc gattgtctgt   2040
tgtgcccagt catagccgaa tagcctctcc acccaagcgg ccggagaacc tgcgtgcaat   2100
ccatcttgtt caatcatttt agcttcctta gctcctgaaa atctcgataa ctcaaaaaat   2160
acgcccggta gtgatcttat ttcattatgg tgaaagttgg aacctcttac gtgccgatca   2220
agtcaaaagc ctccggtcgg aggcttttga ctttctgcta tggaggtcag gtatg        2275
```

<210> SEQ ID NO 57
<211> LENGTH: 1844
<212> TYPE: DNA
<213> ORGANISM: Artificial
<220> FEATURE:
<223> OTHER INFORMATION: pSMARTGC HCKAN

<400> SEQUENCE: 57

```
ctcgtcgacg aattctctag atatcgctca atactgacca tttaaatcat acctgacctc     60
catagcagaa agtcaaaagc ctccgaccgg aggcttttga cttgatcggc acgtaagagg    120
ttccaacttt caccataatg aaataagatc actaccgggc gtattttttg agttatcgag    180
attttcagga gctaaggaag ctaaaatgag tattcaacat ttccgtgtcg cccttattcc    240
cttttttgcg gcattttgcc ttcctgtttt tgctcaccca gaaacgctgg tgaaagtaaa    300
agatgctgaa gatcagttgg gtgcacgagt gggttacatc gaactggatc tcaacagcgg    360
taagatcctt gagagtttac gccccgaaga acgttttcca atgatgagca cttttaaagt    420
tctgctatgt ggcgcggtat tatcccgtat tgacgccggg caagagcaac tcggtcgccg    480
catacactat tctcagaatg acttggttga gtactcacca gtcacagaaa agcatctcac    540
ggatggcatg acagtaagag aattatgcag tgctgccata accatgagtg ataacactgc    600
ggccaactta cttctggcaa cgatcggagg accgaaggag ctaaccgctt ttttgcacaa    660
catgggggat catgtaactc gccttgatcg ttgggaaccg gagctgaatg aagccatacc    720
aaacgacgag cgtgacacca cgatgcctgt agcaatggca acaacgttgc gcaaactatt    780
aactggcgaa ctacttactc tagcttcccg gcaacaatta atagactgga tggaggcgga    840
taaagttgca ggatcacttc tgcgctcggc cctcccggct ggctggttta ttgctgataa    900
atctggagcc ggtgagcgtg ggtctcgcgg tatcattgca gcactggggc cagatggtaa    960
gccctcccgc atcgtagtta tctacacgac ggggagtcag gcaactatgg atgaacgaaa   1020
tagacagatc gctgagatag gtgcctcact gattaagcat tggtaatgag ggcccaaatg   1080
taatcacctg gctcaccttc gggtgggcct ttctgcgttg ctggcgtttt tccataggct   1140
ccgcccccct gacgagcatc acaaaaatcg atgctcaagt cagaggtggc gaaacccgac   1200
aggactataa agataccagg cgtttccccc tggaagctcc ctcgtgcgct ctcctgttcc   1260
gaccctgccg cttaccggat acctgtccgc ctttctccct tcgggaagcg tggcgctttc   1320
tcatagctca cgctgtaggt atctcagttc ggtgtaggtc gttcgctcca agctgggctg   1380
tgtgcacgaa ccccccgttc agcccgaccg ctgcgcctta tccggtaact atcgtcttga   1440
gtccaacccg gtaagacacg acttatcgcc actggcagca gccactggta acaggattag   1500
cagagcgagg tatgtaggcg gtgctacaga gttcttgaag tggtggccta actacggcta   1560
cactagaaga acagtatttg gtatctgcgc tctgctgaag ccagttacct cggaaaaaga   1620
gttggtagct cttgatccgg caaacaaacc accgctggta gcggtggttt ttttgtttgc   1680
```

```
aagcagcaga ttacgcgcag aaaaaaagga tctcaagaag atcctttgat tttctaccga    1740
agaaaggccc acccgtgaag gtgagccagt gagttgattg cagtccagtt acgctggagt    1800
ctgaggctcg tcctgaatga tatcaagctt gaattcgtcg acga                     1844

<210> SEQ ID NO 58
<211> LENGTH: 2036
<212> TYPE: DNA
<213> ORGANISM: Artificial
<220> FEATURE:
<223> OTHER INFORMATION: pSMARTGC LCKAN

<400> SEQUENCE: 58
ctcgtcgacg aattctctag atatcgctca atactgacca tttaaatcat acctgacctc      60
catagcagaa agtcaaaagc ctccgaccgg aggcttttga cttgatcggc acgtaagagg     120
ttccaacttt caccataatg aaataagatc actaccgggc gtatttttg agttatcgag      180 attttcagga gctaaggaag ctaaaatgag tattcaacat ttccgtgtcg cccttattcc     240
cttttttgcg gcattttgcc ttcctgtttt tgctcaccca gaaacgctgg tgaaagtaaa     300
agatgctgaa gatcagttgg gtgcacgagt gggttacatc gaactggatc tcaacagcgg    360
taagatcctt gagagtttac gccccgaaga acgttttcca atgatgagca cttttaaagt    420
tctgctatgt ggcgcggtat tatcccgtat tgacgccggg caagagcaac tcggtcgccg    480
catacactat tctcagaatg acttggttga gtactcacca gtcacagaaa agcatctcac    540
ggatggcatg acagtaagag aattatgcag tgctgccata accatgagtg ataacactgc    600
ggccaactta cttctggcaa cgatcggagg accgaaggag ctaaccgctt ttttgcacaa    660
catgggggat catgtaactc gccttgatcg ttgggaaccg gagctgaatg aagccatacc    720
aaacgacgag cgtgacacca cgatgcctgt agcaatggca acaacgttgc gcaaactatt    780
aactggcgaa ctacttactc tagcttcccg gcaacaatta atagactgga tggaggcgga    840
taaagttgca ggatcacttc tgcgctcggc cctcccggct ggctggttta ttgctgataa    900
atctggagcc ggtgagcgtg gtctcgcgcg tatcattgca gcactggggc cagatggtaa    960
gccctcccgc atcgtagtta tctacacgac ggggagtcag gcaactatgg atgaacgaaa   1020
tagacagatc gctgagatag gtgcctcact gattaagcat tggtaagtga ccaaacagga   1080
aaaaaccgcc cttaacatgg cccgctttat cagaagccag acattaacgc ttctggagaa   1140
actcaacgag ctggacgcgg atgaacaggc agacatctgt gaatcgcttc acgaccacgc   1200
tgatgagctt taccgcagct gcctcgcgcg tttcggtgat gacggtgaaa acctctgatg   1260
agggcccaaa tgtaatcacc tggctcacct tcgggtgggc cttctgcgt tgctggcgtt    1320 tttccatagg ctccgccccc ctgacgagca tcacaaaaat cgatgctcaa gtcagaggtg   1380
gcgaaacccg acaggactat aaagatacca ggcgtttccc cctggaagct ccctcgtgcg   1440
ctctcctgtt ccgaccctgc cgcttaccgg atacctgtcc gcctttctcc cttcgggaag   1500
cgtggcgctt tctcatagct cacgctgtag gtatctcagt tcggtgtagg tcgttcgctc   1560
caagctgggc tgtgtgcacg aaccccccgt tcagcccgac cgctgcgcct tatccggtaa   1620
ctatcgtctt gagtccaacc cggtaagaca cgacttatcg ccactggcag cagccactgg   1680
taacaggatt agcagagcga ggtatgtagg cggtgctaca gagttcttga agtggtggcc   1740
taactacggc tacactagaa gaacagtatt tggtatctgc gctctgctga agccagttac   1800
ctcggaaaaa gagttggtag ctcttgatcc ggcaaacaaa ccaccgctgg tagcggtggt   1860 tttttgttt gcaagcagca gattacgcgc agaaaaaaag gatctcaaga agatcctttg   1920
```

| | |
|---|---|
| attttctacc gaagaaaggc ccacccgtga aggtgagcca gtgagttgat tgcagtccag | 1980 |
| ttacgctgga gtctgaggct cgtcctgaat gatatcaagc ttgaattcgt cgacga | 2036 |

<210> SEQ ID NO 59
<211> LENGTH: 7434
<212> TYPE: DNA
<213> ORGANISM: Artificial
<220> FEATURE:
<223> OTHER INFORMATION: pBAC 3-12

<400> SEQUENCE: 59

| | |
|---|---|
| gatctagcag aaagtcaaaa gcctccgacc ggaggctttt gacttctgtc acctaggtta | 60 |
| cgccccgccc tgccactcat cgcagtactg ttgtaattca ttaagcattc tgccgacatg | 120 |
| gaagccatca caaacggcat gatgaacctg aatcgccagc ggcatcagca ccttgtcgcc | 180 |
| ttgcgtataa tatttgccca tggtgaaaac ggggcgaag aagttgtcca tattggccac | 240 |
| gtttaaatca aaactggtga aactcaccca gggattggct gagacgaaaa acatattctc | 300 |
| aataaaccct ttagggaaat aggccaggtt ttcaccgtaa cacgccacat cttgcgaata | 360 |
| tatgtgtaga aactgccgga aatcgtcgtg gtattcactc cagagcgatg aaaacgtttc | 420 |
| agtttgctca tggaaaacgg tgtaacaagg gtgaacacta tcccatatca ccagctcacc | 480 |
| gtctttcatt gccatacgaa attccggatg agcattcatc aggcgggcaa gaatgtgaat | 540 |
| aaaggccgga taaaacttgt gcttattttt ctttacggtc tttaaaaagg ccgtaatatc | 600 |
| cagctgaacg gtctggttat aggtacattg agcaactgac tgaaatgcct caaaatgttc | 660 |
| tttacgatgc cattgggata tatcaacggt ggtatatcca gtgatttttt tctccatttt | 720 |
| agcttcctta gctcctgaaa atctcgataa ctcaaaaaat acgcccggta gtgatcttat | 780 |
| ttcattatgg tgaaagttgg aacctcttac gtgccgatca gattaaaacg aaaggcccag | 840 |
| tctttcgact gagcctttcg ttttatttga ccatgttggt atgatttaaa tggtcagtgc | 900 |
| ggccgcgact tcaagtctgg cgcgccaatg gcccgggagg cctacttaag aatgccggca | 960 |
| atgctagctc aggcgccatt cgccattcag ctgcgcaact gttgggaagg gcgatcggtg | 1020 |
| cgggcctctt cgctattacg ccagctggcg aaaggggat gtgctgcaag gcgattaagt | 1080 |
| tgggtgacgc cagggttttc ccagtcacga cgttgtaaaa cgacggccag tgaattgtaa | 1140 |
| tacgactcac tatagggcga attcgcacgt gcgtcggatc catcgttaac gatacgtatc | 1200 |
| gcatgcaagc ttgagtattc tatagtctca cctaaatagc ttggcgtaat catggtcata | 1260 |
| gctgttcct gtgtgaaatt gttgtccgct cacaattcca cacaacatac gagccggaag | 1320 |
| cataaagtgt aaagcctggg gtgcctaatg agtgagctaa ctcacattaa ttgcgttgcg | 1380 |
| ctcactgccc gctttccagt cgggaaacct gtcccgctag ctaagccggc ttacttaagt | 1440 |
| aggcctcccg ggccattggg ccctagacaa gttgtcgcgg ccgcactagt gactccagcg | 1500 |
| taactggact ggccacagtt aggccgcaaa tgtaatcaca ctggctcacc ttcgggtggg | 1560 |
| cctttctgcg tcggattatg tcagcaatgg acagaacaac ctaatgaaca cagaaccatg | 1620 |
| atgtggtctg tccttttaca gccagtagtg ctcgccgcag tcgagcgaca gggcgaagcc | 1680 |
| ctcggctggt tgccctcgcc gctgggctgg cggccgtcta tggccctgca aacgcgccag | 1740 |
| aaacgccgtc gaagccgtgt gcgagacacc gcggccggcc gccggcgttg tggataccta | 1800 |
| gcggaaaact tggccctcac tgacagatga ggggcggacg ttgacacttg aggggccgac | 1860 |
| tcacccggcg cggcgttgac agatgagggg caggctcgat ttcggccggc gacgtggagc | 1920 |

```
tggccagcct cgcaaatcgg cgaaaacgcc tgattttacg cgagtttccc acagatgatg    1980
tggacaagcc tggggataag tgccctgcgg tattgacact tgagggggcgc gactactgac   2040 agatgagggg cgcgatcctt gacacttgag gggcagagtg ctgacagatg agggcgcac    2100 ctattgacat ttgagggggct gtccacaggc agaaaatcca gcatttgcaa gggtttccgc   2160 ccgttttcg gccaccgcta acctgtcttt taacctgctt ttaaaccaat atttataaac    2220
cttgttttta accagggctg cgccctgtgc gcgtgaccgc gcacgccgaa gggggtgcc    2280 cccccttctc gaaccctccc ggtcgagtga gcgaggaagc accagggaac agcacttata   2340
tattctgctt acacacgatg cctgaaaaaa cttcccttgg ggttatccac ttatccacgg   2400
ggatattttt ataattattt tttttatagt ttttagatct tctttttag agcgccttgt    2460 aggcctttat ccatgctggt tctagagaag gtgttgtgac aaattgccct ttcagtgtga   2520
caaatcaccc tcaaatgaca gtcctgtctg tgacaaattg cccttaaccc tgtgacaaat   2580
tgccctcaga agaagctgtt ttttcacaaa gttatccctg cttattgact cttttttatt   2640
tagtgtgaca atctaaaaac ttgtcacact tcacatggat ctgtcatggc ggaaacagcg   2700
gttatcaatc acaagaaacg taaaaatagc ccgcgaatcg tccagtcaaa cgacctcact   2760
gaggcggcat atagtctctc ccgggatcaa aaacgtatgc tgtatctgtt cgttgaccag   2820
atcagaaaat ctgatggcac cctacaggaa catgacggta tctgcgagat ccatgttgct   2880
aaatatgctg aaatattcgg attgacctct gcggaagcca gtaaggatat acggcaggca   2940
ttgaagagtt tcgcggggaa ggaagtggtt tttatcgcc ctgaagagga tgccggcgat    3000
gaaaaaggct atgaatcttt tccttggttt atcaaacgtg cgcacagtcc atccagaggg   3060
ctttacagtg tacatatcaa cccatatctc attcccttct ttatcgggtt acagaaccgg   3120
tttacgcagt ttcggcttag tgaaacaaaa gaaatcacca atccgtatgc catgcgttta   3180
tacgaatccc tgtgtcagta tcgtaagccg gatggctcag gcatcgtctc tctgaaaatc   3240
gactggatca tagagcgtta ccagctgcct caaagttacc agcgtatgcc tgacttccgc   3300
cgccgcttcc tgcaggtctg tgttaatgag atcaacagca gaactccaat gcgcctctca   3360
tacattgaga aaagaaagg ccgccagacg actcatatcg tattttcctt ccgcgatatc    3420
acttccatga cgacaggata gtctgagggt tatctgtcac agatttgagg gtggttcgtc   3480
acatttgttc tgacctactg agggtaattt gtcacagttt gctgtttcc ttcagcctgc    3540 atggattttc tcatactttt tgaactgtaa ttttaagga agccaaattt gagggcagtt   3600
tgtcacagtt gatttccttc tctttcccct cgtcatgtga cctgatatcg ggggttagtt   3660
cgtcatcatt tgatgagggt tgattatcaca gtttattact ctgaattggc tatccgcgtg   3720
tgtacctcta cctggagttt ttcccacggt ggatatttct tcttgcgctg agcgtaagag   3780
ctatctgaca gaacagttct tctttgcttc ctcgccagtt cgctcgctat gctcggttac   3840 acggctgcg cgagcgctag tgataataag tgactgaggt atgtgctctt cttatctcct    3900
tttgtagtgt tgctcttatt ttaaacaact ttgcggtttt ttgatgactt tgcgatttg    3960 ttgttgcttt gcagtaaatt gcaagattta ataaaaaaac gcaaagcaat gattaaagga   4020
tgttcagaat gaaactcatg gaaacactta accagtgcat aaacgctggt catgaaatga   4080
cgaaggctat cgccattgca cagtttaatg atgcagccc ggaagcgagg aaaataaccc    4140
ggcgctggag aataggtgaa gcagcggatt tagttgggggt ttcttctcag gctatcagag   4200
atgccgagaa agcagggcga ctaccgcacc cggatatgga aattcgagga cgggttgagc   4260
aacgtgttgg ttatacaatt gaacaaatta atcatatgcg tgatgtgttt ggtacgcgat   4320
```

```
tgcgacgtgc tgaagacgta tttccaccgg tgatcggggt tgctgcccat aaaggtggcg    4380
tttacaaaac ctcagtttct gttcatcttg ctcaggatct ggctctgaag gggctacgtg    4440
ttttgctcgt ggaaggtaac gaccccccagg gaacagcctc aatgtatcac ggatgggtac    4500
cagatcttca tattcatgca gaagacactc tcctgccttt ctatcttggg gaaaaggacg    4560
atgtcactta tgcaataaag cccacttgct ggccggggct tgacattatt ccttcctgtc    4620
tggctctgca ccgtattgaa actgagttaa tgggcaaatt tgatgaaggt aaactgccca    4680
ccgatccaca cctgatgctc cgactggcca ttgaaactgt tgctcatgac tatgatgtca    4740
tagttattga cagcgcgcct aacctgggta tcggcacgat taatgtcgta tgtgctgctg    4800
atgtgctgat tgttcccacg cctgctgagt tgtttgacta cacctccgca ctgcagtttt    4860
tcgatatgct tcgtgatctg ctcaagaacg ttgatcttaa agggttcgag cctgatgtac    4920
gtattttgct taccaaatac agcaaatagta atggctctca gtccccgtgg atggaggagc    4980
aaattcggga tgcctgggga agcatggttc taaaaaatgt tgtacgtgaa acggatgaag    5040
ttggtaaagg tcagatccgg atgagaactg ttttttgaaca ggccattgat caacgctctt    5100
caactggtgc ctggagaaat gctctttcta tttgggaacc tgtctgcaat gaaattttcg    5160
atcgtctgat taaaccacgc tgggagatta gataatgaag cgtgcgcctg ttattccaaa    5220
acatacgctc aatactcaac cggttgaaga tacttcgtta tcgacaccag ctgccccgat    5280
ggtggattcg ttaattgcgc gcgtaggagt aatggctcgc ggtaatgcca ttactttgcc    5340
tgtatgtggt cgggatgtga agtttactct tgaagtgctc cggggtgata gtgttgagaa    5400
gacctctcgg gtatggtcag gtaatgaacg tgaccaggag ctgcttactg aggacgcact    5460
ggatgatctc atcccttctt ttctactgac tggtcaacag acaccggcgt tcggtcgaag    5520
agtatctggt gtcatagaaa ttgccgatgg gagtcgccgt cgtaaagctg ctgcacttac    5580
cgaaagtgat tatcgtgttc tggttggcga gctggatgat gagcagatgg ctgcattatc    5640
cagattgggt aacgattatc gcccaacaag tgcttatgaa cgtggtcagc gttatgcaag    5700
ccgattgcag aatgaatttg ctggaaatat ttctgcgctg gctgatgcgg aaaatatttc    5760
acgtaagatt attacccgct gtatcaacac cgccaaattg cctaaatcag ttgttgctct    5820
tttttctcac cccggtgaac tatctgcccg gtcaggtgat gcacttcaaa aagcctttac    5880
agataaagag gaattactta agcagcaggc atctaacctt catgagcaga aaaaagctgg    5940
ggtgatattt gaagctgaag aagttatcac tcttttaact tctgtgctta aaacgtcatc    6000
tgcatcaaga actagtttaa gctcacgaca tcagtttgct cctggagcga cagtattgta    6060
taagggcgat aaaatggtgc ttaacctgga caggtctcgt gttccaactg agtgtataga    6120
gaaaattgag gccattctta aggaacttga aaagccagca ccctgatgcg accacgtttt    6180
agtctacgtt tatctgtctt tacttaatgt cctttgttac aggccagaaa gcataactgg    6240
cctgaatatt ctctctgggc ccactgttcc acttgtatcg tcggtctgat aatcagactg    6300
ggaccacggt cccactcgta tcgtcggtct gattattagt ctgggaccac ggtcccactc    6360
gtatcgtcgg tctgattatt agtctgggac cacggtccca ctcgtatcgt cggtctgata    6420
atcagactgg gaccacggtc ccactcgtat cgtcggtctg attattagtc tgggaccatg    6480
gtcccactcg tatcgtcggt ctgattatta gtctgggacc acggtcccac tcgtatcgtc    6540
ggtctgatta ttagtctgga accacggtcc cactcgtatc gtcggtctga ttattagtct    6600
gggaccacgg tcccactcgt atcgtcggtc tgattattag tctgggacca cgatcccact    6660
```

-continued

```
cgtgttgtcg gtctgattat cggtctggga ccacggtccc acttgtattg tcgatcagac    6720
tatcagcgtg agactacgat tccatcaatg cctgtcaagg gcaagtattg acatgtcgtc    6780
gtaacctgta gaacggagta acctcggtgt gcggttgtat gcctgctgtg gattgctgct    6840
gtgtcctgct tatccacaac attttgcgca cggttatgtg gacaaaatac ctggttaccc    6900
aggccgtgcc ggcacgttaa ccgggctgca tccgatgcaa gtgtgtcgct gtcgacgagc    6960
tcgcgagctc ggacatgagg ttgccccgta ttcagtgtcg ctgatttgta ttgtctgaag    7020
ttgcttttac gttaagttga tgcagatcaa ttaatacgat acctgcgtca taattgatta    7080
tttgacgtgg tttgatggcc tccacgcacg ttgtgatatg tagatgataa tcattatcac    7140
tttacgggtc ctttccggtg atccgacagg ttacggggcg cgacctcgc gggttttcgc     7200 tatttatgaa aattttccgg tttaaggcgt ttccgttctt cttcgtcata acttaatgtt    7260
tttatttaaa ataccctctg aaaagaaagg aaacgacagg tgctgaaagc gagcttttg     7320 gcctctgtcg tttcctttct ctgttttttgt ccgtggaatg aacaatgaa gtccgagctc    7380 atcgctaata acttcgtata gcatacatta tacgaagtta tattcgatgc ggcc         7434
```

<210> SEQ ID NO 60
<211> LENGTH: 8280
<212> TYPE: DNA
<213> ORGANISM: Artificial
<220> FEATURE:
<223> OTHER INFORMATION: pSMART BAC GC (BOL4.2)

<400> SEQUENCE: 60

```
gatctagcag aaagtcaaaa gcctccgacc ggaggctttt gacttctgtc acctaggtta      60
cgccccgccc tgccactcat cgcagtactg ttgtaattca ttaagcattc tgccgacatg     120
gaagccatca caaacggcat gatgaacctg aatcgccagc ggcatcagca ccttgtcgcc     180
ttgcgtataa tatttgccca tggtgaaaac ggggggcgaag aagttgtcca tattggccac    240
gtttaaatca aaactggtga aactcaccca gggattggct gagacgaaaa acatattctc     300
aataaaccct ttagggaaat aggccaggtt ttcaccgtaa cacgccacat cttgcgaata    360
tatgtgtaga aactgccgga atcgtcgtg gtattcactc cagagcgatg aaaacgtttc      420
agtttgctca tggaaaacgg tgtaacaagg gtgaacacta tcccatatca ccagctcacc    480
gtctttcatt gccatacgaa attccggatg agcattcatc aggcgggcaa gaatgtgaat    540
aaaggccgga taaaacttgt gcttattttt ctttacggtc tttaaaaagg ccgtaatatc    600
cagctgaacg gtctggttat aggtacattg agcaactgac tgaaatgcct caaaatgttc    660
tttacgatgc cattgggata tatcaacggt ggtatatcca gtgatttttt tctccatttt    720
agcttcctta gctcctgaaa atctcgataa ctcaaaaaat acgcccggta gtgatcttat    780
ttcattatgg tgaaagttgg aacctcttac gtgccgatca gattaaaacg aaaggcccag     840
tctttcgact gagcctttcg ttttatttga ccatgttggt atgatttaaa tggtcagtgc     900
ggccgcgact tcaagtcacg tgaattccaa gcttcggatc ccactgtgat ggctatgcgg    960
catcagagca gattgtactg agagtgcacc atatgcggtg tgaaataccg cacagatgcg    1020
taaggagaaa ataccgcatc aggcgccatt cgccattcag ctgcgcaac tgttgggaag     1080 ggcgatcggt gcgggcctct tcgctattac gccagctggc gaaaggggga tgtgctgcaa    1140
ggcgattaag ttgggtaacg ccagggtttt cccagtcacg acgttgtaaa acgacggcca    1200
gtgaattcga gctcggtacc cggggatcct ctagagtcga cctgcaggca tgcaagcttg    1260
gcgtaatcat ggtcatagct gtttcctgtg tgaaattgtt atccgctcac aattccacac    1320
```

-continued

```
aacatacgag ccggaagcat aaagtgtaaa gcctggggtg cctaatgagt gagctaactc   1380
acattaattg cgttgcgctc actgcccgct ttccagtcgg gaaacctgtc gtgccagctg   1440
cattaatgaa tcggccaacg cgcgggggaga ggcggtttgc gtattgggcg ctcttccgct   1500
tcctcgctca ctgactcgct gcgctcggtc gttcggctgc ggcgagcggt atcagctcac   1560
tcaaaggcgg taatacggtt atccacagaa tcaggggata acgcaggaaa gaacatgtga   1620
gcaaaaggcc agcaaaaggc caggaaccgt aaaaaggccg cgttgctggc gttttTccat   1680
aggctccgcc cccctgacga gcatcacaaa aatcgacgct caagtcagag gtggcgaaac   1740
ccgacaggac tataaagata ccaggcgttt ccccctggaa gctccctcgt gcgctctcct   1800
gttccgaccc tgccgcttac cggatacctg tccgcctttc tcccttcggg aagcgtggcg   1860
ctttctcata gctcacgctg taggtatctc agttcggtgt aggtcgttcg ctccaagctg   1920
ggctgtgtgc acgaaccccc cgttcagccc gaccgctgcg ccttatccgg taactatcgt   1980
cttgagtcca acccggtaag acacgactta tcgccactgg cagcagccac tggtaacagg   2040
attagcagag cgaggtatgt aggcggtgct acagagttct tgaagtggtg cctaactac    2100 ggctacacta gaagaacagt atttggtatc tgcgctctgc tgaagccagt taccttcgga   2160
aaaagagttg gtagctcttg atccggcaaa caaaccaccg ctggtagcgg tggtttttTT   2220
gtttgcaagc agcagattac gcgcagaaaa aaaggatctc aagaagatcc tttgatcttt   2280
tctaccagca cattgggatc ctaagcttag aattccacgt ggacaagttg tcgcggccgc   2340
actagtgact ccagcgtaac tggactggcc gcaaatgtaa tcacactggc tcaccttcgg   2400
gtgggccttt ctgcgtcgga ttatgtcagc aatggacaga caacctaat gaacacagaa     2460 ccatgatgtg gtctgtcctt ttacagccag tagtgctcgc cgcagtcgag cgacagggcg   2520
aagccctcgg ctggttgccc tcgccgctgg gctggcggcc gtctatggcc ctgcaaacgc   2580
gccagaaacg ccgtcgaagc cgtgtgcgag acaccgcggc cggccgccgg cgttgtggat   2640
acctcgcgga aaacttggcc ctcactgaca gatgaggggc ggacgttgac acttgagggg   2700
ccgactcacc cggcgcggcg ttgacagatg aggggcaggc tcgatttcgg ccggcgacgt   2760
ggagctggcc agcctcgcaa atcggcgaaa acgcctgatt ttacgcgagt ttcccacaga   2820
tgatgtggac aagcctgggg ataagtgccc tgcggtattg acacttgagg ggcgcgacta   2880
ctgacagatg aggggcgcga tccttgacac ttgagggggca gagtgctgac agatgagggg   2940
cgcacctatt gacatttgag gggctgtcca caggcagaaa atccagcatt tgcaagggtt   3000
tccgcccgtt tttcggccac cgctaacctg tcttttaacc tgcttttaaa ccaatattta   3060
taaaccttgt ttttaaccag ggctgcgccc tgtgcgcgtg accgcgcacg ccgaaggggg   3120
gtgccccccc ttctcgaacc ctcccggtcg agtgagcgag gaagcaccag ggaacagcac   3180
ttatatattc tgcttacaca cgatgcctga aaaaacttcc cttggggtta tccacttatc   3240 cacgggata ttttttataat tattttttTTT atagtttta gatcttcttt tttagagcgc    3300
cttgtaggcc tttatccatg ctggttctag agaaggtgtt gtgacaaatt gccctttcag   3360
tgtgacaaat caccctcaaa tgacagtcct gtctgtgaca aattgccctt aaccctgtga   3420
caaattgccc tcagaagaag ctgttttttTC acaaagttat ccctgcttat tgactctttt   3480
ttatttagtg tgacaatcta aaaacttgtc acacttcaca tggatctgtc atggcggaaa   3540
cagcggttat caatcacaag aaacgtaaaa atagcccgcg aatcgtccag tcaaacgacc   3600
tcactgaggc ggcatatagt ctctcccggg atcaaaaacg tatgctgtat ctgttcgttg   3660
```

```
accagatcag aaaatctgat ggcaccctac aggaacatga cggtatctgc gagatccatg    3720
ttgctaaata tgctgaaata ttcggattga cctctgcgga agccagtaag gatatacggc    3780
aggcattgaa gagtttcgcg gggaaggaag tggttttta tcgccctgaa gaggatgccg    3840
gcgatgaaaa aggctatgaa tcttttcctt ggtttatcaa acgtgcgcac agtccatcca    3900
gagggcttta cagtgtacat atcaacccat atctcattcc cttctttatc gggttacaga    3960
accggtttac gcagtttcgg cttagtgaaa caaaagaaat caccaatccg tatgccatgc    4020
gtttatacga atccctgtgt cagtatcgta agccggatgg ctcaggcatc gtctctctga    4080
aaatcgactg gatcatagag cgttaccagc tgcctcaaag ttaccagcgt atgcctgact    4140
tccgccgccg cttcctgcag gtctgtgtta atgagatcaa cagcagaact ccaatgcgcc    4200
tctcatacat tgagaaaaag aaaggccgcc agacgactca tatcgtattt ccttccgcg    4260 atatcacttc catgacgaca ggatagtctg agggttatct gtcacagatt tgagggtggt    4320
tcgtcacatt tgttctgacc tactgagggt aatttgtcac agttttgctg tttccttcag    4380
cctgcatgga ttttctcata cttttttgaac tgtaattttt aaggaagcca aatttgaggg    4440
cagtttgtca cagttgattt ccttctcttt cccttcgtca tgtgacctga tatcgggggt    4500
tagttcgtca tcattgatga gggttgatta tcacagttta ttactctgaa ttggctatcc    4560
gcgtgtgtac ctctacctgg agttttttccc acggtggata tttcttcttg cgctgagcgt    4620
aagagctatc tgacagaaca gttcttcttt gcttcctcgc cagttcgctc gctatgctcg    4680
gttacacggc tgcggcgagc gctagtgata taagtgact gaggtatgtg ctcttcttat    4740 ctcctttgt agtgttgctc ttattttaaa caactttgcg gttttttgat gactttgcga    4800
ttttgttgtt gctttgcagt aaattgcaag atttaataaa aaaacgcaaa gcaatgatta    4860
aaggatgttc agaatgaaac tcatggaaac acttaaccag tgcataaacg ctggtcatga    4920
aatgacgaag gctatcgcca ttgcacagtt taatgatgac agcccggaag cgaggaaaat    4980
aacccggcgc tggagaatag gtgaagcagc ggatttagtt ggggtttctt ctcaggctat    5040
cagagatgcc gagaaagcag gcgactacc gcacccggat atggaaattc gaggacgggt    5100
tgagcaacgt gttggttata caattgaaca aattaatcat atgcgtgatg tgtttggtac    5160
gcgattgcga cgtgctgaag acgtatttcc accggtgatc ggggttgctg cccataaagg    5220
aggcgtttac aaaacctcag tttctgttca tcttgctcag gatctggctc tgaaggggct    5280
acgtgttttg ctcgtggaag gtaacgaccc ccagggaaca gcctcaatgt atcacggatg    5340
ggtaccagat cttcatattc atgcagaaga cactctcctg cctttctatc ttggggaaaa    5400
ggacgatgtc acttatgcaa taaagcccac ttgctggccg gggcttgaca ttattccttc    5460
ctgtctggct ctgcaccgta ttgaaactga gttaatgggc aaatttgatg aaggtaaact    5520
gcccaccgat ccacacctga tgctccgact ggccattgaa actgttgctc atgactatga    5580
tgtcatagtt attgacagcg cgcctaacct gggtatcggc acgattaatg tcgtatgtgc    5640
tgctgatgtg ctgattgttc ccacgcctgc tgagttgttt gactacacct ccgcactgca    5700 gttttttcgat atgcttcgtg atctgctcaa gaacgttgat cttaaagggt tcgagcctga    5760
tgtacgtatt ttgcttacca aatacagcaa tagtaatggc tctcagtccc cgtggatgga    5820
ggagcaaatt cgggatgcct ggggaagcat ggttctaaaa aatgttgtac gtgaaacgga    5880
tgaagttggt aaaggtcaga tccggatgag aactgttttt gaacaggcca ttgatcaacg    5940
ctcttcaact ggtgcctgga gaaatgctct ttctatttgg gaacctgtct gcaatgaaat    6000
tttcgatcgt ctgattaaac cacgctggga gattagataa tgaagcgtgc gcctgttatt    6060
```

```
ccaaaacata cgctcaatac tcaaccggtt gaagatactt cgttatcgac accagctgcc    6120
ccgatggtgg attcgttaat tgcgcgcgta ggagtaatgg ctcgcggtaa tgccattact    6180
ttgcctgtat gtggtcggga tgtgaagttt actcttgaag tgctccgggg tgatagtgtt    6240
gagaagacct ctcgggtatg gtcaggtaat gaacgtgacc aggagctgct tactgaggac    6300
gcactggatg atctcatccc ttcttttcta ctgactggtc aacagacacc ggcgttcggt    6360
cgaagagtat ctggtgtcat agaaattgcc gatgggagtc gccgtcgtaa agctgctgca    6420
cttaccgaaa gtgattatcg tgttctggtt ggcgagctgg atgatgagca gatggctgca    6480
ttatccagat tgggtaacga ttatcgccca acaagtgctt atgaacgtgg tcagcgttat    6540
gcaagccgat tgcagaatga atttgctgga aatatttctg cgctggctga tgcggaaaat    6600
atttcacgta agattattac ccgctgtatc aacaccgcca aattgcctaa atcagttgtt    6660 gctcttttt ctcaccccgg tgaactatct gcccggtcag gtgatgcact tcaaaaagcc    6720
tttacagata aagaggaatt acttaagcag caggcatcta accttcatga gcagaaaaaa    6780
gctggggtga tatttgaagc tgaagaagtt atcactcttt taacttctgt gcttaaaacg    6840
tcatctgcat caagaactag tttaagctca cgacatcagt ttgctcctgg agcgacagta    6900
ttgtataagg gcgataaaat ggtgcttaac ctggacaggt ctcgtgttcc aactgagtgt    6960
atagagaaaa ttgaggccat tcttaaggaa cttgaaaagc cagcaccctg atgcgaccac    7020
gttttagtct acgtttatct gtctttactt aatgtccttt gttacaggcc agaaagcata    7080
actggcctga atattctctc tgggcccact gttccacttg tatcgtcggt ctgataatca    7140
gactgggacc acggtcccac tcgtatcgtc ggtctgatta ttagtctggg accacggtcc    7200
cactcgtatc gtcggtctga ttattagtct gggaccacgg tcccactcgt atcgtcggtc    7260
tgataatcag actgggacca cggtcccact cgtatcgtcg gtctgattat tagtctggga    7320
ccatggtccc actcgtatcg tcggtctgat tattagtctg gaccacggt cccactcgta    7380 tcgtcggtct gattattagt ctggaaccac ggtcccactc gtatcgtcgg tctgattatt    7440
agtctgggac cacggtccca ctcgtatcgt cggtctgatt attagtctgg accacgatc    7500 ccactcgtgt tgtcggtctg attatcggtc tgggaccacg gtcccacttg tattgtcgat    7560
cagactatca gcgtgagact acgattccat caatgcctgt caagggcaag tattgacatg    7620
gtcgtcgtaa cctgtagaac ggagtaacct cggtgtgcgg ttgtatgcct gctgtggatt    7680
gctgctgtgt cctgcttatc cacaacattt tgcgcacggt tatgtggaca aaatacctgg    7740
ttacccaggc cgtgccggca cgttaaccgg gctgcatccg atgcaagtgt gtcgctgtcg    7800
acgagctcgc gagctcggac atgaggttgc cccgtattca gtgtcgctga tttgtattgt    7860
ctgaagttgc ttttacgtta agttgatgca gatcaattaa tacgatacct gcgtcataat    7920
tgattatttg acgtggtttg atggcctcca cgcacgttgt gatatgtaga tgataatcat    7980
tatcacttta cgggtccttt ccggtgatcc gacaggttac ggggcggcga cctcgcgggt    8040
tttcgctatt tatgaaaatt ttccggttta aggcgtttcc gttcttcttc gtcataactt    8100
aatgttttta tttaaaatac cctctgaaaa gaaaggaaac gacaggtgct gaaagcgagc    8160
tttttggcct ctgtcgtttc ctttctctgt ttttgtccgt ggaatgaaca atggaagtcc    8220
gagctcatcg ctaataactt cgtatagcat acattatacg aagttatatt cgatgcggcc    8280
```

<210> SEQ ID NO 61
<211> LENGTH: 14744
<212> TYPE: DNA

<213> ORGANISM: Artificial
<220> FEATURE:
<223> OTHER INFORMATION: NZAhd

<400> SEQUENCE: 61

```
gcgtataatg gactattgtg tgctgataag gagaacataa gcgcagaaca atatgtatct      60
attccggtgt tgtgttcctt tgttattctg ctattatgtt ctcttatagt gtgacgaaag     120
cagcataatt aatcgtcact tgttctttga ttgtgttacg atatccagag acttagaaac     180
gggggaaccg ggatgagcaa ggtaaaaatc ggtgagttga tcaacacgct tgtgaatgag     240
gtagaggcaa ttgatgcctc agaccgccca caaggcgaca aaacgaagag aattaaagcc     300
gcagccgcac ggtataagaa cgcgttattt aatgataaaa gaaagttccg tgggaaagga     360
ttgcagaaaa gaataaccgc gaatactttt aacgcctata tgagcagggc aagaaagcgg     420
tttgatgata aattacatca tagctttgat aaaaatatta ataaattatc ggaaaagtat     480
cctctttaca gcgaagaatt atcttcatgg ctttctatgc ctacggctaa tattcgccag     540
cacatgtcat cgttacaatc taaattgaaa gaataatgc cgcttgccga gagttatca     600
aatgtaagaa taggctctaa aggcagtgat gcaaaaatag caagactaat aaaaaaatat     660
ccagattgga gttttgctct tagtgattta acagtgatg attggaagga gcgccgtgac     720
tatctttata agttattcca acaaggctct gcgttgttag aagaactaca ccagctcaag     780
gtcaaccatg aggttctgta ccatctgcag ctaagccctg cggagcgtac atctatacag     840
caacgatggg ccgatgttct gcgcgagaag aagcgtaatg ttgtggttat tgactaccca     900
acatacatgc agtctatcta tgatattttg aataatcctg cgactttatt tagtttaaac     960
actcgttctg gaatggcacc tttggccttt gctctggctg cggtatcagg gcgaagaatg    1020
attgagataa tgtttcaggg tgaatttgcc gtttcaggaa agtatacggt taatttctca    1080
gggcaagcta aaaacgctc tgaagataaa agcgtaacca gaacgattta tactttatgc    1140
gaagcaaaat tattcgttga attattaaca gaattgcgtt cttgctctgc tgcatctgat    1200
ttcgatgagg ttgttaaagg atatggaaag gatgatacaa ggtctgagaa cggcaggata    1260
aatgctattt tagcaaaagc atttaaccct tgggttaaat catttttcgg cgatgaccgt    1320
cgtgttata agatagccg cgctatttac gctcgcatcg cttatgagat gttcttccgc    1380
gtcgatccac ggtggaaaaa cgtcgacgag gatgtgttct tcatggagat tctcggacac    1440
gacgatgaga acacccagct gcactataag cagttcaagc tggccaactt ctccagaacc    1500
tggcgacctg aagttgggga tgaaaacacc aggctggtgg ctctgcagaa actggacgat    1560
gaaatgccag gctttgccag aggtgacgct ggcgtccgtc tccatgaaac cgttaagcag    1620
ctggtggagc aggacccatc agcaaaaata accaacagca ctctccgggc ctttaaattt    1680
agcccgacga tgattagccg gtacctggag tttgccgctg atgcattggg gcagttcgtt    1740
ggcgagaacg ggcagtggca gctgaagata gagacacctg caatcgtcct gcctgatgaa    1800
gaatccgttg agaccatcga cgaaccggat gatgagtccc aagacgacga gctggatgaa    1860
gatgaaattg agctcgacga gggtggcggc gatgaaccaa ccgaagagga agggccagaa    1920
gaacatcagc caactgctct aaaacccgtc ttcaagcctg caaaaaataa cggggacgga    1980
acgtacaaga tagagtttga atacgatgga aagcattatg cctggtccgg ccccgccgat    2040
agccctatgg ccgcaatgcg atccgcatgg gaaacgtact acagctaaaa gaaaagccac    2100
cggtgttaat cggtggcttt tttattgagg cctgtcccta cccatcccct gcaagggacg    2160
gaaggattag gcggaaactg cagctgcaac tacggacatc gccgtcccga ctgcagggac    2220
```

```
ttccccgcgt aaagcggggc ttaaattcgg gctggccaac cctattttc tgcaatcgct    2280 ggcgatgtta gttcgtgga tagcgtttcc agcttttcaa tggccagctc aaaatgtgct    2340
ggcagcacct tctccagttc cgtatcaata tcggtgatcg gcagctctcc acaagacata    2400
ctccggcgac cgccacgaac tacatcgcgc agcagctccc gttcgtagac acgcatgttg    2460
cccagagccg tttctgcagc cgttaatatc cggcgcagct cggcgatgat tgccgggaga    2520
tcatccacgg ttattgggtt cggtgatggg ttcctgcagg cgcggcggag agccatccag    2580
acgccgctaa cccatgcgtt acggtactga aaactttgtg ctatgtcgtt tatcaggccc    2640
cgaagttctt ctttctgccg ccagtccagt ggttcaccgg cgttcttagg ctcaggctcg    2700
acaaaagcat actcgccgtt tttccggata gctggcagaa cctcgttcgt cacccacttg    2760
cggaaccgcc aggctgtcgt cccctgtttc accgcgtcgc ggcagcggag gattatggtg    2820
tagagaccag attccgatac cacatttact ccctggcca tccgatcaag ttttgtgcc     2880 tcggttaaac cgagggtcaa ttttttcatca tgatccagct tacgcaatgc atcagaaggg    2940
ttggctatat tcaatgcagc acagatatcc agcgccacaa accacgggtc accaccgaca    3000
agaaccaccc gtataggtg ctttcctga aatgaaaaga cggagagagc cttcattgcg      3060
cctccccgga tttcagctgc tcagaaaggg acaggagca gccgcgagct tcctgcgtga      3120
gttcgcgcgc gacctgcaga agttccgcag cttcctgcaa atacagcgtg gcctcataac    3180
tggagatagt gcggtgagca gagcccacaa gcgcttcaac ctgcagcagg cgttcctcaa    3240
tcgtctccag caggccctgg gcgtttaact gaatctggtt catgcgatca cctcgctgac    3300
cgggatacgg gctgacagaa cgaggacaaa acggctggcg aactggcgac gagcttctcg    3360
ctcggatgat gcaatggtgg aaaggcgtg gatatgggat tttttgtccg tgcggacgac     3420
agctgcaaat ttgaattttga acatggtatg cattcctatc ttgtataggg tgctaccacc    3480
agagttgaga atctctatag gggtggtagc ccagacaggt ttctcaacac cggtacaaga    3540
agaaaccggc ccaaccgaag ttggccccat ctgagccacc ataattcagg tatgcgcaga    3600
tttaacacac aaaaaaacac gctggcgcgt gttgtgcgct tcttgtcatt cggggttgag    3660
aggcccggct gcagattttg ctgcagcggg gtaactctac cgccaaagca gaacgcacgt    3720 caataaattta ggtggatatt ttaccccgtg accagtcacg tgcacaggtg ttttatagt    3780 ttgctttact gactgatcag aacctgatca gttattggag tccggtaatc ttattgatga    3840
ccgcagccac cttagatgtt gtctcaaacc ccatacggcc acgaatgagc cactggaacg    3900
gaatagtcag caggtacagc ggaacgaacc acaaacggtt cagacgctgc cagaacgtcg    3960
catcacgacg ttccatccat tcggtattgt cgacgacctg gtaagcgtat tgtcctggcg    4020 ttttgctgc ttccgagtag caatcctctt caccacaaag aaagttactt atctgcttcc      4080
agttttcgaa cccttcttct ttgagccgct tttccagctc attcctccac aaaacaggca    4140
cccatcctct gcgataaatc atgattattt gtcctttaaa taaggctgta gaactgcaaa    4200
atcgctctcg ttcacatgct gtacgtagat gcgtagcaaa ttgccgttcc atccctgtaa    4260
tccaccttct ttggaaagat cgtccttgac ctcacgaaga accttatcca atagccctgc    4320
ggcacaagaa attgcctgct ctggatcagc aaattcatat tgattaatag gtgattgcca    4380
cacaccaaaa acaggaatca tcttttcggc taaacgcctc tcctgttctt tcttaatctc    4440
aagttgtaag cggaccagct caccatccat cattttttgt agatcatgcg ccactattca    4500 ccccccactgg ccatcagcaa ataaagcttc atactcggac accggcaggc ggcttccacg    4560
```

```
gattgaaagg tcaagccaac cacgtccaga tgggtcagcc ttatccgatt cttcccaccg    4620
ttctgcagct gtagcaacca ggcattctac cgccttcatg tagtcttctg tacggaacca    4680
gccgtagtta atgccaccat cagtaactgc ccaggccatc ttttctctt cggcctcaat     4740 agcccggatg cggttatcgc acagctcgcg acagtacttc agctgttcgt aatccagttg    4800
cttcaggaac tctggtgtcg acgtcatagt ggcttcacct tataggcttt tagaagcgcc    4860
ctggcttcgt ctgtgtggtc ttccatgctc ttatcgctgg caatgcagca ataaactccc    4920
tcactatctg agaacccgtt catccgaatg atcgtgaatg gaagttcccg gccagttttta   4980 taatcgctat agcttgtcgc gtcgtggctg acccttgacca cataagggtc gtagccctcc   5040
acgatgacaa ggcattcccg ttgttttccc attacccctc cggttatatc gccacggctt    5100
gccgctggct tagaaacgct tcagcagcc ttatttcgcg tactgatagc aggtccataa     5160
attcggtcat gtacagcgag gcgaacgttc tcgcgatgct ggccactggc cacaggcgta    5220
ccgcctccat ttcggttgct ggcaacgcgt tctccgccca cgcctccggt accgccaccg    5280
ggatagcctc cagtgcctgg ataattactg attgtggggc gtccggaacg tgctctgttt    5340
tggatcgagg gttaccatgt atatctatat ttagatccaa atcgcgatcc acttcgatgg    5400
tggttttttc caccttacgt gcgtgaattg ataaaccggc ctcgcggcgc ttctccacga    5460
tattcatgag gaactcgacc gagtccgggt caatggaacg catcgtgggg cgtgcatcgc    5520
cgtctctggc gcgtctggtc ttactggata gccccataga ctccaggatg cctatgcaga    5580
ggtctgcagg cgcttcttc ttgcctttct ctgtgttgaa gccgccgatg cgtaaaacgt     5640
tgtttagcag atcgcgccgt tccggcgtga gcaggttatc tctggcgcgt ttgagggcgt    5700
ccatgtctgc ttcaccttcc agggttttg gatcgatacc gcagtcgcgg aagtactgct     5760
gcagcgtcgc cgatttgagg gtgtagaaac cacgcatgcc tatctcaaca gcagggtcg     5820 atttcactcg gtaatcggtt atggccggga atttagcctg gaactctgcg tcggcctgtt    5880
cccgcgtcat ggccgtagtg acgaactgct gccatcttcc ggcaacgcga taagcgtagg    5940
taaagtgaat caacgcttct tcacggtcaa ggcgacgggc ggttatctca tccagctgca    6000
tggtttcaaa caggcgcact ttttttcaggc cgccgtcgaa atagaatttt aacgccacct   6060
cgtcgacatc cagctgcagc tcctttttcga tgtcccagcg gaccagctgg gcctgctcat   6120
ccagggacag ggtgcgtttt tttatcaact catcgtgttc ggcctggtca ggagtatcga    6180
cactcaggtg gcgctccata agctgctcaa agaccagttc acgggcttct ttacgtaaat    6240
ccttaccgat gctgtttgca agcgcgtcgg tggccatagg cgcgacctga tagccatcat    6300
catgcatgat gcaaatcatg ttgctggcat aatcatttct ggccgatgcc tcgagcgcgg    6360
cggctttaat tttgagctgc atgaatgaag agttagccac gccgagtgaa attcggtcac    6420
cgtcaaagac aacgtctgtc agcagcccgg agtggccagc cgtttcgagc aaggcctgcg    6480
cgtaggcgcg tttgattttt tccggatcgg tttcacgttt accgcgaagc ttgtcgaaac    6540
cgataatgta ttcctgagct gtacggtcgc ggcgcagcat ctggatggcg tcgctgggga    6600
ccacttcgcc gcagaacatg ccgaaatggc ggtggaagtg tttctcctca atcgatacac    6660
ctgaagatat cgacgggctg tagatgaggc cgtcatattt tttccaccatc actttaggct   6720 ggttggtgaa atcgtcgact tccttctcct gttttgtttt ctggttaacg cagagaaact    6780
ttttgtcagg gaactgtagt ctcagctgca tggtaacgtc ttcggcgaac gtcgaactgt    6840
cggtggccag catgattcgt tcgccgcgtt gcactcagc gataacctcg gtcatgatcc      6900 gattttctc ggtataaaat acgcggatag gcttgttggt ttcgcggttg cgaacgtcga     6960
```

-continued

```
ccgggagttc aatcacgtga atttgcagcc aggcaggtag gcccagctcc tcgcgtcgct    7020
tcatcgccag ttcagccagg tcaacaagca gatcgttggc atcggcatcc accataatgg    7080
catgctcttc agtacgcgcc agcgcgtcga taagcgtgtt gaatacgcct accgggtttt    7140
ccatcgcacg cccggccaga atggcacgca ggccctgtgt tgcttcatcg aagccgaaga    7200
agtcatgctg gcgcatcagc ggttgccagc agcctttaag tatggagttg atgcaaatag    7260
tcagcttgtt ggcatatggc gccatttcct gatagccggg atcctgataa tgcagaatgt    7320
cggctttcgc gccttttccct tcggtcatca tttcatgcag gccgcctatc agggatacgc    7380
ggtgcgcgac ggaaacgcca cgcgtggact gcagcatcag tggacgcagg aggcctgtcg    7440
atttacccga ccccatcccg gcgcggacaa taacgatgcc ctgcagctgt gcggcgtatg    7500
tcatcacctc atcggtcatc ctggaggttt caaaccgttt gtaagtgatg tgtgacgggc    7560
gaaggttcgg gttggtgatg cgttcactga acgaacgtga tgtttgcgcg cacggcatt    7620 tgcgattcaa ccggcgcgta atgtgatctt taacggtacc gttataaatt tctgcgatac    7680
ccatatcccg cagcgtgctg ctgaaaaggc gcataagttc tttcgggctg tttggtaccg    7740
ggcatgtcag catgccaata tcaacggcgc gaagcagttc tttggcaaaa gtgcgtctgt    7800
tcagacgcgg gagagtacgc agcttattca gcgtgatcga caacaggtcg gttgcacggc    7860
tcagatgatt tctcgttaac tggcgagcga cttccttcag ccctctcagg ctgtgcaggt    7920
cgttaaaatc gctgcattcc agctcagggt catcctcaaa agttgggtaa acacatttga    7980
cgccggaaaa cttctccatg atgtcgaatc cggtgcggag gcctgtgttg ccttttcctt    8040
cagctgagga tttgcggtcg ttatcgagag cgcaagtgat ttgcgcagcc gggtacatgt    8100
tcaccagctg ctcgacaacg tgaatcatgt tgttagcgga aaccgcaatg actaccgcgt    8160
caaagcgttt tttcgggtcg tttctggtcg ccagccagat ggatgccccg gtggcgaaac    8220
cctctgcagt cgcaatttttt tgcgccccct gcaggtcgcc aataacaaag catgcaccga    8280
cgaaatcacc gttagtgatg gcgctggtct ggaacttgcc accattcaga tcgatacgtt    8340
gccagccaac aatccgcccg tcttttcttc cgtccaggtg ggacagaggt atcgccatgt    8400
aagttgttgg tccacggctc catttcgcac tgtcgtgact ggtcacgcga cgtatatcac    8460
aagcgccaaa tacgtcacga attccctttt ttaccgcata aggccaggag ccatcttcag    8520
ctggcgaatg ttcccaggcg cgatggaaag ccaaccatcc aagcaggcgt tcctgctcca    8580
tctgattgtt ttttaaatca ttaacgcgtt gttgttcagc tcggaggcgg cgtgcttcag    8640
cctggcgctc catgcgtgca cgttcttctt ccggctgagc gaccacggtc gcaccattcc    8700
gttgctgttc acggcgatac tccgaaaaca ggaatgaaaa gccactccag agccagcgt    8760 catcgcgcttt ttcaacgaag ttaacgaaag gataactgat gccatccttg ctctgctcaa    8820
ggcgtgaata gatttccaca cggcctttaa ggctcttctg cagagcttcc ggggaggaat    8880
tattgtaggt ggtatagcgc tctacaccac cgcgcggatt gagctgaatc ttatcagcac    8940
acgcaggcca gttgataccg gccatcttcg ccagctcagt cagctcatca cgtgccgcgt    9000
caagcagtga aaacggatcg ctgccaaagc gctccgcgta gaattcttgt aaggtcattt    9060
tttagccttt ccatgcgaat tagcattttt tcggttgaa aaaatccgca ggagcagcca    9120
caataaacgc actatctttc tgaaggacgt atctgcgtta tcgtgctac ttcctgaaaa    9180 aggcccgagt tgccgactc gggttttttt tcgtcttttt tcggctgcta cggtctggtt    9240
caaccccgac aaagtataga tcggattaaa ccagaattat agtcagcaat aaaccctgtt    9300
```

```
attgtatcat ctaccctcaa ccatgaacga tttgatcgta ccgactactt ggtgcacaaa    9360
ttgaagatca ctttatcat ggataacccg ttgagagtta gcactatcaa ggtagtaatg    9420
ctgctcgtca taacgggcta atcgttgaat tgtgatctcg ccgttattat cacaaaccag    9480
tacatcctca cccggtacaa gcgtaagtga agaatcgacc aggataacgt ctcccggctg    9540
gtagtttcgc tgaatctggt tcccgaccgt cagtgcgtaa acggtgttcc gttgactcac    9600
gaacggcagg aatcgctctg tgttggcagg ttctccaggc tgccagtctc tatccggtcc    9660
ggtctctgtc gtaccaataa caggaacgcg gtctggatca gattcagtgc catacagtat    9720
ccattgcacg ggcttacgca ggcattttgc cagcgatagc ccgatctcca gcgacggcat    9780
cacgtcgcca cgttctaagt tttggacgcc cggaagagag attcctacag cttctgccac    9840
ttgcttcagc gtcagtttca gctctaaacg gcgtgctttc agtcgttcgc ctcgtgtttt    9900 catacccctta atcataaatg atctctttat agctggctat aattttata aattatacct    9960 agctttaatt ttcacttatt gattataata atccccatga aacccgaaga acttgtgcgc   10020
catttcggcg atgtggaaaa agcagcggtt ggcgtgggcg tgacacccgg cgcagtctat   10080
caatggctgc aagctgggga gattccacct ctacgacaaa gcgatataga ggtccgtacc   10140
gcgtacaaat taaagagtga tttcacctct cagcgcatgg gtaaggaagg gcataacagg   10200
ggatcctcta gagtcgacct gcaggcatgc aagcttcctg aatcgcccca tcatccagcc   10260
agaaagtgag ggagccacgg ttgatgagag ctttgttgta ggtggaccag ttggtgattt   10320
tgaacttttg ctttgccacg gaacggtctg cgttgtcggg aagatgcgtg atctgatcct   10380
tcaactcagc aaaagttcga tttattcaac aaagccgccg tcccgtcaag tcagcgtaat   10440
gctctgccag tgttacaacc aattaaccaa ttctgattag aaaaactcat cgagcatcaa   10500
atgaaactgc aatttattca tatcaggatt atcaatacca tatttttgaa aaagccgttt   10560
ctgtaatgaa ggagaaaact caccgaggca gttccatagg atggcaagat cctggtatcg   10620
gtctgcgatt ccgactcgtc caacatcaat acaacctatt aatttcccct cgtcaaaaat   10680
aaggttatca agtgagaaat caccatgagt gacgactgaa tccggtgaga atggcaaaag   10740
cttatgcatt tctttccaga cttgttcaac aggccagcca ttacgctcgt catcaaaatc   10800
actcgcatca accaaaccgt tattcattcg tgattgcgcc tgagcgagac gaaatacgcg   10860
atcgctgtta aaaggacaat tacaaacagg aatcgaatgc aaccggcgca ggaacactgc   10920
cagcgcatca acaatatttt cacctgaatc aggatattct tctaatacct ggaatgctgt   10980
tttccctggg atcgcagtgg tgagtaacca tgcatcatca ggagtacgga taaaatgctt   11040
gatggtcgga agaggcataa attccgtcag ccagtttagt ctgaccatct catctgtaac   11100
atcattggca acgctacctt tgccatgttt cagaaacaac tctggcgcat cgggcttccc   11160
atacaatcga tagattgtcg cacctgattg cccgacatta tcgcgagccc atttataccc   11220
atataaatca gcatccatgt tggaatttaa tcgcggcctc gagcaagacg tttcccgttg   11280
aatatggctc ataacacccc ttgtattact gtttatgtaa gcagacagtt ttattgttca   11340
tgatgatata tttttatctt gtgcaatgta acatcagaga ttttgagaca acgtggct    11400 ttgttgaata aatcgaactt ttgctgagtt gaaggatcag atcacgcatc ttcccgacaa   11460
cgcagaccgt tccgtggcaa agcaaaagtt caaaatcacc aactggtcca cctacaacaa   11520
agctctcatc aaccgtggct ccctcacttt ctggctggat gatgggcga ttcaggaagc    11580 ttgcatgcct gcaggtcgac tctagaggat ccccagaaac ccgataatcg ctaccagtga   11640
tgatggctgt tttgcggcgg cgtgagccat cggcaatttc gataatgcct gacgtccttc   11700
```

```
tggcgaacgc ggggttctgc tgtcctgaag tgaggaatga agggataagg tcggccagcg   11760
ctgattcgtt cagcaattcc tgatcacgtt cattaccgag ccaaaccatt gtggccttttt  11820 cgactttatc agcaggaatg gtttccagct taaaagtcac gttgcggcca tcaagcttga   11880
attcgtacgc agaaaggccc acccgaaggt gagccagtgt gattacattt gcggccagtc   11940
cagttacgct ggagtcacta gtgcggccgc gacaacttgt ctagggccca atggcccggg   12000
aggcctactt aagtaagccg gcttagctag cgggacaggt ttcccgactg gaaagcgggc   12060
agtgagcgca acgcaattaa tgtgagttag ctcactcatt aggcacccca ggctttacac   12120
tttatgcttc cggctcgtat gttgtgtgga attgtgagcg acaacaatt tcacacagga    12180 aacagctatg accatgatta cgccaagcta tttaggtgag actatagaat actcaagctt   12240
gcatgcgata cgtatcgtta acgatggatc cgacgcacgt gcgaattcgc cctatagtga   12300
gtcgtattac aattcactgg ccgtcgtttt acaacgtcgt gactgggaaa accctggcgt   12360
cacccaactt aatcgccttg cagcacatcc ccctttcgcc agctggcgta atagcgaaga   12420
ggcccgcacc gatcgccctt ccaacagttg cgcagctga atggcgaatg gcgcctgagc    12480
tagcattgcc ggcattctta agtaggcctc ccgggccatt ggcgcgccat gacttgaagt   12540
cgcggccgca ctgaccattt aaatcatacc aacatggtca aataaaacga aaggctcagt   12600
cgaaagactg ggcctttcgt tttaatctga tcggcacgta agaggttcca actttcacca   12660
taatgaaata agatcactac cgggcgtatt ttttgagtta tcgagatttt caggagctaa   12720
ggaagctaaa atgagtattc aacatttccg tgtcgccctt attcccttttt ttgcggcatt  12780 ttgccttcct gttttttgctc acccagaaac gctggtgaaa gtaaaagatg ctgaagatca   12840
gttgggtgca cgagtgggtt acatcgaact ggatctcaac agcggtaaga tccttgagag   12900
tttacgcccc gaagaacgtt ttccaatgat gagcactttt aaagttctgc tatgtggcgc   12960
ggtattatcc cgtattgacg ccgggcaaga gcaactcggt cgccgcatac actattctca   13020
gaatgacttg gttgagtact caccagtcac agaaaagcat ctcacggatg gcatgacagt   13080
aagagaatta tgcagtgctg ccataaccat gagtgataac actgcggcca acttacttct   13140
ggcaacgatc ggaggaccga aggagctaac cgcttttttg cacaacatgg ggatcatgt    13200 aactcgcctt gatcgttggg aaccggagct gaatgaagcc ataccaaacg acgagcgtga   13260
caccacgatg cctgtagcaa tggcaacaac gttgcgcaaa ctattaactg gcgaactact   13320
tactctagct tcccggcaac aattaataga ctggatggag gcggataaag ttgcaggatc   13380
acttctgcgc tcggcccctcc cggctggctg gtttattgct gataaatctg gagccggtga   13440
gcgtgggtct cgcggtatca ttgcagcact ggggccagat ggtaagccct cccgcatcgt   13500
agttatctac acgacgggga gtcaggcaac tatggatgaa cgaaatagac agatcgctga   13560
gataggtgcc tcactgatta agcattggta atgacagaag tcaaaagcct ccggtcggag   13620
gcttttgact ttctgctaga tctgtttcaa tgcggtgaag ggccaggcag ctggggatta   13680
tgtcgagacc cggccagcat gttggttttta tcgcatattc agcgttgtcg cgtttaccca   13740
ggtaaaatgg aagcagtgta tcgtctgcgt gaatgtgcaa atcaggaacg taaccgtggt   13800
acatagatgc agtcccttgc gggtcgttcc cttcaacgag taggacgcgg tgcccttgca   13860
aggctaacca ttgcgcctgg tgtactgcag atgaggtttt ataaaccct cccttgtgtg    13920 acataacgga aagtacaacc gggttttat cgtcaggtct ttggtttggg ttaccaaaca    13980
cactccgcat atggctaatt tggtcaattg tgtagccagc gcgacgttct actcggcccc   14040
```

```
tcatctcaaa atcaggagcc ggtagacgac cagcttttc cgcgtctctg atagcctgcg    14100
gtgttacgcc gatcaggtct gcaacttctg ttataccca cgcgcgagta atacgacgcg    14160
cttccgggct gtcatcgccg aactgtgcga tggcaatagc gcgcgtcatt tcctgaccgc    14220
gattgataca gtctttcagc aaattaatta acgacatcct gtttcctctc aaacatgccc    14280
ttatctttgt gttttcatc atactttacg tttttaaagc aaagcaacat aaaaaaagca    14340
aagtgactta gaaaacgcaa agttaaggtt caaatcaatt ttttgatgcg ctacagaagc    14400
tatttagctt catctaagcg caacggtatt acttacgttg gtatatttaa aacctaactt    14460
aatgatttta aatgataata aatcatacca attgctatca aaagttaagc gaacatgctg    14520
attttcacgc tgtttataca ctttgaggca tctctatctc ttccgtctct atattgaaac    14580
acaatcaaag aacatcaatc catgtgacat cccccactat ctaagaacac ataacagaa    14640 cacaacatag gaatgcaaca ttaatgtatc aataattcgg aacatatgca ctatatcata    14700
tctcaattac ggaacatatc agcacacaat tgcccattat acgc                    14744
```

<210> SEQ ID NO 62
<211> LENGTH: 14673
<212> TYPE: DNA
<213> ORGANISM: Artificial
<220> FEATURE:
<223> OTHER INFORMATION: NZASA

<400> SEQUENCE: 62

```
gcgtataatg gactattgtg tgctgataag gagaacataa gcgcagaaca atatgtatct      60
attccggtgt tgtgttcctt tgttattctg ctattatgtt ctcttatagt gtgacgaaag     120
cagcataatt aatcgtcact tgttctttga ttgtgttacg atatccagag acttagaaac     180
gggggaaccg ggatgagcaa ggtaaaaatc ggtgagttga tcaacacgct tgtgaatgag     240
gtagaggcaa ttgatgcctc agaccgccca caaggcgaca aaacgaagag aattaaagcc     300
gcagccgcac ggtataagaa cgcgttattt aatgataaaa gaaagttccg tgggaaagga     360
ttgcagaaaa gaataaccgc gaatactttt aacgcctata tgagcagggc aagaaagcgg     420
tttgatgata aattacatca tagctttgat aaaaatatta ataaattatc ggaaaagtat     480 cctctcttaca gcgaagaatt atcttcatgg ctttctatgc ctacggctaa tattcgccag     540
cacatgtcat cgttacaatc taaattgaaa gaaataatgc cgcttgccga agagttatca     600
aatgtaagaa taggctctaa aggcagtgat gcaaaaatag caagactaat aaaaaaatat     660
ccagattgga gttttgctct tagtgattta acagtgatg attggaagga gcgccgtgac     720
tatctttata agttattcca acaaggctct gcgttgttag aagaactaca ccagctcaag     780
gtcaaccatg aggttctgta ccatctgcag ctaagccctg cggagcgtac atctatacag     840
caacgatggg ccgatgttct gcgcgagaag aagcgtaatg ttgtggttat tgactaccca     900
acatacatgc agtctatcta tgatattttg aataatcctg cgactttatt tagtttaaac     960
actcgttctg gaatggcacc tttggccttt gctctggctg cggtatcagg gcgaagaatg    1020
attgagataa tgtttcaggg tgaatttgcc gtttcaggaa agtatacggt taatttctca    1080
gggcaagcta aaaaacgctc tgaagataaa agcgtaacca gaacgattta ctttatgc     1140 gaagcaaaat tattcgttga attattaaca gaattgcgtt cttgctctgc tgcatctgat    1200
ttcgatgagg ttgttaaagg atatggaaag gatgatacaa ggtctgagaa cggcaggata    1260
aatgctattt tagcaaaagc attaaccct tgggttaaat cattttttcgg cgatgaccgt    1320 cgtgtttata agatagccg cgctatttac gctcgcatcg cttatgagat gttcttccgc    1380
```

```
gtcgatccac ggtggaaaaa cgtcgacgag gatgtgttct tcatggagat tctcggacac   1440
gacgatgaga acacccagct gcactataag cagttcaagc tggccaactt ctccagaacc   1500
tggcgacctg aagttgggga tgaaaacacc aggctggtgg ctctgcagaa actggacgat   1560
gaaatgccag gctttgccag aggtgacgct ggcgtccgtc tccatgaaac cgttaagcag   1620
ctggtggagc aggacccatc agcaaaaata accaacagca ctctccgggc ctttaaattt   1680
agcccgacga tgattagccg gtacctggag tttgccgctg atgcattggg gcagttcgtt   1740
ggcgagaacg ggcagtggca gctgaagata gagacacctg caatcgtcct gcctgatgaa   1800
gaatccgttg agaccatcga cgaaccggat gatgagtccc aagacgacga gctggatgaa   1860
gatgaaattg agctcgacga gggtggcggc gatgaaccaa ccgaagagga agggccagaa   1920
gaacatcagc caactgctct aaaacccgtc ttcaagcctg caaaaaataa cggggacgga   1980
acgtacaaga tagagtttga atacgatgga aagcattatg cctggtccgg ccccgccgat   2040
agccctatgg ccgcaatgcg atccgcatgg gaaacgtact acagctaaaa gaaaagccac   2100
cggtgttaat cggtggcttt tttattgagg cctgtcccta cccatcccct gcaagggacg   2160
gaaggattag gcggaaactg cagctgcaac tacgacatc gccgtcccga ctgcagggac   2220
ttccccgcgt aaagcggggc ttaaattcgg gctggccaac cctattttc tgcaatcgct   2280 ggcgatgtta gtttcgtgga tagcgtttcc agcttttcaa tggccagctc aaaatgtgct   2340
ggcagcacct tctccagttc cgtatcaata tcggtgatcg gcagctctcc acaagacata   2400
ctccggcgac cgccacgaac tacatcgcgc agcagctccc gttcgtagac acgcatgttg   2460
cccagagccg tttctgcagc cgttaatatc cggcgcagct cggcgatgat gccgggaga   2520 tcatccacgg ttattgggtt cggtgatggg ttcctgcagg cgcggcggag agccatccag   2580
acgccgctaa cccatgcgtt acggtactga aaactttgtg ctatgtcgtt tatcaggccc   2640
cgaagttctt ctttctgccg ccagtccagt ggttcaccgg cgttcttagg ctcaggctcg   2700
acaaaagcat actcgccgtt tttccggata gctggcagaa cctcgttcgt cacccacttg   2760
cggaaccgcc aggctgtcgt cccctgtttc accgcgtcgc ggcagcggag gattatggtg   2820
tagagaccag attccgatac cacatttact tccctggcca tccgatcaag tttttgtgcc   2880
tcggttaaac cgagggtcaa ttttttcatca tgatccagct tacgcaatgc atcagaaggg   2940
ttggctatat tcaatgcagc acagatatcc agcgccacaa accacgggtc accaccgaca   3000
agaaccaccc gtatagggtg gctttcctga aatgaaaaga cggagagagc cttcattgcg   3060 cctcccgga tttcagctgc tcagaaaggg acagggagca gccgcgagct tcctgcgtga   3120
gttcgcgcgc gacctgcaga gttccgcag cttcctgcaa atacagcgtg gcctcataac   3180
tggagatagt gcggtgagca gagcccacaa gcgcttcaac ctgcagcagg cgttcctcaa   3240
tcgtctccag caggccctgg gcgtttaact gaatctggtt catgcgatca cctcgctgac   3300
cgggatacgg gctgacagaa cgaggacaaa acggctggcg aactggcgac gagcttctcg   3360
ctcggatgat gcaatggtgg aaaggcggtg gatatgggat ttttgtccg tgcggacgac   3420 agctgcaaat ttgaatttga acatggtatg cattcctatc ttgtataggg tgctaccacc   3480
agagttgaga atctctatag gggtggtagc ccagacaggg ttctcaacac cggtacaaga   3540
agaaaccggc ccaaccgaag ttggccccat ctgagccacc ataattcagg tatgcgcaga   3600
tttaacacac aaaaaaacac gctgcgcgcg ttgtgcgct tcttgtcatt cggggttgag   3660
aggcccggct gcagattttg ctgcagcggg gtaactctac cgccaaagca gaacgcacgt   3720
```

```
caataattta ggtggatatt ttaccccgtg accagtcacg tgcacaggtg tttttatagt    3780
ttgctttact gactgatcag aacctgatca gttattggag tccggtaatc ttattgatga    3840
ccgcagccac cttagatgtt gtctcaaacc ccatacggcc acgaatgagc cactggaacg    3900
gaatagtcag caggtacagc ggaacgaacc acaaacggtt cagacgctgc agaacgtcg     3960 catcacgacg ttccatccat tcggtattgt cgacgacctg gtaagcgtat tgtcctggcg    4020
tttttgctgc ttccgagtag caatcctctt caccacaaag aaagttactt atctgcttcc    4080
agttttcgaa cccttcttct ttgagccgct tttccagctc attcctccac aaaacaggca    4140
cccatcctct gcgataaatc atgattattt gtccttttaaa taaggctgta gaactgcaaa   4200
atcgctctcg ttcacatgct gtacgtagat gcgtagcaaa ttgccgttcc atccctgtaa    4260
tccaccttct ttggaaagat cgtccttgac ctcacgaaga accttatcca atagccctgc    4320
ggcacaagaa attgcctgct ctggatcagc aaattcatat tgattaatag gtgattgcca    4380
cacaccaaaa acaggaatca tcttttcggc taaacgcctc tcctgttctt tcttaatctc    4440
aagttgtaag cggaccagct caccatccat catttttttgt agatcatgcg ccactattca    4500
cccccactgg ccatcagcaa ataaagcttc atactcggac accggcaggc ggcttccacg    4560
gattgaaagg tcaagccaac cacgtccaga tgggtcagcc ttatccgatt cttcccaccg    4620
ttctgcagct gtagcaacca ggcattctac cgccttcatg tagtcttctg tacggaacca    4680
gccgtagtta atgccaccat cagtaactgc ccaggccatc ttttttctctt cggcctcaat    4740 agcccggatg cggttatcgc acagctcgcg acagtacttc agctgttcgt aatccagttg    4800
cttcaggaac tctggtgtcg acgtcatagt ggcttcacct tataggcttt tagaagcgcc    4860
ctggcttcgt ctgtgtggtc ttccatgctc ttatcgctgg caatgcagca ataaactccc    4920
tcactatctg agaacccgtt catccgaatg atcgtgaatg gaagttcccg gccagttta     4980 taatcgctat agcttgtcgc gtcgtggctg accttgacca cataagggtc gtagccctcc    5040
acgatgacaa ggcattcccg ttgttttccc attacccctc cggttatatc gccacggctt    5100
gccgctggct tagaaacgct ttcagcagcc ttatttcgcg tactgatagc aggtccataa    5160
attcggtcat gtacagcgag gcgaacgttc tcgcgatgct ggccactggc cacaggcgta    5220
ccgcctccat ttcggttgct ggcaacgcgt tctccgccca cgcctccggt accgccaccg    5280
ggatagcctc cagtgcctgg ataattactg attgtggggc gtccggaacg tgctctgttt    5340
tggatcgagg gttaccatgt atatctatat ttagatccaa atcgcgatcc acttcgatgg    5400
tggttttttc caccttacgt gcgtgaattg ataaaccggc ctcgcggcgc ttctccacga    5460
tattcatgag gaactcgacc gagtccgggt caatggaacg catcgtgggg cgtgcatcgc    5520
cgtctctggc gcgtctggtc ttactggata gccccataga ctccaggatg cctatgcaga    5580
ggtctgcagg cgcttttcttc ttgccttttct ctgtgttgaa gccgccgatg cgtaaaacgt    5640
tgtttagcag atcgcgccgt tccggcgtga gcaggttatc tctggcgcgt ttagggcgt     5700 ccatgtctgc ttcaccttcc agggttttg gatcgatacc gcagtcgcgg aagtactgct     5760
gcagcgtcgc cgatttgagg gtgtagaaac cacgcatgcc tatctcaaca gcaggggtcg    5820
atttcactcg gtaatcggtt atggccggga atttagcctg gaactctgcg tcggcctgtt    5880
cccgcgtcat ggccgtagtg acgaactgct gccatcttcc ggcaacgcga taagcgtagg    5940
taaagtgaat caacgcttct tcacggtcaa ggcgacgggc ggttatctca tccagctgca    6000
tggtttcaaa caggcgcact tttttcaggc cgccgtcgaa atagaatttt aacgccacct    6060
cgtcgacatc cagctgcagc tccttttcga tgtcccagcg gaccagctgg gcctgctcat    6120
```

```
ccagggacag ggtgcgtttt tttatcaact catcgtgttc ggcctggtca ggagtatcga    6180
cactcaggtg gcgctccata agctgctcaa agaccagttc acgggcttct ttacgtaaat    6240
ccttaccgat gctgtttgca agcgcgtcgg tggccatagg cgcgacctga tagccatcat    6300
catgcatgat gcaaatcatg ttgctggcat aatcatttct ggccgatgcc tcgagcgcgg    6360
cggctttaat tttgagctgc atgaatgaag agttagccac gccgagtgaa attcggtcac    6420
cgtcaaagac aacgtctgtc agcagcccgg agtggccagc cgtttcgagc aaggcctgcg    6480
cgtaggcgcg tttgattttt tccggatcgg tttcacgttt accgcgaagc ttgtcgaaac    6540
cgataatgta ttcctgagct gtacggtcgc ggcgcagcat ctggatggcg tcgctgggga    6600
ccacttcgcc gcagaacatg ccgaaatggc ggtggaagtg tttctcctca atcgatacac    6660
ctgaagatat cgacgggctg tagatgaggc cgtcatattt tttcaccatc actttaggct    6720
ggttggtgaa atcgtcgact tccttctcct gtttgttttt ctggttaacg cagagaaact    6780
ttttgtcagg gaactgtagt ctcagctgca tggtaacgtc ttcggcgaac gtcgaactgt    6840
cggtggccag catgattcgt tcgccgcgtt gcactgcagc gataacctcg gtcatgatcc    6900
gatttttctc ggtataaaat acgcggatag gcttgttggt ttcgcggttg cgaacgtcga    6960
ccgggagttc aatcacgtga atttgcagcc aggcaggtag gcccagctcc tcgcgtcgct    7020
tcatcgccag ttcagccagg tcaacaagca gatcgttggc atcggcatcc accataatgg    7080
catgctcttc agtacgcgcc agcgcgtcga taagcgtgtt gaatacgcct accgggtttt    7140
ccatcgcacg cccggccaga atggcacgca ggccctgtgt tgcttcatcg aagccgaaga    7200
agtcatgctg gcgcatcagc ggttgccagc agcctttaag tatggagttg atgcaaatag    7260
tcagcttgtt ggcatatggc gccatttcct gatagccggg atcctgataa tgcagaatgt    7320
cggctttcgc gccttttccct tcggtcatca tttcatgcag gccgcctatc agggatacgc    7380
ggtgcgcgac ggaaacgcca cgcgtggact gcagcatcag tggacgcagg aggcctgtcg    7440
atttacccga ccccatcccg gcgcggacaa taacgatgcc ctgcagctgt gcggcgtatg    7500
tcatcacctc atcggtcatc ctggaggttt caaaccgttt gtaagtgatg tgtgacgggc    7560
gaaggttcgg gttggtgatg cgttcactga acgaacgtga tgtttgcgcg gcacggcatt    7620
tgcgattcaa ccgcgcgta atgtgatctt taacggtacc gttataaatt ctgcgatac    7680 ccatatcccg cagcgtgctg ctgaaaaggc gcataagttc tttcgggctg tttggtaccg    7740
ggcatgtcag catgccaata tcaacggcgc gaagcagttc tttggcaaaa gtgcgtctgt    7800
tcagacgcgg gagagtacgc agcttattca gcgtgatcga caacaggtcg gttgcacggc    7860
tcagatgatt tctcgttaac tggcgagcga cttccttcag ccctctcagg ctgtgcaggt    7920
cgttaaaatc gctgcattcc agctcagggt catcctcaaa agttgggtaa acacatttga    7980
cgccggaaaa cttctccatg atgtcgaatc cggtgcggag gcctgtgttg ccttttcctt    8040
cagctgagga tttgcggtcg ttatcgagag cgcaagtgat ttgcgcagcc gggtacatgt    8100
tcaccagctg ctcgacaacg tgaatcatgt tgttagcgga aaccgcaatg actaccgcgt    8160
caaagcgttt tttcgggtcg tttctggtcg ccagccagat ggatgccccg gtggcgaaac    8220
cctctgcagt cgcaatttttt tgcgcccccct gcaggtcgcc aataacaaag catgcaccga    8280
cgaaatcacc gttagtgatg gcgctggtct ggaacttgcc accattcaga tcgatacgtt    8340
gccagccaac aatccgcccg tcttttcttc cgtccaggtg ggacagaggt atcgccatgt    8400
aagttgttgg tccacggctc catttcgcac tgtcgtgact ggtcacgcga cgtatatcac    8460
```

```
aagcgccaaa tacgtcacga attccctttt ttaccgcata aggccaggag ccatcttcag   8520
ctggcgaatg ttcccaggcg cgatggaaag ccaaccatcc aagcaggcgt tcctgctcca   8580
tctgattgtt ttttaaatca ttaacgcgtt gttgttcagc tcggaggcgg cgtgcttcag   8640
cctggcgctc catgcgtgca cgttcttctt ccggctgagc gaccacggtc gcaccattcc   8700
gttgctgttc acggcgatac tccgaaaaca ggaatgaaaa gccactccag gagccagcgt   8760
catgcgcttt ttcaacgaag ttaacgaaag gataactgat gccatccttg ctctgctcaa   8820
ggcgtgaata gatttccaca cggcctttaa ggctcttctg cagagcttcc ggggaggaat   8880
tattgtaggt ggtatagcgc tctacaccac cgcgcggatt gagctgaatc ttatcagcac   8940
acgcaggcca gttgataccg gccatcttcg ccagctcagt cagctcatca cgtgccgcgt   9000
caagcagtga aaacggatcg ctgccaaagc gctccgcgta gaattcttgt aaggtcattt   9060
tttagccttt ccatgcgaat tagcattttt tcgggttgaa aaaatccgca ggagcagcca   9120
caataaacgc actatctttc tgaaggacgt atctgcgtta tcgtggctac ttcctgaaaa   9180
aggcccgagt ttgccgactc gggtttttt tcgtcttttt tcggctgcta cggtctggtt   9240
caaccccgac aaagtataga tcggattaaa ccagaattat agtcagcaat aaaccctgtt   9300
attgtatcat ctaccctcaa ccatgaacga tttgatcgta ccgactactt ggtgcacaaa   9360
ttgaagatca ctttatcat ggataacccg ttgagagtta gcactatcaa ggtagtaatg   9420
ctgctcgtca taacgggcta atcgttgaat tgtgatctcg ccgttattat cacaaaccag   9480
tacatcctca cccggtacaa gcgtaagtga agaatcgacc aggataacgt ctcccggctg   9540
gtagtttcgc tgaatctggt tcccgaccgt cagtgcgtaa acggtgttcc gttgactcac   9600
gaacggcagg aatcgctctg tgttggcagg ttctccaggc tgccagtctc tatccggtcc   9660
ggtctctgtc gtaccaataa caggaacgcg gtctggatca gattcagtgc catacagtat   9720
ccattgcacg ggcttacgca ggcatttgc cagcgatagc ccgatctcca gcgacggcat   9780
cacgtcgcca cgttctaagt tttggacgcc cggaagagag attcctacag cttctgccac   9840
ttgcttcagc gtcagtttca gctctaaacg gcgtgctttc agtcgttcgc ctcgtgtttt   9900
cataccctta atcataaatg atctctttat agctggctat aattttata aattataacct  9960
agctttaatt ttcacttatt gattataata atccccatga aacccgaaga acttgtgcgc  10020
catttcggcg atgtggaaaa agcagcggtt ggcgtgggcg tgacacccgg cgcagtctat  10080
caatggctgc aagctgggga gattccacct ctacgacaaa gcgatataga ggtccgtacc  10140
gcgtacaaat taaagagtga tttcacctct cagcgcatgg gtaaggaagg gcataacagg  10200
ggatcctcta gagtcgacct gcaggcatgc aagcttcctg aatcgcccca tcatccagcc  10260
agaaagtgag ggagccacgg ttgatgagag ctttgttgta ggtggaccag ttggtgattt  10320
tgaacttttg ctttgccacg gaacggtctg cgttgtcggg aagatgcgtg atctgatcct  10380
tcaactcagc aaaagttcga tttattcaac aaagccgccg tcccgtcaag tcagcgtaat  10440
gctctgccag tgttacaacc aattaaccaa ttctgattag aaaaactcat cgagcatcaa  10500
atgaaactgc aatttattca tatcaggatt atcaatacca tatttttgaa aaagccgttt  10560
ctgtaatgaa ggagaaaact caccgaggca gttccatagg atggcaagat cctggtatcg  10620
gtctgcgatt ccgactcgtc caacatcaat acaacctatt aatttcccct cgtcaaaaat  10680
aaggttatca agtgagaaat caccatgagt gacgactgaa tccggtgaga atggcaaaag  10740
cttatgcatt tctttccaga cttgttcaac aggccagcca ttacgctcgt catcaaaatc  10800
actcgcatca accaaaccgt tattcattcg tgattgcgcc tgagcgagac gaaatacgcg  10860
```

-continued

```
atcgctgtta aaaggacaat tacaaacagg aatcgaatgc aaccggcgca ggaacactgc    10920
cagcgcatca acaatatttt cacctgaatc aggatattct tctaatacct ggaatgctgt    10980
tttccctggg atcgcagtgg tgagtaacca tgcatcatca ggagtacgga taaaatgctt    11040
gatggtcgga agaggcataa attccgtcag ccagtttagt ctgaccatct catctgtaac    11100
atcattggca acgctacctt tgccatgttt cagaaacaac tctggcgcat cgggcttccc    11160
atacaatcga tagattgtcg cacctgattg cccgacatta tcgcgagccc atttataccc    11220
atataaatca gcatccatgt tggaatttaa tcgcggcctc gagcaagacg tttcccgttg    11280
aatatggctc ataacacccc ttgtattact gtttatgtaa gcagacagtt ttattgttca    11340
tgatgatata tttttatctt gtgcaatgta acatcagaga ttttgagaca caacgtggct    11400
tgttgaata aatcgaactt tgctgagtt gaaggatcag atcacgcatc ttcccgacaa    11460
cgcagaccgt tccgtggcaa agcaaaagtt caaaatcacc aactggtcca cctacaacaa    11520
agctctcatc aaccgtggct ccctcacttt ctggctggat gatgggcga ttcaggaagc    11580
ttgcatgcct gcaggtcgac tctagaggat ccccgagaac ccgataatcg ctaccagtga    11640
tgatggctgt tttgcggcgg cgtgagccat cggcaatttc gataatgcct gacgtccttc    11700
tggcgaacgc ggggttctgc tgtcctgaag tgaggaatga agggataagg tcggccagcg    11760
ctgattcgtt cagcaattcc tgatcacgtt cattaccgag ccaaaccatt gtggcctttt    11820
cgactttatc agcaggaatg gtttccagct taaaagtcac gttgcggcca tcaagcttga    11880
attcgtacgc agaaaggccc acccgaaggt gagccagtgt gattacattt gcggccgcat    11940
ttaaatgggc ccaatggccc gggaggccta cttaagtaag ccggcttagc tagcgggaca    12000
ggtttcccga ctgaaaagcg ggcagtgagc gcaacgcaat taatgtgagt tagctcactc    12060
attaggcacc ccaggcttta cactttatgc ttccggctcg tatgttgtgt ggaattgtga    12120
gcggacaaca atttcacaca ggaaacagct atgaccatga ttacgccaag ctatttaggt    12180
gagactatag aatactcaag cttgcatgcg atacgtatcg ttaacgatgg atccgacgca    12240
cgtgcgaatt cgccctatag tgagtcgtat tacaattcac tggccgtcgt tttacaacgt    12300
cgtgactggg aaaaccctgg cgtcacccaa cttaatcgcc ttgcagcaca tccccctttc    12360
gccagctggc gtaatagcga agaggcccgc accgatcgcc cttcccaaca gttgcgcagc    12420
tgaatggcga atggcgcctg agctagcatt gccggcattc ttaagtaggc ctcccgggcc    12480
attggcgcgc catgcggccg ccatggtcaa ataaaacgaa aggctcagtc gaaagactgg    12540
gcctttcgtt ttaatctgat cggcacgtaa gaggttccaa cttttcaccat aatgaaataa    12600
gatcactacc gggcgtattt tttgagttat cgagattttc aggagctaag gaagctaaaa    12660
tgagtattca acatttccgt gtcgccctta ttccctttt tgcggcattt tgccttcctg    12720
tttttgctca cccagaaacg ctggtgaaag taaaagatgc tgaagatcag ttgggtgcac    12780
gagtgggtta catcgaactg gatctcaaca gcggtaagat ccttgagagt ttacgccccg    12840
aagaacgttt tccaatgatg agcactttta aagttctgct atgtggcgcg gtattatccc    12900
gtattgacgc cgggcaagag caactcggtc gccgcataca ctattctcag aatgacttgg    12960
ttgagtactc accagtcaca gaaaagcatc tcacggatgg catgacagta agagaattat    13020
gcagtgctgc cataaccatg agtgataaca ctgcggccaa cttacttctg caacgatcg    13080
gaggaccgaa ggagctaacc gcttttttgc acaacatggg ggatcatgta actcgccttg    13140
atcgttggga accggagctg aatgaagcca taccaaacga cgagcgtgac accacgatgc    13200
```

```
ctgtagcaat ggcaacaacg ttgcgcaaac tattaactgg cgaactactt actctagctt    13260
cccggcaaca attaatagac tggatggagg cggataaagt tgcaggatca cttctgcgct    13320
cggccctccc ggctggctgg tttattgctg ataaatctgg agccggtgag cgtgggtctc    13380
gcggtatcat tgcagcactg ggccagatg gtaagccctc ccgcatcgta gttatctaca    13440
cgacggggag tcaggcaact atggatgaac gaaatagaca gatcgctgag ataggtgcct    13500
cactgattaa gcattggtaa tgacagaagt caaaagcctc cggtcggagg cttttgactt    13560
tctgctagat ctgtttcaat gcggtgaagg gccaggcagc tggggattat gtcgagaccc    13620
ggccagcatg ttggttttat cgcatattca gcgttgtcgc gtttacccag gtaaaatgga    13680
agcagtgtat cgtctgcgtg aatgtgcaaa tcaggaacgt aaccgtggta catgagatgca    13740 gtcccttgcg ggtcgttccc ttcaacgagt aggacgcggt gcccttgcaa ggctaaccat    13800
tgcgcctggt gtactgcaga tgaggtttta taaacccctc ccttgtgtga cataacggaa    13860
agtacaaccg ggtttttatc gtcaggtctt tggtttgggt taccaaacac actccgcata    13920
tggctaattt ggtcaattgt gtagccagcg cgacgttcta ctcggcccct catctcaaaa    13980
tcaggagccg gtagacgacc agcttttcc gcgtctctga tagcctgcgg tgttacgccg    14040
atcaggtctg caacttctgt tataccccag cggcgagtaa tacgacgcgc ttccgggctg    14100
tcatcgccga actgtgcgat ggcaatagcg cgcgtcattt cctgaccgcg attgatacag    14160
tctttcagca aattaattaa cgacatcctg tttcctctca acatgccct tatctttgtg    14220 tttttcatca tactttacgt ttttaaagca aagcaacata aaaaaagcaa agtgacttag    14280
aaaacgcaaa gttaaggttc aaatcaattt tttgatgcgc tacagaagct atttagcttc    14340
atctaagcgc aacggtatta cttacgttgg tatatttaaa acctaactta atgattttaa    14400
atgataataa atcataccaa ttgctatcaa aagttaagcg aacatgctga ttttcacgct    14460
gtttatacac tttgaggcat ctctatctct tccgtctcta tattgaaaca caatcaaaga    14520
acatcaatcc atgtgacatc ccccactatc taagaacacc ataacagaac acaacatagg    14580
aatgcaacat taatgtatca ataattcgga acatatgcac tatatcatat ctcaattacg    14640
gaacatatca gcacacaatt gcccattata cgc                                 14673
```

<210> SEQ ID NO 63  
<211> LENGTH: 14549  
<212> TYPE: DNA  
<213> ORGANISM: Artificial  
<220> FEATURE:  
<223> OTHER INFORMATION: NZCK3

<400> SEQUENCE: 63

```
gcgtataatg gactattgtg tgctgataag gagaacataa gcgcagaaca atatgtatct      60
attccggtgt tgtgttcctt tgttattctg ctattatgtt ctcttatagt gtgacgaaag     120
cagcataatt aatcgtcact tgttctttga ttgtgttacg atatccagag acttagaaac     180
gggggaaccg ggatgagcaa ggtaaaaatc ggtgagttga tcaacacgct tgtgaatgag     240
gtagaggcaa ttgatgcctc agaccgccca caaggcgaca aaacgaagag aattaaagcc     300
gcagccgcac ggtataagaa cgcgttattt aatgataaaa gaaagttccg tgggaaagga     360
ttgcagaaaa gaataaccgc gaatactttt aacgcctata tgagcagggc aagaaagcgg     420
tttgatgata aattacatca tagctttgat aaaaatatta ataaattatc ggaaaagtat     480 cctctcttaca gcgaagaatt atcttcatgg ctttctatgc ctacggctaa tattcgccag     540
cacatgtcat cgttacaatc taaattgaaa gaaataatgc cgcttgccga agagttatca     600
```

```
aatgtaagaa taggctctaa aggcagtgat gcaaaaatag caagactaat aaaaaaatat     660
ccagattgga gttttgctct tagtgattta aacagtgatg attggaagga gcgccgtgac     720
tatctttata agttattcca acaaggctct gcgttgttag aagaactaca ccagctcaag     780
gtcaaccatg aggttctgta ccatctgcag ctaagccctg cggagcgtac atctatacag     840
caacgatggg ccgatgttct gcgcgagaag aagcgtaatg ttgtggttat tgactaccca     900
acatacatgc agtctatcta tgatattttg aataatcctg cgactttatt tagtttaaac     960
actcgttctg gaatggcacc tttggccttt gctctggctg cggtatcagg gcgaagaatg    1020
attgagataa tgtttcaggg tgaatttgcc gtttcaggaa agtatacggt taatttctca    1080
gggcaagcta aaaacgctc tgaagataaa agcgtaacca gaacgattta tactttatgc     1140
gaagcaaaat tattcgttga attattaaca gaattgcgtt cttgctctgc tgcatctgat    1200
ttcgatgagg ttgttaaagg atatggaaag gatgatacaa ggtctgagaa cggcaggata    1260
aatgctattt tagcaaaagc atttaaccct tgggttaaat cattttttcgg cgatgaccgt   1320
cgtgttata aagatagccg cgctatttac gctcgcatcg cttatgagat gttcttccgc     1380
gtcgatccac ggtggaaaaa cgtcgacgag gatgtgttct tcatggagat tctcggacac    1440
gacgatgaga cacccagct gcactataag cagttcaagc tggccaactt ctccagaacc     1500
tggcgacctg aagttgggga tgaaaacacc aggctggtgg ctctgcagaa actggacgat    1560
gaaatgccag gctttgccag aggtgacgct ggcgtccgtc tccatgaaac cgttaagcag    1620
ctggtggagc aggaccccatc agcaaaaata accaacagca ctctccgggc ctttaaattt   1680
agcccgacga tgattagccg gtacctggag tttgccgctg atgcattggg gcagttcgtt    1740
ggcgagaacg ggcagtggca gctgaagata gagacacctg caatcgtcct gcctgatgaa    1800
gaatccgttg agaccatcga cgaaccggat gatgagtccc aagacgacga gctggatgaa    1860
gatgaaattg agctcgacga gggtggcggc gatgaaccaa ccgaagagga agggccagaa    1920
gaacatcagc caactgctct aaaacccgtc ttcaagcctg caaaaaataa cggggacgga    1980
acgtacaaga tagagtttga atacgatgga aagcattatg cctggtccgg ccccgccgat    2040
agccctatgg ccgcaatgcg atccgcatgg gaaacgtact acagctaaaa gaaaagccac    2100
cggtgttaat cggtggcttt ttttattgagg cctgtcccta cccatcccct gcaagggacg    2160
gaaggattag gcggaaactg cagctgcaac tacggacatc gccgtcccga ctgcagggac    2220
ttccccgcgt aaagcggggc ttaaattcgg gctggccaac cctattttc tgcaatcgct    2280
ggcgatgtta gtttcgtgga tagcgtttcc agcttttcaa tggccagctc aaaatgtgct    2340
ggcagcacct tctccagttc cgtatcaata tcggtgatcg gcagctctcc acaagacata    2400
ctccggcgac cgccacgaac tacatcgcgc agcagctccc gttcgtagac acgcatgttg    2460
cccagagccg tttctgcagc cgttaatatc cggcgcagct cggcgatgat tgccgggaga    2520
tcatccacgg ttattgggtt cggtgatggg ttcctgcagg cgcggcggag agccatccag    2580
acgccgctaa cccatgcgtt acggtactga aaactttgtg ctatgtcgtt tatcaggccc    2640
cgaagttctt ctttctgccg ccagtccagt ggttcaccgg cgttcttagg ctcaggctcg    2700
acaaaagcat actcgccgtt tttccggata gctggcagaa cctcgttcgt cacccacttg    2760
cggaaccgcc aggctgtcgt ccctgtttc accgcgtcgc ggcagcggag gattatggtg    2820
tagagaccag attccgatac cacatttact tccctggcca tccgatcaag ttttttgtgcc    2880
tcggttaaac cgagggtcaa ttttttcatca tgatccagct tacgcaatgc atcagaaggg    2940
```

```
ttggctatat tcaatgcagc acagatatcc agcgccacaa accacgggtc accaccgaca    3000
agaaccaccc gtataggtg gctttcctga aatgaaaaga cggagagagc cttcattgcg     3060
cctccccgga tttcagctgc tcagaaaggg acaggagca gccgcgagct tcctgcgtga     3120
gttcgcgcgc gacctgcaga agttccgcag cttcctgcaa atacagcgtg gcctcataac    3180
tggagatagt gcggtgagca gagcccacaa gcgcttcaac ctgcagcagg cgttcctcaa    3240
tcgtctccag caggccctgg gcgtttaact gaatctggtt catgcgatca cctcgctgac    3300
cgggatacgg gctgacagaa cgaggacaaa acggctggcg aactggcgac gagcttctcg    3360
ctcggatgat gcaatggtgg aaaggcggtg gatatgggat ttttgtccg tgcggacgac     3420 agctgcaaat ttgaatttga acatggtatg cattcctatc ttgtataggg tgctaccacc    3480
agagttgaga atctctatag gggtggtagc ccagacaggg ttctcaacac cggtacaaga    3540
agaaaccggc ccaaccgaag ttggccccat ctgagccacc ataattcagg tatgcgcaga    3600
tttaacacac aaaaaaacac gctggcgcgt gttgtgcgct tcttgtcatt cggggttgag    3660
aggcccggct gcagattttg ctgcagcggg gtaactctac cgccaaagca gaacgcacgt    3720
caataattta ggtggatatt ttaccccgtg accagtcacg tgcacaggtg tttttatagt    3780
ttgctttact gactgatcag aacctgatca gttattggag tccggtaatc ttattgatga    3840
ccgcagccac cttagatgtt gtctcaaacc ccatacggcc acgaatgagc cactggaacg    3900
gaatagtcag caggtacagc ggaacgaacc acaaacggtt cagacgctgc cagaacgtcg    3960
catcacgacg ttccatccat tcggtattgt cgacgacctg gtaagcgtat tgtcctggcg    4020
tttttgctgc ttccgagtag caatcctctt caccacaaag aaagttactt atctgcttcc    4080
agttttcgaa cccttcttct ttgagccgct tttccagctc attcctccac aaaacaggca    4140
cccatcctct gcgataaatc atgattattt gtcctttaaa taaggctgta gaactgcaaa    4200
atcgctctcg ttcacatgct gtacgtagat gcgtagcaaa ttgccgttcc atccctgtaa    4260
tccaccttct ttggaaagat cgtccttgac ctcacgaaga accttatcca atagccctgc    4320
ggcacaagaa attgcctgct ctggatcagc aaattcatat tgattaatag gtgattgcca    4380
cacaccaaaa acaggaatca tcttttcggc taaacgcctc tcctgttctt tcttaatctc    4440
aagttgtaag cggaccagct caccatccat cattttttgt agatcatgcg ccactattca    4500 ccccactgg ccatcagcaa ataaagcttc atactcggac accggcaggc ggcttccacg     4560
gattgaaagg tcaagccaac cacgtccaga tgggtcagcc ttatccgatt cttcccaccg    4620
ttctgcagct gtagcaacca ggcattctac cgccttcatg tagtcttctg tacggaacca    4680
gccgtagtta atgccaccat cagtaactgc ccaggccatc ttttctctt cggcctcaat     4740 agcccggatg cggttatcgc acagctcgcg acagtacttc agctgttcgt aatccagttg    4800
cttcaggaac tctggtgtcg acgtcatagt ggcttcacct tataggcttt tagaagcgcc    4860
ctggcttcgt ctgtgtggtc ttccatgctc ttatcgctgg caatgcagca ataaactccc    4920
tcactatctg agaacccgtt catccgaatg atcgtgaatg gaagttcccg gccagttta     4980 taatcgctat agcttgtcgc gtcgtggctg accttgacca cataagggtc gtagccctcc    5040
acgatgacaa ggcattcccg ttgttttccc attacccctc cggttatatc gccacggctt    5100
gccgctggct tagaaacgct ttcagcagcc ttatttcgcg tactgatagc aggtccataa    5160
attcggtcat gtacagcgag gcgaacgttc tcgcgatgct ggccactggc cacaggcgta    5220
ccgcctccat ttcggttgct ggcaacgcgt tctccgccca cgcctccggt accgccaccg    5280
ggatagcctc cagtgcctgg ataattactg attgtgggc gtccggaacg tgctctgttt     5340
```

```
tggatcgagg gttaccatgt atatctatat ttagatccaa atcgcgatcc acttcgatgg    5400
tggttttttc caccttacgt gcgtgaattg ataaaccggc ctcgcggcgc ttctccacga    5460
tattcatgag gaactcgacc gagtccgggt caatggaacg catcgtgggg cgtgcatcgc    5520
cgtctctggc gcgtctggtc ttactggata gccccataga ctccaggatg cctatgcaga    5580
ggtctgcagg cgctttcttc ttgcctttct ctgtgttgaa gccgccgatg cgtaaaacgt    5640
tgtttagcag atcgcgccgt tccggcgtga gcaggttatc tctggcgcgt ttgagggcgt    5700
ccatgtctgc ttcaccttcc agggttttttg gatcgatacc gcagtcgcgg aagtactgct   5760
gcagcgtcgc cgatttgagg gtgtagaaac cacgcatgcc tatctcaaca gcagggggtcg  5820
atttcactcg gtaatcggtt atggccggga atttagcctg gaactctgcg tcggcctgtt    5880
cccgcgtcat ggccgtagtg acgaactgct gccatcttcc ggcaacgcga taagcgtagg    5940
taaagtgaat caacgcttct tcacggtcaa ggcgacgggc ggttatctca tccagctgca    6000
tggtttcaaa caggcgcact ttttcaggc cgccgtcgaa atagaatttt aacgccacct     6060
cgtcgacatc cagctgcagc tccttttcga tgtcccagcg gaccagctgg gcctgctcat    6120
ccagggacag ggtgcgtttt tttatcaact catcgtgttc ggcctggtca ggagtatcga    6180
cactcaggtg gcgctccata agctgctcaa agaccagttc acgggcttct ttacgtaaat    6240
ccttaccgat gctgtttgca agcgcgtcgg tggccatagg cgcgacctga tagccatcat    6300
catgcatgat gcaaatcatg ttgctggcat aatcatttct ggccgatgcc tcgagcgcgg    6360
cggctttaat tttgagctgc atgaatgaag agttagccac gccgagtgaa attcggtcac    6420
cgtcaaagac aacgtctgtc agcagcccgg agtggccagc cgtttcgagc aaggcctgcg    6480
cgtaggcgcg tttgattttt tccggatcgg tttcacgttt accgcgaagc ttgtcgaaac    6540
cgataatgta ttcctgagct gtacggtcgc ggcgcagcat ctggatggcg tcgctgggga    6600
ccacttcgcc gcagaacatg ccgaaatggc ggtggaagtg tttctcctca atcgatacac    6660
ctgaagatat cgacgggctg tagatgaggc cgtcatattt tttcaccatc actttaggct    6720
ggttggtgaa atcgtcgact tccttctcct gtttgttttt ctggttaacg cagagaaact    6780
ttttgtcagg gaactgtagt ctcagctgca tggtaacgtc ttcggcgaac gtcgaactgt    6840
cggtggccag catgattcgt tcgccgcgtt gcactgcagc gataacctcg gtcatgatcc    6900
gattttctc ggtataaaat acgcggatag gcttgttggt ttcgcggttg cgaacgtcga     6960
ccgggagttc aatcacgtga atttgcagcc aggcaggtag gcccagctcc tcgcgtcgct    7020
tcatcgccag ttcagccagg tcaacaagca gatcgttggc atcggcatcc accataatgg    7080
catgctcttc agtacgcgcc agcgcgtcga taagcgtgtt gaatacgcct accgggtttt    7140
ccatcgcacg cccggccaga atggcacgca ggccctgtgt tgcttcatcg aagccgaaga    7200
agtcatgctg gcgcatcagc ggttgccagc agcctttaag tatggagttg atgcaaatag    7260
tcagcttgtt ggcatatggc gccatttcct gatagccggg atcctgataa tgcagaatgt    7320
cggctttcgc gccttttccct tcggtcatca tttcatgcag gccgcctatc agggatacgc    7380
ggtgcgcgac ggaaacgcca cgcgtggact gcagcatcag tggacgcagg aggcctgtcg    7440
atttaccccga ccccatcccg gcgcggacaa taacgatgcc ctgcagctgt gcggcgtatg   7500
tcatcacctc atcggtcatc ctggaggttt caaaccgttt gtaagtgatg tgtgacgggc    7560
gaaggttcgg gttggtgatg cgttcactga acgaacgtga tgtttgcgcg cacggcatt    7620
tgcgattcaa ccggcgcgta atgtgatctt taacggtacc gttataaatt tctgcgatac    7680
```

```
ccatatcccg cagcgtgctg cttaaaaggc gcataagttc tttcgggctg tttggtaccg   7740
ggcatgtcag catgccaata tcaacggcgc gaagcagttc tttggcaaaa gtgcgtctgt   7800
tcagacgcgg gagagtacgc agcttattca gcgtgatcga caacagatcg gttgcacggc   7860
tcagatgatt tctcgttaat ctggcgagcg acttccttca gccctctcag gctgtgcagg   7920
tcgttaaaat cgctgcattc cagctcaggg tcatcctcaa aagttgggta aacacattgg   7980
acgccggaaa acttctccat gatgtcgaat ccggtgcgga ggcctgtgtt gccttttcct   8040
tcagctgagg atttgcggtc gttatcgaga gcgcaagtga tttgcgcagc cgggtacatg   8100
ttcaccagct gctcgacaac gtgaatcatg ttgttagcgg aaaccgcaat gactaccgcg   8160
tcaaagcgtt ttttcgggtc gtttctggtc gccagccaga tggatgcccc ggtggcgaaa   8220
ccctctgcag tcgcaatttt ttgcgccccc tgcaggtcgc caataacaaa gcatgcaccg   8280
acgaaatcac cgttagtgat ggcgctggtc tggaacttgc caccattcag atcgatacgt   8340
tgccagccaa caatccgccc gtcttttctt ccgtccaggt gggacagagg tatcgccatg   8400
taagttgttg gtccacggct ccatttcgca ctgtcgtgac tggtcacgcg acgtatatca   8460
caagcgccaa atacgtcacg aattcccttt tttaccgcat aaggccagga gccatcttca   8520
gctggcgaat gttcccaggc gcgatggaaa gccaaccatc caagcaggcg ttcctgctcc   8580
atctgattgt ttttttaaatc attaacgcgt tgttgttcag ctcggaggcg gcgtgcttca   8640
gcctggcgct ccatgcgtgc acgttcttct tccggctgag cgaccacggt cgcaccattc   8700
cgttgctgtt cacggcgata ctccgaaaac aggaatgaaa agccactcca ggagccagcg   8760
tcatgcgctt tttcaacgaa gttaacgaaa ggataactga tgccatcctt gctctgctca   8820
aggcgtgaat agatttccac acggccttta aggctcttct gcagagcttc cggggaggaa   8880
ttattgtagg tggtatagcg ctctacacca ccgcgcggat tgagctgaat cttatcagca   8940
cacgcaggcc agttgatacc ggccatcttc gccagctcag tcagctcatc acgtgccgcg   9000
tcaagcagtg aaaacggatc gctgccaaag cgctccgcgt agaattcttg taaggtcatt   9060
ttttagcctt tccatgcgaa ttagcatttt ttcgggttga aaaaatccgc aggagcagcc   9120
acaataaacg cactatcttt ctgaaggacg tatctgcgtt atcgtggcta cttcctgaaa   9180
aaggcccgag tttgccgact cgggtttttt ttcgtctttt ttcggctgct acggtctggt   9240
tcaaccccga caaagtatag atcggattaa accagaatta tagtcagcaa taaaccctgt   9300
tattgtatca tctaccctca accatgaacg atttgatcgt accgactact tggtgcacaa   9360
attgaagatc acttttatca tggataaccc gttgagagtt agcactatca aggtagtaat   9420
gctgctcgtc ataacgggct aatcgttgaa ttgtgatctc gccgttatta tcacaaacca   9480
gtacatcctc acccggtaca agcgtaagtg aagaatcgac caggataacg tctcccggct   9540
ggtagtttcg ctgaatctgg ttcccgaccg tcagtgcgta aacggtgttc cgttgactca   9600
cgaacggcag gaatcgctct gtgttggcag gttctccagg ctgccagtct ctatccggtc   9660
cggtctctgt cgtaccaata acaggaacgc ggtctggatc agattcagtg ccatacagta   9720
tccattgcac gggcttacgc aggcattttg ccagcgatag cccgatctcc agcgacggca   9780
tcacgtcgcc acgttctaag ttttggacgc ccggaagaga gattcctaca gcttctgcca   9840
cttgcttcag cgtcagtttc agctctaaac ggcgtgcttt cagtcgttcg cctcgtgttt   9900
tcatacccct aatcataaat gatctcttta gctggctact aattttttat aaattatacc   9960
tagctttaat tttcacttat tgattataat aatcccccatg aaacccgaag aacttgtgcg  10020
ccatttcggc gatgtggaaa aagcagcggt tggcgtgggc gtgacacccg gcgcagtcta  10080
```

```
tcaatggctg caagctgggg agattccacc tctacgacaa agcgatatag aggtccgtac  10140
cgcgtacaaa ttaaagagtg atttcacctc tcagcgcatg ggtaaggaag gcataacag   10200
gggatcctct agagtcgacc tgcaggcatg caagcttcct gaatcgcccc atcatccagc  10260
cagaaagtga gggagccacg gttgatgaga gctttgttgt aggtggacca gttggtgatt  10320
ttgaactttt gctttgccac ggaacggtct gcgttgtcgg gaagatgcgt gatctgatcc  10380
ttcaactcag caaaagttcg atttattcaa caaagccgcc gtcccgtcaa gtcagcgtaa  10440
tgctctgcca gtgttacaac caattaacca attctgatta gaaaaactca tcgagcatca  10500
aatgaaactg caatttattc atatcaggat tatcaatacc atattttga aaaagccgtt   10560
tctgtaatga aggagaaaac tcaccgaggc agttccatag gatggcaaga tcctggtatc  10620
ggtctgcgat tccgactcgt ccaacatcaa tacaacctat taatttcccc tcgtcaaaaa  10680
taaggttatc aagtgagaaa tcaccatgag tgacgactga atccggtgag aatggcaaaa  10740
gcttatgcat ttctttccag acttgttcaa caggccagcc attacgctcg tcatcaaaat  10800
cactcgcatc aaccaaaccg ttattcattc gtgattgcgc ctgagcgaga cgaaatacgc  10860
gatcgctgtt aaaaggacaa ttacaaacag gaatcgaatg caaccggcgc aggaacactg  10920
ccagcgcatc aacaatattt tcacctgaat caggatattc ttctaatacc tggaatgctg  10980
ttttccctgg gatcgcagtg gtgagtaacc atgcatcatc aggagtacgg ataaaatgct  11040
tgatggtcgg aagaggcata aattccgtca gccagtttag tctgaccatc tcatctgtaa  11100
catcattggc aacgctacct ttgccatgtt tcagaaacaa ctctggcgca tcgggcttcc  11160
catacaatcg atagattgtc gcacctgatt gcccgacatt atcgcgagcc catttatacc  11220
catataaatc agcatccatg ttggaattta atcgcggcct cgagcaagac gtttcccgtt  11280
gaatatggct cataacaccc cttgtattac tgtttatgta agcagacagt tttattgttc  11340
atgatgatat attttatct tgtgcaatgt aacatcagag attttgagac acaacgtggc   11400
tttgttgaat aaatcgaact tttgctgagt tgaaggatca gatcacgcat cttcccgaca  11460
acgcagaccg ttccgtggca aagcaaaagt tcaaaatcac caactggtcc acctacaaca  11520
aagctctcat caaccgtggc tccctcactt tctggctgga tgatggggcg attcaggaag  11580
cttgcatgcc tgcaggtcga ctctagagga tccccgagaa cccgataatc gctaccagtg  11640
atgatggctg ttttgcggcg gcgtgagcca tcggcaattt cgataatgcc tgacgtcctt  11700
ctggcgaacg cggggttctg ctgtcctgaa gtgaggaatg aagggataag gtcggccagc  11760
gctgattcgt tcagcaattc ctgatcacgt tcattaccga gccaaaccat tgtggccttt  11820
tcgactttat cagcaggaat ggtttccagc ttaaaagtca cgttgcggcc atcaagcttg  11880
aattcgtacg cagaaaggcc caccogaagg tgagccagtg tgattacatt tgcggccagt  11940
ccagttacgc tggagtcact agtgcggccg cgacaacttg tctagggccc aatgcccgg   12000
gaggcctact taagtaagcc ggcttagcta gcgggacagg tttcccgact ggaaagcggg  12060
cagtgagcgc aacgcaatta atgtgagtta gctcactcat taggcacccc aggctttaca  12120
ctttatgctt ccggctcgta tgttgtgtgg aattgtgagc ggacaacaat ttcacacagg  12180
aaacagctat gaccatgatt acgccaagct atttaggtga gactatagaa tactcaagct  12240
tgcatgcgat acgtatcgtt aacgatggat ccgacgcacg tgcgaattcg ccctatagtg  12300
agtcgtatta caattcactg gccgtcgttt tacaacgtcg tgactgggaa accctggcg   12360
tcacccaact taatcgcctt gcagcacatc cccctttcgc cagctggcgt aatagcgaag  12420
```

```
aggcccgcac cgatcgccct tcccaacagt tgcgcagctg aatggcgaat ggcgcctgag   12480
ctagcattgc cggcattctt aagtaggcct cccgggccat tggcgcgcca gacttgaagt   12540
cgcggccgca ctgaccattt aaatcatacc aacatggtca aataaaacga aaggctcagt   12600
cgaaagactg ggcctttcgt tttaatctga tcggcacgta agaggttcca actttcacca   12660
taatgaaata agatcactac cgggcgtatt ttttgagtta tcgagatttt caggagctaa   12720
ggaagctaaa atggagaaaa aaatcactgg atataccacc gttgatatat cccaatggca   12780
tcgtaaagaa cattttgagg catttcagtc agttgctcaa tgtacctata accagaccgt   12840
tcagctggat attacggcct ttttaaagac cgtaaagaaa aataagcaca gttttatcc    12900 ggcctttatt cacattcttg cccgcctgat gaatgctcat ccggaatttc gtatggcaat   12960
gaaagacggt gagctggtga tatgggatag tgttcaccct tgttacaccg ttttccatga   13020
gcaaactgaa acgttttcat cgctctggag tgaataccac gacgatttcc ggcagtttct   13080
acacatatat tcgcaagatg tggcgtgtta cggtgaaaac ctggcctatt tccctaaagg   13140
gtttattgag aatatgtttt tcgtctcagc caatccctgg gtgagtttca ccagttttga   13200
tttaaacgtg gccaatatgg acaacttctt cgccccccgtt ttcaccatgg gcaaatatta   13260
tacgcaaggc gacaaggtgc tgatgccgct ggcgattcag gttcatcatg ccgtttgtga   13320
tggcttccat gtcggcagaa tgcttaatga attacaacag tactgcgatg agtggcaggg   13380
cggggcgtaa cctaggtgac agaagtcaaa agcctccggt cggaggcttt tgactttctg   13440
ctagatctgt ttcaatgcgg tgaagggcca ggcagctggg gattatgtcg agacccggcc   13500
agcatgttgg ttttatcgca tattcagcgt tgtcgcgttt acccaggtaa aatggaagca   13560
gtgtatcgtc tgcgtgaatg tgcaaatcag gaacgtaacc gtggtacata gatgcagtcc   13620
cttgcgggtc gttcccttca acgagtagga cgcggtgccc ttgcaaggct aaccattgcg   13680
cctggtgtac tgcagatgag gttttataaa cccctcccct gtgtgacata acggaaagta   13740
caaccgggtt tttatcgtca ggtctttggt ttgggttacc aaacacactc cgcatatggc   13800
taatttggtc aattgtgtag ccagcgcgac gttctactcg gcccctcatc tcaaaatcag   13860
gagccggtag acgaccagct ttttccgcgt ctctgatagc ctgcggtgtt acgccgatca   13920
ggtctgcaac ttctgttata ccccagcggc gagtaatacg acgcgcttcc gggctgtcat   13980
cgccgaactg tgcgatggca atagcgcgcg tcatttcctg accgcgattg atacagtctt   14040
tcagcaaatt aattaacgac atcctgtttc ctctcaaaca tgcccttatc tttgtgtttt   14100
tcatcatact ttacgttttt aaagcaaagc aacataaaaa aagcaaagtg acttagaaaa   14160
cgcaaagtta aggttcaaat caattttttg atgcgctaca gaagctattt agcttcatct   14220
aagcgcaacg gtattactta cgttggtata tttaaaacct aacttaatga ttttaaatga   14280
taataaatca taccaattgc tatcaaaagt taagcgaaca tgctgatttt cacgctgttt   14340
atacactttg aggcatctct atctcttccg tctctatatt gaaacacaat caagaacat    14400 caatccatgt gacatccccc actatctaag aacaccataa cagaacacaa cataggaatg   14460
caacattaat gtatcaataa ttcggaacat atgcactata tcatatctca attacggaac   14520
atatcagcac acaattgccc attatacgc                                    14549
```

<210> SEQ ID NO 64
<211> LENGTH: 12873
<212> TYPE: DNA
<213> ORGANISM: Artificial
<220> FEATURE:
<223> OTHER INFORMATION: NZTC2

<400> SEQUENCE: 64

```
gcgtataatg gactattgtg tgctgataag gagaacataa gcgcagaaca atatgtatct      60
attccggtgt tgtgttcctt tgttattctg ctattatgtt ctcttatagt gtgacgaaag     120
cagcataatt aatcgtcact tgttctttga ttgtgttacg atatccagag acttagaaac     180
gggggaaccg ggatgagcaa ggtaaaaatc ggtgagttga tcaacacgct tgtgaatgag     240
gtagaggcaa ttgatgcctc agaccgccca caaggcgaca aaacgaagag aattaaagcc     300
gcagccgcac ggtataagaa cgcgttattt aatgataaaa gaaagttccg tgggaaagga     360
ttgcagaaaa gaataaccgc gaatactttt aacgcctata tgagcagggc aagaaagcgg     420
tttgatgata aattacatca tagctttgat aaaaatatta ataaattatc ggaaaagtat     480
cctcttttaca gcgaagaatt atcttcatgg ctttctatgc ctacggctaa tattcgccag     540
cacatgtcat cgttacaatc taaattgaaa gaaataatgc cgcttgccga agagttatca     600
aatgtaagaa taggctctaa aggcagtgat gcaaaaatag caagactaat aaaaaaatat     660
ccagattgga gttttgctct tagtgattta acagtgatg attggaagga gcgccgtgac      720
tatctttata agttattcca acaaggctct gcgttgttag aagaactaca ccagctcaag     780
gtcaaccatg aggttctgta ccatctgcag ctaagccctg cggagcgtac atctatacag     840
caacgatggg ccgatgttct gcgcgagaag aagcgtaatg ttgtggttat tgactaccca     900
acatacatgc agtctatcta tgatattttg aataatcctg cgactttatt tagtttaaac     960
actcgttctg gaatggcacc tttggccttt gctctggctg cggtatcagg gcgaagaatg    1020
attgagataa tgtttcaggg tgaatttgcc gtttcaggaa agtatacggt taatttctca    1080
gggcaagcta aaaacgctc tgaagataaa agcgtaacca gaacgattta ctttatgc      1140
gaagcaaaat tattcgttga attattaaca gaattgcgtt cttgctctgc tgcatctgat    1200
ttcgatgagg ttgttaaagg atatggaaag gatgatacaa ggtctgagaa cggcaggata    1260
aatgctattt tagcaaaagc atttaacccct tgggttaaat catttttcgg cgatgaccgt    1320
cgtgtttata agatagccg cgctatttac gctcgcatcg cttatgagat gttcttccgc    1380
gtcgatccac ggtggaaaaa cgtcgacgag gatgtgttct tcatggagat tctcggacac    1440
gacgatgaga acacccagct gcactataag cagttcaagc tggccaactt ctccagaacc    1500
tggcgacctg aagttgggga tgaaaacacc aggctggtgg ctctgcagaa actggacgat    1560
gaaatgccag gctttgccag aggtgacgct ggcgtccgtc tccatgaaac cgttaagcag    1620
ctggtggagc aggacccatc agcaaaaata accaacagca ctctccgggc ctttaaattt    1680
agcccgacga tgattagccg gtacctggag tttgccgctg atgcattggg gcagttcgtt    1740
ggcgagaacg ggcagtggca gctgaagata gagacacctg caatcgtcct gcctgatgaa    1800
gaatccgttg agaccatcga cgaaccggat gatgagtccc aagacgacga gctggatgaa    1860
gatgaaattg agctcgacga gggtggcggc gatgaaccaa ccgaagagga agggccagaa    1920
gaacatcagc caactgctct aaaacccgtc ttcaagcctg caaaaaataa cggggacgga    1980
acgtacaaga tagagtttga atacgatgga aagcattatg cctggtccgg ccccgccgat    2040
agccctatgg ccgcaatgcg atccgcatgg gaaacgtact acagctaaaa gaaaagccac    2100
cggtgttaat cggtggcttt tttattgagg cctgtcccta cccatcccct gcaagggacg    2160
gaaggattag gcgaaactg cagctgcaac tacggacatc gccgtcccga ctgcagggac     2220
ttccccgcgt aaagcggggc ttaaattcgg gctggccaac cctatttttc tgcaatcgct    2280
```

```
ggcgatgtta gtttcgtgga tagcgtttcc agcttttcaa tggccagctc aaaatgtgct    2340
ggcagcacct tctccagttc cgtatcaata tcggtgatcg gcagctctcc acaagacata    2400
ctccggcgac cgccacgaac tacatcgcgc agcagctccc gttcgtagac acgcatgttg    2460
cccagagccg tttctgcagc cgttaatatc cggcgcagct cggcgatgat tgccgggaga    2520
tcatccacgg ttattgggtt cggtgatggg ttcctgcagg cgcggcggag agccatccag    2580
acgccgctaa cccatgcgtt acggtactga aaactttgtg ctatgtcgtt tatcaggccc    2640
cgaagttctt ctttctgccg ccagtccagt ggttcaccgg cgttcttagg ctcaggctcg    2700
acaaaagcat actcgccgtt tttccggata gctggcagaa cctcgttcgt cacccacttg    2760
cggaaccgcc aggctgtcgt cccctgtttc accgcgtcgc ggcagcggag gattatggtg    2820
tagagaccag attccgatac cacatttact tccctggcca tccgatcaag ttttttgtgcc    2880
tcggttaaac cgagggtcaa ttttttcatca tgatccagct tacgcaatgc atcagaaggg    2940
ttggctatat tcaatgcagc acagatatcc agcgccacaa accacgggtc accaccgaca    3000
agaaccaccc gtataggggtg gctttcctga aatgaaaaga cggagagagc cttcattgcg    3060
cctccccgga tttcagctgc tcagaaaggg acagggagca gccgcgagct tcctgcgtga    3120
gttcgcgcgc gacctgcaga agttccgcag cttcctgcaa atacagcgtg gcctcataac    3180
tggagatagt gcggtgagca gagcccacaa gcgcttcaac ctgcagcagg cgttcctcaa    3240
tcgtctccag caggccctgg gcgtttaact gaatctggtt catgcgatca cctcgctgac    3300
cgggatacgg gctgacagaa cgaggacaaa acggctggcg aactggcgac gagcttctcg    3360
ctcggatgat gcaatggtgg aaaggcggtg gatatgggat ttttttgtccg tgcggacgac    3420
agctgcaaat ttgaatttga acatggtatg cattcctatc ttgtataggg tgctaccacc    3480
agagttgaga atctctatag gggtggtagc ccagacaggg ttctcaacac cggtacaaga    3540
agaaaccggc ccaaccgaag ttggcccccat ctgagccacc ataattcagg tatgcgcaga    3600
tttaacacac aaaaaaacac gctggcgcgt gttgtgcgct tcttgtcatt cggggttgag    3660
aggcccggct gcagattttg ctgcagcggg gtaactctac cgccaaagca gaacgcacgt    3720
caataattta ggtggatatt ttaccccgtg accagtcacg tgcacaggtg tttttatagt    3780
ttgctttact gactgatcag aacctgatca gttattggag tccggtaatc ttattgatga    3840
ccgcagccac cttagatgtt gtctcaaacc ccatacggcc acgaatgagc cactggaacg    3900
gaatagtcag caggtacagc ggaacgaacc acaaacggtt cagacgctgc cagaacgtcg    3960
catcacgacg ttccatccat tcggtattgt cgacgacctg gtaagcgtat tgtcctggcg    4020
tttttgctgc ttccgagtag caatcctctt caccacaaag aaagttactt atctgcttcc    4080
agttttcgaa cccttcttct ttgagccgct tttccagctc attcctccac aaaacaggca    4140
cccatcctct gcgataaatc atgattattt gtcctttaaa taaggctgta gaactgcaaa    4200
atcgctctcg ttcacatgct gtacgtagat gcgtagcaaa ttgccgttcc atccctgtaa    4260
tccaccttct ttggaaagat cgtccttgac ctcacgaaga accttatcca atagccctgc    4320
ggcacaagaa attgcctgct ctggatcagc aaattcatat tgattaatag gtgattgcca    4380
cacaccaaaa acaggaatca tcttttcggc taaacgcctc tcctgttctt tcttaatctc    4440
aagttgtaag cggaccagct caccatccat cattttttgt agatcatgcg ccactattca    4500
cccccactgg ccatcagcaa ataaagcttc atactcggac accggcaggc ggcttccacg    4560
gattgaaagg tcaagccaac cacgtccaga tgggtcagcc ttatccgatt cttcccaccg    4620
ttctgcagct gtagcaacca ggcattctac cgccttcatg tagtcttctg tacggaacca    4680
```

```
gccgtagtta atgccaccat cagtaactgc ccaggccatc tttttctctt cggcctcaat    4740
agcccggatg cggttatcgc acagctcgcg acagtacttc agctgttcgt aatccagttg    4800
cttcaggaac tctggtgtcg acgtcatagt ggcttcacct tataggcttt tagaagcgcc    4860
ctggcttcgt ctgtgtggtc ttccatgctc ttatcgctgg caatgcagca ataaactccc    4920
tcactatctg agaacccgtt catccgaatg atcgtaatg gaagttcccg ccagttttta     4980
taatcgctat agcttgtcgc gtcgtggctg accttgacca cataagggtc gtagccctcc    5040
acgatgacaa ggcattcccg ttgttttccc attaccctc cggttatatc gccacggctt     5100
gccgctggct tagaaacgct ttcagcagcc ttatttcgcg tactgatagc aggtccataa    5160
attcggtcat gtacagcgag gcgaacgttc tcgcgatgct ggccactggc cacaggcgta    5220
ccgcctccat ttcggttgct ggcaacgcgt tctccgccca cgcctccggt accgccaccg    5280
ggatagcctc cagtgcctgg ataattactg attgtgggc gtccggaacg tgctctgttt      5340
tggatcgagg gttaccatgt atatctatat ttagatccaa atcgcgatcc acttcgatgg    5400
tggttttttc caccttacgt gcgtgaattg ataaaccggc ctcgcggcgc ttctccacga    5460
tattcatgag gaactcgacc gagtccgggt caatggaacg catcgtgggg cgtgcatcgc    5520
cgtctctggc gcgtctggtc ttactggata gccccataga ctccaggatg cctatgcaga    5580
ggtctgcagg cgctttcttc ttgcctttct ctgtgttgaa gccgccgatg cgtaaaacgt    5640
tgtttagcag atcgcgccgt tccggcgtga gcaggttatc tctggcgcgt ttgagggcgt    5700
ccatgtctgc ttcaccttcc agggttttg gatcgatacc gcagtcgcgg aagtactgct      5760
gcagcgtcgc cgatttgagg gtgtagaaac cacgcatgcc tatctcaaca gcaggggtcg    5820
atttcactcg gtaatcggtt atggccggga atttagcctg gaactctgcg tcggcctgtt    5880
cccgcgtcat ggccgtagtg acgaactgct gccatcttcc ggcaacgcga taagcgtagg    5940
taaagtgaat caacgcttct tcacggtcaa ggcgacgggc ggttatctca tccagctgca    6000
tggtttcaaa caggcgcact ttttcaggc cgccgtcgaa atagaatttt aacgccacct     6060
cgtcgacatc cagctgcagc tccttttcga tgtcccagcg gaccagctgg gcctgctcat    6120
ccagggacag ggtgcgtttt tttatcaact catcgtgttc ggcctggtca ggagtatcga    6180
cactcaggtg gcgctccata agctgctcaa agaccagttc acgggcttct ttacgtaaat    6240
ccttaccgat gctgtttgca agcgcgtcgg tggccatagg cgcgacctga tagccatcat    6300
catgcatgat gcaaatcatg ttgctggcat aatcatttct ggccgatgcc tcgagcgcgg    6360
cggctttaat tttgagctgc atgaatgaag agttagccac gccgagtgaa attcggtcac    6420
cgtcaaagac aacgtctgtc agcagcccgg agtggccagc cgtttcgagc aaggcctgcg    6480
cgtaggcgcg tttgatttt tccggatcgg tttcacgttt accgcgaagc ttgtcgaaac      6540
cgataatgta ttcctgagct gtacggtcgc ggcgcagcat ctggatggcg tcgctgggga    6600
ccacttcgcc gcagaacatg ccgaaatggc ggtggaagtg tttctcctca atcgatacac    6660
ctgaagatat cgacgggctg tagatgaggc cgtcatattt tttcaccatc actttaggct    6720
ggttggtgaa atcgtcgact tccttctcct gtttgttttt ctggttaacg cagagaaact    6780
ttttgtcagg gaactgtagt ctcagctgca tggtaacgtc ttcggcgaac gtcgaactgt    6840
cggtggccag catgattcgt tcgccgcgtt gcactgcagc gataacctcg gtcatgatcc    6900
gattttctc ggtataaaat acgcggatag gcttgttggt ttcgcggttg cgaacgtcga     6960
ccgggagttc aatcacgtga atttgcagcc aggcaggtag gcccagctcc tcgcgtcgct    7020
```

```
tcatcgccag ttcagccagg tcaacaagca gatcgttggc atcggcatcc accataatgg   7080
catgctcttc agtacgcgcc agcgcgtcga taagcgtgtt gaatacgcct accgggtttt   7140
ccatcgcacg cccggccaga atggcacgca ggccctgtgt tgcttcatcg aagccgaaga   7200
agtcatgctg gcgcatcagc ggttgccagc agcctttaag tatggagttg atgcaaatag   7260
tcagcttgtt ggcatatggc gccatttcct gatagccggg atcctgataa tgcagaatgt   7320
cggctttcgc gcctttccct tcggtcatca tttcatgcag gccgcctatc agggatacgc   7380
ggtgcgcgac ggaaacgcca cgcgtggact gcagcatcag tggacgcagg aggcctgtcg   7440
atttacccga ccccatcccg gcgcggacaa taacgatgcc ctgcagctgt gcggcgtatg   7500
tcatcacctc atcggtcatc ctggaggttt caaaccgttt gtaagtgatg tgtgacgggc   7560
gaaggttcgg gttggtgatg cgttcactga acgaacgtga tgtttgcgcg cacggcatt   7620 tgcgattcaa ccggcgcgta atgtgatctt taacggtacc gttataaatt tctgcgatac   7680
ccatatcccg cagcgtgctg ctkaaaaggc gcataagttc tttcgggctg tttggtaccg   7740
ggcatgtcag catgccaata tcaacggcgc gaagcagttc tttggcaaaa gtgcgtctgt   7800
tcagacgcgg gagagtacgc agcttattca gcgtgatcga caacaggtcg gttgcacggc   7860
tcagatgatt tctcgttaac tggcgagcga cttccttcag ccctctcagg ctgtgcaggt   7920
cgttaaaatc gctgcattcc agctcagggt catcctcaaa agttgggtaa acacatttga   7980
cgccggaaaa cttctccatg atgtcgaatc cggtgcggag gcctgtgttg cctttttcctt   8040 cagctgagga tttgcggtcg ttatcgagag cgcaagtgat ttgcgcagcc gggtacatgt   8100
tcaccagctg ctcgacaacg tgaatcatgt tgttagcgga aaccgcaatg actaccgcgt   8160
caaagcgttt tttcgggtcg tttctggtcg ccagccagat ggatgccccg gtggcgaaac   8220
cctctgcagt cgcaatttttt tgcgccccct gcaggtcgcc aataacaaag catgcaccga   8280
cgaaatcacc gttagtgatg gcgctggtct ggaacttgcc accattcaga tcgatacgtt   8340
gccagccaac aatccgcccg tcttttcttc cgtccaggtg ggacagaggt atcgccatgt   8400
aagttgttgg tccacggctc catttcgcac tgtcgtgact ggtcacgcga cgtatatcac   8460
aagcgccaaa tacgtcacga attccctttt ttaccgcata aggccaggag ccatcttcag   8520
ctggcgaatg ttcccaggcg cgatggaaag ccaaccatcc aagcaggcgt tcctgctcca   8580
tctgattgtt ttttaaatca ttaacgcgtt gttgttcagc tcggaggcgg cgtgcttcag   8640
cctggcgctc catgcgtgca cgttcttctt ccggctgagc gaccacggtc gcaccattcc   8700
gttgctgttc acggcgatac tccgaaaaca ggaatgaaaa gccactccag gagccagcgt   8760
catgcgcttt ttcaacgaag ttaacgaaag gataactgat gccatccttg ctctgctcaa   8820
ggcgtgaata gatttccaca cggcctttaa ggctcttctg cagagcttcc ggggaggaat   8880
tattgtaggt ggtatagcgc tctacaccac cgcgcggatt gagctgaatc ttatcagcac   8940
acgcaggcca gttgataccg gccatcttcg ccagctcagt cagctcatca cgtgccgcgt   9000
caagcagtga aaacggatcg ctgccaaagc gctccgcgta gaattcttgt aaggtcattt   9060
tttagccttt ccatgcgaat tagcattttt tcgggttgaa aaaatccgca ggagcagcca   9120
caataaacgc actatctttc tgaaggacgt atctgcgtta tcgtggctac ttcctgaaaa   9180
aggcccgagt tgccgactc gggttttttt tcgtctttt tcggctgcta cggtctggtt   9240
caaccccgac aaagtatcag tcggattaaa ccagaattat agtcagcaat aaaccctgtt   9300
attgtatcat ctaccctcaa ccatgaacga tttgatcgta ccgactactt ggtgcacaaa   9360
ttgaagatca cttttatcat ggataacccg ttgagagtta gcactatcaa ggtagtaatg   9420
```

```
ctgctcgtca taacgggcta atcgttgaat tgtgatctcg ccgttattat cacaaaccag    9480
tacatcctca cccggtacaa gcgtaagtga agaatcgacc aggataacgt ctcccggctg    9540
gtagtttcgc tgaatctggt tcccgaccgt cagtgcgtaa acggtgttcc gttgactcac    9600
gaacggcagg aatcgctctg tgttggcagg ttctccaggc tgccagtctc tatccggtcc    9660
ggtctctgtc gtaccaataa caggaacgcg gtctggatca gattcagtgc catacagtat    9720
ccattgcacg ggcttacgca ggcattttgc cagcgatagc ccgatctcca gcgacggcat    9780
cacgtcgcca cgttctaagt tttggacgcc cggaagagag attcctacag cttctgccac    9840
ttgcttcagc gtcagtttca gctctaaacg gcgtgctttc agtcgttcgc ctcgtgtttt    9900
cataccctta atcataaatg atctctttat agctggctat aattttata aattatacct     9960
agctttaatt ttcacttatt gattataata atccccatga aacccgaaga acttgtgcgc   10020
catttcggcg atgtggaaaa agcagcggtt ggcgtgggcg tgacacccgg cgcagtctat   10080
caatggctgc aagctgggga gattccacct ctacgacaaa gcgatataga ggtccgtacc   10140
gcgtacaaat taaagagtga tttcacctct cagcgcatgg gtaaggaagg cataacagg    10200
ggatcctcta gacgcagaaa ggcccacccg aaggtgagcc agtgtgatta catttgcggc   10260
cagtccagtt acgctggagt cactagtgcg gccgcgacaa cttgtctagg gcccaatggc   10320
ccgggaggcc tacttaagta agccggctta gctagcggga caggtttccc gactggaaag   10380
cgggcagtga gcgcaacgca attaatgtga gttagctcac tcattaggca ccccaggctt   10440
tacactttat gcttccggct cgtatgttgt gtggaattgt gagcggacaa caatttcaca   10500
caggaaacag ctatgaccat gattacgcca agctatttag gtgagactat agaatactca   10560
agcttgcatg cgatacgtat cgttaacgat ggatccgacg cacgtgcgaa ttcgccctat   10620
agtgagtcgt attacaattc actggccgtc gttttacaac gtcgtgactg gaaaaccct    10680
ggcgtcaccc aacttaatcg ccttgcagca catccccctt tcgccagctg gcgtaatagc   10740
gaagaggccc gcaccgatcg cccttcccaa cagttgcgca gctgaatggc gaatggcgcc   10800
tgagctagca ttgccggcat tcttaagtag gcctcccggg ccattggcgc gccagacttg   10860
aagtcgcggc cgcactgacc atttaaatca taccaacatg gtcaaataaa acgaaaggct   10920
cagtcgaaag actgggcctt tcgttttaat ctgatcggca cgtaagaggt tccaactttc   10980
accataatga aataagatca ctaccgggcg tattttttga gttatcgaga ttttcaggag   11040
ctaaggaagc taaaatggag aaaaaaatca ctggatatac caccgttgat atatcccaat   11100
ggcatcgtaa agaacatttt gaggcatttc agtcagttgc tcaatgtacc tataaccaga   11160
ccgttcagct ggatattacg gcctttttaa agaccgtaaa gaaaaataag cacaagtttt   11220
atccggcctt tattcacatt cttgcccgcc tgatgaatgc tcatccggaa tttcgtatgg   11280
caatgaaaga cggtgagctg gtgatatggg atagtgttca cccttgttac accgttttcc   11340
atgagcaaac tgaaacgttt tcatcgctct ggagtgaata ccacgacgat ttccggcagt   11400
ttctacacat atattcgcaa gatgtggcgt gttacggtga aaacctggcc tatttcccta   11460
aagggtttat tgagaatatg ttttcgtct cagccaatcc ctgggtgagt ttcaccagtt    11520
ttgatttaaa cgtggccaat atggacaact tcttcgcccc cgttttcacc atgggcaaat   11580
attatacgca aggcgacaag gtgctgatgc cgctggcgat tcaggttcat catgccgttt   11640
gtgatggctt ccatgtcggc agaatgctta atgaattaca acagtactgc gatgagtggc   11700
agggcggggc gtaacctagg tgacagaagt caaaagcctc cggtcggagg cttttgactt   11760
```

```
tctgctagat ctgtttcaat gcggtgaagg gccaggcagc tggggattat gtcgagaccc   11820
ggccagcatg ttggttttat cgcatattca gcgttgtcgc gtttacccag gtaaaatgga   11880
agcagtgtat cgtctgcgtg aatgtgcaaa tcaggaacgt aaccgtggta catagatgca   11940
gtcccttgcg ggtcgttccc ttcaacgagt aggacgcggt gcccttgcaa ggctaaccat   12000
tgcgcctggt gtactgcaga tgaggtttta taaacccctc ccttgtgtga cataacggaa   12060
agtacaaccg ggttttttatc gtcaggtctt tggtttgggt taccaaacac actccgcata   12120
tggctaattt ggtcaattgt gtagccagcg cgacgttcta ctcggcccct catctcaaaa   12180
tcaggagccg gtagacgacc agcttttttcc gcgtctctga tagcctgcgg tgttacgccg   12240
atcaggtctg caacttctgt tataccccag cggcgagtaa tacgacgcgc ttccgggctg   12300
tcatcgccga actgtgcgat ggcaatagcg cgcgtcattt cctgaccgcg attgatacag   12360
tctttcagca aattaattaa cgacatcctg tttcctctca acatgccct tatctttgtg    12420 tttttcatca tactttacgt ttttaaagca aagcaacata aaaaaagcaa agtgacttag   12480
aaaacgcaaa gttaaggttc aaatcaattt tttgatgcgc tacagaagct atttagcttc   12540
atctaagcgc aacggtatta cttacgttgg tatatttaaa acctaactta atgattttaa   12600
atgataataa atcataccaa ttgctatcaa aagttaagcg aacatgctga ttttcacgct   12660
gtttatacac tttgaggcat ctctatctct tccgtctcta tattgaaaca caatcaaaga   12720
acatcaatcc atgtgacatc ccccactatc taagaacacc ataacagaac acaacatagg   12780
aatgcaacat taatgtatca ataattcgga acatatgcac tatatcatat ctcaattacg   12840
gaacatatca gcacacaatt gcccattata cgc                                12873

<210> SEQ ID NO 65
<211> LENGTH: 12827
<212> TYPE: DNA
<213> ORGANISM: Artificial
<220> FEATURE:
<223> OTHER INFORMATION: Vector NZTC3

<400> SEQUENCE: 65
gcgtataatg gactattgtg tgctgataag gagaacataa gcgcagaaca atatgtatct     60
attccggtgt tgtgttcctt tgttattctg ctattatgtt ctcttatagt gtgacgaaag    120
cagcataatt aatcgtcact tgttctttga ttgtgttacg atatccagag acttagaaac    180 ggggaaccg ggatgagcaa ggtaaaaatc ggtgagttga tcaacacgct tgtgaatgag     240
gtagaggcaa ttgatgcctc agaccgccca caaggcgaca aaacgaagag aattaaagcc    300
gcagccgcac ggtataagaa cgcgttattt aatgataaaa gaaagttccg tgggaaagga    360
ttgcagaaaa gaataaccgc gaatactttt aacgcctata tgagcagggc aagaaagcgg    420
tttgatgata aattacatca tagctttgat aaaaatatta taaattatc ggaaaagtat     480 cctctcttaca gcgaagaatt atcttcatgg cttttctatgc ctacggctaa tattcgccag   540
cacatgtcat cgttacaatc taaattgaaa gaataatgc cgcttgccga agagttatca    600
aatgtaagaa taggctctaa aggcagtgat gcaaaaatag caagactaat aaaaaaatat    660
ccagattgga gttttgctct tagtgattta aacagtgatg attggaagga gcgccgtgac    720
tatctttata gttattcca acaaggctct gcgttgttag aagaactaca ccagctcaag     780
gtcaaccatg aggttctgta ccatctgcag ctaagcccgc ggagcgtac atctatacag    840 caacgatggg ccgatgttct gcgcgagaag aagcgtaatg ttgtggttat tgactaccca    900
acatacatgc agtctatcta tgatatttg aataatcctg cgactttatt tagtttaaac    960
```

```
actcgttctg gaatggcacc tttggccttt gctctggctg cggtatcagg gcgaagaatg    1020
attgagataa tgtttcaggg tgaatttgcc gtttcaggaa agtatacggt taatttctca    1080
gggcaagcta aaaaacgctc tgaagataaa agcgtaacca gaacgattta tactttatgc    1140
gaagcaaaat tattcgttga attattaaca gaattgcgtt cttgctctgc tgcatctgat    1200
ttcgatgagg ttgttaaagg atatggaaag gatgatacaa ggtctgagaa cggcaggata    1260
aatgctattt tagcaaaagc atttaaccct tgggttaaat cattttttcgg cgatgaccgt   1320 cgtgtttata aagatagccg cgctatttac gctcgcatcg cttatgagat gttcttccgc    1380
gtcgatccac ggtggaaaaa cgtcgacgag gatgtgttct tcatggagat tctcggacac    1440
gacgatgaga acacccagct gcactataag cagttcaagc tggccaactt ctccagaacc    1500
tggcgacctg aagttgggga tgaaaacacc aggctggtgg ctctgcagaa actggacgat    1560
gaaatgccag gctttgccag aggtgacgct ggcgtccgtc tccatgaaac cgttaagcag    1620
ctggtggagc aggacccatc agcaaaaata accaacagca ctctccgggc ctttaaattt    1680
agcccgacga tgattagccg gtacctggag tttgccgctg atgcattggg gcagttcgtt    1740
ggcgagaacg ggcagtggca gctgaagata gagacacctg caatcgtcct gcctgatgaa    1800
gaatccgttg agaccatcga cgaaccggat gatgagtccc aagacgacga gctggatgaa    1860
gatgaaattg agctcgacga gggtggcggc gatgaaccaa ccgaagagga agggccagaa    1920
gaacatcagc caactgctct aaaacccgtc ttcaagcctg caaaaaataa cggggacgga    1980
acgtacaaga tagagtttga atacgatgga aagcattatg cctggtccgg ccccgccgat    2040
agccctatgg ccgcaatgcg atccgcatgg gaaacgtact acagctaaaa gaaaagccac    2100
cggtgttaat cggtggcttt tttattgagg cctgtcccta cccatcccct gcaagggacg    2160
gaaggattag gcggaaactg cagctgcaac tacggacatc gccgtcccga ctgcagggac    2220
ttccccgcgt aaagcggggc ttaaattcgg gctggccaac cctattttc tgcaatcgct    2280 ggcgatgtta gtttcgtgga tagcgttcc agcttttcaa tggccagctc aaaatgtgct    2340
ggcagcacct tctccagttc cgtatcaata tcggtgatcg gcagctctcc acaagacata    2400
ctccggcgac cgccacgaac tacatcgcgc agcagctccc gttcgtagac acgcatgttg    2460
cccagagccg tttctgcagc cgttaatatc cggcgcagct cggcgatgat tgccgggaga    2520
tcatccacgg ttattgggtt cggtgatggg ttcctgcagg cgcggcggag agccatccag    2580
acgccgctaa cccatgcgtt acggtactga aaactttgtg ctatgtcgtt tatcaggccc    2640
cgaagttctt ctttctgccg ccagtccagt ggttcaccgg cgttcttagg ctcaggctcg    2700
acaaaagcat actcgccgtt tttccggata gctggcagaa cctcgttcgt cacccacttg    2760
cggaaccgcc aggctgtcgt cccctgtttc accgcgtcgc ggcagcggag gattatggtg    2820
tagagaccag attccgatac cacatttact tccctggcca tccgatcaag tttttgtgcc    2880
tcggttaaac cgagggtcaa tttttcatca tgatccagct tacgcaatgc atcagaaggg    2940
ttggctatat tcaatgcagc acagatatcc agcgccacaa accacgggtc accaccgaca    3000
agaaccaccc gtataggtgt gctttcctga aatgaaaaga cggagagagc cttcattgcg    3060
cctccccgga tttcagctgc tcagaaaggg acagggagca gccgcgagct tcctgcgtga    3120
gttcgcgcgc gacctgcaga agttccgcag cttcctgcaa atacagcgtg gcctcataac    3180
tggagatagt gcggtgagca gagcccacaa gcgcttcaac ctgcagcagg cgttcctcaa    3240
tcgtctccag caggccctgg gcgtttaact gaatctggtt catgcgatca cctcgctgac    3300
```

```
cgggatacgg gctgacagaa cgaggacaaa acggctggcg aactggcgac gagcttctcg    3360
ctcggatgat gcaatggtgg aaaggcggtg gatatgggat ttttgtccg tgcggacgac     3420
agctgcaaat ttgaatttga acatggtatg cattcctatc ttgtataggg tgctaccacc   3480
agagttgaga atctctatag gggtggtagc ccagacaggg ttctcaacac cggtacaaga   3540
agaaaccggc ccaaccgaag ttggccccat ctgagccacc ataattcagg tatgcgcaga   3600
tttaacacac aaaaaaacac gctggcgcgt gttgtgcgct tcttgtcatt cggggttgag   3660
aggcccggct gcagattttg ctgcagcggg gtaactctac cgccaaagca gaacgcacgt   3720
caataattta ggtggatatt ttaccccgtg accagtcacg tgcacaggtg tttttatagt   3780
ttgctttact gactgatcag aacctgatca gttattggag tccggtaatc ttattgatga   3840
ccgcagccac cttagatgtt gtctcaaacc ccatacggcc acgaatgagc cactggaacg   3900
gaatagtcag caggtacagc ggaacgaacc acaaacggtt cagacgctgc cagaacgtcg   3960
catcacgacg ttccatccat tcggtattgt cgacgacctg gtaagcgtat tgtcctggcg   4020
tttttgctgc ttccgagtag caatcctctt caccacaaag aaagttactt atctgcttcc   4080
agttttcgaa cccttcttct ttgagccgct tttccagctc attcctccac aaaacaggca   4140
cccatcctct gcgataaatc atgattattt gtcctttaaa taaggctgta gaactgcaaa   4200
atcgctctcg ttcacatgct gtacgtagat gcgtagcaaa ttgccgttcc atccctgtaa   4260
tccaccttct ttggaaagat cgtccttgac ctcacgaaga accttatcca atagccctgc   4320
ggcacaagaa attgcctgct ctggatcagc aaattcatat tgattaatag gtgattgcca   4380
cacaccaaaa acaggaatca tctttcggc taaacgcctc tcctgttctt tcttaatctc     4440
aagttgtaag cggaccagct caccatccat cattttttgt agatcatgcg ccactattca   4500
cccccactgg ccatcagcaa ataaagcttc atactcggac accggcaggc ggcttccacg   4560
gattgaaagg tcaagccaac cacgtccaga tgggtcagcc ttatccgatt cttcccaccg   4620
ttctgcagct gtagcaacca ggcattctac cgccttcatg tagtcttctg tacggaacca   4680
gccgtagtta atgccaccat cagtaactgc ccaggccatc tttttctctt cggcctcaat   4740
agcccggatg cggttatcgc acagctcgcg acagtacttc agctgttcgt aatccagttg   4800
cttcaggaac tctggtgtcg acgtcatagt ggcttcacct tataggcttt tagaagcgcc   4860
ctggcttcgt ctgtgtggtc ttccatgctc ttatcgctgg caatgcagca ataaactccc   4920
tcactatctg agaacccgtt catccgaatg atcgtgaatg gaagttcccg gccagtttta   4980
taatcgctat agcttgtcgc gtcgtggctg accttgacca cataagggtc gtagccctcc   5040
acgatgacaa ggcattcccg ttgttttccc attacccctc cggttatatc gccacggctt   5100
gccgctggct tagaaacgct ttcagcagcc ttatttcgcg tactgatagc aggtccataa   5160
attcggtcat gtacagcgag gcgaacgttc tcgcgatgct ggccactggc cacaggcgta   5220
ccgcctccat ttcggttgct ggcaacgcgt tctccgccca cgcctccggt accgccaccg   5280
ggatagcctc cagtgcctgg ataattactg attgtggggc gtccggaacg tgctctgttt   5340
tggatcgagg gttaccatgt atatctatat ttagatccaa atcgcgatcc acttcgatgg   5400
tggttttttc caccttacgt gcgtgaattg ataaaccggc ctcgcggcgc ttctccacga   5460
tattcatgag gaactcgacc gagtccgggt caatggaacg catcgtgggg cgtgcatcgc   5520
cgtctctggc gcgtctggtc ttactggata gccccataga ctccaggatg cctatgcaga   5580
ggtctgcagg cgctttcttc ttgccttct ctgtgttgaa gccgccgatg cgtaaaacgt     5640
tgtttagcag atcgcgccgt tccggcgtga gcaggttatc tctggcgcgt ttgagggcgt   5700
```

```
ccatgtctgc ttcaccttcc agggttttg  gatcgatacc gcagtcgcgg aagtactgct   5760
gcagcgtcgc cgatttgagg gtgtagaaac cacgcatgcc tatctcaaca gcagggtcg    5820
atttcactcg gtaatcggtt atggccggga atttagcctg gaactctgcg tcggcctgtt   5880
cccgcgtcat ggccgtagtg acgaactgct gccatcttcc ggcaacgcga taagcgtagg   5940
taaagtgaat caacgcttct tcacggtcaa ggcgacgggc ggttatctca tccagctgca   6000
tggtttcaaa caggcgcact tttttcaggc cgccgtcgaa atagaatttt aacgccacct   6060
cgtcgacatc cagctgcagc tccttttcga tgtcccagcg gaccagctgg gcctgctcat   6120
ccagggacag ggtgcgtttt tttatcaact catcgtgttc ggcctggtca ggagtatcga   6180
cactcaggtg gcgctccata agctgctcaa agaccagttc acgggcttct ttacgtaaat   6240
ccttaccgat gctgtttgca agcgcgtcgg tggccatagg cgcgacctga tagccatcat   6300
catgcatgat gcaaatcatg ttgctggcat aatcatttct ggccgatgcc tcgagcgcgg   6360
cggctttaat tttgagctgc atgaatgaag agttagccac gccgagtgaa attcggtcac   6420
cgtcaaagac aacgtctgtc agcagcccgg agtggccagc cgtttcgagc aaggcctgcg   6480
cgtaggcgcg tttgatttt  tccggatcgg tttcacgttt accgcgaagc ttgtcgaaac   6540
cgataatgta ttcctgagct gtacggtcgc ggcgcagcat ctggatggcg tcgctgggga   6600
ccacttcgcc gcagaacatg ccgaaatggc ggtggaagtg tttctcctca atcgatacac   6660
ctgaagatat cgacgggctg tagatgaggc cgtcatattt tttccaccat actttaggct   6720
ggttggtgaa atcgtcgact tccttctcct gtttgttttt ctggttaacg cagagaaact   6780
ttttgtcagg gaactgtagt ctcagctgca tggtaacgtc ttcggcgaac gtcgaactgt   6840
cggtggccag catgattcgt tcgccgcgtt gcactgcagc gataacctcg gtcatgatcc   6900
gattttctc  ggtataaaat acgcggatag gcttgttggt ttcgcggttg cgaacgtcga   6960
ccgggagttc aatcacgtga atttgcagcc aggcaggtag gcccagctcc tcgcgtcgct   7020
tcatcgccag ttcagccagg tcaacaagca gatcgttggc atcggcatcc accataatgg   7080
catgctcttc agtacgcgcc agcgcgtcga taagcgtgtt gaatacgcct accgggtttt   7140
ccatcgcacg cccggccaga atggcacgca ggccctgtgt tgcttcatcg aagccgaaga   7200
agtcatgctg gcgcatcagc ggttgccagc agcctttaag tatggagttg atgcaaatag   7260
tcagcttgtt ggcatatggc gccatttcct gatagccggg atcctgataa tgcagaatgt   7320
cggctttcgc gcctttccct tcggtcatca tttcatgcag gccgcctatc agggatacgc   7380
ggtgcgcgac ggaaacgcca cgcgtggact gcagcatcag tggacgcagg aggcctgtcg   7440
atttacccga ccccatcccg gcgcggacaa taacgatgcc ctgcagctgt gcggcgtatg   7500
tcatcacctc atcggtcatc ctggaggttt caaaccgttt gtaagtgatg tgtgacgggc   7560
gaaggttcgg gttggtgatg cgttcactga acgaacgtga tgtttgcgcg gcacggcatt   7620
tgcgattcaa ccggcgcgta atgtgatctt taacggtacc gttataaatt tctgcgatac   7680
ccatatcccg cagcgtgctg ctgaaaaggc gcataagttc tttcgggctg tttggtaccg   7740
ggcatgtcag catgccaata tcaacggcgc gaagcagttc tttggcaaaa gtgcgtctgt   7800
tcagacgcgg gagagtacgc agcttattca gcgtgatcga caacaggtcg gttgcacggc   7860
tcagatgatt tctcgttaac tggcgagcga cttccttcag ccctctcagg ctgtgcaggt   7920
cgttaaaatc gctgcattcc agctcagggt catcctcaaa agttgggtaa acacatttga   7980
cgccggaaaa cttctccatg atgtcgaatc cggtgcggag gcctgtgttg ccttttcctt   8040
```

```
cagctgagga tttgcggtcg ttatcgagag cgcaagtgat ttgcgcagcc gggtacatgt    8100
tcaccagctg ctcgacaacg tgaatcatgt tgttagcgga aaccgcaatg actaccgcgt    8160
caaagcgttt tttcggtcg tttctggtcg ccagccagat ggatgccccg gtggcgaaac    8220
cctctgcagt cgcaattttt tgcgccccct gcaggtcgcc aataacaaag catgcaccga    8280
cgaaatcacc gttagtgatg cgctggtct ggaacttgcc accattcaga tcgatacgtt    8340
gccagccaac aatccgcccg tcttttcttc cgtccaggtg ggacagaggt atcgccatgt    8400
aagttgttgg tccacggctc catttcgcac tgtcgtgact ggtcacgcga cgtatatcac    8460
aagcgccaaa tacgtcacga attcccttt ttaccgcata aggccaggag ccatcttcag    8520
ctggcgaatg ttcccaggcg cgatggaaag ccaaccatcc aagcaggcgt tcctgctcca    8580
tctgattgtt ttttaaatca ttaacgcgtt gttgttcagc tcggaggcgg cgtgcttcag    8640
cctggcgctc catgcgtgca cgttcttctt ccggctgagc gaccacggtc gcaccattcc    8700
gttgctgttc acggcgatac tccgaaaaca ggaatgaaaa gccactccag gagccagcgt    8760
catgcgcttt ttcaacgaag ttaacgaaag gataactgat gccatccttg ctctgctcaa    8820
ggcgtgaata gatttccaca cggcctttaa ggctcttctg cagagcttcc ggggaggaat    8880
tattgtaggt ggtatagcgc tctacaccac cgcgcggatt gagctgaatc ttatcagcac    8940
acgcaggcca gttgataccg gccatcttcg ccagctcagt cagctcatca cgtgccgcgt    9000
caagcagtga aaacggatcg ctgccaaagc gctccgcgta gaattcttgt aaggtcattt    9060
tttagccttt ccatgcgaat tagcattttt tcgggttgaa aaaatccgca ggagcagcca    9120
caataaacgc actatctttc tgaaggacgt atctgcgtta tcgtggctac ttcctgaaaa    9180
aggcccgagt ttgccgactc gggtttttt tcgtctttt tcggctgcta cggtctggtt    9240
caaccccgac aaagtataga tcggattaaa ccagaattat agtcagcaat aaaccctgtt    9300
attgtatcat ctaccctcaa ccatgaacga tttgatcgta ccgactactt ggtgcacaaa    9360
ttgaagatca cttttatcat ggataacccg ttgagagtta gcactatcaa ggtagtaatg    9420
ctgctcgtca taacgggcta atcgttgaat tgtgatctcg ccgttattat cacaaaccag    9480
tacatcctca cccggtacaa gcgtaagtga agaatcgacc aggataacgt ctcccggctg    9540
gtagtttcgc tgaatctggt tcccgaccgt cagtgcgtaa acggtgttcc gttgactcac    9600
gaacggcagg aatcgctctg tgttggcagg ttctccaggc tgccagtctc tatccggtcc    9660
ggtctctgtc gtaccaataa caggaacgcg gtctggatca gattcagtgc catacagtat    9720
ccattgcacg ggcttacgca ggcattttgc cagcgatagc ccgatctcca cgacggcat    9780 cacgtcgcca cgttctaagt tttgacgcc cggaagagag attcctacag cttctgccac    9840
ttgcttcagc gtcagtttca gctctaaacg gcgtgctttc agtcgttcgc ctcgtgtttt    9900
cataccctta atcataaatg atctctttat agctggctat aattttata aattatacct    9960 agctttaatt ttcacttatt gattataata atccccatga aacccgaaga acttgtgcgc   10020
catttcggcg atgtggaaaa agcagcggtt ggcgtgggcg tgacacccgg cgcagtctat   10080
caatggctgc aagctgggga gattccacct ctacgacaaa gcgatataga ggtccgtacc   10140
gcgtacaaat taagagtga tttcacctct cagcgcatgg gtaaggaagg gcataacagg   10200
ggatcctcta gacagtccag ttacgctgga gtcactagtg cggccgcgac aacttgtcta   10260
gggcccaatg gcccgggagg cctacttaag taagccggct tagctagcgg gacaggtttc   10320
ccgactggaa agcgggcagt gagcgcaacg caattaatgt gagttagctc actcattagg   10380
cacccccagg ctttacactt tatgcttccg gctcgtatgt tgtgtggaatt gtgagcggac   10440
```

-continued

```
aacaatttca cacaggaaac agctatgacc atgattacgc caagctattt aggtgagact   10500
atagaatact caagcttgca tgcgatacgt atcgttaacg atggatccga cgcacgtgcg   10560
aattcgccct atagtgagtc gtattacaat tcactggccg tcgttttaca acgtcgtgac   10620
tgggaaaacc ctggcgtcac ccaacttaat cgccttgcag cacatccccc tttcgccagc   10680
tggcgtaata gcgaagaggc ccgcaccgat cgcccttccc aacagttgcg cagctgaatg   10740
gcgaatctta agtaggcctc ccgggccatt agacttgaag tcaagcggcc gctacaactg   10800
gaccttgctg gtacatagaa ctgattaact gaccatttaa atcataccaa catggtcaaa   10860
taaaacgaaa ggctcagtcg aaagactggg cctttcgttt taatctgatc ggcacgtaag   10920
aggttccaac tttcaccata atgaaataag atcactaccg gcgtattttt ttgagttatc   10980
gagattttca ggagctaagg aagctaaaat ggagaaaaaa atcactggat ataccaccgt   11040
tgatatatcc caatggcatc gtaaagaaca ttttgaggca tttcagtcag ttgctcaatg   11100
tacctataac cagaccgttc agctggatat tacggccttt ttaaagaccg taagaaaaaa   11160
taagcacaag ttttatccgg cctttattca cattcttgcc cgcctgatga atgctcatcc   11220
ggaatttcgt atggcaatga agacggtga gctggtgata tgggatagtg ttcacccttg   11280
ttacaccgtt ttccatgagc aaactgaaac gttttcatcg ctctggagtg aataccacga   11340
cgatttccgg cagtttctac acatatattc gcaagatgtg gcgtgttacg gtgaaaacct   11400
ggcctatttc cctaaagggt ttattgagaa tatgtttttc gtctcagcca atccctgggt   11460
gagtttcacc agttttgatt taaacgtggc caatatggac aacttcttcg ccccgttt   11520 caccatgggc aaatattata cgcaaggcga caggtgctg atgccgctgg cgattcaggt   11580
tcatcatgcc gtttgtgatg gcttccatgt cggcagaatg cttaatgaat tacaacagta   11640
ctgcgatgag tggcagggcg gggcgtaacc taggtgacag aagtcaaaag cctccggtcg   11700
gaggcttttg actttctgct agatctgttt caatgcggtg aagggccagg cagctgggga   11760
ttatgtcgag acccggccag catgttggtt ttatcgcata ttcagcgttg tcgcgtttac   11820
ccaggtaaaa tggaagcagt gtatcgtctg cgtgaatgtg caaatcagga acgtaaccgt   11880
ggtacataga tgcagtccct tgcgggtcgt tcccttcaac gagtaggacg cggtgccctt   11940
gcaaggctaa ccattgcgcc tggtgtactg cagatgaggt tttataaacc cctcccttgt   12000
gtgacataac ggaaagtaca accgggtttt tatcgtcagg tctttggttt gggttaccaa   12060
acacactccg catatggcta atttggtcaa ttgtgtagcc agcgcgacgt tctactcggc   12120
ccctcatctc aaaatcagga gccggtagac gaccagcttt ttccgcgtct ctgatagcct   12180
gcggtgttac gccgatcagg tctgcaactt ctgttatacc ccagcggcga gtaatacgac   12240
gcgcttccgg gctgtcatcg ccgaactgtg cgatggcaat agcgcgcgtc atttcctgac   12300
cgcgattgat acagtctttc agcaaattaa ttaacgacat cctgtttcct ctcaaacatg   12360
cccttatctt tgtgttttc atcatacttt acgttttaa agcaaagcaa cataaaaaaa   12420
gcaaagtgac ttagaaaacg caaagttaag gttcaaatca attttttgat gcgctacaga   12480
agctatttag cttcatctaa gcgcaacggt attacttacg ttggtatatt taaaacctaa   12540
cttaatgatt ttaaatgata ataaatcata ccaattgcta tcaaaagtta agcgaacatg   12600
ctgattttca cgctgtttat acactttgag gcatctctat ctcttccgtc tctatattga   12660
aacacaatca aagaacatca atccatgtga catcccccac tatctaagaa caccataaca   12720
gaacacaaca taggaatgca acattaatgt atcaataatt cggaacatat gcactatatc   12780
```

-continued

| | |
|---|---|
| atatctcaat tacggaacat atcagcacac aattgcccat tatacgc | 12827 |

<210> SEQ ID NO 66
<211> LENGTH: 8139
<212> TYPE: DNA
<213> ORGANISM: Artificial
<220> FEATURE:
<223> OTHER INFORMATION: pCC1FOS

<400> SEQUENCE: 66

| | |
|---|---|
| gcggccgcaa ggggttcgcg tcagcgggtg ttggcgggtg tcggggctgg cttaactatg | 60 |
| cggcatcaga gcagattgta ctgagagtgc accatatgcg gtgtgaaata ccgcacagat | 120 |
| gcgtaaggag aaaataccgc atcaggcgcc attcgccatt cagctgcgca actgttggga | 180 |
| agggcgatcg gtgcgggcct cttcgctatt acgccagctg gcgaaagggg gatgtgctgc | 240 |
| aaggcgatta agttgggtaa cgccagggtt ttcccagtca cgacgttgta aaacgacggc | 300 |
| cagtgaattg taatacgact cactataggg cgaattcgag ctcggtaccc ggggatccca | 360 |
| cgtgggatcc tctagagtcg acctgcaggc atgcaagctt gagtattcta tagtctcacc | 420 |
| taaatagctt ggcgtaatca tggtcatagc tgtttcctgt gtgaaattgt tatccgctca | 480 |
| caattccaca acatacga gccggaagca taaagtgtaa agcctggggt gcctaatgag | 540 |
| tgagctaact cacattaatt gcgttgcgct cactgcccgc tttccagtcg ggaaacctgt | 600 |
| cgtgccagct gcattaatga atcggccaac gcgaacccct tgcggccgcc cgggccgtcg | 660 |
| accaattctc atgtttgaca gcttatcatc gaatttctgc cattcatccg cttattatca | 720 |
| cttattcagg cgtagcaacc aggcgtttaa gggcaccaat aactgcctta aaaaaattac | 780 |
| gccccgccct gccactcatc gcagtactgt tgtaattcat taagcattct gccgacatgg | 840 |
| aagccatcac aaacggcatg atgaacctga atcgccagcg gcatcagcac cttgtcgcct | 900 |
| tgcgtataat atttgcccat ggtgaaaacg ggggcgaaga agttgtccat attggccacg | 960 |
| tttaaatcaa aactggtgaa actcacccag ggattggctg agacgaaaaa catattctca | 1020 |
| ataaacccctt tagggaaata ggccaggttt tcaccgtaac acgccacatc ttgcgaatat | 1080 |
| atgtgtagaa actgccggaa atcgtcgtgg tattcactcc agagcgatga aaacgtttca | 1140 |
| gtttgctcat ggaaaacggt gtaacaaggg tgaacactat cccatatcac cagctcaccg | 1200 |
| tctttcattg ccatacgaaa ttccggatga gcattcatca ggcgggcaag aatgtgaata | 1260 |
| aaggccggat aaaacttgtg cttatttttc tttacggtct ttaaaaaggc cgtaatatcc | 1320 |
| agctgaacgg tctggttata ggtacattga gcaactgact gaaatgcctc aaaatgttct | 1380 |
| ttacgatgcc attgggatat atcaacggtg gtatatccag tgatttttt ctccatttta | 1440 |
| gcttccttag ctcctgaaaa tctcgataac tcaaaaaata cgcccggtag tgatcttatt | 1500 |
| tcattatggt gaaagttgga acctcttacg tgccgatcaa cgtctcattt tcgccaaaag | 1560 |
| ttggcccagg gcttcccggt atcaacaggg acaccaggat ttatttattc tgcgaagtga | 1620 |
| tcttccgtca caggtattta ttcgcgataa gctcatggag cggcgtaacc gtcgcacagg | 1680 |
| aaggacagag aaagcgcgga tctgggaagt gacggacaga acggtcagga cctggattgg | 1740 |
| ggaggcggtt gccgccgctg ctgctgacgg tgtgacgttc tctgttccgg tcacaccaca | 1800 |
| tacgttccgc cattcctatg cgatgcacat gctgtatgcc ggtataccgc tgaaagttct | 1860 |
| gcaaagcctg atgggacata agtccatcag ttcaacggaa gtctacacga aggttttgc | 1920 |
| gctgatgtg gctgcccggc accgggtgca gtttgcgatg ccggagtctg atgcggttgc | 1980 |
| gatgctgaaa caattatcct gagaataaat gccttggcct ttatatggaa atgtggaact | 2040 |

```
gagtggatat gctgtttttg tctgttaaac agagaagctg gctgttatcc actgagaagc    2100
gaacgaaaca gtcgggaaaa tctcccatta tcgtagagat ccgcattatt aatctcagga    2160
gcctgtgtag cgtttatagg aagtagtgtt ctgtcatgat gcctgcaagc ggtaacgaaa    2220
acgatttgaa tatgccttca ggaacaatag aaatcttcgt gcggtgttac gttgaagtgg    2280
agcggattat gtcagcaatg gacagaacaa cctaatgaac acagaaccat gatgtggtct    2340
gtccttttac agccagtagt gctcgccgca gtcgagcgac agggcgaagc cctcggctgg    2400
ttgccctcgc cgctgggctg gcggccgtct atggccctgc aaacgcgcca gaaacgccgt    2460
cgaagccgtg tgcgagacac cgcggccggc cgccggcgtt gtggatacct cgcggaaaac    2520
ttggcccctca ctgacagatg aggggcggac gttgacactt gaggggccga ctcacccggc    2580
gcggcgttga cagatgaggg gcaggctcga tttcggccgg cgacgtggag ctggccagcc    2640
tcgcaaatcg gcgaaaacgc ctgatttttac gcgagtttcc cacagatgat gtggacaagc    2700
ctggggataa gtgccctgcg gtattgacac ttgaggggcg cgactactga cagatgaggg    2760
gcgcgatcct tgacacttga ggggcagagt gctgacagat gaggggcgca cctattgaca    2820
tttgaggggc tgtccacagg cagaaaatcc agcatttgca agggtttccg cccgttttc    2880
ggccaccgct aacctgtctt ttaacctgct tttaaaccaa tatttataaa ccttgttttt    2940
aaccagggct gcgccctgtg cgcgtgaccg cgcacgccga aggggggtgc ccccccttct    3000
cgaaccctcc cggtcgagtg agcgaggaag caccagggaa cagcacttat atattctgct    3060
tacacacgat gcctgaaaaa acttcccttg gggttatcca cttatccacg gggatatttt    3120
tataattatt ttttttatag tttttagatc ttctttttta gagcgccttg taggccttta    3180
tccatgctgg ttctagagaa ggtgttgtga caaattgccc tttcagtgtg acaaatcacc    3240
ctcaaatgac agtcctgtct gtgacaaatt gcccttaacc ctgtgacaaa ttgccctcag    3300
aagaagctgt tttttcacaa agttatccct gcttattgac tcttttttat ttagtgtgac    3360
aatctaaaaa cttgtcacac ttcacatgga tctgtcatgg cggaaacagc ggttatcaat    3420
cacaagaaac gtaaaaatag cccgcgaatc gtccagtcaa acgacctcac tgaggcggca    3480
tatagtctct cccgggatca aaaacgtatg ctgtatctgt tcgttgacca gatcagaaaa    3540
tctgatggca ccctacagga acatgacggt atctgcgaga tccatgttgc taaatatgct    3600
gaaatattcg gattgacctc tgcggaagcc agtaaggata tacggcaggc attgaagagt    3660
ttcgcgggga aggaagtggt ttttatcgc cctgaagagg atgccggcga tgaaaaaggc    3720
tatgaatctt ttccttggtt tatcaaacgt gcgcacagtc catccagagg gctttacagt    3780
gtacatatca acccatatct cattcccttc tttatcgggt tacagaaccg gtttacgcag    3840
tttcggctta gtgaaacaaa agaaatcacc aatccgtatg ccatgcgttt atacgaatcc    3900
ctgtgtcagt atcgtaagcc ggatggctca ggcatcgtct ctctgaaaat cgactggatc    3960
atagagcgtt accagctgcc tcaaagttac cagcgtatgc ctgacttccg ccgccgcttc    4020
ctgcaggtct gtgttaatga gatcaacagc agaactccaa tgcgcctctc atacattgag    4080
aaaaagaaag gccgccagac gactcatatc gtatttttcct tccgcgatat cacttccatg    4140
acgacaggat agtctgaggg ttatctgtca cagatttgag ggtggttcgt cacatttgtt    4200
ctgacctact gagggtaatt tgtcacagtt ttgctgtttc cttcagcctg catggatttt    4260
ctcatacttt ttgaactgta attttttaagg aagccaaatt tgaggcagt ttgtcacagt    4320
tgatttcctt ctcttttccct tcgtcatgtg acctgatatc gggggttagt tcgtcatcat    4380
```

```
tgatgagggt tgattatcac agtttattac tctgaattgg ctatccgcgt gtgtacctct    4440
acctggagtt tttcccacgg tggatatttc ttcttgcgct gagcgtaaga gctatctgac    4500
agaacagttc ttctttgctt cctcgccagt tcgctcgcta tgctcggtta cacggctgcg    4560
gcgagcgcta gtgataataa gtgactgagg tatgtgtctc tcttatctcc ttttgtagtg    4620
ttgctcttat tttaaacaac tttgcggttt tttgatgact ttgcgatttt gttgttgctt    4680
tgcagtaaat tgcaagattt aataaaaaaa cgcaaagcaa tgattaaagg atgttcagaa    4740
tgaaactcat ggaaacactt aaccagtgca taaacgctgg tcatgaaatg acgaaggcta    4800
tcgccattgc acagtttaat gatgacagcc cggaagcgag gaaaataacc cggcgctgga    4860
gaataggtga agcagcggat ttagttgggg tttcttctca ggctatcaga gatgccgaga    4920
aagcagggcg actaccgcac ccggatatgg aaattcgagg acgggttgag caacgtgttg    4980
gttatacaat tgaacaaatt aatcatatgc gtgatgtgtt tggtacgcga ttgcgacgtg    5040
ctgaagacgt atttccaccg gtgatcgggg ttgctgccca taaggtggc gtttacaaaa    5100 cctcagtttc tgttcatctt gctcaggatc tggctctgaa ggggctacgt gttttgctcg    5160
tggaaggtaa cgaccccag ggaacagcct caatgtatca cggatgggta ccagatcttc    5220
atattcatgc agaagacact ctcctgcctt tctatcttgg ggaaaaggac gatgtcactt    5280
atgcaataaa gcccacttgc tggccggggc ttgacattat tccttcctgt ctggctctgc    5340
accgtattga aactgagtta atgggcaaat tgatgaagg taaactgccc accgatccac    5400
acctgatgct ccgactggcc attgaaactg ttgctcatga ctatgatgtc atagttattg    5460
acagcgcgcc taacctgggt atcggcacga ttaatgtcgt atgtgctgct gatgtgctga    5520
ttgttcccac gcctgctgag ttgtttgact acacctccgc actgcagttt tcgatatgc    5580 ttcgtgatct gctcaagaac gttgatctta aagggttcga gcctgatgta cgtatttgc    5640 ttaccaaata cagcaatagt aatggctctc agtccccgtg gatggaggag caaattcggg    5700
atgcctgggg aagcatggtt ctaaaaatg ttgtacgtga acggatgaa gttggtaaag    5760 gtcagatccg gatgagaact gttttttgaac aggccattga tcaacgctct tcaactggtg    5820
cctggagaaa tgctctttct atttgggaac ctgtctgcaa tgaaatttc gatcgtctga    5880 ttaaaccacg ctgggagatt agataatgaa gcgtgcgcct gttattccaa aacatacgct    5940
caatactcaa ccggttgaag atacttcgtt atcgacacca gctgccccga tggtggattc    6000
gttaattgcg cgcgtaggag taatggctcg cggtaatgcc attactttgc ctgtatgtgg    6060
tcgggatgtg aagtttactc ttgaagtgct ccggggtgat agtgttgaga agacctctcg    6120
ggtatggtca ggtaatgaac gtgaccagga gctgcttact gaggacgcac tggatgatct    6180
catcccttct tttctactga ctggtcaaca gacaccggcg ttcggtcgaa gagtatctgg    6240
tgtcatagaa attgccgatg ggagtcgccg tcgtaaagct gctgcactta ccgaaagtga    6300
ttatcgtgtt ctggttggcg agctggatga tgagcagatg gctgcattat ccagattggg    6360
taacgattat cgcccaacaa gtgcttatga acgtggtcag cgttatgcaa gccgattgca    6420
gaatgaattt gctggaaata tttctgcgct ggctgatgcg gaaaatattt cacgtaagat    6480
tattacccgc tgtatcaaca ccgccaaatt gcctaaatca gttgttgctc ttttttctca    6540
ccccggtgaa ctatctgccc ggtcaggtga tgcacttcaa aaagccttta cagataaaga    6600
ggaattactt aagcagcagg catctaacct tcatgagcag aaaaaagctg gggtgatatt    6660
tgaagctgaa gaagttatca ctccttttaac ttctgtgctt aaaacgtcat ctgcatcaag    6720
aactagttta agctcacgac atcagtttgc tcctggagcg acagtattgt ataagggcga    6780
```

```
taaaatggtg cttaacctgg acaggtctcg tgttccaact gagtgtatag agaaaattga    6840
ggccattctt aaggaacttg aaaagccagc accctgatgc gaccacgttt tagtctacgt    6900
ttatctgtct ttacttaatg tcctttgtta caggccagaa agcataactg gcctgaatat    6960
tctctctggg cccactgttc cacttgtatc gtcggtctga taatcagact gggaccacgg    7020
tcccactcgt atcgtcggtc tgattattag tctgggacca cggtcccact cgtatcgtcg    7080
gtctgattat tagtctggga ccacggtccc actcgtatcg tcggtctgat aatcagactg    7140
ggaccacggt cccactcgta tcgtcggtct gattattagt ctgggaccat ggtcccactc    7200
gtatcgtcgg tctgattatt agtctgggac cacggtccca ctcgtatcgt cggtctgatt    7260
attagtctgg aaccacggtc ccactcgtat cgtcggtctg attattagtc tgggaccacg    7320
gtcccactcg tatcgtcggt ctgattatta gtctgggacc acgatcccac tcgtgttgtc    7380
ggtctgatta tcggtctggg accacggtcc cacttgtatt gtcgatcaga ctatcagcgt    7440
gagactacga ttccatcaat gcctgtcaag gcaagtatt gacatgtcgt cgtaacctgt    7500
agaacggagt aacctcggtg tgcggttgta tgcctgctgt ggattgctgc tgtgtcctgc    7560
ttatccacaa cattttgcgc acggttatgt ggacaaaata cctggttacc caggccgtgc    7620
cggcacgtta accgggctgc atccgatgca agtgtgtcgc tgtcgacgag ctcgcgagct    7680
cggacatgag gttgccccgt attcagtgtc gctgatttgt attgtctgaa gttgttttta    7740
cgttaagttg atgcagatca attaatacga tacctgcgtc ataattgatt atttgacgtg    7800
gtttgatggc ctccacgcac gttgtgatat gtagatgata tcattatca ctttacgggt    7860 cctttccggt gatccgacag gttacggggc ggcgacctcg cgggttttcg ctatttatga    7920
aaattttccg gtttaaggcg tttccgttct tcttcgtcat aacttaatgt ttttatttaa    7980 aatacctct gaaagaaag gaaacgacag gtgctgaaag cgagcttttt ggcctctgtc    8040
gtttcctttc tctgttttg tccgtggaat gaacaatgga agtccgagct catcgctaat    8100
aacttcgtat agcatacatt atacgaagtt atattcgat                          8139
```

<210> SEQ ID NO 67
<211> LENGTH: 14600
<212> TYPE: DNA
<213> ORGANISM: Artificial
<220> FEATURE:
<223> OTHER INFORMATION: pJAZZ-OC

<400> SEQUENCE: 67

```
gcgtataatg gactattgtg tgctgataag gagaacataa gcgcagaaca atatgtatct     60
attccggtgt tgtgttcctt tgttattctg ctattatgtt ctcttatagt gtgacgaaag    120
cagcataatt aatcgtcact tgttctttga ttgtgttacg atatccagag acttagaaac    180
gggggaaccg ggatgagcaa ggtaaaaatc ggtgagttga tcaacacgct tgtgaatgag    240
gtagaggcaa ttgatgcctc agaccgccca caaggcgaca aaacgaagag aattaaagcc    300
gcagccgcac ggtataagaa cgcgttattt aatgataaaa gaaagttccg tgggaaagga    360
ttgcagaaaa gaataaccgc gaatactttt aacgcctata tgagcagggc aagaaagcgg    420
tttgatgata aattacatca tagctttgat aaaaatatta ataaattatc ggaaaagtat    480 cctctcttaca gcgaagaatt atcttcatgg ctttctatgc ctacggctaa tattcgccag    540
cacatgtcat cgttacaatc taaattgaaa gaaataatgc cgcttgccga agagttatca    600
aatgtaagaa taggctctaa aggcagtgat gcaaaaatag caagactaat aaaaaatat    660
```

```
ccagattgga gttttgctct tagtgattta aacagtgatg attggaagga gcgccgtgac    720
tatctttata agttattcca acaaggctct gcgttgttag aagaactaca ccagctcaag    780
gtcaaccatg aggttctgta ccatctgcag ctaagccctg cggagcgtac atctatacag    840
caacgatggg ccgatgttct gcgcgagaag aagcgtaatg ttgtggttat tgactaccca    900
acatacatgc agtctatcta tgatattttg aataatcctg cgactttatt tagtttaaac    960
actcgttctg gaatggcacc tttggccttt gctctggctg cggtatcagg gcgaagaatg   1020
attgagataa tgtttcaggg tgaatttgcc gtttcaggaa agtatacggt taatttctca   1080
gggcaagcta aaaaacgctc tgaagataaa agcgtaacca gaacgattta tactttatgc   1140
gaagcaaaat tattcgttga attattaaca gaattgcgtt cttgctctgc tgcatctgat   1200
ttcgatgagg ttgttaaagg atatggaaag gatgatacaa ggtctgagaa cggcaggata   1260
aatgctattt tagcaaaagc atttaaccct tgggttaaat cattttttcgg cgatgaccgt   1320
cgtgtttata aagatagccg cgctatttac gctcgcatcg cttatgagat gttcttccgc   1380
gtcgatccac ggtggaaaaa cgtcgacgag gatgtgttct tcatggagat tctcggacac   1440
gacgatgaga acacccagct gcactataag cagttcaagc tggccaactt ctccagaacc   1500
tggcgacctg aagttgggga tgaaaacacc aggctggtgg ctctgcagaa actggacgat   1560
gaaatgccag gctttgccag aggtgacgct ggcgtccgtc tccatgaaac cgttaagcag   1620
ctggtggagc aggacccatc agcaaaaata accaacagca ctctccgggc ctttaaattt   1680
agcccgacga tgattagccg gtacctggag tttgccgctg atgcattggg gcagttcgtt   1740
ggcgagaacg ggcagtggca gctgaagata gagacacctg caatcgtcct gcctgatgaa   1800
gaatccgttg agaccatcga cgaaccggat gatgagtccc aagacgacga gctggatgaa   1860
gatgaaattg agctcgacga gggtggcggc gatgaaccaa ccgaagagga agggccagaa   1920
gaacatcagc caactgctct aaaacccgtc ttcaagcctg caaaaaataa cggggacgga   1980
acgtacaaga tagagtttga atacgatgga aagcattatg cctggtccgg ccccgccgat   2040
agccctatgg ccgcaatgcg atccgcatgg gaaacgtact acagctaaaa gaaaagccac   2100
cggtgttaat cggtggcttt tttattgagg cctgtcccta cccatcccct gcaagggacg   2160
gaaggattag gcggaaactg cagctgcaac tacggacatc gccgtcccga ctgcagggac   2220
ttccccgcgt aaagcggggc ttaaattcgg gctggccaac cctatttttc tgcaatcgct   2280
ggcgatgtta gtttcgtgga tagcgttttcc agcttttcaa tggccagctc aaaatgtgct   2340
ggcagcacct tctccagttc cgtatcaata tcggtgatcg gcagctctcc acaagacata   2400
ctccggcgac cgccacgaac tacatcgcgc agcagctccc gttcgtagac acgcatgttg   2460
cccagagccg tttctgcagc cgttaatatc cggcgcagct cggcgatgat tgccgggaga   2520
tcatccacgg ttattgggtt cggtgatggg ttcctgcagg gcggcggag agccatccag   2580
acgccgctaa cccatgcgtt acggtactga aaactttgtg ctatgtcgtt tatcaggccc   2640
cgaagttctt ctttctgccg ccagtccagt ggttcaccgg cgttcttagg ctcaggctcg   2700
acaaaagcat actcgccgtt tttccggata gctggcagaa cctcgttcgt cacccacttg   2760
cggaaccgcc aggctgtcgt cccctgtttc accgcgtcgc ggcagcggag gattatggtg   2820
tagagaccag attccgatac cacatttact tccctggcca tccgatcaag ttttttgtgcc   2880
tcggttaaac cgagggtcaa ttttttcatca tgatccagct tacgcaatgc atcagaaggg   2940
ttggctatat tcaatgcagc acagatatcc agcgccacaa accacgggtc accaccgaca   3000
agaaccaccc gtataggggtg gctttcctga aatgaaaaga cggagagagc cttcattgcg   3060
```

```
cctcccggga tttcagctgc tcagaaaggg acagggagca gccgcgagct tcctgcgtga    3120
gttcgcgcgc gacctgcaga agttccgcag cttcctgcaa atacagcgtg gcctcataac    3180
tggagatagt gcggtgagca gagcccacaa gcgcttcaac ctgcagcagg cgttcctcaa    3240
tcgtctccag caggccctgg gcgtttaact gaatctggtt catgcgatca cctcgctgac    3300
cgggatacgg gctgacagaa cgaggacaaa acggctggcg aactggcgac gagcttctcg    3360
ctcggatgat gcaatggtgg aaaggcggtg gatatgggat tttttgtccg tgcggacgac    3420
agctgcaaat ttgaatttga acatggtatg cattcctatc ttgtataggg tgctaccacc    3480
agagttgaga atctctatag gggtggtagc ccagacaggg ttctcaacac cggtacaaga    3540
agaaaccggc ccaaccgaag ttggccccat ctgagccacc ataattcagg tatgcgcaga    3600
tttaacacac aaaaaaacac gctggcgcgt gttgtgcgct tcttgtcatt cggggttgag    3660
aggcccggct gcagattttg ctgcagcggg gtaactctac cgccaaagca gaacgcacgt    3720
caataattta ggtggatatt ttaccccgtg accagtcacg tgcacaggtg tttttatagt    3780
ttgctttact gactgatcag aacctgatca gttattggag tccggtaatc ttattgatga    3840
ccgcagccac cttagatgtt gtctcaaacc ccatacggcc acgaatgagc cactggaacg    3900
gaatagtcag caggtacagc ggaacgaacc acaaacggtt cagacgctgc cagaacgtcg    3960
catcacgacg ttccatccat tcggtattgt cgacgacctg gtaagcgtat tgtcctggcg    4020
tttttgctgc ttccgagtag caatcctctt caccacaaag aaagttactt atctgcttcc    4080
agttttcgaa cccttcttct ttgagccgct tttccagctc attcctccac aaaacaggca    4140
cccatcctct gcgataaatc atgattattt gtcctttaaa taaggctgta gaactgcaaa    4200
atcgctctcg ttcacatgct gtacgtagat gcgtagcaaa ttgccgttcc atccctgtaa    4260
tccaccttct ttggaaagat cgtccttgac ctcacgaaga accttatcca atagccctgc    4320
ggcacaagaa attgcctgct ctggatcagc aaattcatat tgattaatag gtgattgcca    4380
cacaccaaaa acaggaatca tcttttcggc taaacgcctc tcctgttctt tcttaatctc    4440
aagttgtaag cggaccagct caccatccat catttttgt agatcatgcg ccactattca    4500
cccccactgg ccatcagcaa ataaagcttc atactcggac accggcaggc ggcttccacg    4560
gattgaaagg tcaagccaac cacgtccaga tgggtcagcc ttatccgatt cttcccaccg    4620
ttctgcagct gtagcaacca ggcattctac cgccttcatg tagtcttctg tacggaacca    4680
gccgtagtta atgccaccat cagtaactgc ccaggccatc ttttctctt cggcctcaat    4740 agcccggatg cggttatcgc acagctcgcg acagtacttc agctgttcgt aatccagttg    4800
cttcaggaac tctggtgtcg acgtcatagt ggcttcacct tataggcttt tagaagcgcc    4860
ctggcttcgt ctgtgtggtc ttccatgctc ttatcgctgg caatgcagca ataaactccc    4920
tcactatctg agaacccgtt catccgaatg atcgtgaatg gaagttcccg gccagtttta    4980
taatcgctat agcttgtcgc gtcgtggctg accttgacca cataagggtc gtagccctcc    5040
acgatgacaa ggcattcccg ttgttttccc attaccctc cggttatatc gccacggctt    5100
gccgctggct tagaaacgct tcagcagcc ttatttcgcg tactgatagc aggtccataa    5160
attcggtcat gtacagcgag gcgaacgttc tcgcgatgct ggccactggc cacaggcgta    5220
ccgcctccat ttcggttgct ggcaacgcgt tctccgccca cgcctccggt accgccaccg    5280
ggatagcctc cagtgcctgg ataattactg attgtgggc gtccggaacg tgctctgttt    5340
tggatcgagg gttaccatgt atatctatat ttagatccaa atcgcgatcc acttcgatgg    5400
```

```
tggttttttc caccttacgt gcgtgaattg ataaaccggc ctcgcggcgc ttctccacga    5460
tattcatgag gaactcgacc gagtccgggt caatggaacg catcgtgggg cgtgcatcgc    5520
cgtctctggc gcgtctggtc ttactggata gccccataga ctccaggatg cctatgcaga    5580
ggtctgcagg cgctttcttc ttgcctttct ctgtgttgaa gccgccgatg cgtaaaacgt    5640
tgtttagcag atcgcgccgt tccggcgtga gcaggttatc tctggcgcgt ttgagggcgt    5700
ccatgtctgc ttcaccttcc agggttttg gatcgatacc gcagtcgcgg aagtactgct     5760
gcagcgtcgc cgatttgagg gtgtagaaac cacgcatgcc tatctcaaca gcagggtcg     5820
atttcactcg gtaatcggtt atggccggga atttagcctg gaactctgcg tcggcctgtt    5880
cccgcgtcat ggccgtagtg acgaactgct gccatcttcc ggcaacgcga taagcgtagg    5940
taaagtgaat caacgcttct tcacggtcaa ggcgacgggc ggttatctca tccagctgca    6000
tggtttcaaa caggcgcact ttttcaggc cgccgtcgaa atagaatttt aacgccacct     6060
cgtcgacatc cagctgcagc tccttttcga tgtcccagcg gaccagctgg gcctgctcat    6120
ccagggacag ggtgcgtttt tttatcaact catcgtgttc ggcctggtca ggagtatcga    6180
cactcaggtg gcgctccata agctgctcaa agaccagttc acgggcttct ttacgtaaat    6240
ccttaccgat gctgtttgca agcgcgtcgg tggccatagg cgcgacctga tagccatcat    6300
catgcatgat gcaaatcatg ttgctggcat aatcatttct ggccgatgcc tcgagcgcgg    6360
cggctttaat tttgagctgc atgaatgaag agttagccac gccgagtgaa attcggtcac    6420
cgtcaaagac aacgtctgtc agcagcccgg agtggccagc cgtttcgagc aaggcctgcg    6480
cgtaggcgcg tttgattttt tccggatcgg tttcacgttt accgcgaagc ttgtcgaaac    6540
cgataatgta ttcctgagct gtacggtcgc ggcgcagcat ctggatggcg tcgctgggga    6600
ccacttcgcc gcagaacatg ccgaaatggc ggtggaagtg tttctcctca atcgatacac    6660
ctgaagatat cgacgggctg tagatgaggc cgtcatattt tttcaccatc actttaggct    6720
ggttggtgaa atcgtcgact tccttctcct gtttgttttt ctggttaacg cagagaaact    6780
ttttgtcagg gaactgtagt ctcagctgca tggtaacgtc ttcggcgaac gtcgaactgt    6840
cggtggccag catgattcgt tcgccgcgtt gcactgcagc gataacctcg gtcatgatcc    6900
gattttctc ggtataaaat acgcggatag gcttgttggt ttcgcggttg cgaacgtcga     6960
ccgggagttc aatcacgtga atttgcagcc aggcaggtag gcccagctcc tcgcgtcgct    7020
tcatcgccag ttcagccagg tcaacaagca gatcgttggc atcggcatcc accataatgg    7080
catgctcttc agtacgcgcc agcgcgtcga taagcgtgtt gaatacgcct accgggtttt    7140
ccatcgcacg cccggccaga atggcacgca ggccctgtgt tgcttcatcg aagccgaaga    7200
agtcatgctg gcgcatcagc ggttgccagc agcctttaag tatggagttg atgcaaatag    7260
tcagcttgtt ggcatatggc gccatttcct gatagccggg atcctgataa tgcagaatgt    7320
cggctttcgc gcctttccct tcggtcatca tttcatgcag gccgcctatc agggatacgc    7380
ggtgcgcgac ggaaacgcca cgcgtggact gcagcatcag tggacgcagg aggcctgtcg    7440
atttacccga ccccatcccg cgcggacaa taacgatgcc ctgcagctgt gcggcgtatg     7500
tcatcacctc atcggtcatc ctggaggttt caaaccgttt gtaagtgatg tgtgacgggc    7560
gaaggttcgg gttggtgatg cgttcactga acgaacgtga tgtttgcgcg cacggcatt    7620
tgcgattcaa ccggcgcgta atgtgatctt taacggtacc gttataaatt tctgcgatac    7680
ccatatcccg cagcgtgctg ctgaaaaggc gcataagttc tttcgggctg tttggtaccg    7740
ggcatgtcag catgccaata tcaacggcgc gaagcagttc tttggcaaaa gtgcgtctgt    7800
```

```
tcagacgcgg gagagtacgc agcttattca gcgtgatcga caacaggtcg gttgcacggc    7860
tcagatgatt tctcgttaac tggcgagcga cttccttcag ccctctcagg ctgtgcaggt    7920
cgttaaaatc gctgcattcc agctcagggt catcctcaaa agttgggtaa acacatttga    7980
cgccggaaaa cttctccatg atgtcgaatc cggtgcggag gcctgtgttg ccttttcctt    8040
cagctgagga tttgcggtcg ttatcgagag cgcaagtgat ttgcgcagcc gggtacatgt    8100
tcaccagctg ctcgacaacg tgaatcatgt tgttagcgga aaccgcaatg actaccgcgt    8160
caaagcgttt tttcggtcg tttctggtcg ccagccagat ggatgccccg gtggcgaaac     8220
cctctgcagt cgcaattttt tgcgccccct gcaggtcgcc aataacaaag catgcaccga    8280
cgaaatcacc gttagtgatg gcgctggtct ggaacttgcc accattcaga tcgatacgtt    8340
gccagccaac aatccgcccg tcttttcttc cgtccaggtg ggacagaggt atcgccatgt    8400
aagttgttgg tccacggctc catttcgcac tgtcgtgact ggtcacgcga cgtatatcac    8460
aagcgccaaa tacgtcacga attccctttt ttaccgcata aggccaggag ccatcttcag    8520
ctggcgaatg ttcccaggcg cgatggaaag ccaaccatcc aagcaggcgt tcctgctcca    8580
tctgattgtt ttttaaatca ttaacgcgtt gttgttcagc tcggaggcgg cgtgcttcag    8640
cctggcgctc catgcgtgca cgttcttctt ccggctgagc gaccacggtc gcaccattcc    8700
gttgctgttc acggcgatac tccgaaaaca ggaatgaaaa gccactccag gagccagcgt    8760
catgcgcttt ttcaacgaag ttaacgaaag gataactgat gccatccttg ctctgctcaa    8820
ggcgtgaata gatttccaca cggcctttaa ggctcttctg cagagcttcc ggggaggaat    8880
tattgtaggt ggtatagcgc tctacaccac cgcgcggatt gagctgaatc ttatcagcac    8940
acgcaggcca gttgataccg gccatcttcg ccagctcagt cagctcatca cgtgccgcgt    9000
caagcagtga aaacggatcg ctgccaaagc gctccgcgta gaattcttgt aaggtcattt    9060
tttagccttt ccatgcgaat tagcattttt tcgggttgaa aaaatccgca ggagcagcca    9120
caataaacgc actatctttc tgaaggacgt atctgcgtta tcgtggctac ttcctgaaaa    9180
aggcccgagt ttgccgactc gggtttttt tcgtcttttt tcggctgcta cggtctggtt     9240
caaccccgac aaagtataga tcggattaaa ccagaattat agtcagcaat aaaccctgtt    9300
attgtatcat ctaccctcaa ccatgaacga tttgatcgta ccgactactt ggtgcacaaa    9360
ttgaagatca cttttatcat ggataacccg ttgagagtta gcactatcaa ggtagtaatg    9420
ctgctcgtca taacgggcta atcgttgaat tgtgatctcg ccgttattat cacaaaccag    9480
tacatcctca cccggtacaa gcgtaagtga agaatcgacc aggataacgt ctcccggctg    9540
gtagtttcgc tgaatctggt tcccgaccgt cagtgcgtaa acggtgttcc gttgactcac    9600
gaacggcagg aatcgctctg tgttggcagg ttctccaggc tgccagtctc tatccggtcc    9660
ggtctctgtc gtaccaataa caggaacgcg gtctggatca gattcagtgc catacagtat    9720
ccattgcacg ggcttacgca ggcattttgc cagcgatagc ccgatctcca gcgacggcat    9780
cacgtcgcca cgttctaagt tttgacgcc cggaagagag attcctacag cttctgccac      9840
ttgcttcagc gtcagtttca gctctaaacg gcgtgctttc agtcgttcgc ctcgtgtttt    9900
catacccctta atcataaatg atctctttat agctggctat aattttata aattatacct    9960
agctttaatt ttcacttatt gattataata atccccatga aacccgaaga acttgtgcgc    10020
catttcggcg atgtggaaaa agcagcggtt ggcgtgggcg tgacacccgg cgcagtctat    10080
caatggctgc aagctgggga gattccacct ctacgacaaa gcgatataga ggtccgtacc    10140
```

```
gcgtacaaat taaagagtga tttcacctct cagcgcatgg gtaaggaagg gcataacagg    10200
ggatcctcta gagtcgacct gcaggcatgc aagcttcctg aatcgcccca tcatccagcc    10260
agaaagtgag ggagccacgg ttgatgagag ctttgttgta ggtggaccag ttggtgattt    10320
tgaacttttg ctttgccacg gaacggtctg cgttgtcggg aagatgcgtg atctgatcct    10380
tcaactcagc aaaagttcga tttattcaac aaagccgccg tcccgtcaag tcagcgtaat    10440
gctctgccag tgttacaacc aattaaccaa ttctgattag aaaaactcat cgagcatcaa    10500
atgaaactgc aatttattca tatcaggatt atcaatacca tatttttgaa aaagccgttt    10560
ctgtaatgaa ggagaaaact caccgaggca gttccatagg atggcaagat cctggtatcg    10620
gtctgcgatt ccgactcgtc aacatcaat acaacctatt aatttcccct cgtcaaaaat    10680
aaggttatca agtgagaaat caccatgagt gacgactgaa tccggtgaga atggcaaaag    10740
cttatgcatt tctttccaga cttgttcaac aggccagcca ttacgctcgt catcaaaatc    10800
actcgcatca accaaaccgt tattcattcg tgattgcgcc tgagcgagac gaaatacgcg    10860
atcgctgtta aaaggacaat tacaaacagg aatcgaatgc aaccggcgca ggaacactgc    10920
cagcgcatca acaatatttt cacctgaatc aggatattct tctaataccct ggaatgctgt    10980 tttccctggg atcgcagtgg tgagtaacca tgcatcatca ggagtacgga taaaatgctt    11040
gatggtcgga agaggcataa attccgtcag ccagtttagt ctgaccatct catctgtaac    11100
atcattggca acgctacctt tgccatgttt cagaaacaac tctggcgcat cgggcttccc    11160
atacaatcga tagattgtcg cacctgattg cccgacatta tcgcgagccc atttataccc    11220
atataaatca gcatccatgt tggaatttaa tcgcggcctc gagcaagacg tttcccgttg    11280
aatatggctc ataacacccc ttgtattact gtttatgtaa gcagacagtt ttattgttca    11340
tgatgatata ttttatctt gtgcaatgta acatcagaga ttttgagaca caacgtggct    11400
ttgttgaata aatcgaactt tgctgagtt gaaggatcag atcacgcatc ttcccgacaa    11460
cgcagaccgt tccgtggcaa agcaaaagtt caaaatcacc aactggtcca cctacaacaa    11520
agctctcatc aaccgtggct ccctcacttt ctggctggat gatggggcga ttcaggaagc    11580
ttgcatgcct gcaggtcgac tctagaggat ccccgagaac ccgataatcg ctaccagtga    11640
tgatggctgt tttgcggcgg cgtgagccat cggcaatttc gataatgcct gacgtccttc    11700
tggcgaacgc ggggttctgc tgtcctgaag tgaggaatga agggataagg tcggccagcg    11760
ctgattcgtt cagcaattcc tgatcacgtt cattaccgag ccaaaccatt gtggcctttt    11820
cgactttatc agcaggaatg gtttccagct taaaagtcac gttgcggcca tcaagcttga    11880
attcgtacgc agaaaggccc acccgaaggt gagccagtgt gattacattt gcggccgcat    11940
ttaaatgggc ccgggacagg tttcccgact ggaaagcggg cagtgagcgc aacgcaatta    12000
atgtgagtta gctcactcat taggcacccc aggctttaca ctttatgctt ccggctcgta    12060
tgttgtgtgg aattgtgagc ggacaacaat ttcacacagg aaacagctat gaccatgatt    12120
acgccaagct atttaggtga gactatagaa tactcaagct tgcatgcgat acgtatcgtt    12180
tacgatggat ccgacgcacg tgcgaattcg ccctatagtg agtcgtatta caattcactg    12240
gccgtcgttt tacaacgtcg tgactgggaa aaccctggcg tcacccaact aatcgcctt    12300 gcagcacatc ccccttttcgc cagctggcgt aatagcgaag aggcccgcac cgatcgccct    12360
tcccaacagt tgcgcagctg aatggcgaat ggcgcctgag ggcccgggat ggcgcgccat    12420
gcggccgcca tggtcaaata aaacgaaagg ctcagtcgaa agactgggcc tttcgtttta    12480
atctgatcgg cacgtaagag gttccaactt tcaccataat gaaataagat cactaccggg    12540
```

```
cgtattttt  gagttatcga  gattttcagg  agctaaggaa  gctaaaatga  gtattcaaca   12600
tttccgtgtc  gcccttattc  ccttttttgc  ggcattttgc  cttcctgttt  ttgctcaccc   12660
agaaacgctg  gtgaaagtaa  aagatgctga  agatcagttg  ggtgcacgag  tgggttacat   12720
cgaactggat  ctcaacagcg  gtaagatcct  tgagagttta  cgccccgaag  aacgttttcc   12780
aatgatgagc  acttttaaag  ttctgctatg  tggcgcggta  ttatcccgta  ttgacgccgg   12840
gcaagagcaa  ctcggtcgcc  gcatacacta  ttctcagaat  gacttggttg  agtactcacc   12900
agtcacagaa  aagcatctca  cggatggcat  gacagtaaga  gaattatgca  gtgctgccat   12960
aaccatgagt  gataacactg  cggccaactt  acttctggca  acgatcggag  gaccgaagga   13020
gctaaccgct  tttttgcaca  acatggggga  tcatgtaact  cgccttgatc  gttgggaacc   13080
ggagctgaat  gaagccatac  caaacgacga  gcgtgacacc  acgatgcctg  tagcaatggc   13140
aacaacgttg  cgcaaactat  taactggcga  actacttact  ctagcttccc  ggcaacaatt   13200
aatagactgg  atggaggcgg  ataaagttgc  aggatcactt  ctgcgctcgg  cccctccggc   13260
tggctggttt  attgctgata  aatctggagc  cggtgagcgt  gggtctcgcg  gtatcattgc   13320
agcactgggg  ccagatggta  agccctcccg  catcgtagtt  atctacacga  cggggagtca   13380
ggcaactatg  gatgaacgaa  atagacagat  cgctgagata  ggtgcctcac  tgattaagca   13440
ttggtaatga  cagaagtcaa  aagcctccgg  tcggaggctt  ttgactttct  gctagatctg   13500
tttcaatgcg  gtgaagggcc  aggcagctgg  ggattatgtc  gagacccggc  agcatgttg   13560 gttttatcgc  atattcagcg  ttgtcgcgtt  tacccaggta  aaatgaagc  agtgtatcgt   13620 ctgcgtgaat  gtgcaaatca  ggaacgtaac  cgtggtacat  agatgcagtc  ccttgcgggt   13680
cgttcccttc  aacgagtagg  acgcggtgcc  cttcaaggc  taaccattgc  gcctggtgta   13740
ctgcagatga  ggttttataa  acccctccct  tgtgtgacat  aacggaaagt  acaaccgggt   13800
ttttatcgtc  aggtctttgg  tttgggttac  caaacacact  ccgcatatgg  ctaatttggt   13860
caattgtgta  gccagcgcga  cgttctactc  ggcccctcat  ctcaaaatca  ggagccggta   13920
gacgaccagc  ttttccgcg  tctctgatag  cctgcggtgt  tacgccgatc  aggtctgcaa   13980
cttctgttat  accccagcgg  cgagtaatac  gacgcgcttc  cgggctgtca  tcgccgaact   14040
gtgcgatggc  aatagcgcgc  gtcatttcct  gaccgcgatt  gatacagtct  ttcagcaaat   14100
taattaacga  catcctgttt  cctctcaaac  atgcccttat  ctttgtgttt  ttcatcatac   14160
tttacgtttt  taaagcaaag  caacataaaa  aaagcaaagt  gacttagaaa  acgcaaagtt   14220
aaggttcaaa  tcaatttttt  gatgcgctac  agaagctatt  tagcttcatc  taagcgcaac   14280
ggtattactt  acgttggtat  atttaaaacc  taacttaatg  attttaaatg  ataataaatc   14340
ataccaattg  ctatcaaaag  ttaagcgaac  atgctgattt  tcacgctgtt  tatacacttt   14400
gaggcatctc  tatctcttcc  gtctctatat  tgaaacacaa  tcaaagaaca  tcaatccatg   14460
tgacatcccc  cactatctaa  gaacaccata  acagaacaca  acataggaat  gcaacattaa   14520
tgtatcaata  attcggaaca  tatgcactat  atcatatctc  aattacggaa  catatcagca   14580
cacaattgcc  cattatacgc                                                  14600
```

<210> SEQ ID NO 68
<211> LENGTH: 13165
<212> TYPE: DNA
<213> ORGANISM: Artificial
<220> FEATURE:
<223> OTHER INFORMATION: pG591
<220> FEATURE:

```
<221> NAME/KEY: misc_feature
<222> LOCATION: (10741)..(10741)
<223> OTHER INFORMATION: n is a, c, g, or t
<220> FEATURE:
<221> NAME/KEY: misc_feature
<222> LOCATION: (10987)..(10987)
<223> OTHER INFORMATION: n is a, c, g, or t

<400> SEQUENCE: 68
gcgtataatg gactattgtg tgctgataag gagaacataa gcgcagaaca atatgtatct        60
attccggtgt tgtgttcctt tgttattctg ctattatgtt ctcttatagt gtgacgaaag       120
cagcataatt aatcgtcact tgttctttga ttgtgttacg atatccagag acttagaaac       180
gggggaaccg ggatgagcaa ggtaaaaatc ggtgagttga tcaacacgct tgtgaatgag       240
gtagaggcaa ttgatgcctc agaccgccca caaggcgaca aaacgaagag aattaaagcc       300
gcagccgcac ggtataagaa cgcgttattt aatgataaaa gaaagttccg tgggaaagga       360
ttgcagaaaa gaataaccgc gaatactttt aacgcctata tgagcagggc aagaaagcgg       420
tttgatgata aattacatca tagctttgat aaaaatatta ataaattatc ggaaaagtat       480
cctctttaca gcgaagaatt atcttcatgg cttctctgc ctacggctaa tattcgccag       540
cacatgtcat cgttacaatc taaattgaaa gaaataatgc cgcttgccga agagttatca       600
aatgtaagaa taggctctaa aggcagtgat gcaaaaatag caagactaat aaaaaaatat       660
ccagattgga gttttgctct tagtgattta acagtgatg attggaagga gcgccgtgac       720
tatctttata agttattcca acaaggctct gcgttgttag aagaactaca ccagctcaag       780
gtcaaccatg aggttctgta ccatctgcag ctaagccctg cggagcgtac atctatacag       840
caacgatggg ccgatgttct gcgcgagaag aagcgtaatg ttgtggttat tgactaccca       900
acatacatgc agtctatcta tgatattttg aataatcctg cgactttatt tagtttaaac       960
actcgttctg gaatggcacc tttggccttt gctctggctg cggtatcagg gcgaagaatg      1020
attgagataa tgtttcaggg tgaatttgcc gtttcaggaa agtatacggt taatttctca      1080
gggcaagcta aaaacgctc tgaagataaa agcgtaacca gaacgattta cttatgc           1140
gaagcaaaat tattcgttga attattaaca gaattgcgtt cttgctctgc tgcatctgat      1200
ttcgatgagg ttgttaaagg atatggaaag gatgatacaa ggtctgagaa cggcaggata      1260
aatgctattt tagcaaaagc atttaaccct tgggttaaat catttttcgg cgatgaccgt      1320
cgtgtttata agatagccg cgctatttac gctcgcatcg cttatgagat gttcttccgc      1380
gtcgatccac ggtggaaaaa cgtcgacgag gatgtgttct tcatggagat tctcggacac      1440
gacgatgaga acacccagct gcactataag cagttcaagc tggccaactt ctccagaacc      1500
tggcgacctg aagttgggga tgaaaacacc aggctggtgg ctctgcagaa actggacgat      1560
gaaatgccag gctttgccag aggtgacgct ggcgtccgtc tccatgaaac cgttaagcag      1620
ctggtggagc aggaccatc agcaaaaata accaacagca ctctccgggc ctttaaattt      1680
agcccgacga tgattagccg gtacctggag tttgccgctg atgcattggg gcagttcgtt      1740
ggcgagaacg ggcagtggca gctgaagata gagacacctg caatcgtcct gcctgatgaa      1800
gaatccgttg agaccatcga cgaaccggat gatgagtccc aagacgacga gctggatgaa      1860
gatgaaattg agctcgacga gggtggcggc gatgaaccaa ccgaagagga agggccagaa      1920
gaacatcagc caactgctct aaaacccgtc ttcaagcctg caaaaaataa cggggacgga      1980
acgtacaaga tagagtttga atacgatgga aagcattatg cctggtccgg ccccgccgat      2040
agccctatgg ccgcaatgcg atccgcatgg gaaacgtact acagctaaaa gaaaagccac      2100
```

```
cggtgttaat cggtggcttt tttattgagg cctgtcccta cccatcccct gcaagggacg    2160
gaaggattag gcggaaactg cagctgcaac tacggacatc gccgtcccga ctgcagggac    2220
ttccccgcgt aaagcgggc ttaaattcgg gctggccaac cctattttc tgcaatcgct     2280 ggcgatgtta gtttcgtgga tagcgtttcc agcttttcaa tggccagctc aaaatgtgct    2340
ggcagcacct tctccagttc cgtatcaata tcggtgatcg gcagctctcc acaagacata    2400
ctccggcgac cgccacgaac tacatcgcgc agcagctccc gttcgtagac acgcatgttg    2460
cccagagccg tttctgcagc cgttaatatc cggcgcagct cggcgatgat tgccgggaga    2520
tcatccacgg ttattgggtt cggtgatggg ttcctgcagg cgcggcggag agccatccag    2580
acgccgctaa cccatgcgtt acggtactga aaactttgtg ctatgtcgtt tatcaggccc    2640
cgaagttctt ctttctgccg ccagtccagt ggttcaccgg cgttcttagg ctcaggctcg    2700
acaaaagcat actcgccgtt tttccggata gctggcagaa cctcgttcgt cacccacttg    2760
cggaaccgcc aggctgtcgt ccctgtttc accgcgtcgc ggcagcggag gattatggtg     2820
tagagaccag attccgatac cacatttact tccctggcca tccgatcaag ttttgtgcc     2880 tcggttaaac cgagggtcaa ttttcatca tgatccagct tacgcaatgc atcagaaggg     2940
ttggctatat tcaatgcagc acagatatcc agcgccacaa accacgggtc accaccgaca    3000
agaaccaccc gtataggtg gctttcctga atgaaaga cggagagagc cttcattgcg       3060
cctccccgga tttcagctgc tcagaaaggg acagggagca gccgcgagct tcctgcgtga    3120
gttcgcgcgc gacctgcaga agttccgcag cttcctgcaa atacagcgtg gcctcataac    3180
tggagatagt gcggtgagca gagcccacaa gcgcttcaac ctgcagcagg cgttcctcaa    3240
tcgtctccag caggccctgg gcgtttaact gaatctggtt catgcgatca cctcgctgac    3300
cgggatacgg gctgacagaa cgaggacaaa acggctggcg aactggcgac gagcttctcg    3360
ctcggatgat gcaatggtgg aaaggcggtg gatatgggat tttttgtccg tgcggacgac    3420
agctgcaaat ttgaatttga acatggtatg cattcctatc ttgtataggg tgctaccacc    3480
agagttgaga atctctatag gggtggtagc ccagacaggg ttctcaacac cggtacaaga    3540
agaaaccggc ccaaccgaag ttggccccat ctgagccacc ataattcagg tatgcgcaga    3600
tttaacacac aaaaaaacac gctggcgcgt gttgtgcgct tcttgtcatt cggggttgag    3660
aggcccggct gcagattttg ctgcagcggg gtaactctac cgccaaagca gaacgcacgt    3720
caataattta ggtggatatt ttaccccgtg accagtcacg tgcacaggtg tttttatagt    3780
ttgctttact gactgatcag aacctgatca gttattggag tccggtaatc ttattgatga    3840
ccgcagccac cttagatgtt gtctcaaacc ccatacggcc acgaatgagc cactggaacg    3900
gaatagtcag caggtacagc ggaacgaacc acaaacggtt cagacgctgc cagaacgtcg    3960
catcacgacg ttccatccat tcggtattgt cgacgacctg gtaagcgtat tgtcctggcg    4020
tttttgctgc ttccgagtag caatcctctt caccacaaag aaagttactt atctgcttcc    4080
agttttcgaa cccttcttct ttgagccgct tttccagctc attcctccac aaaacaggca    4140
cccatcctct gcgataaatc atgattattt gtcctttaaa taaggctgta gaactgcaaa    4200
atcgctctcg ttcacatgct gtacgtagat gcgtagcaaa ttgccgttcc atccctgtaa    4260
tccaccttct ttggaaagat cgtccttgac ctcacgaaga accttatcca atagccctgc    4320
ggcacaagaa attgcctgct ctggatcagc aaattcatat tgattaatag gtgattgcca    4380
cacaccaaaa acaggaatca tcttttcggc taaacgcctc tcctgttctt tcttaatctc    4440
```

```
aagttgtaag cggaccagct caccatccat cattttttgt agatcatgcg ccactattca   4500
cccccactgg ccatcagcaa ataaagcttc atactcggac accggcaggc ggcttccacg   4560
gattgaaagg tcaagccaac cacgtccaga tgggtcagcc ttatccgatt cttcccaccg   4620
ttctgcagct gtagcaacca ggcattctac cgccttcatg tagtcttctg tacggaacca   4680
gccgtagtta atgccaccat cagtaactgc ccaggccatc ttttctctt cggcctcaat    4740 agcccggatg cggttatcgc acagctcgcg acagtacttc agctgttcgt aatccagttg   4800
cttcaggaac tctggtgtcg acgtcatagt ggcttcacct tataggcttt tagaagcgcc   4860
ctggcttcgt ctgtgtggtc ttccatgctc ttatcgctgg caatgcagca ataaactccc   4920
tcactatctg agaacccgtt catccgaatg atcgtgaatg aagttcccg gccagtttta   4980 taatcgctat agcttgtcgc gtcgtggctg accttgacca cataagggtc gtagccctcc   5040
acgatgacaa ggcattcccg ttgttttccc attacccctc cggttatatc gccacggctt   5100
gccgctggct tagaaacgct tcagcagcc ttatttcgcg tactgatagc aggtccataa    5160
attcggtcat gtacagcgag gcgaacgttc tcgcgatgct ggccactggc cacaggcgta   5220
ccgcctccat ttcggttgct ggcaacgcgt tctccgccca cgcctccggt accgccaccg   5280
ggatagcctc cagtgcctgg ataattactg attgtgggc gtccggaacg tgctctgttt    5340
tggatcgagg gttaccatgt atatctatat ttagatccaa atcgcgatcc acttcgatgg   5400
tggttttttc caccttacgt gcgtgaattg ataaaccggc ctcgcggcgc ttctccacga   5460
tattcatgag gaactcgacc gagtccgggt caatggaacg catcgtgggg cgtgcatcgc   5520
cgtctctggc gcgtctggtc ttactggata gccccataga ctccaggatg cctatgcaga   5580
ggtctgcagg cgctttcttc ttgcctttct ctgtgttgaa gccgccgatg cgtaaaacgt   5640
tgtttagcag atcgcgccgt tccggcgtga gcaggttatc tctggcgcgt ttgagggcgt   5700
ccatgtctgc ttcaccttcc agggttttg gatcgatacc gcagtcgcgg aagtactgct    5760
gcagcgtcgc cgatttgagg gtgtagaaac cacgcatgcc tatctcaaca gcagggtcg    5820 atttcactcg gtaatcggtt atggccggga atttagcctg gaactctgcg tcggcctgtt   5880
cccgcgtcat ggccgtagtg acgaactgct gccatcttcc ggcaacgcga taagcgtagg   5940
taaagtgaat caacgcttct tcacggtcaa ggcgacgggc ggttatctca tccagctgca   6000
tggtttcaaa caggcgcact ttttttcaggc cgccgtcgaa atagaatttt aacgccacct   6060
cgtcgacatc cagctgcagc tccttttcga tgtcccagcg gaccagctgg gcctgctcat   6120
ccagggacag ggtgcgtttt tttatcaact catcgtgttc ggcctggtca ggagtatcga   6180
cactcaggtg gcgctccata agctgctcaa agaccagttc acgggcttct ttacgtaaat   6240
ccttaccgat gctgtttgca agcgcgtcgg tggccatagg cgcgacctga tagccatcat   6300
catgcatgat gcaaatcatg ttgctggcat aatcatttct ggccgatgcc tcgagcgcgg   6360
cggctttaat tttgagctgc atgaatgaag agttagccac gccgagtgaa attcggtcac   6420
cgtcaaagac aacgtctgtc agcagcccgg agtggccagc cgtttcgagc aaggcctgcg   6480
cgtaggcgcg tttgattttt tccggatcgg tttcacgttt accgcgaagc ttgtcgaaac   6540
cgataatgta ttcctgagct gtacggtcgc ggcgcagcat ctggatggcg tcgctgggga   6600
ccacttcgcc gcagaacatg ccgaaatggc ggtggaagtg tttctcctca atcgatacac   6660
ctgaagatat cgacgggctg tagatgaggc cgtcatattt tttccaccat actttaggct   6720
ggttggtgaa atcgtcgact tccttctcct gtttgttttt ctggttaacg cagagaaact   6780
ttttgtcagg gaactgtagt ctcagctgca tggtaacgtc ttcggcgaac gtcgaactgt   6840
```

```
cggtggccag catgattcgt tcgccgcgtt gcactgcagc gataacctcg gtcatgatcc    6900 gattttctc  ggtataaaat acgcggatag gcttgttggt ttcgcggttg cgaacgtcga    6960
ccgggagttc aatcacgtga atttgcagcc aggcaggtag gcccagctcc tcgcgtcgct    7020
tcatcgccag ttcagccagg tcaacaagca gatcgttggc atcggcatcc accataatgg    7080
catgctcttc agtacgcgcc agcgcgtcga taagcgtgtt gaatacgcct accgggtttt    7140
ccatcgcacg cccggccaga atggcacgca ggccctgtgt tgcttcatcg aagccgaaga    7200
agtcatgctg gcgcatcagc ggttgccagc agcctttaag tatggagttg atgcaaatag    7260
tcagcttgtt ggcatatggc gccatttcct gatagccggg atcctgataa tgcagaatgt    7320
cggctttcgc gcctttccct tcggtcatca tttcatgcag gccgcctatc agggatacgc    7380
ggtgcgcgac ggaaacgcca cgcgtggact gcagcatcag tggacgcagg aggcctgtcg    7440
atttacccga ccccatcccg gcgcggacaa taacgatgcc ctgcagctgt gcggcgtatg    7500
tcatcaccct atcggtcatc ctggaggttt caaaccgttt gtaagtgatg tgtgacgggc    7560
gaaggttcgg gttggtgatg cgttcactga acgaacgtga tgtttgcgcg gcacggcatt    7620
tgcgattcaa ccgcgcgta  atgtgatctt taacggtacc gttataaatt tctgcgatac    7680
ccatatcccg cagcgtgctg ctgaaaaggc gcataagttc tttcgggctg tttggtaccg    7740
ggcatgtcag catgccaata tcaacggcgc gaagcagttc tttggcaaaa gtgcgtctgt    7800
tcagacgcgg gagagtacgc agcttattca gcgtgatcga caacaggtcg gttgcacggc    7860
tcagatgatt tctcgttaac tggcgagcga cttccttcag ccctctcagg ctgtgcaggt    7920
cgttaaaatc gctgcattcc agctcagggt catcctcaaa agttgggtaa acacatttga    7980
cgccggaaaa cttctccatg atgtcgaatc cggtgcggag gcctgtgttg ccttttcctt    8040
cagctgagga tttgcggtcg ttatcgagag cgcaagtgat tgcgcagcc  gggtacatgt    8100 tcaccagctg ctcgacaacg tgaatcatgt tgttagcgga aaccgcaatg actaccgcgt    8160
caaagcgttt tttcgggtcg tttctggtcg ccagccagat ggatgccccg gtggcgaaac    8220
cctctgcagt cgcaattttt tgcgccccct gcaggtcgcc aataacaaag catgcaccga    8280
cgaaatcacc gttagtgatg cgctggtct  ggaacttgcc accattcaga tcgatacgtt    8340
gccagccaac aatccgcccg tcttttcttc cgtccaggtg ggacagaggt atcgccatgt    8400
aagttgttgg tccacggctc catttcgcac tgtcgtgact ggtcacgcga cgtatatcac    8460
aagcgccaaa tacgtcacga attccctttt ttaccgcata aggccaggag ccatcttcag    8520
ctggcgaatg ttcccaggcg cgatggaaag ccaaccatcc aagcaggcgt tcctgctcca    8580
tctgattgtt ttttaaatca ttaacgcgtt gttgttcagc tcggaggcgg cgtgcttcag    8640 cctgcgctc  catgcgtgca cgttcttctt ccggctgagc gaccacggtc gcaccattcc    8700
gttgctgttc acggcgatac tccgaaaaca ggaatgaaaa gccactccag gagccagcgt    8760
catgcgcttt ttcaacgaag ttaacgaaag gataactgat gccatccttg ctctgctcaa    8820
ggcgtgaata gatttccaca cggcctttaa ggctcttctg cagagcttcc ggggaggaat    8880
tattgtaggt ggtatagcgc tctacaccac cgcgcggatt gagctgaatc ttatcagcac    8940
acgcaggcca gttgataccg gccatcttcg ccagctcagt cagctcatca cgtgccgcgt    9000
caagcagtga aaacggatcg ctgccaaagc gctccgcgta gaattcttgt aaggtcattt    9060
tttagccttt ccatgcgaat tagcattttt tcgggttgaa aaaatccgca ggagcagcca    9120
caataaacgc actatctttc tgaaggacgt atctgcgtta tcgtggctac ttcctgaaaa    9180
aggcccgagt ttgccgactc gggttttttt tcgtcttttt tcggctgcta cggtctggtt    9240
```

```
caacccccgac aaagtataga tcggattaaa ccagaattat agtcagcaat aaaccctgtt    9300
attgtatcat ctaccctcaa ccatgaacga tttgatcgta ccgactactt ggtgcacaaa    9360
ttgaagatca cttttatcat ggataacccg ttgagagtta gcactatcaa ggtagtaatg    9420
ctgctcgtca taacgggcta atcgttgaat tgtgatctcg ccgttattat cacaaaccag    9480
tacatcctca cccggtacaa gcgtaagtga agaatcgacc aggataacgt ctcccggctg    9540
gtagtttcgc tgaatctggt tcccgaccgt cagtgcgtaa acggtgttcc gttgactcac    9600
gaacggcagg aatcgctctg tgttggcagg ttctccaggc tgccagtctc tatccggtcc    9660
ggtctctgtc gtaccaataa caggaacgcg gtctggatca gattcagtgc catacagtat    9720
ccattgcacg ggcttacgca ggcattttgc cagcgatagc ccgatctcca gcgacggcat    9780
cacgtcgcca cgttctaagt tttggacgcc cggaagagag attcctacag cttctgccac    9840
ttgcttcagc gtcagtttca gctctaaacg gcgtgctttc agtcgttcgc ctcgtgtttt    9900 catacccttta atcataaatg atctctttat agctggctat aattttttata aattataacct   9960 agctttaatt ttcacttatt gattataata atccccatga aacccgaaga acttgtgcgc   10020
catttcggcg atgtggaaaa agcagcggtt ggcgtgggcg tgacacccgg cgcagtctat   10080
caatggctgc aagctgggga gattccacct ctacgacaaa gcgatataga ggtccgtacc   10140
gcgtacaaat taaagagtga tttcacctct cagcgcatgg gtaaggaagg gcataacagg   10200
ggatcctcta gagtcgacct gcaggcatgc aagcttcctg aatcgcccca tcatccagcc   10260
agaaagtgag ggagccacgg ttgatgagag cttttgttgta ggtggaccag ttggtgattt   10320
tgaacttttg ctttgccacg gaacggtctg cgttgtcggg aagatgcgtg atctgatcct   10380
tcaactcagc aaaagttcga tttattcaac aaagccgccg tcccgtcaag tcagcgtaat   10440
gctctgccag tgttacaacc aattaaccaa ttctgattag aaaaactcat cgagcatcaa   10500
atgaaactgc aatttattca tatcaggatt atcaatacca tatttttgaa aaagccgttt   10560
ctgtaatgaa ggagaaaact caccgaggca gttccatagg atggcaagat cctggtatcg   10620
gtctgcgatt ccgactcgtc caacatcaat acaacctatt aatttcccct cgtcaaaaat   10680
aaggttatca agtgagaaat caccatgagt gacgactgaa tccggtgaga atggcaaaag   10740
nttatgcatt tctttccaga cttgttcaac aggccagcca ttacgctcgt catcaaaatc   10800
actcgcatca accaaaccgt tattcattcg tgattgcgcc tgagcgagac gaaatacgcg   10860
atcgctgtta aaaggacaat acaaacagg aatcgaatgc aaccggcgca ggaacactgc   10920
cagcgcatca acaatatttt cacctgaatc aggatattct tctaatacct ggaatgctgt   10980
tttcccnggg atcgcagtgg tgagtaacca tgcatcatca ggagtacgga taaaatgctt   11040
gatggtcgga agaggcataa attccgtcag ccagtttagt ctgaccatct catctgtaac   11100
atcattggca acgctacctt tgccatgttt cagaaacaac tctggcgcat cgggcttccc   11160
atacaatcga tagattgtcg cacctgattg cccgacatta tcgcgagccc atttatacccc   11220 atataaatca gcatccatgt tggaatttaa tcgcggcctc gagcaagacg tttcccgttg   11280
aatatggctc ataacacccc ttgtattact gtttatgtaa gcagacagtt ttattgttca   11340
tgatgatata ttttttatctt gtgcaatgta acatcagaga ttttgagaca caacgtggct   11400
ttgttgaata aatcgaactt tgctgagtt gaaggatcag atcacgcatc ttcccgacaa   11460
cgcagaccgt tccgtggcaa agcaaaagtt caaaatcacc aactggtcca cctacaacaa   11520
agctctcatc aaccgtggct ccctcacttt ctggctggat gatggggcga ttcaggaagc   11580
ttgcatgcct gcaggtcgac tctagaggat ccccgagaac ccgataatcg ctaccagtga   11640
```

-continued

```
tgatggctgt tttgcggcgg cgtgagccat cggcaatttc gataatgcct gacgtccttc    11700
tggcgaacgc ggggttctgc tgtcctgaag tgaggaatga agggataagg tcggccagcg    11760
ctgattcgtt cagcaattcc tgatcacgtt cattaccgag ccaaaccatt gtggccttttt   11820 cgactttatc agcaggaatg gtttccagct taaaagtcac gttgcggccg caaaccggta    11880
gcgtaatgct attcccggac aacgaactta atttgctctg taagtcgcca accatcggcg    11940
aaaccgatgg cgcttttttgc ggcgcattat ggttattgct catgaacgtt tcgatgttgg   12000
gcgcattttt taatatagag cgattcttca tagttagtcc tcccaacgag gtttgattag    12060
atctgtttca atgcggtgaa gggccaggca gctgggggatt atgtcgagac ccggccagca   12120
tgttggtttt atcgcatatt cagcgttgtc gcgtttaccc aggtaaaatg gaagcagtgt    12180
atcgtctgcg tgaatgtgca aatcaggaac gtaaccgtgg tacatagatg cagtcccttg    12240
cgggtcgttc ccttcaacga gtaggacgcg gtgcccttgc aaggctaacc attgcgcctg    12300
gtgtactgca gatgaggttt tataaacccc tcccttgtgt gacataacgg aaagtacaac    12360
cgggttttta tcgtcaggtc tttggtttgg gttaccaaac acactccgca tatggctaat    12420
ttggtcaatt gtgtagccag cgcgacgttc tactcggccc ctcatctcaa aatcaggagc    12480
cggtagacga ccagcttttt ccgcgtctct gatagcctgc ggtgttacgc cgatcaggtc    12540
tgcaacttct gttataccccc agcggcgagt aatacgacgc gcttccgggc tgtcatcgcc    12600
gaactgtgcg atggcaatag cgcgcgtcat ttcctgaccg cgattgatac agtctttcag    12660
caaattaatt aacgacatcc tgtttcctct caaacatgcc cttatctttg tgttttttcat    12720 catactttac gttttaaaag caaagcaaca taaaaaaagc aaagtgactt agaaaacgca    12780
aagttaaggt tcaaatcaat ttttttgatgc gctacagaag ctattttagct tcatctaagc    12840 gcaacggtat tacttacgtt ggtatattta aaacctaact taatgattttt aaatgataat    12900 aaatcatacc aattgctatc aaaagttaag cgaacatgct gatttttcacg ctgtttatac    12960 actttgaggc atctctatct cttccgtctc tatattgaaa cacaatcaaa gaacatcaat    13020
ccatgtgaca tcccccacta tctaagaaca ccataacaga acacaacata ggaatgcaac    13080
attaatgtat caataattcg gaacatatgc actatatcat atctcaatta cggaacatat    13140
cagcacacaa ttgcccatta tacgc                                           13165
```

<210> SEQ ID NO 69
<211> LENGTH: 588
<212> TYPE: PRT
<213> ORGANISM: Artificial
<220> FEATURE:
<223> OTHER INFORMATION: 3173 mutant D49A

<400> SEQUENCE: 69

```
Met Gly Glu Asp Gly Leu Ser Leu Pro Lys Met Met Asn Thr Pro Lys
1               5                   10                  15

Pro Ile Leu Lys Pro Gln Pro Lys Ala Leu Val Glu Pro Val Leu Cys
            20                  25                  30

Asp Ser Ile Asp Glu Ile Pro Ala Lys Tyr Asn Glu Pro Val Tyr Phe
        35                  40                  45

Ala Leu Glu Thr Asp Glu Asp Arg Pro Val Leu Ala Ser Ile Tyr Gln
    50                  55                  60

Pro His Phe Glu Arg Lys Val Tyr Cys Leu Asn Leu Leu Lys Glu Lys
65                  70                  75                  80

Val Ala Arg Phe Lys Asp Trp Leu Leu Lys Phe Ser Glu Ile Arg Gly
                85                  90                  95
```

```
Trp Gly Leu Asp Phe Asp Leu Arg Val Leu Gly Tyr Thr Tyr Glu Gln
            100                 105                 110

Leu Arg Asn Lys Lys Ile Val Asp Val Gln Leu Ala Ile Lys Val Gln
            115                 120                 125

His Tyr Glu Arg Phe Lys Gln Gly Gly Thr Lys Gly Glu Gly Phe Arg
            130                 135                 140

Leu Asp Asp Val Ala Arg Asp Leu Leu Gly Ile Glu Tyr Pro Met Asn
145                 150                 155                 160

Lys Thr Lys Ile Arg Glu Thr Phe Lys Asn Asn Met Phe His Ser Phe
                165                 170                 175

Ser Asn Glu Gln Leu Leu Tyr Ala Ser Leu Asp Ala Tyr Ile Pro His
            180                 185                 190

Leu Leu Tyr Glu Gln Leu Thr Ser Ser Thr Leu Asn Ser Leu Val Tyr
            195                 200                 205

Gln Leu Asp Gln Gln Ala Gln Lys Val Val Ile Glu Thr Ser Gln His
            210                 215                 220

Gly Met Pro Val Lys Leu Lys Ala Leu Glu Glu Ile His Arg Leu
225                 230                 235                 240

Thr Gln Leu Arg Ser Glu Met Gln Lys Gln Ile Pro Phe Asn Tyr Asn
                245                 250                 255

Ser Pro Lys Gln Thr Ala Lys Phe Phe Gly Val Asn Ser Ser Ser Lys
            260                 265                 270

Asp Val Leu Met Asp Leu Ala Leu Gln Gly Asn Glu Met Ala Lys Lys
            275                 280                 285

Val Leu Glu Ala Arg Gln Ile Glu Lys Ser Leu Ala Phe Ala Lys Asp
            290                 295                 300

Leu Tyr Asp Ile Ala Lys Arg Ser Gly Gly Arg Ile Tyr Gly Asn Phe
305                 310                 315                 320

Phe Thr Thr Thr Ala Pro Ser Gly Arg Met Ser Cys Ser Asp Ile Asn
                325                 330                 335

Leu Gln Gln Ile Pro Arg Arg Leu Arg Ser Phe Ile Gly Phe Asp Thr
            340                 345                 350

Glu Asp Lys Lys Leu Ile Thr Ala Asp Phe Pro Gln Ile Glu Leu Arg
            355                 360                 365

Leu Ala Gly Val Ile Trp Asn Glu Pro Lys Phe Ile Glu Ala Phe Arg
            370                 375                 380

Gln Gly Ile Asp Leu His Lys Leu Thr Ala Ser Ile Leu Phe Asp Lys
385                 390                 395                 400

Asn Ile Glu Glu Val Ser Lys Glu Glu Arg Gln Ile Gly Lys Ser Ala
                405                 410                 415

Asn Phe Gly Leu Ile Tyr Gly Ile Ala Pro Lys Gly Phe Ala Glu Tyr
            420                 425                 430

Cys Ile Ala Asn Gly Ile Asn Met Thr Glu Glu Gln Ala Tyr Glu Ile
            435                 440                 445

Ser Gln Lys Val Glu Glu Val Leu His Lys Asp Cys Arg Gln His Gln
            450                 455                 460

Val Ala Tyr Glu Arg Phe Lys Tyr Asn Glu Tyr Val Asp Asn Glu Thr
465                 470                 475                 480

Trp Leu Asn Arg Thr Tyr Arg Ala Trp Lys Pro Gln Asp Leu Leu Asn
                485                 490                 495

Tyr Gln Ile Gln Gly Ser Gly Ala Glu Leu Phe Lys Lys Ala Ile Val
            500                 505                 510
```

```
Leu Leu Lys Glu Thr Lys Pro Asp Leu Lys Ile Val Asn Leu Val His
        515                 520                 525

Asp Glu Ile Val Val Glu Ala Asp Ser Lys Glu Ala Gln Asp Leu Ala
        530                 535                 540

Lys Leu Ile Lys Glu Lys Met Glu Glu Ala Trp Asp Trp Cys Leu Glu
545                 550                 555                 560

Lys Ala Glu Glu Phe Gly Asn Arg Val Ala Lys Ile Lys Leu Glu Val
                565                 570                 575

Glu Glu Pro His Val Gly Asn Thr Trp Glu Lys Pro
                580                 585

<210> SEQ ID NO 70
<211> LENGTH: 588
<212> TYPE: PRT
<213> ORGANISM: Artificial
<220> FEATURE:
<223> OTHER INFORMATION: 3173 mutant D49A/F418Y

<400> SEQUENCE: 70

Met Gly Glu Asp Gly Leu Ser Leu Pro Lys Met Met Asn Thr Pro Lys
1               5                   10                  15

Pro Ile Leu Lys Pro Gln Pro Lys Ala Leu Val Glu Pro Val Leu Cys
                20                  25                  30

Asp Ser Ile Asp Glu Ile Pro Ala Lys Tyr Asn Glu Pro Val Tyr Phe
            35                  40                  45

Ala Leu Glu Thr Asp Glu Asp Arg Pro Val Leu Ala Ser Ile Tyr Gln
        50                  55                  60

Pro His Phe Glu Arg Lys Val Tyr Cys Leu Asn Leu Leu Lys Glu Lys
65                  70                  75                  80

Val Ala Arg Phe Lys Asp Trp Leu Leu Lys Phe Ser Glu Ile Arg Gly
                85                  90                  95

Trp Gly Leu Asp Phe Asp Leu Arg Val Leu Gly Tyr Thr Tyr Glu Gln
                100                 105                 110

Leu Arg Asn Lys Lys Ile Val Asp Val Gln Leu Ala Ile Lys Val Gln
            115                 120                 125

His Tyr Glu Arg Phe Lys Gln Gly Gly Thr Lys Gly Glu Gly Phe Arg
        130                 135                 140

Leu Asp Asp Val Ala Arg Asp Leu Leu Gly Ile Glu Tyr Pro Met Asn
145                 150                 155                 160

Lys Thr Lys Ile Arg Glu Thr Phe Lys Asn Asn Met Phe His Ser Phe
                165                 170                 175

Ser Asn Glu Gln Leu Leu Tyr Ala Ser Leu Asp Ala Tyr Ile Pro His
                180                 185                 190

Leu Leu Tyr Glu Gln Leu Thr Ser Ser Thr Leu Asn Ser Leu Val Tyr
        195                 200                 205

Gln Leu Asp Gln Gln Ala Gln Lys Val Val Ile Glu Thr Ser Gln His
        210                 215                 220

Gly Met Pro Val Lys Leu Lys Ala Leu Glu Glu Glu Ile His Arg Leu
225                 230                 235                 240

Thr Gln Leu Arg Ser Glu Met Gln Lys Gln Ile Pro Phe Asn Tyr Asn
                245                 250                 255

Ser Pro Lys Gln Thr Ala Lys Phe Phe Gly Val Asn Ser Ser Ser Lys
                260                 265                 270

Asp Val Leu Met Asp Leu Ala Leu Gln Gly Asn Glu Met Ala Lys Lys
            275                 280                 285
```

Val Leu Glu Ala Arg Gln Ile Glu Lys Ser Leu Ala Phe Ala Lys Asp
    290                 295                 300

Leu Tyr Asp Ile Ala Lys Arg Ser Gly Gly Arg Ile Tyr Gly Asn Phe
305                 310                 315                 320

Phe Thr Thr Thr Ala Pro Ser Gly Arg Met Ser Cys Ser Asp Ile Asn
                325                 330                 335

Leu Gln Gln Ile Pro Arg Arg Leu Arg Ser Phe Ile Gly Phe Asp Thr
            340                 345                 350

Glu Asp Lys Lys Leu Ile Thr Ala Asp Phe Pro Gln Ile Glu Leu Arg
        355                 360                 365

Leu Ala Gly Val Ile Trp Asn Glu Pro Lys Phe Ile Glu Ala Phe Arg
    370                 375                 380

Gln Gly Ile Asp Leu His Lys Leu Thr Ala Ser Ile Leu Phe Asp Lys
385                 390                 395                 400

Asn Ile Glu Glu Val Ser Lys Glu Glu Arg Gln Ile Gly Lys Ser Ala
                405                 410                 415

Asn Tyr Gly Leu Ile Tyr Gly Ile Ala Pro Lys Gly Phe Ala Glu Tyr
            420                 425                 430

Cys Ile Ala Asn Gly Ile Asn Met Thr Glu Gln Ala Tyr Glu Ile
        435                 440                 445

Ser Gln Lys Val Glu Glu Val Leu His Lys Asp Cys Arg Gln His Gln
    450                 455                 460

Val Ala Tyr Glu Arg Phe Lys Tyr Asn Glu Tyr Val Asp Asn Glu Thr
465                 470                 475                 480

Trp Leu Asn Arg Thr Tyr Arg Ala Trp Lys Pro Gln Asp Leu Leu Asn
                485                 490                 495

Tyr Gln Ile Gln Gly Ser Gly Ala Glu Leu Phe Lys Lys Ala Ile Val
            500                 505                 510

Leu Leu Lys Glu Thr Lys Pro Asp Leu Lys Ile Val Asn Leu Val His
        515                 520                 525

Asp Glu Ile Val Val Glu Ala Asp Ser Lys Glu Ala Gln Asp Leu Ala
    530                 535                 540

Lys Leu Ile Lys Glu Lys Met Glu Glu Ala Trp Asp Trp Cys Leu Glu
545                 550                 555                 560

Lys Ala Glu Glu Phe Gly Asn Arg Val Ala Lys Ile Lys Leu Glu Val
                565                 570                 575

Glu Glu Pro His Val Gly Asn Thr Trp Glu Lys Pro
            580                 585

<210> SEQ ID NO 71
<211> LENGTH: 28
<212> TYPE: DNA
<213> ORGANISM: Artificial
<220> FEATURE:
<223> OTHER INFORMATION: 28T

<400> SEQUENCE: 71
gatgcggccg cttgtatctg atactgct                                      28

<210> SEQ ID NO 72
<211> LENGTH: 30
<212> TYPE: DNA
<213> ORGANISM: Artificial
<220> FEATURE:
<223> OTHER INFORMATION: 30B
<400> SEQUENCE: 72
ggagcagtat cagatacaag cggccgcatc                                    30

VECTORS, KITS AND METHODS FOR CLONING DNA

STATEMENT REGARDING FEDERALLY SPONSORED RESEARCH

The invention was made with United States government support awarded by the Department of Health and Human Services National Human Genome Research Institute (Grant No. 2R44HG002627-02). The United States has certain rights in this invention.

INTRODUCTION

Molecular biology is founded on technology that facilitates cloning and sequencing of polynucleotide sequences. Although rapid advances have been made in obtaining and assembling vast amounts of sequence information, there have been very few improvements in the vectors used for generating plasmid libraries for shotgun sequencing or for conventional cloning of individual genes. Common vectors are typically maintained at high copy number and induce transcription and translation of inserted fragments, causing instability and/or loss of recombinants. Subsequent deletion or rearrangement of "unstable" DNA may result in sequence stacking, clone gaps, or other difficulties in creating plasmid libraries, especially from DNA with a high percentage (e.g., >65%) of adenine and thymine bases ("AT-rich DNA").

By far, the most common plasmids used for cloning are pUC18 and its closely related derivatives. These plasmid vectors have several notable features, such as their blue/white screening capacity, large multiple cloning site, high copy number, and the ability to generate RNA transcripts and single-stranded DNA. However, potential disadvantages of these vectors make them unsuitable for certain applications. For example, the blue/white screen causes a high level of transcription and translation of cloned insert DNA, which often selects against the clones containing open reading frames. Inserts containing multiple tandem copies of trinucleotide repeats are rendered unstable upon transcription, as are regions containing long polyT tracts. The screen is also unreliable for detecting small inserts and inserts containing active promoters, both of which may lead to production of false negative or blue colonies. Further, transcription from promoters in the cloning site may interfere with expression of the antibiotic selection gene or the origin of replication of the plasmid, causing loss of the clone. Finally, the supercoiling of pUC plasmids may induce rearrangement of some recombinant sequences, particularly those with strong secondary structure.

One commonly used method for cloning polymerase chain reaction (PCR) products, described in U.S. Pat. Nos. 5,847,993 and 5,827,657, involves the use of circular plasmids that can be cut with restriction endonucleases to produce single 3' deoxythymidine monophosphate ("dTMP"). This method relies on the ability of Taq DNA polymerase and other non-proofreading DNA polymerases to introduce a single deoxyadenosine monophosphate ("dAMP") overhang at the 3' end of polynucleotides during PCR amplification in the presence of all four nucletotides. Another commonly used method for making plasmids that have a single 3' dTMP, deoxyuridine monophosphate ("dUMP") or deoxyinosine monophosphate ("dIMP"), described in U.S. Pat. No. 5,856,144, is to incubate any blunt ended DNA with Taq DNA polymerase and either dTTP, dUTP, or dITP to create the single base pair overhangs. An "A-tailed" PCR-amplified polynucleotide can then be ligated to any of the complementary base-tailed vectors using standard methods, without the need for prior purification of the insert. Accordingly, all the vectors that have been developed to directly clone PCR products contain either a single 3'T- or 3'U-, or 3'I-overhang. Examples include plasmids pCR2001, pCR. II, pTOPO TA (Invitrogen, Carlsbad, Calif.); pKRX (ATCC, Rockville, Md.); pSC-A (Stratagene, La Jolla, Calif.); and the original pTA12 vector (Invitrogen). T-tailing or U-tailing can be also accomplished using a non-proofreading polymerase such as Taq DNA polymerase to add a dTTP or dUTP to a blunt-ended vector, as found in, e.g., pGEM-T (Promega, Madison, Wis.), or pT7Blue (Novagen, Madison, Wis.).

Despite the usefulness of TA and TU cloning, the ligation reactions are extremely slow, due to the inherently low ligation efficiency of DNA containing single 3'T and 3'A overhangs. The length of time required to complete the ligation reaction has been addressed by the covalent coupling of topoisomerase from vaccinia virus to each terminus of the T-tailed cloning vector, as described in U.S. Pat. No. 6,916,632. This alteration decreases the required ligation time to as little as five minutes, but significantly increases the cost to the user. Moreover, the available TA cloning vectors possess further limitations, including a frequent inability to clone large fragments (e.g., >8 kb) or fragments that contain AT-rich regions. A very high background of empty vector clones has also been observed. These problems are exacerbated when cloning toxic genes, such as viral gene products and nucleases.

Another challenge frequently encountered during cloning is the formation of recombinants containing more than one insert fragment per recombinant event. It is important to minimize or eliminate multiple inserts to facilitate accurate assembly of large sequences, for example, contiguous sequences ("contigs") from many smaller clones in shotgun sequencing projects. Blunt-ended fragments readily form concatamers in ligation reactions, generating multiple unrelated insert products. It is generally understood that in a typical reaction containing blunt inserts and a blunt vector, up to 10-20% of the recombinant clones may contain multiple inserts. Multiple inserts greatly complicate sequence analysis and assembly of multiple fragments into a proper contiguous assembly.

One method that has been used to avoid cloning multiple inserts in libraries of blunt, random fragments (e.g., those generated by shearing or by degenerate PCR) involves ligating linkers with an asymmetric endonuclease recognition sequence, e.g., a BstXI site, to the insert DNA. The linker-ligated fragments are then gel purified and ligated to a vector with termini that are compatible with those of the asymmetric linker sequence. A major disadvantage of this method is that removal of the unligated linkers is difficult, time-consuming, and inefficient. Considerable effort and expertise is required to generate a library that has a high level of true recombinants and low levels of inserts containing linker only. Thus, a need exists for a convenient and reliable method of producing libraries of random inserts that are substantially free of multiple insert recombinants or recombinants that contain only linkers.

BRIEF SUMMARY OF THE INVENTION

In general, the invention provides universal and efficient molecular cloning methods and compositions employing single 3' deoxy- and dideoxy-nucleotide overhangs. The method and compositions are particularly suitable for cloning PCR-amplified sequences, but any polynucleotide sequence may be cloned by way of the invention.

In one aspect, the invention provides a vector preparation for cloning. The vector preparation is a double-stranded DNA molecule having two 3' termini, each 3' terminus having an overhang that is complementary to a deoxyguanosine monophospate ("dGMP"). The overhang is a single, unpaired deoxycytidine monophospate ("dCMP"), or alternatively, is a nucleotide analog capable of hybridizing to an unpaired dGMP. The invention also provides a cloning construct configured to produce the vector preparation upon cleavage with a restriction endonuclease. The cloning construct includes two restriction endonuclease sites for producing the overhang at each 3' terminus.

In another aspect, the invention provides a kit containing instructions for use of the kit, and the vector preparation or cloning construct of the invention.

In yet another aspect, the invention provides a method of preparing a double-stranded polynucleotide for cloning. In one embodiment, the method encompasses treating the polynucleotide to provide an overhang at each 3' terminus, where each overhang is a single unpaired dGMP, or is a nucleotide analog capable of hybridizing to an unpaired dCMP. In another embodiment, the method encompasses treating the polynucleotide to provide an overhang at each 3' terminus, where each overhang is a single unpaired dideoxynucleotide monophosphate ("ddNMP").

In a further aspect, the invention provides a method of cloning a double-stranded polynucleotide. The method encompasses steps of preparing the polynucleotide for cloning, ligating the prepared target polynucleotide to a vector preparation to provide a recombinant molecule, transforming a cell with the recombinant molecule to provide a transformed cell, and incubating the transformed cell under conditions suitable for cloning the polynucleotide. In this aspect of the invention, the vector preparation is a double-stranded DNA molecule having two 3' termini, each 3' terminus having an overhang that is complementary to an unpaired dGMP.

In another aspect, the invention provides a method of cloning a double-stranded polynucleotide. The method includes steps of preparing the polynucleotide for cloning according to the invention, ligating the prepared target polynucleotide to a vector preparation of the invention to provide a recombinant molecule, transforming a cell with the recombinant molecule to provide a transformed cell, and incubating the transformed cell under conditions suitable for cloning the polynucleotide. In this aspect of the invention, the vector preparation is a double-stranded DNA molecule having two 3' termini, each 3' terminus having an overhang that is capable of hybridizing to an unpaired ddNMP.

In yet a further aspect, the invention provides a method of preparing a library of recombinant molecules. In some embodiments, the steps of the method include randomly shearing a plurality of polynucleotides and cloning each polynucleotide according to any of the cloning methods described herein. In some embodiments, less than about 5% of the recombinant molecules comprise more than one target polynucleotide per vector preparation.

DETAILED DESCRIPTION OF SEVERAL EMBODIMENTS

The invention provides a universal cloning system that variously encompasses the following attributes: 1) it substantially prevents recombinant molecules from including more than one insert per vector; 2) it provides rapid, reliable, and cost-effective cloning of DNA fragments, including fragments that are otherwise difficult to clone (e.g., large and/or AT-rich PCR products); 3) it permits direct cloning of PCR products; 4) it permits cloning of blunt fragments without requiring linker sequences; and 5) it substantially decreases the number of recombinant molecules that do not contain insert, i.e., "background." Several embodiments of this invention are contemplated.

Vector Preparations and Cloning Constructs

Some embodiments of the invention provide vector preparations useful for cloning polynucleotide sequences of interest. As used herein, a "vector" is a DNA molecule to which heterologous DNA may be operatively linked so as to bring about replication of the heterologous DNA. Vectors are conventionally used to deliver DNA molecules to cells, including *E.coli* cells that are typically used in a majority of cloning applications.

Figure 2:
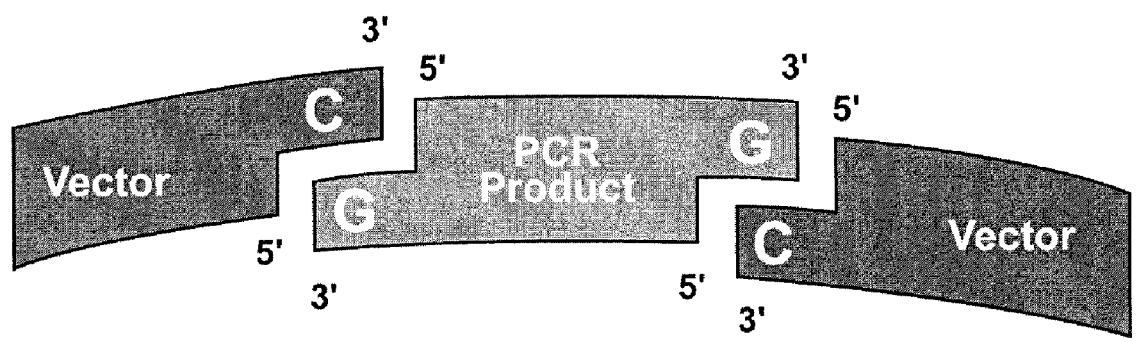
FIG. 2 is a schematic diagram showing the basis for cloning according to several embodiments of the invention.
Figure 3:
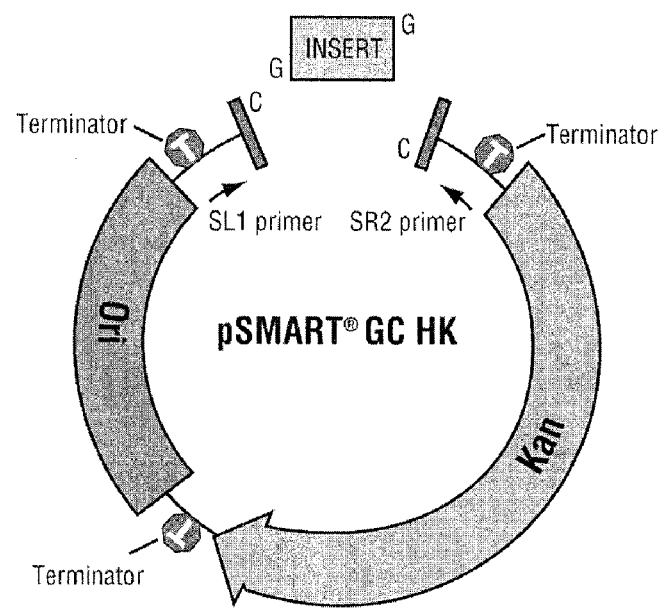
FIG. 3 is a schematic diagram of one embodiment of a cloning construct of the invention, referred to herein as pSMART®GC HK.

The vector preparations are double-stranded DNA molecules having two 3' termini and are constructed to include an overhang at each 3' terminus. Each of the overhangs is capable of hybridizing to an unpaired dGMP on a 3' terminus of an opposing strand of a heterologous double-stranded DNA molecule, i.e., the polynucleotide to be cloned. In some cases, the overhang is a single, unpaired dCMP that base pairs via three hydrogen bonds to a single, unpaired dGMP overhang on the opposing strand, as depicted schematically in FIG. 2. Such vectors are also referred to herein as "C-tailed." In other cases, the overhang is a single, unpaired nucleotide analog that base pairs to an overhanging dGMP on the opposing strand via one or more hydrogen bonds or other intermolecular interactions. As used herein, a "nucleotide analog" is any non-naturally occurring structural analog of a nucleotide that is capable of base pairing to a dGMP (or G-tail). Example of such analogs are known in the art, and include, but are not limited to, inosine, which can form hydrogen bonds with any of the naturally occurring nucleotides, "iso-cytidine," which differs from cytidine by the transposition of the amino and carbonyl groups, as well as various other nucleotide analogs as described by, for example, Day J P, Nucleic Acids Res., 7(8): 1810-1818 (1999), which is incorporated herein by reference. Nucleotide analogs that may hybridize to dGMP also may include chain terminating analogs including acyNTPs, ddNTPs, analogs that have moieties that allow facile detection, including fluorescently labeled nucleotides, e.g., fluorescein or rhodamine derivatives, and/or combinations of chain terminators with detectable moieties, e.g., dye terminators. Suitable nucleotide analogs may also have alternative backbone chemistries, e.g., O-methyl or 2'azido linkages, and/or alternative ring chemistries.

A principle feature of the vector preparation is the single base (either the dCMP or nucleotide analog) overhang on the 3' terminus of each strand of the double-stranded DNA. It is this overhang that provides the cohesive termini for base pairing with the cohesive termini of the double-stranded polynucleotide to be cloned. The overhang is suitably generated by restriction digestion of a plasmid construct or linear vector construct, as further described below. Alternatively, the vector preparation may be artificially synthesized using techniques known in the art or may be prepared by PCR amplification. In a further alternative, the single base overhang may be added by use of a terminal deoxynucleotidyl transferase enzyme. However, it is to be understood that the vector preparations are not limited by any particular method of production.

In some embodiments, the vector preparation is a plasmid construct that has been linearized. A "plasmid construct," as the term is used herein, refers to any autonomously replicating, circular DNA molecule which is not found in nature, i.e., it is artificially synthesized or generated using recombinant techniques. The term "plasmid," is used generically herein to encompass any circular DNA molecule, and includes small plasmids (e.g., less than 20 kb), as well as bacterial artificial chromosomes ("BACs"), cosmids and fosmids. A "linearized" plasmid is a circular plasmid construct that has been subjected to restriction endonuclease digestion and/or otherwise treated as described above, such that at least two 3' termini each having a single base overhang are generated.

In other embodiments, the vector preparation is a linear vector construct having dissociated right and left arms. A "linear vector," as used herein, refers to a construct derived from a bacteriophage of $E.$ $coli$ that replicates during lysogeny as an extrachromosomal, double-stranded linear structure. A linear vector is "derived from" a bacteriophage when a linear genomic structure is isolated from the host microorganism and subjected to further molecular manipulation to produce a cloning construct. Suitable linear vectors useful as starting materials for producing vector preparations of the invention include, but are not limited to, derivates of bacteriophages lambda and N15, such as pG591 (SEQ ID NO: 68) and pJAZZ-KA (Lucigen Corp., Middleton, Wis.) (SEQ ID NO: 5). Suitable linear vectors are also described in U.S. Provisional Application Ser. No. 60/747,733 and U.S. Provisional Application Ser. No. 60/758,479, the entire disclosures of which are incorporated herein by reference. Vector preparations are prepared from linear vector constructs by subjecting the constructs to restriction endonuclease digestion such that at least two 3' termini are generated. Upon cleavage by restriction endonucleases, linear vector preparations comprise a "right arm" and a "left arm," wherein the two arms are dissociated from each other, i.e., they are not covalently connected.

The term "cloning construct" refers to either a plasmid construct or linear vector construct that is configured to produce a vector preparation of the invention when subjected to restriction endonuclease digestion and optionally, further steps to append an appropriate 3' single base overhang. Because dCMP does not base pair to itself, the vector preparations are prepared from cloning constructs by removing an intervening segment between two endonuclease restriction sites in the cloning construct. The restriction sites may be the same or different, but should generate single, overhanging 3' dCMPs at each of the sites upon cleavage by the corresponding enzyme. Suitable restriction endonucleases include, but are not limited to, commercially available enzymes Hph I, HpyCH4 III, Hpy188 I, Mbo II, Xcm I, and Ahd I (New England Biolabs catalog, 2005-2006). For example, the restriction enzyme Ahd I recognizes the interrupted palindrome sequence GACNNN/NNGTC, cleaving the DNA after the hash mark, leaving a single base 3' overhang. The letter N in the recognition sequence indicates that any base (A, C, G, or T) can occupy the designated position and still be digested by the enzyme. Selection of an appropriate restriction enzyme depends on several considerations, including whether recognition sequences in addition to the desired recognition sequences (i.e., those that are used to generate the single base overhangs for pairing with the overhangs of the insert) are present in the vector preparation. Screening for such additional sites, as well as removing such sites as desired, e.g., by PCR using appropriate primers, is well within the capabilities of those skilled in the art. Alternatively, the cloning construct is configured to produce the vector upon cleavage at two restriction endonuclease sites that produce blunt termini, followed by incubation with a terminal deoxynucleotidyl transferase.

As will be appreciated, any cloning construct may be modified to provide the vector preparation of the invention. Suitably, the cloning construct is selected or modified to contain appropriate restriction endonuclease recognition sites, as described above.

Suitably, the vector preparations and/or the cloning constructs from which the vector preparations are prepared further include additional elements useful for cloning. Such elements may include, but are not limited to, an origin of replication, a sequence encoding a selectable marker, a sequence encoding a screening marker, one or more transcription termination sequences and/or one or more regulatory sequences.

An "origin of replication," as used herein, refers to a DNA sequence that confers functional replication capabilities to a polynucleotide within a host cell. Origins may be conditional (i.e., requiring the presence of trans-acting factors) or non-conditional. Origins of replication incorporated into the vector preparations of the invention may be a high-copy origin of replication (e.g., colE1 origin of replication), a low copy origin (e.g., the colE1 origin in conjunction with the ROP gene of pBR322) or a single-copy origin of replication (e.g., the ori2 origin of the F plasmid of *E. coli*). A "high copy" origin of replication suitably provides about 100 to about 500 copies/cell. A "low copy" origin of replication suitably provides about 5 to about 40 copies/cell. Selection of an appropriate origin of replication is within the skill in the art. For example, it is appreciated that low copy and single copy origins increase the ability to clone intact polynucleotide sequences that are difficult to maintain due to, e.g., size or AT content.

As used herein, a "selectable marker" refers to a phenotypic trait conferred on transformed cells that protects them from a selective agent in their environment, i.e., the growth media. Examples of selectable markers include, but are not limited to, antibiotic resistance markers (e.g., genes encoding resistance to kanamycin, ampicillin, chloramphenicol, gentamycin, or trimethoprim and metabolic markers (e.g., amino acid synthesis genes or transfer RNA genes). As is appreciated in the art, the origin of replication can also be used as a selectable marker. Use of single or multiple selectable markers is contemplated for use in conjunction with the present invention.

As used herein, a "screening marker" refers to a phenotypic trait that provides a means for distinguishing cells transformed with recombinant molecules that have inserts from cells that do not have recombinants, i.e., those having only "empty" vector. Notable examples suitable for use in the present invention include the lacZ-alpha coding sequence, which confers blue/white screening capability, and toxic product coding sequences (e.g., sacB, ccdB), wherein failure to interrupt the toxic product coding sequence with an insert results in a phenotype that is toxic to the cell.

Optionally, the vector preparations (or cloning constructs) of the invention include a transcriptional termination sequence proximal to each 3' overhang. As used herein and in the art, a "transcriptional termination sequence," is a regulatory sequence which induces dissociation of a transcription complex in prokaryotic cells. A transcriptional termination sequence is "proximal to" a 3' overhang when it is configured to reduce transcription from the insert sequence into the vector after recombination events have taken place. The use of transcriptional terminator sequences most suitably prevents interference with the function of replication origins, selectable markers or screening markers, if present in the vector. Suitable transcriptional termination sequences are palindromic sequences which form hairpin loop structures. The transcriptional termination sequences may be the same or different, but use of different transcriptional termination sequences results in a more stable cloning construct due to a reduced likelihood of recombination between them. Transcriptional termination sequences may be unidirectional or bidirectional. Bidirectional terminators advantageously block transcription into the insert from vector promoters and into the vector from promoters within the insert. Most suitably, the transcriptional terminators are functional in the absence of host factors (i.e., are rho independent). Suitable transcriptional terminator sequences include the trpA terminator, T3 terminator, T7 terminator, rrnB T1 terminator, and others (Reynolds, et. al, J. Mol. Biol. (1992) 224:31-51, incorporated herein by reference in its entirety). Suitably, an additional transcriptional termination sequence may be placed proximal to the origin of replication.

Vector preparations are optionally dephosphorylated prior to ligation with inserts. Dephosphorylation minimizes self ligation and production of "empty background" vectors. As is appreciated in the art, when vector preparations are dephosphorylated, it is necessary to phosphorylate the polynucleotide to be cloned, either by use of phosphorylated primers during PCR amplification, or by incubation with a kinase, e.g., T4 polynucleotide kinase, or by digestion with a restriction enzyme that leaves a terminus compatible with that of the vector. Most suitably, when a kinase is used to phosphorylate the primers or insert DNA, agarose gel purification is performed to remove the kinase prior to ligation with the vector preparations.

Preparing Polynucleotides for Cloning

Polynucleotides that are suitably cloned using the vector preparations of the invention, also referred to herein as "targets," "insert sequences," or simply, "inserts," include any double-stranded DNA fragments. Inserts that may cloned include, but are not limited to, PCR products, polynucleotides from random "shotgun" libraries, sheared polynucleotides obtained from, e.g., an environmental source, and known or unknown target sequences of interest. Inserts of virtually any size, up to about 200 to 300 kb, may be cloned, depending on the particular vector preparation selected.

The inserts are prepared for cloning by treating the polynucleotide to provide an overhang on each 3' terminus that is compatible with (i.e., capable of hybridizing to) the vector preparation to be used. Accordingly, in some embodiments, the overhang is a single, unpaired dGMP that base pairs via three hydrogen bonds to a single, unpaired dCMP overhang on the opposing vector strand, as depicted schematically in FIG. 2. In other cases, the overhang is a single, unpaired nucleotide analog that base pairs to an overhanging dCMP on the opposing vector strand via one or more hydrogen bonds or other intermolecular interactions.

One suitable method of generating single 3' dGMP overhangs on the insert is to amplify the insert using PCR with suitable paired primers, dNTPs and a non-proofreading DNA polymerase. Alternatively, 3' dGMP overhangs may be appended to the insert by first modifying the insert to provide blunt termini (either by suitable restriction endonuclease digestion with a blunt-cutting endonuclease or by PCR using any suitable proofreading or non-proofreading polymerase, paired primers and dNTPs), followed by incubation of the blunt-ended insert with a non-proofreading polymerase and dGTP. As yet another alternative, terminal deoxynucleotidyl transferase can be used according to standard methods to append dGMP or nucleotide analogs to the insert.

"Non-proofreading polymerases" refers to polymerases that have substantially no 3' to 5' exonuclease activity, either natively or by virtue of one or more mutations. It is well within the skill in the art to screen for exonuclease activity, and any polymerase which substantially lacks exonuclease activity may be used in the present invention. Non-proofreading polymerases have been found by the inventors to efficiently append single, 3' overhangs to double-stranded DNA molecules, either during incubation of blunt-ended polynucleotides with the non-proofreading polymerase, or in PCR reactions that contain the non-proofreading polymerase. Examples of non-proofreading polymerases are known in the art and include both native polymerases of, e.g., *Thermus aquaticus, Thermus brockianus, Thermus filiformis, Thermus flavus, Thermus thermophilis* or *Thermotoga maritem*, or any of several polymerases that have been mutated to delete the exonuclease function, as described in, e.g., Kong H, et al., J. Biol. Chem., 268(3):1965-75 (Jan. 25, 1993), the disclosure of which is incorporated herein by reference.

Additional suitable non-proofreading polymerases are described in International Application PCT/US2006/039406, which is incorporated herein by reference. Particularly suitable polymerases for use in the invention are mutants of "polymerase 3173" (also called "PYROPHAGE" polymerases, Lucigen, Middleton, Wis.) that have the native exonuclease function deleted, as described in PCT/US2006/039406 ("exo-minus mutants of 3173"). Suitable exo-minus mutants of 3173 polymerases may have additional mutations as well, useful in further embodiments of the invention as described below. The polypeptide sequences for two suitable 3173 mutant polymerases suitable for use in conjunction with the invention are given in SEQ ID NOS: 69-70.

A further embodiment of the invention is particularly suitable for blocking the addition of more than one insert per vector preparation. In these embodiments, the polynucleotide insert is prepared for cloning by treating the polynucleotide to provide 3' overhangs that are each a single, unpaired, dideoxynucleotide monophosphate (ddNMP), or "dideoxy-tailing," as also used herein. The ddNMP tail used in this embodiment may be any of ddAMP, ddCMP, ddGMP, ddTMP, ddUMP, or ddIMP. The dideoxy-tailed insert can be ligated under standard conditions to any vector preparation that has 3' overhangs that are compatible with the dideoxy-tailed insert, for example, a vector preparation that has a single dAMP appended to each of its 3' termini can be ligated to an insert that is tailed with ddTTP.

Dideoxy-tailed inserts are suitably prepared by incubating the polynucleotide in a reaction comprising a ddNTP and a polymerase that is both non-proofreading and non-discriminating. In some embodiments, the polynucleotide is modified to provide blunt termini prior to the reaction, either by digestion with a blunt-cutting endonuclease, or by incubation with a suitable polymerase (e.g., T4 DNA polymerase) and dNTPs. Alternatively, terminal deoxynucleotidyl transferase can be used to append ddAMP, ddCMP, ddGMP, ddTMP ddUMP, or ddIMP to the 3' termini of the insert.

A "non-discriminating" polymerase is a polymerase that has the ability to incorporate nucleotide analogs, i.e., polymerases that do not discriminate, or exhibit reduced discrimination, against incorporation of nucleotide analogs. Most suitably, no-discriminating polymerases are also non-proofreading as described above, however, it is specifically contemplated that mixtures of polymerases may also be used to achieve equivalent results.

Discrimination of a polymerase for nucleotide analogs can be measured by, e.g., determining kinetics of the incorporation reaction, i.e., the rate of phosphoryl transfer and/or binding affinity for nucleotide analog. Suitable non-discriminating polymerases are described in International Application PCT/US2006/039406, which is incorporated herein by reference in its entirety. Most suitably, a non-proofreading polymerase is mutated in the dNTP binding domain to reduce discrimination against ddNTPs. As is known in the art, the dNTP binding domain of most polymerases may be characterized as having the sequence K N1 N2 N3 N4 N5 N6 N7 Y G/Q, wherein N1-N7 are independently any amino acid and N7 may or may not be present, depending on the polymerase. Most suitably, a substitution is introduced at position N4 of the dNTP binding domain. Most suitably, the amino acid at position N4 is substituted to tyrosine or a functionally equivalent amino acid that may be chosen by routine experimentation. The sequence of a particularly suitable non-proofreading, non-discriminating polymerase for use in the invention is a double mutant of polymerase 3173, the polypeptide sequence of which is shown in SEQ ID NO: 70.

Cloning Methods

Using the above-described vector preparations and methods of preparing polynucleotides for cloning, any double-stranded polynucleotide sequence of interest may be cloned in electrocompetent or chemically competent cells (both of which are referred to herein as "competent cells") capable of maintaining and/or replicating the recombinant polynucleotides under standard conditions. For any given cloning application, selection and design of the appropriate vector is within the skill of the artisan.

Accordingly, methods of cloning a polynucleotide in accordance with the invention include steps of preparing the polynucleotide for cloning as detailed herein, ligating the prepared polynucleotide to a vector preparation to provide a recombinant molecule, transforming a competent cell to provide a transformed cell, and incubating the transformed cell under conditions suitable for cloning the polynucleotide. Selection of appropriate means for carrying out these steps is well within the skill in the art in view of the present disclosure.

Preparation of Libraries

In another embodiment of the invention, the above-described cloning methods are used to prepare libaries. Suitably, for preparation of libraries from high molecular weight DNA (e.g., genomic DNA from prokaryotic or eukaryotic organisms; bacterial artificial chromosome ("BAC"), P1-derived artificial chromosome ("PAC"), or yeast artificial chromosome ("YAC") clones), or environmental sources, randomly sheared DNA inserts are prepared according to the above methods, ligated under standard conditions to vector preparations of the invention to form recombinant molecules, and transformed into competent cells to generate a library of recombinant clones. In particularly suitable embodiments of the invention, less than about 5% of the recombinant molecules comprise more than one target polynucleotide per vector preparation. More preferably, less than about 1% of the recombinant molecules comprise more than one target polynucleotide per vector preparation.

Kits for Cloning

Particular embodiments of the invention provide kits useful in cloning one or more polynucleotides. In addition to either the vector preparation or cloning construct of the invention, kits include instructions for informing the user how to use the kit. Further additional components suitably provided with the kits include a non-proofreading polymerase; a non-proofreading, non-discriminating polymerase; or a terminal deoxynucleotidyl transferase; and one or more components selected from a ligase, a kinase, a proofreading polymerase, one or more sequencing primer pairs, one or more amplification primer pairs, competent cells, dNTPs, ddNTPs, nucleotide analogs and reaction buffers suitable for use in carrying out any of the steps for modifying and cloning a polynucleotide of interest according to the present disclosure.

EXAMPLES

The following examples are provided to assist in a further understanding of the invention. The particular materials and conditions employed are intended to be further illustrative of the invention and are not limiting upon the reasonable scope of the appended claims.

Example 1

G-tailing of Blunt-ended DNA Using the Non-proofreading Polymerase from *Thermus aquaticus* (Taq DNA Polymerase)

Bacteriophage lambda DNA (48,502 bp) digested with Hinc II generates 35 fragments with blunt ends containing 5' phosphates. These fragments were treated with Taq DNA polymerase in four separate reactions, containing dATP, dTTP, dGTP or dCTP for 30 minutes at 70° C. The four reactions each contained 10 mM Tris-HCl (pH 9.0), 50 mM KCl, 1.5 mM MgCl2, 0.1% TRITON® X-100 (a nonionic surfactant), 2.5 U Taq DNA polymerase and 200 μM of one of the four dNTPs.

Figure 1:
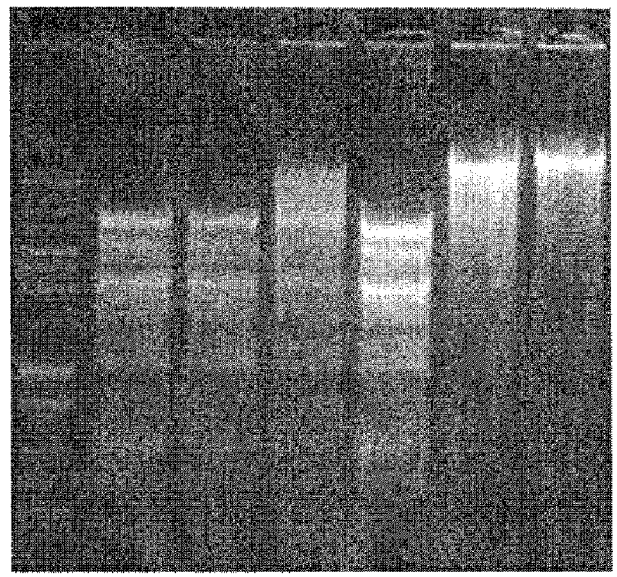
FIG. 1 is a photograph of an agarose gel showing protection of blunt DNA from self-ligation by A or G tailing using Taq DNA polymerase.

The reactions were precipitated using sodium acetate and ethanol, resuspended in water, and incubated with T4 DNA ligase, ligase buffer and riboATP (FIG. 1, Lanes A, T, C, or G). Control reactions contained no ligase (Lane 0) or were ligated as blunt fragments without Taq DNA polymerase treatment (Lane "Blunt"). The self-ligated A- and G-tailed DNA fragments (Lanes A and G) showed no observable mobility shift compared to the unligated control (Lane 0), indicating that most of the ends were not able to ligate efficiently. The ends presumably did not ligate efficiently due to blocking of the end-joining reaction by the single 3'A or 3'G extension. The T-tailed DNA fragments showed moderate mobility shifts (Lane T), and the C-tailed DNA showed significant mobility shifts (lane C). The mobility shifts indicated that very little C-tailing occurs, so the blunt ends remained unmodified and thus were free to self-ligate. A 1 kb ladder was included for size reference (Lane M).

The results, shown in FIG. 1, demonstrate that G-tailing appears to be as efficient as A-tailing for blocking self-ligation of blunt DNA fragments, when the blocking reaction uses Taq DNA polymerase and a single nucleotide.

Example 2

Construction of C-tailed Vectors for Cloning G-tailed DNA

Figure 4:
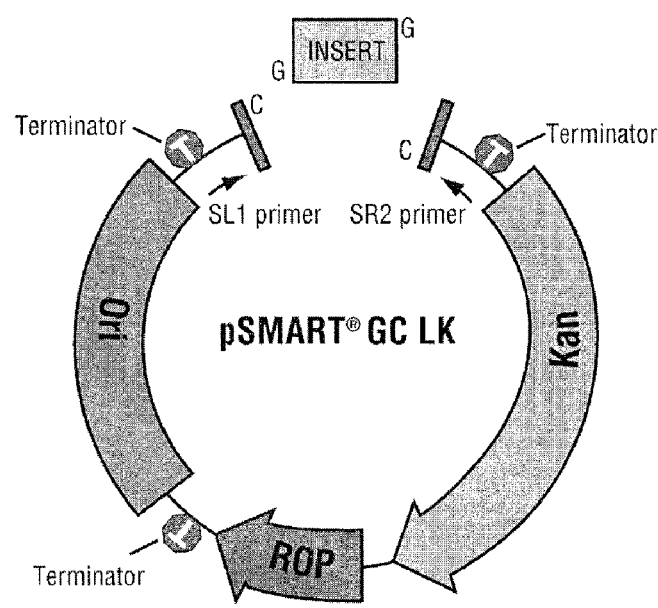
FIG. 4 is a schematic diagram of one embodiment of a cloning construct of the invention, referred to herein as pSMART®GC LK.
Figure 5:
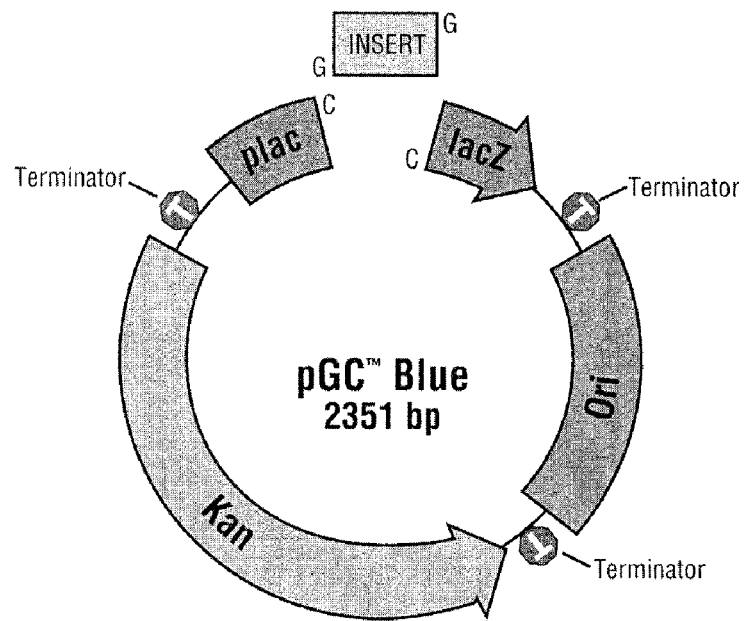
FIG. 5 is a schematic diagram of one embodiment of a cloning construct of the invention, referred to herein as pGC BLUE.
Figure 7:
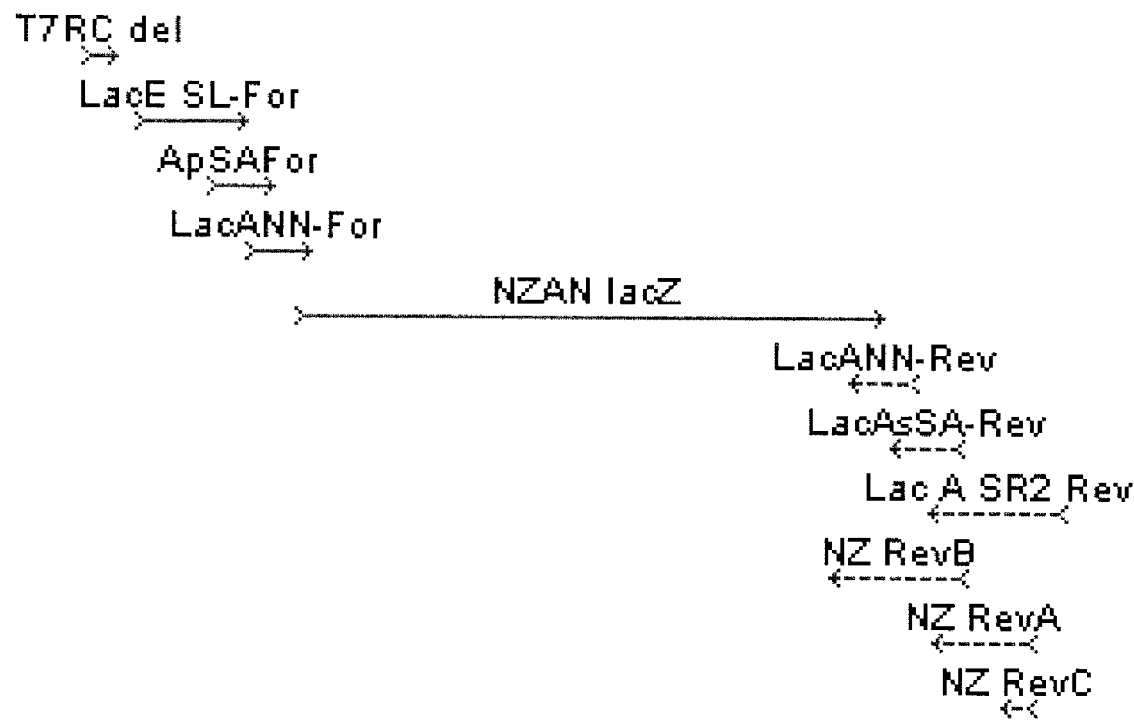
FIG. 7 is a schematic diagram of the position and orientation of primers used for amplification of the lacZ region, used in the preparation of one embodiment of the invention.
Figure 8:
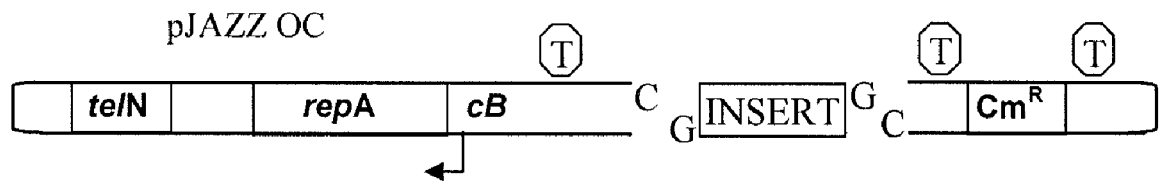
FIG. 8 is a schematic diagram of one embodiment of a cloning construct of the invention, referred to herein as pJAZZ® OC.

Five different cloning constructs were prepared, each having two asymmetric Ahd I sites, designed such that single 3' dCMP overhangs were present on both termini of the linearized plasmid after removal of the intervening region by Ahd I digestion. Two of the cloning constructs were based on pSMART® HK and pSMART® LK plasmids (see FIGS. 4 and 5), and are transcription-free and translation-free to maintain otherwise deleterious DNAs. In the third cloning construct, designated pGC BLUE (see FIG. 6), the Ahd I sites were engineered in-frame with a lacZα peptide coding region. This cloning construct permits use of the blue/white visual screening assay. The fourth cloning construct was a modification of a transcription-free BAC vector, and is designated pSMART® BAC GC (see FIG. 7). The fifth cloning construct, designated pJAZZ® OC (see FIG. 8) is adapted from a linear cloning construct, modified to provide Ahd I sites.

a) Preparation of pSMART®GC HK and pSMART®GC LK transcription-free C-tailed cloning constructs.

pSMART®GC HK and pSMART®GC LK were constructed by modifying pSMART® HCKan (NCBI accession number AF532107) (SEQ ID NO:1) or pSMART® LCKan (NCBI accession number AF532106) (SEQ ID NO:2) respectively. A beta lactamase gene cassette (encoding ampicillin resistance) was obtained by amplifying the ampicillin resistance gene of pUC19 with PCR primers AHDAMPL (SEQ ID NO:7) and ADHAMPR (SEQ ID NO:8), which contain asymmetric Ahd I sites. The PCR amplification reaction was performed with VENT$_R$® DNA polymerase (New England Biolabs, Ipswich, Mass.), a high-fidelity thermophilic DNA polymerase, so the ends would be blunt. The PCR product was ligated a HincII digest of pSMART® HCKan or pSMART® LCKan, transformed into high efficiency, electrocompetent E. Coli cells (E. CLONI® 10G cells, Lucigen, Middleton, Wis.), and plated on agar plates containing ampicillin plus kanamycin. Recombinant clones were assayed for size by agarose gel electrophoresis, and one clone was chosen for DNA sequence analysis for each of the two cloning constructs. The sequences of the resulting clones, designated pSMART®GC HK and pSMART®GC LK, are given in SEQ ID NO:57 and SEQ ID NO:58, respectively.

The final pSMART®GC HK and pSMART®GC LK cloning constructs were prepared for ligation to G-tailed insert DNA by restriction with Ahd I, dephosphorylation with calf intestinal alkaline phosphatase, and gel purification of the vector backbone.

b) Preparation of a lacZ based pGCBlue cloning construct.

pGCBlue (SEQ ID NO: 56) was constructed in three steps. First the LacZα gene and promoter from pCRII-TOPO (SEQ ID NO:3, nucleotides 108-612) were added to the backbone of pSMART® HCKan (SEQ ID NO:1, nucleotides 27-1753). The backbone of the pSMART® HCKan vector was obtained by amplifying with PCR primers S-MCSL (SEQ ID NO:9) and S-MCSR (SEQ ID NO:10). The LacZα gene and promoter were amplified with PCR primers CR2ZL (SEQ ID NO:11) and CR2ZR (SEQ ID NO:12). PCR was performed under standard conditions using VENT$_R$® DNA polymerase. The two PCR products were purified by agarose gel electrophoresis, ligated in the presence of T4 DNA ligase, transformed into E. CLONI cells (Lucigen, Middleton, Wis.), and plated on kanamycin plus XGAL agar plates. Blue recombinant colonies were assayed by restriction analysis and one clone was confirmed by DNA sequence analysis.

In the second step AhdI restriction sites were added to the vector resulting from step one using PCR primers AhdMCSL (SEQ ID NO:13) and AhdMCSR (SEQ ID NO:14). The PCR amplification reaction was performed using standard conditions and purified by agarose gel electrophoresis, self-ligated in the presence of T4 DNA ligase, transformed into E. CLONI cells (Lucigen, Middleton, Wis.) and plated on kanamycin plus XGAL agar plates. Blue recombinant colonies were assayed by restriction analysis and one clone was chosen for DNA sequence analysis.

The third step was replacing the kanamycin open reading frame (ORF) in the pSMART® HCKan backbone (SEQ ID NO:1, nucleotides 200-1024)), which contains a HindIII site, with the kanamycin ORF from pCRII-TOPO (SEQ ID NO:3, nucleotides 1361-2155), which has no HindIII site. This was done to make the HindIII restriction site in the multiple cloning site of the vector unique. The pSMART® HCKan backbone without a kanamycin ORF was made by amplifying the clone from the second step with PCR primers HCKanNoKL (SEQ ID NO:15) and HCKanNoKR (SEQ ID NO:16). The kanamycin ORF from pCRII was amplified using PCR primers CR2ResL (SEQ ID NO:17) and CR2ResR (SEQ ID NO:18). Both PCR amplification reactions were performed using the conditions described above. The two PCR products were purified by agarose gel electrophoresis, ligated in the presence of T4 DNA ligase, transformed into E. CLONI cells (Lucigen, Middleton, Wis.) and plated on kanamycin plus XGAL agar plates. Blue recombinant colonies were assayed by restriction analysis and one clone was chosen for DNA sequence analysis.

The final pGCBlue construct (SEQ ID NO:56) was prepared for ligation to G-tailed insert DNA by restriction with Ahd I, dephosphorylation with calf intestinal alkaline phosphatase, and gel purification of the primary vector backbone.

c) Preparation of a single-copy, transcription-free, C-tailed BAC/FOSMID cloning construct.

Figure 6:
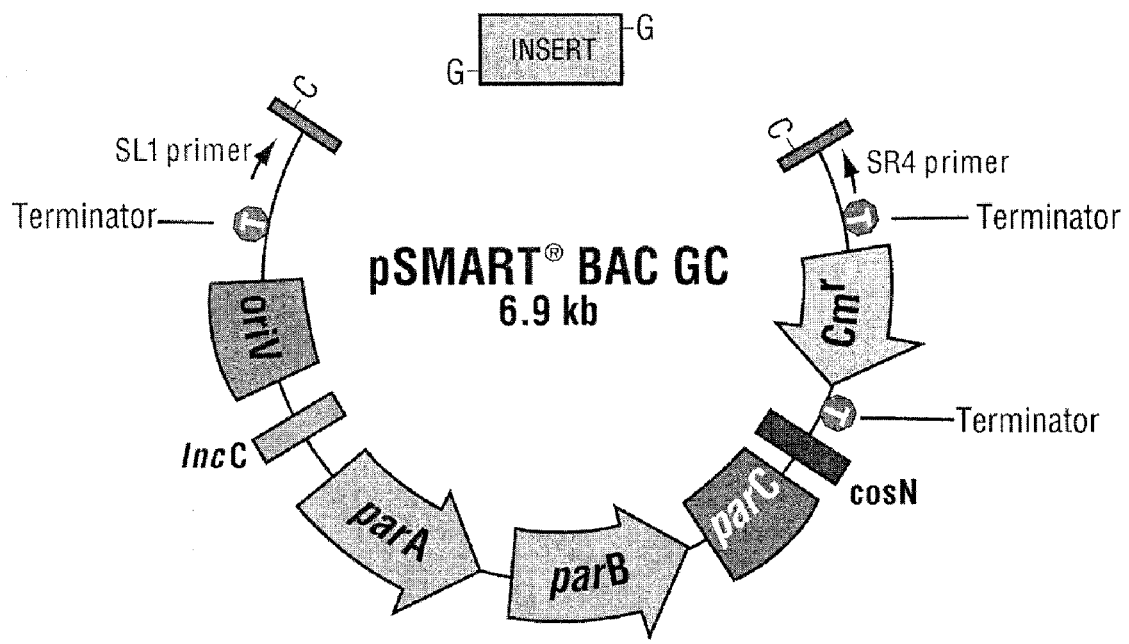
FIG. 6 is a schematic diagram of one embodiment of a cloning construct of the invention, referred to herein as pSMART® BAC GC.

The vector BOL4.2 (SEQ ID NO:60) is a transcription-free BAC/fosmid vector used for G-tailed cloning, referred to herein as pSMART® BAC GC (See FIG. 6). This vector contains the single-copy origin of replication and the partitioning genes of the F plasmid of *E. coli*, which are common to nearly all BAC and fosmid vectors. It also contains the oriV inducible origin of replication.

The pSMART® BAC GC vector was created through a series of nucleic acid cloning steps. First, the plasmid pCC1FOS (Epicentre, Madison, Wis.) (SEQ ID NO:66) was digested with Ahd I, which cuts once within the vector backbone. The linear product was treated to produce blunt termini with DNATERMINATOR® (Lucigen, Middleton, Wis.), a commercially available end modification kit. The end-repaired vector was re-ligated, thereby destroying the Ahd I site. The resulting plasmid, called pCCdAhd3, was digested with Not I and Bsr BI. The digest generated three fragments, including a fragment of ~6 kb that contained the F plasmid partitioning genes and the single-copy ori2 origin of replication. This fragment was made blunt with the DNATERMINATOR® Kit and ligated to a second fragment, which was called "T-CM-T".

A second fragment, called "T-CM-T", was created by multiple rounds of PCR. Fragment T-CM-T contained the T7 terminator, a LacZα gene flanked by multiple cloning sites (MCSs), the rrn terminator, the chloramphenicol resistance gene (camR), and the TonB terminator. In the first set of PCRs, the coding sequence of lacZα gene, the flanking MCSs and transcription terminators, and the promoter of the camR gene were amplified from the vector NZCK3 (SEQ ID NO:63, See Example 2d) using the primers SL1 (SEQ ID NO:19) and pCmOR (SEQ ID NO:20). The promoter and coding region of the camR gene of the vector pSMART® VC (Lucigen, Middleton, Wis.) (SEQ ID NO:4, nucleotides 825-1587) were amplified using the primers pCmF (SEQ ID NO:21) and CamTonB-Rev (SEQ ID NO:22). The resulting lacZ and CamR PCR products were purified, combined, and fused by re-amplification in a PCR containing the primers T7RC-del (SEQ ID NO:23) and CamTonB-Rev (SEQ ID NO:22) to create the fragment T-CM-T. After treating with the DNATERMINATOR® kit, the T-CM-T fragment was ligated to the blunt NotI-Bsr GI fragment of pCCdAhd3, generating the plasmid pBAC3-12 (SEQ ID NO:59).

A BstXI cloning site in the backbone pBAC3-12 was deleted as follows: using pBAC3-12 as a template, a PCR was performed with the primers 2370F (SEQ ID NO:24) and dBstX4382R (SEQ ID NO:25); another PCR reaction was done with the primers dBstXI5185F (SEQ ID NO:26) and Stu5741R (SEQ ID NO:27). The two PCR products were purified, combined, and fused by re-amplification with primers 2370F (SEQ ID NO:24) and Stu5741R (SEQ ID NO:27). The fusion fragment, which contained a mutation in the Bst XI site, was digested with BsrGI and KpnI. pBAC3-12 was also digested with BsrGI and KpnI, and the ~6 kb fragment was ligated to the digested fusion fragment, generating the plasmid pBK2.

A fragment containing the colE1 high-copy origin of replication and the LacZα gene was amplified from pUC19 using the primers dPRHBBlacR (SEQ ID NO:28) and dPRHBBoriF (SEQ ID NO:29). The PCR product was re-amplified with the primers NotLacR (SEQ ID NO:30) and NotOriF (SEQ ID NO:31) to add additional restriction sites to the termini. The product was cut with Not I and ligated to a Not I digest of pBK2 to generate the pSMART BAC GC (SEQ ID NO: 60).

All of the PCR reactions performed here to make the various vector components was done using the proofreading enzyme from *Thermococcus litoralis* VENT$_R$® DNA polymerase, New England Biolabs) using conditions described above. The constructs were all sequenced to verify the correct fusions and sequence changes.

The pSMART BAC GC construct was prepared for ligation to G-tailed insert DNA by restriction with Ahd I, dephosphorylation with calf intestinal alkaline phosphatase, and gel purification of the vector backbone.

d) Preparation of a transcription-free, C-tailed linear cloning construct.

A linear vector cloning construct was created through multiple rounds of PCR amplification and cloning. PCR was performed using according to the manufacture's recommendations, using the VENT® or PHUSION® proofreading polymerases (New England Biolabs). The lacZ fragment of the vector NZAN (SEQ ID NO:5) (sold commercially as pJAZZ®-KA, Lucigen, Middleton, Wis.) was amplified by PCR with the primers LacANN-For (SEQ ID NO:32) and LacANN-Rev (SEQ ID NO:33). The resulting PCR product was re-amplified with the primers LacApSA-For (SEQ ID NO:34) and LacAsSA-Rev (SEQ ID NO:35). See FIG. 7 for the position and orientation of primers used for amplification of the lacZ region. The product was digested with ApaI and AscI, ligated to the 12 kb ApaI fragment and the 2 kb AscI fragment of the vector NZAN, transformed into E. CLONI® 10G-pTel cells (Lucigen, Middleton, Wis.), and selected on plates containing ampicillin plus kanamycin. The resulting linear vector was designated NZASA (SEQ ID NO:62).

To add additional cloning sites and binding sites for sequencing primers, the lacZ fragment was amplified from NZASA using primers LacE-SL1-F (SEQ ID NO:36) and LacA SR2-Rev (SEQ ID NO:37). The resulting PCR product was digested with AflIII, ligated to the end-repaired 10-kb NotI fragment and the 3-kb NcoI fragment of the vector NZASA (SEQ ID NO:61), transformed into E. CLONI® 10G-pTel cells, and selected on plates containing ampicillin plus kanamycin. The resulting linear vector was designated NZAhd (SEQ ID NO:62).

E. CLONI® 10G-pTel cells are a derivative of the E. CLONI® 10G strain (Lucigen, Middleton, Wis.). E. CLONI® 10G-pTel cells contain a plasmid expressing protelomerase (the telN gene product of N15) to allow efficient transformation with the linear vector. To create the E. CLONI® 10G-pTel strain, the telN gene (SEQ ID NO: 6), was PCR-amplified from phage N15 DNA using the following primers: telN-For (SEQ ID NO:38) and telN-Rev (SEQ ID NO:39). The resulting PCR product was digested with BamHI and HindIII. The digested product was cloned into the BamHI/HindIII sites of pGZ119EH, which expresses the target gene under control of IPTG-inducible Ptac promoter (Lessl et al., 1992, J. Bacteriol., 174: 2493-2500). The recombinant vector, named pGZ telN, expresses telN protein and encodes resistance to chloramphenicol. pGZ-telN DNA was transformed into E. CLONI® 10G cells by electroporation to create the strain E. CLONI® 10G-pTel.

A cassette containing the telN gene, the sopBA operon, and the antA gene was subsequently integrated onto the chromosome of E. CLONI® 10G cells as follows: a DNA fragment comprising phage N15 sopBA operon (under control of its own promoter) and the antA antirepressor gene (under control of arabinose-inducible araPBAD promoter) was excised from plasmid pCD31sop (Mardanov A. V., and Ravin N. V. (2004) Abstracts of the conference "Lomonosov-2004", v. 1, p. 21, Moscow, Russia) as an XhoI-MroNI fragment and cloned into the HindIII site of plasmid pJWtelN. The resulting vector, pJW-telN31sop, was partially digested with NotI to excise the fragment containing telN-sopBA-antA, which was purified by gel-electrophoresis and circularized by self-ligation. The circularized fragment was transformed into E.

CLONI® 10G cells carrying the lambda integrase-producing plasmid pJW289t. Colonies that contained an integrated fragment comprising telN gene, sopBA operon and antA antirepressor, and which had lost the pJW289t plasmid were selected as described by Wild J, Hradecna Z, and Szybalski W (2002), Genome 12:1434-44, the disclosure of which is incorporated herein by reference. The resulting ampicillin resistant strain, designated E. CLONI® 10G-telN31S or BIGEASY TSA (Lucigen, Middleton, Wis.), allows efficient transformation with the linear vector and permit induction of copy number.

To create a version of the linear vector for use with the BIGEASY TSA cells, the ampicillin resistance gene of the NZAhd vector was replaced with a chloramphenicol resistance gene, and the AhdI restriction site in the vector backbone was also destroyed. The resulting vector, designated NZCK3 (SEQ ID NO:63), was created by ligation of four fragments as follows:

The first (left-most) fragment was the 7.8 kb AhdI fragment of NZAhd encompassing the left telomere, telN gene, and part of the repA gene. The second fragment was a region of ~4.5 kb amplified from NZAhd by PCR with the primers 7847-F2 (SEQ ID NO:40), which introduces a mutation that destroys the AhdI site, and LacA-SR2-Rev (SEQ ID NO:37). This fragment was treated with Tfl DNA polymerase in the presence of dGTP to add a 3'G tail to the termini. It was further digested with SpeI to remove the lacZ region from the right side of the fragment. The third fragment was a region of ~1.3 kb containing the lacZ region flanked by MCSs, followed by the chloramphenicol resistance gene. This fragment was amplified from NZAhd by PCR with the primers lacE-SL1-F (SEQ ID NO:36) and CamTonB-Rev (SEQ ID NO:22) and was subsequently digested with SpeI and BglII. The fourth fragment was the 1.3 kb BglII fragment of the NZAN vector that contains the right telomere. The ligation reaction of these four fragments was transformed into E. CLONI® 10G-pTel cells, and recombinants containing NZCK3 were selected on plates containing chloramphenicol plus kanamycin.

Another linear vector, which lacks the kanamycin resistance gene, was created by ligation of three fragments. This vector was designated NZTC2 (SEQ ID NO:64). The first (left-most fragment) was a 10 kb XbaI fragment from the NZASA vector, containing the left telomere, telN gene, and repA gene. The XbaI restriction site was made blunt by treatment with T4 DNA polymerase in the presence of dNTPs. The second fragment, containing the lacZ gene and flanking DNA, was amplified from the NZCK3 vector by PCR with the primers T7-RC-Del (SEQ ID NO:41) and pCmOR (SEQ ID NO:20) and digested with AscI. The third fragment was a ~2.2 kb AscI fragment from the NZCK3 vector containing the right telomere and chloramphenicol resistance gene. The ligation reaction of these fragments was transformed into E. CLONI® iTel cells.

E. CLONI® iTel cells were derived by integrating the telN gene into the attB site in the chromosome of E. CLONI® 10G cells. The fragment containing Ptac-telN was excised from pGZ-telN and cloned into the chromosome-integration vector pJW22 (as described by Wild J, Hradecna Z, and Szybalski W (2002), Genome 12:1434-44), which encodes resistance to ampicillin. The resulting integration vector, pJW-telN, was digested with NotI to excise the fragment containing Ptac-telN, which was purified by gel-electrophoresis and circularized by self-ligation. The circularized fragment was transformed into E. CLONI® 10G cells carrying the integrase-producing plasmid pJW289t. Colonies that contained an integrated telN gene and which had lost the pJW289t plasmid were selected (as described by Wild J, Hradecna Z, and Szybalski W (2002), Genome 12:1434-44). The resulting ampicillin resistant strain was designated E. CLONI® iTel.

NZTC2 contained an AhdI site in the repA gene. A derivative lacking this site was created from three fragments. The first (left-most) fragment was the 7.8 kb AhdI fragment of NZAhd encompassing the left telomere, telN gene, and part of the repA gene. The second fragment was a region of ~4.5 kb amplified from NZTC2 by PCR, using as forward primers a mixture of the primers NZg7847a-F2 (SEQ ID NO:42) and NZg7847a-F3 (SEQ ID NO:43), which introduce a mutation that destroys the AhdI site, and the reverse primer NZ-RevB (SEQ ID NO:44). This fragment was re-amplified with NZg7847a-F2 as a forward primer and a mixture of NZ-RevA (SEQ ID NO:45) and NZ-RevC (SEQ ID NO:46) as reverse primers. This fragment was treated with Tfl DNA polymerase in the presence of dGTP to add a 3'G tail to the ends, and further digested with SwaI to generate a blunt site on the right side of the fragment. The third fragment was the ~2.2 kb SwaI fragment of NZTC2 that contains the right telomere. The ligation reaction of these three fragments was transformed into E. CLONI® BIGEASY® TSA cells, and recombinants containing NZTC3 (SEQ ID NO:65) were selected on plates containing chloramphenicol.

The linear construct, designated pJAZZ-OC (SEQ ID NO:67), was prepared for ligation to G-tailed DNA by restriction with Ahd I and dephosphorylation with calf intestinal alkaline phosphatase.

Example 3

Cloning a PCR Product Encoding Single Stranded DNA Binding Protein (SSB) from *Thermus brokanius* (Tbr)

Non-proofreading thermostable DNA polymerases such as those from Thermus aquatics, *Thermus flavus*, and a new bacteriophage DNA polymerase enzyme developed at Lucigen, Middleton, Wis., PYROPHAGE® 3173, have been shown to produce single 3'A ends but not single 3'G ends. To demonstrate cloning using the vector preparations of the invention with these same enzymes, primers specific for a Tbr SSB gene were used to amplify a 677-bp product using an exonuclease minus mutant of PYROPHAGE® DNA polymerase 3173. The PCR primers SSB L (SEQ ID NO:47) and SSB R (SEQ ID NO:48) were phosphorlyated in a reaction containing 1.5 U T4 polynucleotide kinase, 400 pmol SSB L, 400 pmol SSB R, 10 mM NaCl, 5 mM Tris-HCl, 1 mM MgCl2, 0.1 mM dithiothreitol in a 10 microliter reaction volume incubated at 37° C. for 10 minutes. The PCR included 100 ng of *Thermus brockianus* genomic DNA (Lucigen, Middleton, Wis.), 50 mM Tris HCl (pH 9.0 at 25° C.), 50 mM KCl, 10 mM $(NH_4)_2SO_4$, 1.5 mM $MgSO_4$, 1.5 mM $MgCl_2$, 0.1% TRITON®-X100, 250 mM ectoine, 0.2 mM each of dGTP, dATP, dTTP and dCTP, and the exonuclease minus mutant of PYROPHAGE® DNA polymerase 3173 (5 U).

After thermal cycling (25 cycles of 94° C. for 15 seconds, 60° C. for 15 seconds, 72° C. for 60 seconds), reactions were resolved using agarose gel electrophoresis to confirm the presence of the expected 0.7 kb fragment. The PCR reaction mix was used without further treatment in a cloning reaction. The ligation reaction contained 1 ul PCR reaction, 25 ng of Ahd I restricted and dephosphorylated pSMART®GC HK, ligase buffer, and 2 U T4 DNA ligase. The reaction was incubated at room temperature for 2 hours, heat treated for 15 minutes at 70° C., and transformed into E. CLONI® 10G electrocompetent cells. Transformants were selected on agarose plates containing kanamycin, and sequence analysis confirmed the presence of the correct gene. The fusion point of the vector and insert contained the expected GC base pair at the junction.

Example 4

Cloning a PCR Amplified Gene for DNA Polymerase I (PolA) from *Thermus brockanius*

To demonstrate cloning using the vector preparations of the invention with non-proofreading thermostable DNA polymerase enzymes, primers specific for the Tbr PolA gene were used to amplify a 2513 bp product using an exonuclease deficient mutant of PYROPHAGE DNA polymerase 3173 (Lucigen, Middleton, Wis.). The PCR primers TBRPOLAL (SEQ ID NO:49) and TBRPOLAR (SEQ ID NO:50) were phosphorlyated in a reaction containing 1.5 U T4 polynucleotide kinase, 400 pmol TBRPOLA, 400 pmol TBRPOLA, 10 mM NaCl, 5 mM Tris-HCl, 1 mM MgCl2, 0.1 mM dithiothreitol in a 10 microliter reaction volume incubated at 37° C. for 10 minutes. The polymerase chain reaction included 100 ng of *Thermus brockianus* genomic DNA (Lucigen strain), 50 mM Tris HCl (pH 9.0 at 25° C.), 50 mM KCl, 10 mM $(NH_4)_2SO_4$, 1.5 mM $MgSO_4$, 1.5 mM $MgCl_2$, 0.1% TRITON®-X100, 250 mM ectoine, 0.2 mM each of dGTP, dATP, dTTP and dCTP, and the exonuclease minus mutant of PYROPHAGE® DNA polymerase 3173 (5 U) (Lucigen) (SEQ ID NO:69).

After thermal cycling (25 cycles of 94° C. for 15 seconds, 60° C. for 15 seconds, 72° C. for 60 seconds), the presence of the expected 2513 bp fragment was confirmed by gel electrophoresis. The PCR reaction was used without further treatment in a cloning reaction. The ligation reaction contained 1 ul of the unpurified PCR reaction, 25 ng of pSMART®GC HK, ligase buffer, and 2 U T4 DNA ligase. The reaction was incubated at room temperature for 2 hours, heat treated for 15 minutes at 70 C, and used to transform electrocompetent E. CLONI® cells. Transformants were selected on an agar plate containing 30 ug/ml kanamycin. Numerous colonies containing the expected 2513 bp insert were found and one was confirmed by DNA sequencing.

Example 5

Cloning a PCR Amplified Gene Encoding Chloramphenicol Resistance

A PCR fragment containing the chloramphenicol resistance gene with phosphorylated ends was directly ligated into pSMART®GC HK and pGC Blue vectors, transformed into E. CLONI cells (Lucigen, Middleton, Wis.), and plated on kanamycin plates to determine total colony forming units per ligation. Colonies were subsequently patched to chloramphenicol plates to assess the percent of complete chloramphenicol expressing inserts. The phosphorylated chloramphenicol resistance PCR fragment was generated by amplifying the resistance gene from pSMART® VC (Lucigen, Middleton, Wis.) (SEQ ID NO:4) with phosphorylated primers CAp29F (SEQ ID NO:51) and cam792R (SEQ ID NO:52). The PCR primers were phosphorlyated in a reaction containing 1.5 U T4 polynucleotide kinase, 400 pmol CAp29 primer, 400 pmol cam792R, 10 mM NaCl, 5 mM Tris-HCl, 1 mM MgCl2, 0.1 mM dithiothreitol in a 10 microliter reaction volume incubated at 37° C. for 10 minutes. The phosphorylation reaction was added to a PCR mix that included 40 ng of pSMART® VC DNA, 50 mM Tris HCl (pH 9.0 at 25° C.), 50 mM KCl, 1.5 mM $MgCl_2$, 0.1% TRITON®-X100, 0.2 mM each of dGTP, dATP, dTTP and dCTP, and Taq DNA polymerase (5 U).

After thermal cycling (25 cycles of 94° C. for 15 seconds, 60° C. for 15 seconds, 72° C. for 60 seconds), reactions were resolved using agarose gel electrophoresis. The expected 781 bp fragment was observed. Aliquots of the PCR reaction were used without purification in cloning reactions. The first ligation reaction contained 1 ul PCR reaction, 25 ng of pSMART®GC HK, ligase buffer, and 2 U T4 DNA ligase. A second ligation reaction contained 1 ul PCR reaction, 25 ng of pGC Blue, ligase buffer, and 2 U T4 DNA ligase. The reactions were incubated at room temperature for 30 minutes, heat treated for 15 minutes at 70° C., and used to transform electrocompetent E. CLONI® 10G cells.

The following day, 50 colonies were picked and streaked onto an agar plate containing 12.5 µg/ml chloramphenicol. The results showed that 43/50 streaks grew on chloramphenicol. The pGC Blue transformation was spread onto an agar plate containing 30 ug/ml kanamycin and XGAL. White colonies that arose were subsequently patched onto chloramphenicol agarose plates, and 56/70 of them grew.

A non-phosphorylated, PCR-amplified chloramphenicol resistance gene fragment was directly ligated to a TOPO TA cloning vector (pCRII-TOPO) (Invitrogen, Carlsbad, Calif.), plated on kanamycin and patched to chloramphenicol plates for a benchmark comparison to the GC cloning constructs prepared in Example 2. The non-phosphorylated chloramphenicol resistance PCR fragment was generated following the protocol outlined above but without phosphorylation of the primers. The ligation reaction contained 1 µl PCR product, 1 µl of TOPO vector premix, 1 µl diluted salt solution and 2 µl water. The ligation reaction was incubated at room temperature for five minutes, placed on ice and then transformed into E. CLONI 10G electrocompetent cells (Lucigen, Middleton, Wis.) as described above. The pCRII-TOPO transformation was spread onto an agar plate containing 30 ug/ml kanamycin and XGAL. The following day 25 white colonies were picked and streaked onto an agar plate containing 12.5 µg/ml chloramphenicol; 22/25 streaks grew from this experiment.

Figure 9:
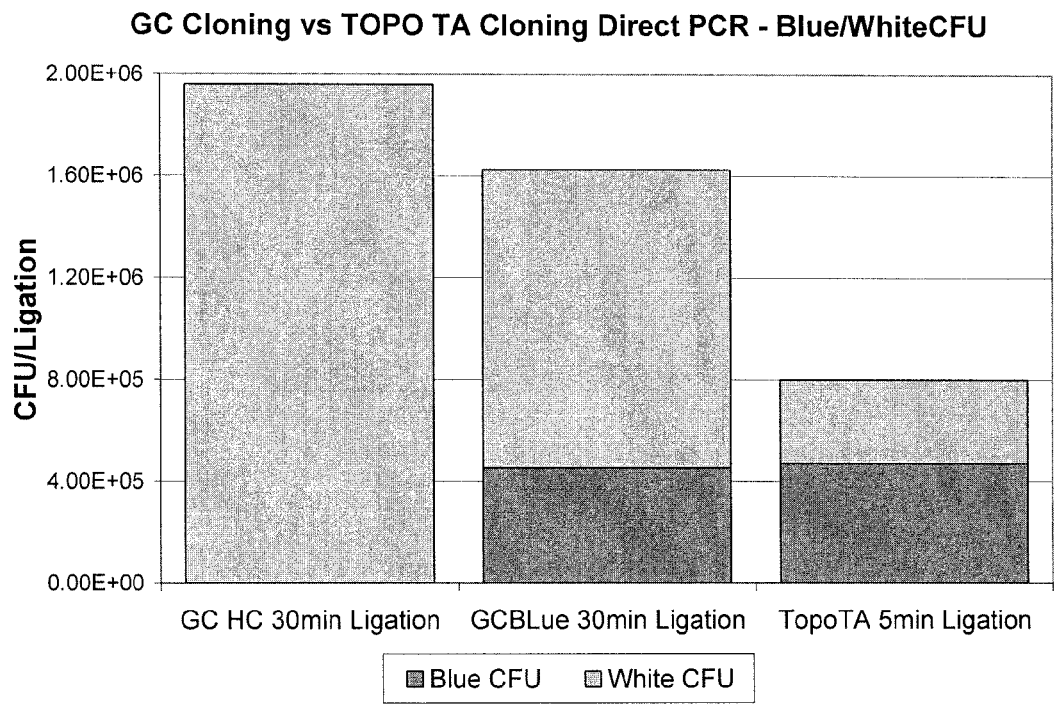
FIG. 9 shows results of a comparison of cloning methods of the invention to TOPO TA cloning of a PCR amplified chloramphenicol resistance gene. Panel A is a bar graph comparing colony forming units per ligation reaction using pSMART®GC HK and pGC BLUE in comparison to pCRII TOPO TA vector. Panel B is a bar graph showing numbers of non-chloramphenicol-resistant and chloramphenicol-expressing colonies (background) produced per ligation reaction when using pSMART®GC HK and pGC BLUE as compared to pCRII TOPO TA vector.
Figure 9:
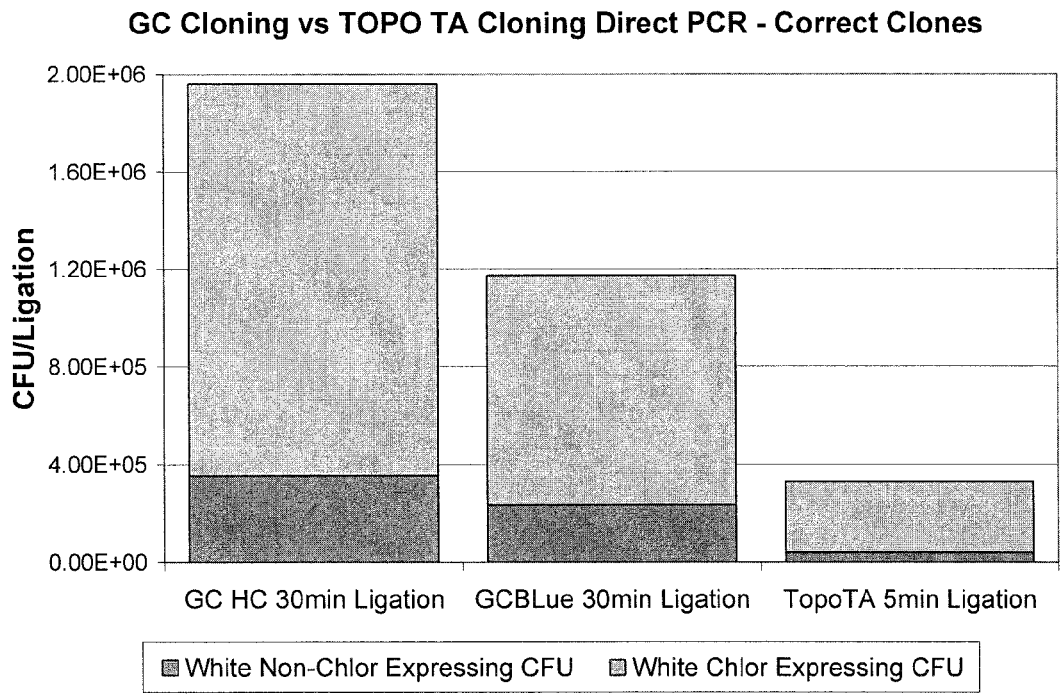

The data obtained for this comparison of GC cloning versus TA cloning is compiled in FIG. 9. It demonstrates that GC cloning works well, in contradiction to the central dogma of TA cloning. GC cloning resulted in more recombinant clones with the correct insert than TOPO TA cloning did, by a margin of approximately 3- and 8-fold for pGC BLUE and pSMART®GC HK, respectively (FIG. 9, panel B).

Example 6

Cloning a PCR Amplified Gene Encoding the lacZ Alpha Peptide

A 497 bp lacZα PCR fragment with phosphorylated ends was amplified, directly ligated into pSMART®GC HK, transformed into E. CLONI 10G cells (Lucigen, Middleton, Wis.) and plated on agarose containing kanamycin, XGAL and IPTG to determine total colony forming units per ligation. The phosphorylated lacZα PCR fragment was generated by amplifying the lacZα gene from pJAZZ®-KA (Lucigen, Middleton, Wis.) (SEQ ID NO: 5) with phosphorylated primers ANNLacFor (SEQ ID NO:53) and ANNLacRev (SEQ ID NO:54). The PCR primers were phosphorlyated in a reaction containing 1.5 U T4 polynucleotide kinase, 400 pmol ANNLacFor primer, 400 pmol ANNLacRev, 10 mM NaCl, 5 mM Tris-HCl, 1 mM MgCl2, 0.1 mM dithiothreitol in a 10 microliter reaction volume incubated at 37° C. for 10 minutes. The polymerase chain reaction included 5 ng of pJAZZ®-KA vector DNA, 1× buffer specific for each enzyme, and 0.2 mM each of dGTP, dATP, dTTP and dCTP, and 2.5 units of Taq, Tfl, or a non-proofreading mutant of PYROPHAGE® 3173 DNA polymerase (SEQ ID NO:69). The 1× buffer for Taq DNAP is 10 mM Tris-HCl (pH 9.0), 50 mM KCl, 1.5 mM $MgCl_2$, and 0.1% TRITON® X-100. The 1× buffer for Tfl DNAP is 20 mM Tris-acetate (pH 8.9), 10 mM ammonium sulfate, 1.5 mM $MgSO_4$. The 1× buffer for PYROPHAGE® 3173 DNAP is 50 mM Tris HCl (pH 9.0 at 25° C.), 50 mM KCl, 10 mM $(NH_4)_2SO_4$, 1.5 mM $MgSO_4$, 1.5 mM $MgCl_2$, 0.1% TRITON®-X100, 250 mM ectoine. After thermal cycling (25 cycles of 94° C. for 15 seconds, 60° C. for 15 seconds, 72° C. for 60 seconds), reactions were resolved using agarose gel electrophoresis. The expected 497 bp fragment was observed in all three cases.

Three ligation reactions were performed, each containing 2 ul of product from one of the PCRs, 25 ng of pSMARTOGC HCKan, ligase buffer, and 2 U T4 DNA ligase. The reactions were incubated at room temperature for 30 minutes, heat treated for 15 minutes at 70° C. and used to transform electrocompetent E. CLONI® cells. A 5 ul aliquot of each transformation was spread onto an agar plate containing 30 ug/ml kanamycin, XGAL and IPTG. The Taq DNA polymerase product yielded 117 white colonies and 171 blue colonies, the Tfl DNA polymerase product yielded 34 white colonies and 426 blue colonies, and the PYROPHAGE® 3173 DNA polymerase product yielded 34 white colonies and 566 blue colonies.

Example 7

Cloning of Blunt PCR Amplified DNA

The following example illustrates that blunt-ended DNA can be efficiently G-tailed for ligation to pSMART®GC vectors by incubation with Taq DNA Polymerase. A phosphorylated lacZα PCR fragment was generated by amplifying the gene from pJAZZ®-KA (SEQ ID NO: 5, nucleotides 11952-12399) with phosphorylated primers ANNLacFor (SEQ ID NO:53) and ANNLacRev (SEQ ID NO:54). The PCR primers were phosphorlyated in a reaction containing 1.5 U T4 polynucleotide kinase, 400 pmol ANNLacFor primer, 400 pmol ANNLacRev, 10 mM NaCl, 5 mM Tris-HCl, 1 mM MgCl2, 0.1 mM dithiothreitol in a 10 microliter reaction volume incubated at 37° C. for 10 minutes. The polymerase chain reaction included 5 ng of pJAZZ®-KA Vector DNA, 20 mM Tris HCl (pH 9.0 at 25° C.), 10 mM KCl, 10 mM $(NH_4)_2SO_4$, 2 mM $MgSO_4$, 0.1% TRITON®-X100, and 0.2 mM each of dGTP, dATP, dTTP and dCTP, and 5 U of VENT$_R$® DNA polymerase.

A control PCR reaction contained the same phosphorylated primers, 5 ng of pSMART® VC BAC vector DNA, 50 mM Tris HCl (pH 9.0 at 25° C.), 50 mM KCl, 1.5 mM $MgCl_2$, 0.1% TRITON®-X100, and 0.2 mM each of dGTP, dATP, dTTP and dCTP, and 5 units of Taq DNA polymerase. After thermal cycling (25 cycles of 94° C. for 15 seconds, 60° C. for 15 seconds, 72° C. for 60 seconds), an aliquot of the reactions were resolved using agarose gel electrophoresis and the expected 497 bp fragment was observed.

G-tailing reactions were performed on 25 μl of VENT$_R$® DNA polymerase PCR reaction by adding 2.5 U of Taq DNA Polymerase directly to the amplification reaction and incubating at 72° C. for 10 minutes. An aliquot of the untailed VENT$_R$® DNA polymerase PCR reaction was used as a ligation control.

The Vent PCR product, with or without G-tailing, or the Taq PCR product were ligated to the 25 ng of pSMART®GC HK vector. The reactions were incubated at room temperature for 30 minutes, heat treated for 15 minutes at 70° C., transformed into E. CLONI® 10G cells and spread onto agar plates containing 30 ug/ml kanamycin, XGAL and IPTG. Direct cloning of the blunt PCR product into a C-tailed vector resulted in 71 blue colonies and 29 white colonies. Direct cloning of the G-tailed product into a C-tailed vector resulted in 787 blue colonies and 23 white colonies. Direct cloning of Taq amplified DNA (G-tailed endogenously) into a C-tailed vector resulted in 1188 blue colonies and 116 white colonies.

Example 8

Cloning of 40-kb, Randomly Sheared DNA Fragments Using a C-tailed Single-copy, BAC/Fosmid Cloning Vector Large (>20 kb) randomly sheared potato DNA fragments were G-tailed for ligation to a C-tailed single copy BAC/fosmid vector preparation. Potato nuclei were extracted, washed, and re-suspended in the nuclear preparation buffer (0.8 M KCl, 0.1 M Tris, 0.1 M EDTA, 10 mM spermidine, 10 mM spermine, pH to 9.5 and 0.15% β-mercaptoethanol). The nuclei suspension was embedded in low-melting-point agarose plugs and lysed in 0.5 M EDTA, pH 9.0, 1% sodium lauryl sarcosine, and 0.1-0.5 mg/ml proteinase K at 55° C. for 2 hours, resulting in purified high molecular weight (HMW) genomic DNA in the agarose plugs.

The DNA plugs were physically sheared to 50-300 kb by pipetting, end repaired with the DNATERMINATOR® Kit (Lucigen, Middleton, Wis.) and G-tailed with Taq DNA polymerase as described above. The end-repaired and G-tailed high molecular weight (HMW) DNA was fractionated by pulse field gel electrophoresis (PFGE). Three gel fractions containing DNA fragments of 50-70 kb, 70-100 kb, and 100-200 kb were excised, electroeluted, and dialyzed into TE buffer. DNA from each of the fractions were ligated into the C-tailed single copy BAC/fosmid cloning vector pSMART® BAC GC cut with AhdI at an equal molar ratio using 5 U T4 DNA ligase (Invitrogen, Carlsbad, Calif.) at 16° C. for 12 h. Ligated DNA was transformed into E. CLONI 10G cells (Lucigen, Middleton, Wis.) by electroporation, using a Cell Porator System (Whatman Biometra Goettingen, Germany). The setting conditions were 350V, 330 pF, low-ohms, and 4 kΩ with fast charge. Recombinant transformants were selected on an LB agar plate containing 5% sucrose, 12.5 μg/ml chloramphenicol, 0.5 mM IPTG, and 50 μg/ml XGAL. After a 32 h incubation at 37° C., white colonies were randomly selected, and BAC DNA was isolated, digested with NotI, and subjected to size analysis by PFGE (FIG. 10).

Figure 10:
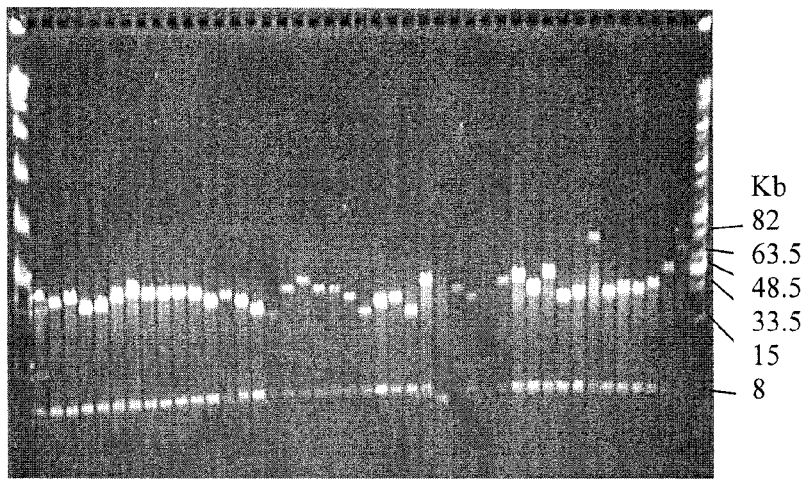
FIG. 10 is a photograph of an agarose electrophoresis gel showing recombinants of a 40 kb potato genomic library cloned using pSMART®BAC GC. M1 is a lambda ladder and M2 is a Mid Range ladder (New England Biolabs).

The 50-70 kb and 70-100 kb fractions had a transformation efficiency of more than 300 white colonies/μl ligation and 81/82 (98.8%) of randomly selected samples contained inserts with an average size of 40 kb (FIG. 10). The 100-200 kb ligation was not as efficient but still contained recombinant inserts larger than 150 kb.

Example 9

Cloning of 10-20 kb, Randomly Sheared, ddG-tailed DNA in a C-tailed Linear Vector

*Lactobacillus helveticus* are Gram-positive bacteria. The genomic DNA from these microbes is approximately 65% AT, and cloning fragments larger than 4-5 kb is very difficult in standard vectors and in pSMART® vectors as well. In contrast, fragments of this genome as large as 20-30 kb could be successfully cloned in the pJAZZ® linear vectors. The pJAZZ® OC vector was therefore used to demonstrate the efficiency of cloning with large, AT rich DNA fragments from *L. helveticus.*

Ten micrograms of *Lactobacillus helveticus* DNA was physically sheared to 10-20 kb using a HydroShear Device (Gene Machines), and the ends were repaired using the DNA-TERMINATOR® kit (Lucigen, Middleton, Wis.). This blunt DNA was tailed with 2',3'-dideoxyguanosine 5'-triphosphate (ddGTP) in a tailing reaction containing 10 μg of blunt sheared *L. helveticus* DNA, 10 mM KCl, 20 mM Tris-HCl (pH 8.8 at 25° C.), 10 mM $(NH_4)_2SO_4$, 2 mM MgSO4 and 0.1% TRITON® X-100, 400 μM ddGTP, 2.5U exonuclease minus 3173 DNA polymerase with an F/Y mutation. The ddGTP tailing reaction was incubated at 70° C. for 30 minutes, then size selected for 10-20 kb by gel purification. The DNA was quantitated against a DNA mass standard using gel densitometry software (Alpha Innotech, San Leandro, Calif.).

The ddGTP tailed insert DNAs were ligated to the pJAZZ® OC vector that was Ahd I restricted and dephosphorylated. The ligation reaction contained 98 ng of insert DNA, 50 ng of digested pJAZZ® OC, ligase buffer, and 2 U T4 DNA ligase. The reaction was incubated at room temperature for 2 hours, heat treated for 15 minutes at 70° C. and used to transform electrocompetent E. CLONI® BIGEASY® TSA cells. Cells were spread on to an agar plate containing 12.5 ug/ml chloramphenicol, XGAL and IPTG. Linear plasmid DNA was isolated using standard alkaline lysis purification with binding to diatomaceous earth. The DNA was digested with Not I and assayed by agarose gel electrophoresis.

Figure 11:
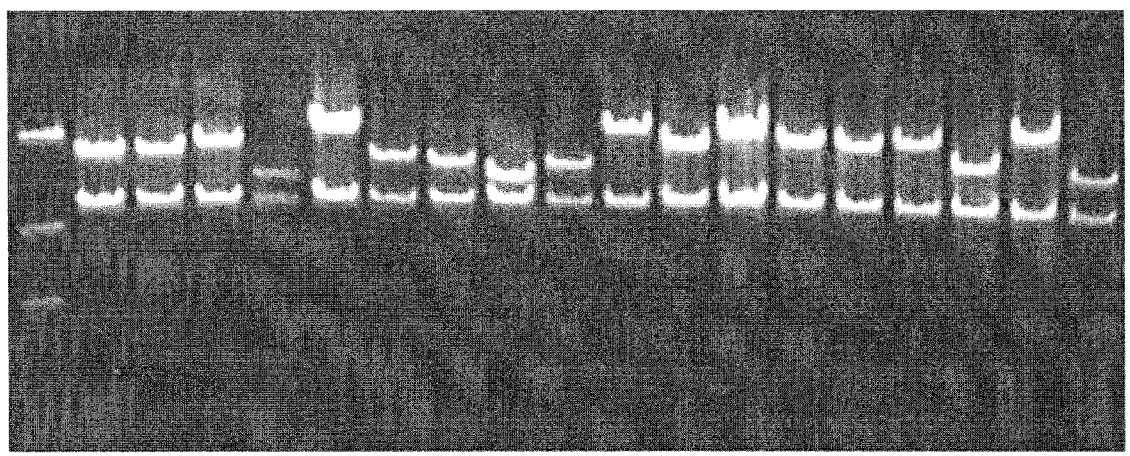
FIG. 11 is a photograph of an agarose gel of 10-20 kb *Lactobacillus helveticus* recombinants prepared according to the invention and restricted by Not I endonuclease.

The results are shown in FIG. 11. Nearly all of the recombinant clones contained inserts of 10-20 kb, and 97 samples were sequenced to confirm that they contained genomic DNA from *L. helveticus.*

Example 10

Chimera-free Cloning Using ddG-tailed DNA Inserts and C-tailed Vectors

Thirty micrograms of lambda phage genomic DNA (Promega Cat# D150A, Madison, Wis.) was physically sheared to 1-3 kb using a HydroShear Device (Gene Machines, San Carlos, Calif.), split into three aliquots, and end-repaired with the DNATERMINATOR Kit (Lucigen, Middleton, Wis.).

The first sample (#1) remained untreated. The second sample was tailed with 2',3'-dideoxyguanosine 5'-triphosphate (ddGTP), as described in Example 9. The third sample was tailed with 2'-deoxyguanosine 5'-triphosphate (dGTP), under similar reaction conditions. All three samples were size selected for 2 kb fragments by gel purification and quantitated.

The ddGTP and dGTP tailed insert DNAs were then ligated to a low copy pSMART®GC vector and the blunt insert DNA was ligated to a blunt low copy pSMART® vector. The ligation reaction contained 300 ng of insert DNA, 25 ng of pSMART®GC LK or 25 ng of pSMART® LCKan, ligase buffer, and 2 U T4 DNA ligase. The reaction was incubated at room temperature for 2 hours, heat treated for 15 minutes at 70° C. and used to transform E. CLONI® 10G cells. Transformed cells were spread onto an agar plate containing 30 ug/ml kanamycin. The plasmid DNA was isolated and its size assayed by agarose gel electrophoresis.

Figure 12:
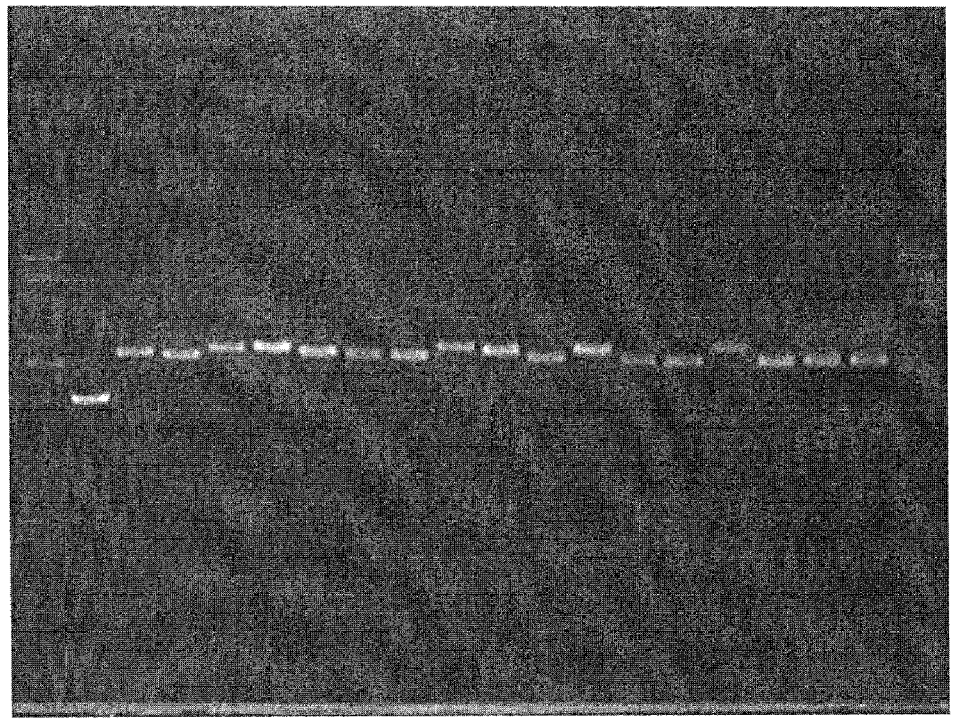
FIG. 12 is a photograph of an agarose gel showing results of a method of cloning according to one embodiment of the invention (Panel A) compared to conventional blunt cloning (Panel B).
Figure 12:
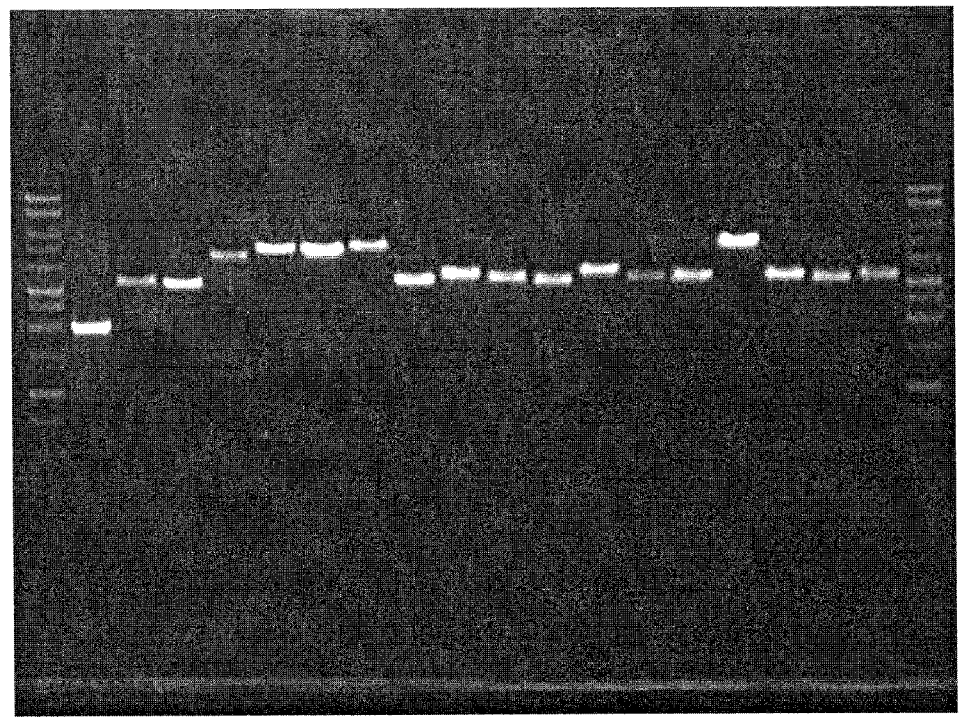

The results are shown in FIG. 12. Clones with single inserts were obvious from their tight banding centered between 3 and 4 kb (FIG. 12A). The first and last lanes of FIGS. 12A and B contain a 1 kb size standard, the second lane contains the empty vector and lanes 3-19 contain randomly picked clones from the chimera-free cloning experiment (FIG. 12A) or normal blunt end cloning (FIG. 12B). Clones with multiple inserts (chimeras) were obvious by their increased size relative to single-insert clones (FIG. 12B, lanes 5-8 and 16). ddGTP-tailed insert DNA ligated to pSMART®GC LK vector had 1/102 clones with a chimeric insert (1.0%) and 1/102 clones that were self-ligated (1.0%). dGTP tailed insert DNA ligated to pSMART®GC LK vector had 3/93 clones with a chimeric insert (3.2%) and 0/93 clones that were self-ligated (0%). Blunt-ended insert DNA ligated to pSMART® LK vector had 12/102 chimeric inserts (11.8%) and 0/102 clones that were self-ligated (0%).

Example 11

Construction of an Environmental Viral DNA Library Using Cloning

Viral particles were isolated from a thermal spring, commonly known as Octopus Spring, in Yellowstone National Park (temperature 80° C., pH 8; map coordinates N 44.53416, W 110.79812). Hot spring water was filtered using a 100 kiloDalton molecular weight cut-off (mwco) tangential flow filter (A/G Technology, GE Healthcare Life Sciences, Piscataway, N.J.) and viruses and microbes from 630 liters were concentrated to 2 liters. The resulting concentrate was filtered through a 0.2 μm tangential flow filter to remove microbial cells. The viral fraction was further concentrated to 100 ml using a 100 kD tangential flow filter. Viruses from 40 ml were further concentrated to 400 μl and transferred to SM buffer (0.1 M NaCl, 8 mM MgSO4, 50 mM Tris HCl 7.5) by filtration in a 30 kD mwco spin filter (CENTRICON®, Millipore, Billerica, Mass.).

*Serratia marcescens* endonuclease (10 U, Sigma, St. Louis, Mo.) was added to the viral preparation to remove non-encapsidated (non-viral) DNA. The reaction was incubated for 30 min. at 23° C. Subsequently, EDTA (20 mM), sodium dodecyl sulfate (SDS) (0.5%) and Proteinase K (100 U) was added and the reaction was incubated for 3 hours at 56° C. Sodium chloride (0.7M) and cetyltrimethylammonium bromide (CTAB) (1%) were added. The DNA was extracted once with chloroform, once with phenol, once with a phenol:chloroform (1:1) mixture and again with chloroform. The DNA was precipitated with 1 ml of ethanol and washed with 70% ethanol. The yield of DNA was 20 nanograms.

Ten nanograms of viral DNA were physically sheared to 2-4 kb using a HydroShear Device (Gene Machines, San Carlos, Calif.). The fragments were ligated to a double-stranded asymmetrical linker having one blunt phosphorylated end and one non-phosphorylated staggered end, created by annealing primers 28T (SEQ ID NO:71) and 30B (SEQ ID NO:72) using standard methods. The ligation mix was separated by agarose gel electrophoresis, and fragments in the size range of 1-2 kb were isolated. These fragments were amplified by standard PCR methods using the primer 28T4 (SEQ ID NO:55). The amplification products were gel purified, and 100 ng of this DNA was ligated to 25 ng of a dephosphorylated, C-tailed preparation of the vector pSMART®GC HK in a ten microliter reaction. The reaction was incubated for 2 hours at room temperature, heated to 70° C. for 15 minutes, and electroporated into E. CLONI® 10G cells. Transformants were selected on plates containing 30 ug/ml kanamycin.

As used in this specification and the appended claims, the singular forms "a," "an," and "the" include plural referents unless the content clearly dictates otherwise. Thus, for example, reference to a composition containing "a polynucleotide" includes a mixture of two or more polynucleotides. It should also be noted that the term "or" is generally employed in its sense including "and/or" unless the content clearly dictates otherwise. All publications, patents and patent applications referenced in this specification are indicative of the level of ordinary skill in the art to which this invention pertains. All publications, patents and patent applications are herein expressly incorporated by reference to the same extent as if each individual publication or patent application was specifically and individually indicated by reference. In case of conflict between the present disclosure and the incorporated patents, publications and references, the present disclosure should control.

It also is specifically understood that any numerical value recited herein includes all values from the lower value to the upper value, i.e., all possible combinations of numerical values between the lowest value and the highest value enumerated are to be considered to be expressly stated in this application. For example, if a concentration range is stated as 1% to 50%, it is intended that values such as 2% to 40%, 10% to 30%, or 1% to 3%, etc., are expressly enumerated in this specification. These are only examples of what is specifically intended.

The invention has been described with reference to various specific embodiments and techniques. However, it should be understood that many variations and modifications may be made while remaining within the spirit and scope of the invention.

We claim:

1. A cloning construct configured to produce a vector preparation comprising a double-stranded DNA molecule having two 3' termini, each 3' terminus comprising an overhang, each overhang comprising a single, unpaired dCMP or nucleotide analog capable of hybridizing to an unpaired dGMP, the cloning construct comprising a sequence selected from the group consisting of SEQ ID NO:56, SEQ ID NO:57, SEQ ID NO:58, SEQ ID NO:60 and SEQ ID NO:67.

2. The cloning construct of claim 1, wherein the vector preparation comprises:
   a) a linearized plasmid; or
   b) a right arm and a left arm of a linear vector construct, wherein the right and left arms are dissociated.

3. The cloning construct of claim 1, wherein the vector preparation comprises a transcription termination sequence proximal to each overhang.

4. The cloning construct of claim 1, wherein the DNA molecule of the vector preparation is dephosphorylated.

5. The cloning construct of claim 1, comprising a plasmid construct.

6. The cloning construct of claim 1, comprising a linear vector construct.

7. The cloning construct of claim 1, comprising two restriction endonuclease sites for producing the overhang at each 3' terminus selected from Ahd I, Hph I, HpyCH4 III, Hpy188 I, Mbo II, or Xcm I.

8. A kit comprising instructions for use of the kit, and the cloning construct of claim 1.

9. The kit of claim 8, further comprising a non-proofreading polymerase; a non-proofreading, non-discriminating polymerase; or a terminal deoxynucleotidyl transferase.

10. The kit of claim 9, wherein the non-proofreading polymerase comprises a polymerase of *Thermus aquaticus, Thermus brockianus, Thermus filiformis, Thermus flavus, Thermus thermophilis* or *Thermotoga maritem*, or a polymerase comprising the sequence of SEQ ID NO:69 or SEQ ID NO:70.

11. The kit of claim 9, further comprising a component selected from the group consisting of a ligase, a kinase, a proofreading polymerase, a sequencing primer pair, an amplification primer pair, competent cells, dNTPs, ddNTPs and a reaction buffer.

* * * * *